United States Patent
Jebrail et al.

(10) Patent No.: US 11,992,842 B2
(45) Date of Patent: May 28, 2024

(54) CONTROL OF EVAPORATION IN DIGITAL MICROFLUIDICS

(71) Applicant: mirOculus Inc., San Francisco, CA (US)

(72) Inventors: Mais Jehan Jebrail, Toronto (CA); Mathieu Gabriel-Emmanuel Chauleau, San Francisco, CA (US); Poornasree Kumar, San Francisco, CA (US); Eduardo Cervantes, San Francisco, CA (US); Foteini Christodoulou, San Francisco, CA (US); Nikolay Sergeev, San Francisco, CA (US); Spencer Seiler, San Francisco, CA (US); Alejandro Tocigl Domeyko, San Francisco, CA (US); Ana Eugenia Carvajal, San Francisco, CA (US)

(73) Assignee: mirOculus Inc., San Francisco, CA (US)

( * ) Notice: Subject to any disclaimer, the term of this patent is extended or adjusted under 35 U.S.C. 154(b) by 762 days.

(21) Appl. No.: 17/088,572

(22) Filed: Nov. 3, 2020

(65) Prior Publication Data
US 2021/0069714 A1    Mar. 11, 2021

Related U.S. Application Data

(63) Continuation of application No. PCT/US2019/033794, filed on May 23, 2019.
(Continued)

(51) Int. Cl.
*B01L 3/00* (2006.01)
*C12M 3/06* (2006.01)
*G01N 27/447* (2006.01)

(52) U.S. Cl.
CPC ....... *B01L 3/502792* (2013.01); *C12M 23/16* (2013.01); *G01N 27/44791* (2013.01);
(Continued)

(58) Field of Classification Search
None
See application file for complete search history.

(56) References Cited

U.S. PATENT DOCUMENTS

| 4,469,863 A | 9/1984 | Ts'o et al. |
| 4,492,322 A | 1/1985 | Hieftje et al. |

(Continued)

FOREIGN PATENT DOCUMENTS

| CA | 2470847 A1 | 7/2003 |
| CA | 2740113 A1 | 4/2010 |

(Continued)

OTHER PUBLICATIONS

Jensen et al.; Free-running enzymatic oligonucleotide synthesis for data storage applications; bioRxiv; 1:355719; 7 pages; Jan. 2018.
(Continued)

*Primary Examiner* — J. Christopher Ball
(74) *Attorney, Agent, or Firm* — Shay Glenn LLP

(57) ABSTRACT

Air-matrix digital microfluidics (DMF) apparatuses and methods of using them. These methods and apparatuses may include the use of a liquid wax coating material and/or pinning the encapsulated reaction droplet within the air gap using pinning features. Any of these methods may also include separating the liquid wax from an encapsulated aqueous droplet, e.g., using an oil absorbent wick to selectively separate the liquid oil or wax from the aqueous droplet by adsorbing and/or absorbing the liquid wax into the absorbent wick while leaving the aqueous droplet behind.

24 Claims, 61 Drawing Sheets

Related U.S. Application Data

(60) Provisional application No. 62/675,749, filed on May 23, 2018.

(52) U.S. Cl.
CPC ... *B01L 2200/027* (2013.01); *B01L 2200/142* (2013.01); *B01L 2300/042* (2013.01); *B01L 2300/0874* (2013.01); *B01L 2300/1822* (2013.01); *B01L 2400/0415* (2013.01)

(56) References Cited

U.S. PATENT DOCUMENTS

| | | |
|---|---|---|
| 4,569,575 A | 2/1986 | Le Pesant et al. |
| 4,636,785 A | 1/1987 | Le Pesant |
| 4,818,052 A | 4/1989 | Le Pesant et al. |
| 5,034,506 A | 7/1991 | Summerton et al. |
| 5,130,238 A | 7/1992 | Malek et al. |
| 5,216,141 A | 6/1993 | Benner |
| 5,235,033 A | 8/1993 | Summerton et al. |
| 5,270,185 A | 12/1993 | Margolskee |
| 5,386,023 A | 1/1995 | Sanghvi et al. |
| 5,399,491 A | 3/1995 | Kacian et al. |
| 5,409,818 A | 4/1995 | Davey et al. |
| 5,411,876 A | 5/1995 | Bloch et al. |
| 5,455,166 A | 10/1995 | Walker |
| 5,486,337 A | 1/1996 | Ohkawa |
| 5,602,240 A | 2/1997 | De Mesmaeker et al. |
| 5,637,684 A | 6/1997 | Cook et al. |
| 5,644,048 A | 7/1997 | Yau |
| 5,681,702 A | 10/1997 | Collins et al. |
| 5,705,365 A | 1/1998 | Ryder et al. |
| 5,710,029 A | 1/1998 | Ryder et al. |
| 5,888,779 A | 3/1999 | Kacian et al. |
| 6,007,690 A | 12/1999 | Nelson et al. |
| 6,074,725 A | 6/2000 | Kennedy |
| 6,294,063 B1 | 9/2001 | Becker et al. |
| 6,352,838 B1 | 3/2002 | Krulevitch et al. |
| 6,401,552 B1 | 6/2002 | Elkins |
| 6,495,369 B1 | 12/2002 | Kercso et al. |
| 6,565,727 B1 | 5/2003 | Shenderov |
| 6,596,988 B2 | 7/2003 | Corso et al. |
| 6,723,985 B2 | 4/2004 | Schultz et al. |
| 6,773,566 B2 | 8/2004 | Shenderov |
| 6,787,111 B2 | 9/2004 | Roach et al. |
| 6,887,384 B1 | 5/2005 | Frechet et al. |
| 6,911,132 B2 | 6/2005 | Pamula et al. |
| 6,989,234 B2 | 1/2006 | Kolar et al. |
| 7,057,031 B2 | 6/2006 | Olejnik et al. |
| 7,147,763 B2 | 12/2006 | Elrod et al. |
| 7,163,612 B2 | 1/2007 | Sterling et al. |
| 7,214,302 B1 | 5/2007 | Reihs et al. |
| 7,323,345 B1 | 1/2008 | Stjerstrom |
| 7,328,979 B2 | 2/2008 | Decre et al. |
| 7,329,545 B2 | 2/2008 | Pamula et al. |
| 7,349,014 B2 | 3/2008 | Higashihara |
| 7,390,463 B2 | 6/2008 | He et al. |
| 7,391,020 B2 | 6/2008 | Bousse et al. |
| 7,439,014 B1 | 10/2008 | Pamula et al. |
| 7,445,926 B2 | 11/2008 | Mathies et al. |
| 7,531,120 B2 | 5/2009 | Van Rijn et al. |
| D599,832 S | 9/2009 | Chapin et al. |
| 7,713,456 B2 | 5/2010 | Dodd et al. |
| 7,727,723 B2 | 6/2010 | Pollack et al. |
| 7,745,207 B2 | 6/2010 | Jovanovich et al. |
| 7,763,471 B2 | 7/2010 | Pamula et al. |
| 7,815,871 B2 | 10/2010 | Pamula et al. |
| 7,816,121 B2 | 10/2010 | Pollack et al. |
| 7,822,510 B2 | 10/2010 | Paik et al. |
| 7,851,184 B2 | 12/2010 | Pollack et al. |
| 7,897,737 B2 | 3/2011 | Wu et al. |
| 7,901,947 B2 | 3/2011 | Pollack et al. |
| 7,919,330 B2 | 4/2011 | de Guzman et al. |
| 7,939,021 B2 | 5/2011 | Smith et al. |
| 7,998,436 B2 | 8/2011 | Pollack et al. |
| 8,007,739 B2 | 8/2011 | Pollack et al. |
| 8,041,463 B2 | 10/2011 | Pollack et al. |
| 8,053,239 B2 | 11/2011 | Wheeler et al. |
| 8,088,578 B2 | 1/2012 | Hua et al. |
| 8,093,062 B2 | 1/2012 | Winger |
| 8,137,917 B2 | 3/2012 | Pollack et al. |
| 8,187,864 B2 | 5/2012 | Wheeler et al. |
| 8,190,371 B2 | 5/2012 | Allawi et al. |
| 8,202,686 B2 | 6/2012 | Pamula et al. |
| 8,202,736 B2 | 6/2012 | Mousa et al. |
| 8,208,146 B2 | 6/2012 | Srinivasan et al. |
| 8,268,246 B2 | 9/2012 | Srinivasan et al. |
| 8,304,253 B2 | 11/2012 | Yi et al. |
| 8,317,990 B2 | 11/2012 | Pamula et al. |
| 8,349,276 B2 | 1/2013 | Pamula et al. |
| 8,364,315 B2 | 1/2013 | Sturmer et al. |
| 8,367,370 B2 | 2/2013 | Wheeler et al. |
| 8,389,297 B2 | 3/2013 | Pamula et al. |
| 8,394,641 B2 | 3/2013 | Winger |
| 8,399,222 B2 | 3/2013 | Siva et al. |
| 8,426,213 B2 | 4/2013 | Eckhardt et al. |
| 8,440,392 B2 | 5/2013 | Pamula et al. |
| 8,454,905 B2 | 6/2013 | Pope et al. |
| 8,460,528 B2 | 6/2013 | Pollack et al. |
| 8,470,153 B2 | 6/2013 | Feiglin et al. |
| 8,470,606 B2 | 6/2013 | Srinivasan et al. |
| 8,481,125 B2 | 7/2013 | Yi et al. |
| 8,492,168 B2 | 7/2013 | Srinivasan et al. |
| 8,562,807 B2 | 10/2013 | Srinivasan et al. |
| 8,591,830 B2 | 11/2013 | Sudarsan et al. |
| 8,592,217 B2 | 11/2013 | Eckhardt |
| 8,613,889 B2 | 12/2013 | Pollack et al. |
| 8,637,317 B2 | 1/2014 | Pamula et al. |
| 8,637,324 B2 | 1/2014 | Pollack et al. |
| 8,653,832 B2 | 2/2014 | Hadwen et al. |
| 8,658,111 B2 | 2/2014 | Srinivasan et al. |
| 8,685,344 B2 | 4/2014 | Sudarsan et al. |
| 8,685,754 B2 | 4/2014 | Pollack et al. |
| 8,702,938 B2 | 4/2014 | Srinivasan et al. |
| 8,716,015 B2 | 5/2014 | Pollack et al. |
| 8,809,068 B2 | 8/2014 | Sista et al. |
| 8,821,705 B2 | 9/2014 | Bjornson et al. |
| 8,845,872 B2 | 9/2014 | Pollack et al. |
| 8,846,414 B2 | 9/2014 | Sista et al. |
| 8,852,952 B2 | 10/2014 | Pollack et al. |
| 8,872,527 B2 | 10/2014 | Sturmer et al. |
| 8,877,512 B2 | 11/2014 | Srinivasan et al. |
| 8,888,969 B2 | 11/2014 | Soleymani et al. |
| 8,901,043 B2 | 12/2014 | Eckhardt et al. |
| 8,926,065 B2 | 1/2015 | Winger |
| 8,927,296 B2 | 1/2015 | Sista et al. |
| 8,936,708 B2 | 1/2015 | Feiglin et al. |
| 8,951,732 B2 | 2/2015 | Pollack et al. |
| 8,980,198 B2 | 3/2015 | Srinivasan et al. |
| 9,005,544 B2 | 4/2015 | Van Dam et al. |
| 9,011,662 B2 | 4/2015 | Wang et al. |
| 9,039,973 B2 | 5/2015 | Watson et al. |
| 9,046,514 B2 | 6/2015 | Sista et al. |
| 9,091,649 B2 | 7/2015 | Pollack et al. |
| 9,140,635 B2 | 9/2015 | Graham et al. |
| 9,188,615 B2 | 11/2015 | Sturmer et al. |
| 9,223,317 B2 | 12/2015 | Winger |
| 9,238,222 B2 | 1/2016 | Delattre et al. |
| 9,248,450 B2 | 2/2016 | Bauer |
| 9,377,439 B2 | 6/2016 | Lee et al. |
| 9,435,765 B2 | 9/2016 | Reimitz et al. |
| 9,446,404 B2 | 9/2016 | Bauer et al. |
| 9,476,811 B2 | 10/2016 | Mudrik et al. |
| 9,476,856 B2 | 10/2016 | Pamula et al. |
| 9,513,253 B2 | 12/2016 | Winger |
| 9,517,469 B2 | 12/2016 | Shenderov et al. |
| 9,594,056 B2 | 3/2017 | Fobel et al. |
| 9,851,365 B2 | 12/2017 | Mousa et al. |
| 9,975,117 B2 | 5/2018 | Lee et al. |
| 10,232,374 B2 | 3/2019 | Jebrail et al. |
| 10,464,067 B2 | 11/2019 | Jebrail et al. |
| 10,596,572 B2 | 3/2020 | Hong et al. |
| 10,695,762 B2 | 6/2020 | Jebrail et al. |
| 11,772,093 B2 | 10/2023 | Jebrail et al. |

(56) References Cited

U.S. PATENT DOCUMENTS

| | | |
|---|---|---|
| 2002/0150683 A1 | 10/2002 | Troian et al. |
| 2003/0017551 A1 | 1/2003 | Parthasarathy et al. |
| 2003/0136451 A1 | 7/2003 | Beebe et al. |
| 2003/0194716 A1 | 10/2003 | Knoll |
| 2004/0171169 A1 | 9/2004 | Kallury et al. |
| 2004/0211659 A1 | 10/2004 | Velev |
| 2005/0115836 A1 | 6/2005 | Reihs |
| 2005/0133370 A1 | 6/2005 | Park et al. |
| 2005/0148091 A1 | 7/2005 | Kitaguchi et al. |
| 2005/0191759 A1 | 9/2005 | Pedersen Bjergaard et al. |
| 2005/0220675 A1 | 10/2005 | Reed et al. |
| 2006/0091015 A1 | 5/2006 | Lau |
| 2006/0132542 A1 | 6/2006 | Bruker et al. |
| 2006/0231398 A1 | 10/2006 | Sarrut et al. |
| 2006/0272942 A1 | 12/2006 | Sirringhaus |
| 2007/0023292 A1 | 2/2007 | Kim et al. |
| 2007/0095407 A1 | 5/2007 | Chen et al. |
| 2007/0148763 A1 | 6/2007 | Huh et al. |
| 2007/0258864 A1 | 11/2007 | Braymer et al. |
| 2007/0269825 A1 | 11/2007 | Wang et al. |
| 2008/0110753 A1 | 5/2008 | Fourrier et al. |
| 2008/0131904 A1 | 6/2008 | Parce et al. |
| 2008/0156983 A1 | 7/2008 | Fourrier et al. |
| 2008/0169197 A1 | 7/2008 | McRuer et al. |
| 2008/0185339 A1 | 8/2008 | Delapierre et al. |
| 2008/0210558 A1 | 9/2008 | Sauter-Starace et al. |
| 2008/0241831 A1 | 10/2008 | Fan et al. |
| 2008/0293051 A1 | 11/2008 | Levy et al. |
| 2009/0017197 A1 | 1/2009 | Zhang et al. |
| 2009/0017453 A1 | 1/2009 | Maples et al. |
| 2009/0207206 A1 | 8/2009 | Harada |
| 2009/0286297 A1 | 11/2009 | Pihl et al. |
| 2010/0015614 A1 | 1/2010 | Beer et al. |
| 2010/0022414 A1 | 1/2010 | Link et al. |
| 2010/0025250 A1 | 2/2010 | Pamula et al. |
| 2010/0032293 A1 | 2/2010 | Pollack et al. |
| 2010/0048410 A1 | 2/2010 | Shenderov et al. |
| 2010/0087012 A1 | 4/2010 | Shenderov |
| 2010/0120130 A1 | 5/2010 | Srinivasan et al. |
| 2010/0130369 A1 | 5/2010 | Shenderov et al. |
| 2010/0136544 A1 | 6/2010 | Agresti et al. |
| 2010/0206094 A1 | 8/2010 | Shenderov |
| 2010/0236927 A1 | 9/2010 | Pope et al. |
| 2010/0236928 A1 | 9/2010 | Srinivasan et al. |
| 2010/0236929 A1 | 9/2010 | Pollack et al. |
| 2010/0270156 A1 | 10/2010 | Srinivasan et al. |
| 2010/0288368 A1 | 11/2010 | Beebe et al. |
| 2010/0311599 A1 | 12/2010 | Wheeler et al. |
| 2011/0024793 A1 | 2/2011 | Jeon |
| 2011/0076685 A1 | 3/2011 | Moeller et al. |
| 2011/0097763 A1 | 4/2011 | Pollack et al. |
| 2011/0104725 A1 | 5/2011 | Pamula et al. |
| 2011/0104747 A1 | 5/2011 | Pollack et al. |
| 2011/0107822 A1 | 5/2011 | Bunner et al. |
| 2011/0147216 A1 | 6/2011 | Fan et al. |
| 2011/0220501 A1 | 9/2011 | Witkowski et al. |
| 2011/0240471 A1 | 10/2011 | Wheeler et al. |
| 2011/0247934 A1 | 10/2011 | Wang et al. |
| 2011/0293851 A1 | 12/2011 | Bollström et al. |
| 2011/0303542 A1 | 12/2011 | Srinivasan et al. |
| 2011/0311980 A1 | 12/2011 | Pollack et al. |
| 2012/0000777 A1 | 1/2012 | Garrell et al. |
| 2012/0045748 A1 | 2/2012 | Willson et al. |
| 2012/0045768 A1 | 2/2012 | Arunachalam et al. |
| 2012/0149018 A1 | 6/2012 | Dahlberg et al. |
| 2012/0190027 A1 | 7/2012 | Loeffert et al. |
| 2012/0208705 A1 | 8/2012 | Steemers et al. |
| 2012/0208724 A1 | 8/2012 | Steemers et al. |
| 2012/0259233 A1 | 10/2012 | Chan et al. |
| 2012/0261264 A1 | 10/2012 | Srinivasan et al. |
| 2012/0289581 A1 | 11/2012 | Chang et al. |
| 2012/0325665 A1 | 12/2012 | Chiou et al. |
| 2013/0017544 A1 | 1/2013 | Eckhardt et al. |
| 2013/0018611 A1 | 1/2013 | Sturmer |
| 2013/0062205 A1 | 3/2013 | Hadwen et al. |
| 2013/0068622 A1 | 3/2013 | Schertzer et al. |
| 2013/0105318 A1 | 5/2013 | Bhattacharya et al. |
| 2013/0123979 A1 | 5/2013 | Elliot et al. |
| 2013/0157259 A1 | 6/2013 | Choi et al. |
| 2013/0168250 A1 | 7/2013 | Fogleman et al. |
| 2013/0171546 A1 | 7/2013 | White et al. |
| 2013/0177915 A1 | 7/2013 | Too et al. |
| 2013/0203606 A1 | 8/2013 | Pollack et al. |
| 2013/0215492 A1 | 8/2013 | Steckl et al. |
| 2013/0217113 A1 | 8/2013 | Srinivasan et al. |
| 2013/0225450 A1 | 8/2013 | Pollack et al. |
| 2013/0236377 A1 | 9/2013 | Kim et al. |
| 2013/0270114 A1 | 10/2013 | Feiglin |
| 2013/0284956 A1 | 10/2013 | Kwon |
| 2013/0288254 A1 | 10/2013 | Pollack et al. |
| 2013/0293246 A1 | 11/2013 | Pollack et al. |
| 2013/0306480 A1 | 11/2013 | Chang et al. |
| 2014/0005066 A1 | 1/2014 | Boles et al. |
| 2014/0054174 A1 | 2/2014 | Wang |
| 2014/0124037 A1 | 5/2014 | Foley |
| 2014/0141409 A1 | 5/2014 | Foley et al. |
| 2014/0161686 A1 | 6/2014 | Bort et al. |
| 2014/0174926 A1 | 6/2014 | Bort et al. |
| 2014/0179539 A1 | 6/2014 | Lohman et al. |
| 2014/0194305 A1 | 7/2014 | Kayyem et al. |
| 2014/0216559 A1 | 8/2014 | Foley |
| 2014/0273100 A1 | 9/2014 | Saito et al. |
| 2014/0335069 A1 | 11/2014 | Graham et al. |
| 2014/0353157 A1 | 12/2014 | Hoffmeyer et al. |
| 2015/0001078 A1 | 1/2015 | Feiglin |
| 2015/0008123 A1 | 1/2015 | Cheng et al. |
| 2015/0021182 A1 | 1/2015 | Rival et al. |
| 2015/0075986 A1 | 3/2015 | Cyril et al. |
| 2015/0111237 A1 | 4/2015 | Graham et al. |
| 2015/0144489 A1 | 5/2015 | Hoffmeyer et al. |
| 2015/0148549 A1 | 5/2015 | Van dam et al. |
| 2015/0198604 A1 | 6/2015 | Ermantraut et al. |
| 2015/0205272 A1 | 7/2015 | Yi et al. |
| 2015/0212043 A1 | 7/2015 | Pollack |
| 2015/0238959 A1 | 8/2015 | Prakash et al. |
| 2015/0258520 A1 | 9/2015 | Griffiths et al. |
| 2015/0267242 A1 | 9/2015 | Foegeding et al. |
| 2015/0322272 A1 | 11/2015 | Pokroy et al. |
| 2016/0068901 A1 | 3/2016 | Eckhardt et al. |
| 2016/0108432 A1 | 4/2016 | Punnamaraju et al. |
| 2016/0108433 A1 | 4/2016 | Fair et al. |
| 2016/0116438 A1 | 4/2016 | Pamula et al. |
| 2016/0129437 A1 | 5/2016 | Kayyem et al. |
| 2016/0161343 A1 | 6/2016 | Smith et al. |
| 2016/0175859 A1 | 6/2016 | Yi et al. |
| 2016/0199832 A1 | 7/2016 | Jamshidi et al. |
| 2016/0298173 A1 | 10/2016 | Wang et al. |
| 2016/0319354 A1 | 11/2016 | Tocigl et al. |
| 2016/0370317 A9 | 12/2016 | Sudarsan et al. |
| 2017/0184546 A1 | 6/2017 | Fobel et al. |
| 2017/0315090 A1 | 11/2017 | Wheeler et al. |
| 2017/0354973 A1 | 12/2017 | Sustarich et al. |
| 2018/0001286 A1 | 1/2018 | Wu |
| 2018/0015469 A1 | 1/2018 | Reiter et al. |
| 2018/0059056 A1 | 3/2018 | Taylor et al. |
| 2018/0095067 A1 | 4/2018 | Huff et al. |
| 2018/0099275 A1 | 4/2018 | Wu et al. |
| 2018/0120335 A1 | 5/2018 | Mousa et al. |
| 2018/0221882 A1 | 8/2018 | Roberts et al. |
| 2018/0250672 A1 | 9/2018 | Jamshidi et al. |
| 2019/0060900 A1 | 2/2019 | Breinlinger et al. |
| 2019/0168223 A1 | 6/2019 | Soto-Moreno et al. |
| 2019/0210026 A1 | 7/2019 | Jebrail et al. |
| 2020/0016597 A1 | 1/2020 | Jebrail et al. |
| 2020/0061621 A1 | 2/2020 | Jebrail et al. |
| 2020/0114359 A1 | 4/2020 | Jebrail et al. |
| 2020/0164367 A1 | 5/2020 | Wunsch et al. |
| 2020/0179933 A1 | 6/2020 | Jebrail et al. |
| 2020/0254458 A1 | 8/2020 | Hong et al. |
| 2020/0316606 A1 | 10/2020 | Soto-Moreno et al. |
| 2020/0324290 A1 | 10/2020 | Jebrail et al. |
| 2021/0370304 A1 | 12/2021 | Jebrail et al. |
| 2022/0118455 A1 | 4/2022 | Jebrail et al. |
| 2022/0401957 A1 | 12/2022 | Jebrail et al. |

(56) References Cited

U.S. PATENT DOCUMENTS

| | | |
|---|---|---|
| 2023/0049633 A1 | 2/2023 | Jebrail et al. |
| 2023/0219083 A1 | 7/2023 | Jebrail et al. |
| 2023/0249185 A1 | 8/2023 | Jebrail et al. |

FOREIGN PATENT DOCUMENTS

| | | |
|---|---|---|
| CA | 2881783 A1 | 2/2014 |
| CN | 1668527 A | 9/2005 |
| CN | 101609063 A | 12/2009 |
| CN | 102549804 A | 7/2012 |
| CN | 102719526 A | 10/2012 |
| CN | 102740976 A | 10/2012 |
| CN | 102836653 A | 12/2012 |
| CN | 103014148 A | 4/2013 |
| CN | 103170383 A | 6/2013 |
| CN | 103502386 A | 1/2014 |
| CN | 103946712 A | 7/2014 |
| CN | 104144748 A | 11/2014 |
| CN | 104321141 A | 1/2015 |
| CN | 104995261 A | 10/2015 |
| CN | 105764490 A | 7/2016 |
| CN | 105849032 A | 8/2016 |
| CN | 106092865 A | 11/2016 |
| DE | 19949735 A1 | 5/2001 |
| EP | 2111554 B1 | 5/2013 |
| GB | 2533952 A | 7/2016 |
| JP | 2002321449 A | 11/2002 |
| JP | 2006220606 A | 8/2006 |
| JP | 2010500596 A | 1/2010 |
| JP | 2010098133 A | 4/2010 |
| JP | 2010515877 A | 5/2010 |
| JP | 2010180222 A | 8/2010 |
| JP | 2012525687 A | 10/2012 |
| JP | 2015529615 A | 10/2015 |
| WO | WO2000/067907 A2 | 11/2000 |
| WO | WO2001/025137 A1 | 4/2001 |
| WO | WO2003/045556 A2 | 6/2003 |
| WO | WO2004/074169 A1 | 9/2004 |
| WO | WO2005/068993 A1 | 7/2005 |
| WO | WO2005/118129 A1 | 12/2005 |
| WO | WO2006/000828 A2 | 1/2006 |
| WO | WO2006/102309 A2 | 9/2006 |
| WO | WO2007/120240 A2 | 10/2007 |
| WO | WO2007/123908 A2 | 11/2007 |
| WO | WO2007/130294 A2 | 11/2007 |
| WO | WO2007/136386 A2 | 11/2007 |
| WO | WO2008/066828 A2 | 6/2008 |
| WO | WO2009/026339 A2 | 2/2009 |
| WO | WO2009/052348 A2 | 4/2009 |
| WO | WO2009/111723 A1 | 9/2009 |
| WO | WO2009/111769 A2 | 9/2009 |
| WO | WO2009/140671 A2 | 11/2009 |
| WO | WO2010/003188 A1 | 1/2010 |
| WO | WO2010/006166 A2 | 1/2010 |
| WO | WO2010/027894 A2 | 3/2010 |
| WO | WO2010/042637 A2 | 4/2010 |
| WO | WO2010/069977 A1 | 6/2010 |
| WO | WO2010/091334 A2 | 8/2010 |
| WO | WO2010/111265 A1 | 9/2010 |
| WO | WO2011/002957 A2 | 1/2011 |
| WO | WO2011/062557 A1 | 5/2011 |
| WO | WO2012/061832 A1 | 5/2012 |
| WO | WO2012/172172 A1 | 12/2012 |
| WO | WO2013/006312 A2 | 1/2013 |
| WO | WO2013/040562 A2 | 3/2013 |
| WO | WO2013/090889 A1 | 6/2013 |
| WO | WO2013/096839 A1 | 6/2013 |
| WO | WO2013/116039 A1 | 8/2013 |
| WO | WO2013/176767 A1 | 11/2013 |
| WO | WO2014/078100 A1 | 5/2014 |
| WO | WO2014/083622 A1 | 6/2014 |
| WO | WO2014/100473 A1 | 6/2014 |
| WO | WO2014/106167 A1 | 7/2014 |
| WO | WO2014/108185 A1 | 7/2014 |
| WO | WO2014/183118 A1 | 11/2014 |
| WO | WO2015/023745 A1 | 2/2015 |
| WO | WO2015/077737 A1 | 5/2015 |
| WO | WO2015/172255 A1 | 11/2015 |
| WO | WO2015/172256 A1 | 11/2015 |
| WO | WO2016/094589 A1 | 6/2016 |
| WO | WO2016/128544 A1 | 8/2016 |
| WO | WO2016/182814 A2 | 11/2016 |
| WO | WO2016/197013 A1 | 12/2016 |
| WO | WO2017/094021 A1 | 6/2017 |
| WO | WO2017/223026 A1 | 12/2017 |
| WO | WO2018/119253 A1 | 6/2018 |
| WO | WO2018/126082 A1 | 7/2018 |
| WO | WO2019/023133 A1 | 1/2019 |
| WO | WO2019/046860 A1 | 3/2019 |
| WO | WO2019/075211 A1 | 4/2019 |
| WO | WO2019/226919 A1 | 11/2019 |
| WO | WO2020/160520 A1 | 8/2020 |
| WO | WO2020/176816 A8 | 9/2020 |

OTHER PUBLICATIONS

Davoust et al.; Evaporation rate of drop arrays within a digital microfluidic system; Sensors and Actuators B Chemical; 189; pp. 157-164; Dec. 2013.

Soto-Moreno et al.; U.S. Appl. No. 17/434,531 entitled "Digital microfluidics devices and methods of using them," filed Aug. 27, 2021.

Soto-Moreno et al.; U.S. Appl. No. 17/630,048 entitled "Digital microfluidics devices and methods of use thereof," filed Jan. 25, 2022.

Cervantes et al.; U.S. Appl. No. 17/427,290 entitled "Nonfouling compositions and methods for manipulating and processing encapsulated droplets," filed Jul. 30, 2021.

Leriche et al.; Cleavable linkers in chemical biology; Bioorganic & Medicinal Chemistry; 20(2); pp. 571-582; Jan. 15, 2012.

Davoust et al.; Evaporation Rate of Drop Arrays within a Digital Microsystem; Procedia Engineering; vol. 47; pp. 1-4; Jan. 1, 2012.

Nge et al.; Advances in microfluidic materials, functions, integration, and applications. Chemical reviews; 113(4); pp. 2550-2583; Apr. 10, 2013.

Jebrail et al.; U.S. Appl. No. 17/967,671 entitled "Evaporation Management in Digital Mecrofluidic Devices," filed Oct. 17, 2022.

Soto-Moreno et al.; U.S. Appl. No. 18/064,893 entitled "Digital microfluidics devices and methods of use thereof," filed Dec. 12, 2022.

Soto-Moreno et al.; U.S. Appl. No. 17/728,952 entitled "Digital microfluidics devices and methods of using them," filed Apr. 25, 2022.

Soto-Moreno et al.; U.S. Appl. No. 17/775,373 entitled "Digital microfluidics systems, apparatus and method of using them," filed May 9, 2022.

Palluk et al.; De novo DNA synthesis using polymerase-nucleotide conjugates; Nature biotechnology; 36(7); pp. 645-650; Jun. 18, 2018.

Abdelgawad et al., All-terrain droplet actuation, Lab on a Chip, 8(5), pp. 672-677, May 2008.

Abdelgawad et al.; Low-cost, rapid-prototyping of digital microfluidics devices, Microfluidics and Nanofluidics, 4, pp. 349-355, Apr. 2008.

Abdelgawad et al.; Rapid prototyping in copper substrates for digital microfluidics, Adv. Mater., 19(1), pp. 133-137; Jan. 2007.

Abdelgawad et al.; Hybrid microfluidics: a digital-to-channel interface for in-line sample processing and chemical separations, Lab on a Chip, 9(8), pp. 1046-1051, Apr. 2009.

Abdelgawad; Digital Microfluidics for Integration of Lab-on-a-Chip Devices (Doctoral dissertation); University of Toronto; © 2009.

Albrecht et al.; Laboratory testing of gonadal steroids in children; Pediatric Endocrinology Reviews; 5(suppl 1); pp. 599-607; Oct. 2007.

Analog Devices; 24-bit Capicitance-to-Digital converter with temperature sensor, AD7745/AD7746; Analog Devices; Norwood, MA;

(56) References Cited

OTHER PUBLICATIONS 28 pages; (year of pub. sufficiently earlier than effective US filing date and any foreign priority date) 2005.
Analog Devices; Extending the capacitive input range of AD7745/AD7746 Capicitance-to-Digital converter; Analog Devices; Norwood, MA; 5 pages; (year of pub. sufficiently earlier than effective US filing date and any foreign priority date) 2009.
Ankarberg-Lindren et al.; A purification step prior to commercial sensitive immunoassay is necessary to achieve clinical usefulness when quantifying serum 17 ?-estradiol in prepubertal children. Eur J Endocrinol, 158, pp. 117-124, Jan. 2008.
Armstrong et al.; A study of plasma free amino acid levels. II. Normal values for children and adults, Metabolism, 22(4), pp. 561-569, Apr. 1973.
Asiello et al.; Miniaturized isothermal nucleic acid amplification, a review; Lab Chip; 11(8); pp. 1420-1430; Apr. 2011.
Au et al., Integrated microbioreactor for culture and analysis of bacteria, algae and yeast, Biomedical Microdevices, 13(1), pp. 41-50, Feb. 2011.
Au et al.; A new angle on pluronic additives: Advancing droplets and understanding in digital microfluidics; Langmuir; 27; pp. 8586-8594; Jun. 2011.
Banatvala et al., Rubella, The Lancet, 363(9415), pp. 1127-1137, Apr. 2004.
Banér et al.; Signal amplification of padlock probes by rolling circle replication; Nuc. Acids Res.; 26(22); pp. 5073-5078; Nov. 1998.
Barany; Genetic disease detection and DNA amplification using cloned thermostable ligase; PNAS; 88(1); pp. 189-193; Jan. 1991.
Barbulovic-Nad et al., A microfluidic platform for complete mammalian cell culture, Lab on a Chip, 10(12), pp. 1536-1542; Jun. 2010.
Barbulovic-Nad et al.; Digital microfluidics for cell-based assays, Lab Chip, 8(4), pp. 519-526; Apr. 2008.
Baxendale et al. ; Multistep synthesis using modular flow reactors: bestmann-ohira reagent for the formation of alkynes and triazoles; Angewandle Chemie International Edition; 48(22); pp. 4017-4021; May 2009.
Beattie et al.; Endogenous sex hormones, breast cancer risk, and tamoxifen response: an ancillary study in the NSABP Breast Cancer Prevention Trial P-1, J Natl Cancer Inst, 98(2), pp. 110-115, Jan. 2006.
Beaucage et al., The Functionalization of Oligonucleotides via Phosphoramidite Derivatives, Tetrahedron, 49(10), pp. 1925-1963, Mar. 1993.
Belanger et al.; Omental and subcutaneous adipose tissue steroid levels in obese men. Steroids, 71(8), pp. 674-682, Aug. 2006.
Bergkvist et al., Improved chip design for integrated solid-phase microextraction in on-line proteomic sample preparation, Proteomics, 2(4), pp. 422-429, Apr. 2002.
Bi et al.; Dumbbell probe-mediated cascade isothermal amplification: A novel strategy for label-free detection of microRNAs and its application to real sample assay; Analytica Chimica Acta; 760; pp. 69-74; Jan. 2013.
Blankenstein et al.; Intratumoral levels of estrogens in breast cancer. J Steroid Biochem Mol Biol, 69(1-6), pp. 293-297, Apr.-Jun. 1999.
Bodamer et al.; Expanded newborn screening in Europe, Journal of Inherited Metabolic Disease, 30(4), pp. 439-444, Aug. 2007.
Bohlen et al.; Fluorometric assay of proteins in the nanogram range, Archives of Biochemistry and Biophysics, 155(1), pp. 213-220, Mar. 1973.
Boles et al.; Droplet-Based Pyrosequencing Using Digital Microfluidics; Analytical Chemistry; 83(22); pp. 8439-8447; Oct. 14, 2011.
Bollström et al.; A Multilayer Coated Fiber-Based Substrate Suitable for Printed Functionality; Organic Electronics; 10(5); pp. 1020-1023; Aug. 2009.
Bonneil et al., Integration of solid-phase extraction membranes for sample multiplexing: Application to rapid protein identification from gel-isolated protein extracts, Electrophoresis, 23(20), pp. 3589-3598, Oct. 2002.
Brassard et al.; Water-oil core-shell droplets for electrowetting-based digital microfluidic devices; Lab Chip; 8(8); pp. 1342-1349; Aug. 2008.
Brill et al., Synthesis of oligodeoxynucleoside phosphorodithioates via thioamidites, J. Am. Chem. Soc., 111(6), pp. 2321-2322, Mar. 1989.
Brivio et al.; Integrated microfluidic system enabling (bio)chemical reactions with on-line MALDI-TOF mass spectrometry, Anal. Chem., 74(16), pp. 3972-3976, Aug. 2002.
Burstein; Aromatase inhibitor-associated arthralgia syndrome. Breast, 16(3), pp. 223-234, Jun. 2007.
Carlsson et al., Screening for genetic mutations, Nature, 380(6571), pp. 207, Mar. 1996.
Chace et al.; A biochemical perspective on the use of tandem mass spectrometry for newborn screening and clinical testing, Clinical Biochemistry, 38(4), pp. 296-309; Apr. 2005.
Chace et al.; Rapid diagnosis of maple syrup urine disease in blood spots from newborns by tandem mass spectrometry, Clinical Chemistry, 41(1), pp. 62-68, Jan. 1995.
Chace et al.; Rapid diagnosis of phenylketonuria by quantitative analysis for phenylalanine and tyrosine in neonatal blood spots by tandem mass spectrometry, Clinical Chemistry, 39(1), pp. 66-71; Jan. 1993.
Chace et al.; Use of tandem mass spectrometry for multianalyte screening of dried blood specimens from newborns, Clinical Chemistry, 49(11), pp. 1797-1817, Nov. 2003.
Chace; Mass spectrometry in newborn and metabolic screening: historical perspective and future directions, Journal of Mass Spectrometry, 44(2), pp. 163-170, Feb. 2009.
Chang et al.; Integrated polymerase chain reaction chips utilizing digital microfluidics; Biomedical Microdevices; 8(3); pp. 215-225; Sep. 2006.
Chatterjee et al.; Droplet-based microfluidics with nonaqueous solvents and solutions, Lab Chip, 6(2), pp. 199-206, Feb. 2006.
Chen et al.; Selective Wettability Assisted Nanoliter Sample Generation via Electrowetting-Based Transportation; Proceedings of the 5th International Conference on Nanochannels, Microchannels and Minichannels (ICNMM); Puebla, Mexico; Paper No. ICNMM2007-30184; pp. 147-153; Jun. 18-20, 2007.
Chen et al.; The chemistrode: a droplet-based microfluidic device for stimulation and recording with high temporal, spatial, and chemical resolution: Proceedings of the National Academy of Sciences; 105(44); pp. 16843-16848; Nov. 2004.
Cheng et al., Paper-Based ELISA, Angewandte Chemie, 49(28), pp. 4771-4774, Jun. 2010.
Cheng et al.; Highly Sensitive Determination of microRNA Using Target-Primed and Branched Rolling-Circle Amplification; Angew. Chem.; 121(18); pp. 3318-3322; Apr. 2009.
Chetrite et al.; Estradiol inhibits the estrone sulfatase activity in normal and cancerous human breast tissues. Journal of Steroid Biochemistry and Molecular Biology, 104(3-5), pp. 289-292, May 2007.
Cho et al.; Creating, transporting, cutting, and merging liquid droplets by electrowetting-based actuation for digital microfluidic circuits, J. MEMS 2003, 12(1), pp. 70-80, Feb. 2003.
Choi et al., Automated digital microfluidic platform for magnetic-particle-based immunoassays with optimization by design of experiments, Anal. Chem., 85(20), pp. 9638-9646; Oct. 2013.
Choi et al., Digital Microfluidics, Annu. Rev. Anal. Chem., 5, pp. 413-440, (Epub) Apr. 2012.
Christiansen; Hormone Replacement Therapy and Osteoporosis; Maturitas, 23, Suppl. pp. S71-S76, May 1996.
Chuang et al.; Direct Handwriting Manipulation of Droplets by Self-Aligned Mirror-EWOO Across a Dielectric Sheet; 19th IEEE International Conf. on Micro Electro Mechanical Systems (MEMS); Instanbul, Turkey; pp. 538-541; Jan. 22-26, 2006.
Cipriano et al.; The cost-effectiveness of expanding newborn screening for up to 21 inherited metabolic disorders using tandem mass spectrometry: results from a decision-analytic model, Value in Health, 10(2), pp. 83-97, Mar.-Apr. 2007.
Cooney et al.; Electrowetting droplet microfluidics on a single planar surface, Microfluid. Nanofluid., 2(5), pp. 435-446; Sep. 2006.

(56) References Cited

OTHER PUBLICATIONS

Coregenomics; How do SPRI beads work; 31 pages; retrieved from the internet (http://core-genomics.blogspot.com/2012/04/how-do-spri-beads-work.html); Apr. 28, 2012.

Cottam et al.; Accelerated synthesis of titanium oxide nanostructures using microfluidic chips; Lab on a Chip; 7(2); pp. 167-169; Feb. 2007.

Crabtree et al.; Microchip injection and separation anomalies due to pressure effects, Anal. Chem., 73(17), pp. 4079-4086, Sep. 2001.

Cunningham; Testosterone replacement therapy for late-onset hypogonadism. Nature Clinical Practice Urology, 3(5), pp. 260-267, May 2006.

Cuzick; Chemoprevention of breast cancer. Women's Health, 2(6), pp. 853-861, Nov. 2006.

Dahlin et al.; Poly(dimethylsiloxane)-based microchip for two-dimensional solid-phase extraction-capillary electrophoresis with an integrated electrospray emitter tip, Anal. Chem., 77(16), pp. 5356-5363, Aug. 2005.

Dambrot; Of microchemistry and molecules: Electronic microfluidic device synthesizes biocompatible probes; 4 pages, retrieved from the internet (https://phys.org/news/2012-01-microchemistry-molecules-electronic-microfluidic-device.html); Jan. 26, 2012.

Danton et al.; Porphyrin profiles in blood, urine and faeces by HPLC/electrospray ionization tandem mass spectrometry. Biomedical Chromatography, 20(6-7), pp. 612-621, Jun.-Jul. 2006.

De Mesmaeker et al.; Comparison of rigid and flexible backbones in antisense oligonucleotides; Bioorganic & Medicinal Chem. Lett; 4(3); pp. 395-398; Feb. 1994.

Deligeorgiev et al.; Intercalating Cyanine Dyes for Nucleic Acid Detection; Recent Pat Mat Sci; 2(1); pp. 1-26; Jan. 2006.

Dempcy et al., Synthesis of a thymidyl pentamer of deoxyribonucleic guanidine and binding studies with DNA homopolynucleotides, Proc. Natl. Acad. Sci., 92(13), pp. 6097-6101, Jun. 1995.

Deng et al.; Rapid determination of amino acids in neonatal blood samples based on derivatization with isobutyl chloroformate followed by solid-phase microextraction and gas chromatography/mass spectrometry. Rapid Communications in Mass Spectrometry, 18(1), pp. 2558-2564, Nov. 2004.

Denneulin et al.; Infra-red assisted sintering of inkjet printed silver tracks on paper substrates; J Nanopart Res; 13(9); pp. 3815-3823; Sep. 2011.

Dibbelt et al.; Determination of natural and synthetic estrogens by radioimmunoassay: Comparison of direct and extraction methods for quantification of estrone in human serum. Clinical Laboratory, 44(3), 137-143, Mar. 1998.

Dietzen et al.; National academy of clinical biochemistry laboratory medicine practice guidelines: follow-up testing for metabolic disease identified by expanded newborn screening using tandem mass spectrometry; executive summary, Clinical Chemistry, 55(9), pp. 1615-1626, Sep. 2009.

Diver et al.; Warning on plasma oestradiol measurement. Lancet, 330(8567), p. 1097, Nov. 1987.

Divino Filho et al.; Simultaneous measurements of free amino acid patterns of plasma, muscle and erythrocytes in healthy human subjects, Clinical Nutrition, 16(6), pp. 299-305, Dec. 1997.

Dixon et al.; An inkjet printed, roll-coated digital microfluidic device for inexpensive, miniaturized diagnostic assays; Lab on a Chip; 16(23); pp. 4560-4568; Nov. 2016.

Djerassi; Chemical birth of the pill. American Journal of Obstetrics and Gynecology, 194(1), pp. 290-298, Jan. 2006.

Dobrowolski et al.; DNA microarray technology for neonatal screening, Acta Paediatrica Suppl, 88(432), pp. 61-64, Dec. 1999.

Doebler et al.; Continuous-flow, rapid lysis devices for biodefense nucleic acid diagnostic systems; Journal of the Association for Laboratory Automation; 14(3); pp. 119-125; Jun. 2009.

Dong et al.; Highly sensitive multiple microRNA detection based on flourescence quenching of graphene oxide and isothermal strand-displacement polymerase reaction; Anal Chem; 84; pp. 4587-4593; Apr. 2012.

Dryden et al.; Integrated digital microfluidic platform for voltammetric analysis; Analytical Chemistry; 85(18); pp. 8809-8816; Sep. 2013.

Duffy et al.; Rapid prototyping of microfluidic systems in Poly (dimethylsiloxane), Anal. Chem., 70(23), pp. 4974-4984, Dec. 1998.

Edgar et al.; Capillary electrophoresis separation in the presence of an immiscible boundary for droplet analysis, Anal. Chem., 78(19), pp. 6948-6954 (author manuscript, 15 pgs.), Oct. 2006.

Egholm et al., PNA hybridizes to complementary oligonucleotides obeying the Watson-Crick hydrogen-bonding rules, Nature, 365(6446), pp. 566-568, Oct. 1993.

Egholm et al., Recognition of guanine and adenine in DNA by cytosine and thymine containing peptide nucleic acids (PNA), J. Am. Chem. Soc., 114(24), pp. 9677-9678; Nov. 1992.

Ehrmann; Polycystic ovary syndrome. New England Journal of Medicine; 352 (12); pp. 1223-1236; Mar. 2005.

Ekstrom et al., Miniaturized solid-phase extraction and sample preparation for MALDI MS using a microfabricated integrated selective enrichment target, Journal of Proteome Research, 5(5), pp. 1071-1081, May 2006.

Ekstrom et al., Polymeric integrated selective enrichment target (ISET) for solid-phase-based sample preparation in MALDI-TOF MS, Journal of Mass Spectrometry, 42(11), pp. 1445-1452, Nov. 2007.

Ekstrom et al., On-chip microextraction for proteomic sample preparation of in-gel digests, Proteomics, 2(4), pp. 413-421, Apr. 2002.

El-Ali et al.; Cells on chips; Nature (2006) insight Review; 442(7101); pp. 403-411; Jul. 2006.

Fair; Digital microfluidics: Is a true lab-on-a-chip possible?; Microfluid. Nanofluid.; 3(3); pp. 245-281; Jun. 2007.

Falk et al.; Measurement of Sex Steroid Hormones in Breast Adipocytes: Methods and Implications; Cancer Epidemiol Biomarkers Prev; 17(8); pp. 1891-1895; Aug. 2008.

Fan et al.; Cross-scale electric manipulations of cells and droplets by frequency-modulated dielectrophoresis and electrowetting; Lab Chip; 8(8); pp. 1325-1331; Aug. 2008.

Fan et al.; Electrically Programmable Surfaces for Configurable Patterning of Cells; Advanced Materials; 20(8); pp. 1418-1423; Apr. 2008.

Fan et al.; Integrated barcode chips for rapid, multiplexed analysis of proteins in microliter quanties of blood; Nature Biotechnology; 26(12); pp. 1373-1378; 15 pages (Author Manuscript); Dec. 2008.

Faure et al.; Improved electrochemical detection of a transthyretin synthetic peptide in the nanomolar range with a two-electrode system integrated in a glass/PDMS microchip; Lab on a Chip; 14(15); pp. 2800-2805, Aug. 2014.

Fobel et al.; DropBot: An open-source digital microfluidic control system with precise control of electrostatic driving force and instantaneous drop velocity measurement; Applied Physics Letters; 102(19); 193513 (5 pgs.); May 2013.

Foote et al., Preconcentration of proteins on microfluidic devices using porous silica membranes, Analytical Chemistry, 77(1), pp. 57-63, Jan. 2005.

Freire et al.; A practical interface for microfluidics and nanoelectrospray mass spectrometry, Electrophoresis, 29(9), pp. 1836-1843, May 2008.

Fridley et al., Controlled release of dry reagents in porous media for tunable temporal and spatial distribution upon rehydration, Lab Chip, 12(21), pp. 4321-4327 (author manuscript, 14 pgs.), Nov. 2012.

Fu et al., Controlled Reagent Transport in Disposable 2D Paper Networks, Lab. Chip, 10(7), pp. 918-920 (author manuscript, 9 pgs.), Apr. 2010.

Gao et al.; Unusual conformation of a 3'-thioformacetal linkage in a DNA duplex; J. Biomol. NMR; 4(1); pp. 17-34; Jan. 1994.

Gentili et al.; Analysis of free estrogens and their conjugates in sewage and river waters by solid-phase extraction then liquid chromatography-electrospray-tandem mass spectrometry. Chromatographia 56(1), pp. 25-32, Jul. 2002.

(56) References Cited

OTHER PUBLICATIONS

Gerasimova et al.; Fluorometric method for phenylalanine microplate assay adapted for phenylketonuria screening, Clinical Chemistry, 35(10), pp. 2112-2115, Oct. 1989.
Gong et al., All-Electronic Droplet Generation On-Chip With Real-Time Feedback Control for EWOD Digital Microfluidics, Lab Chip, 8(6), pp. 898-906 (author manuscript, 20 pgs.), Jun. 2008.
Gong et al.; Portable digital microfluidics platform with active but disposable lab-on-chip; 17th IEEE International Conference on Micro Electro Mechanical Systems; Maastricht, Netherlands; pp. 355-358; Jan. 24-29, 2004.
Gong et al.; Two-dimensional digital microfluidic system by multilayer printed circuit board, 18th IEEE International Conference on Micro Electro Mechanical Systems (MEMS 2005); IEEE; pp. 726-729; Jan. 30-Feb. 3, 2005.
Goto et al.; Colorimetric detection of loop-mediated isothermal amplification reaction by using hydroxy naphthol blue; Biotechniques; 46(3); pp. 167-172; Mar. 2009.
Gottschlich et al.; Integrated microchip-device for the digestion, separation and postcolumn labeling of proteins and peptides, J. Chromatogr. B, 745(1), pp. 243-249, Aug. 2000.
Govindarajan et al., A low cost point-of-care viscous sample preparation device for molecular diagnosis in the developing world; an example of microfluidic origami, Lab Chip, 12(1), pp. 174-181, Jan. 2012.
Green et al.; Neonatal screening by DNA microarray: spots and chips, Nature Reviews Genetics, 6(2), pp. 147-151, Feb. 2005.
Hatch et al., Integrated preconcentration SDS-PAGE of proteins in microchips using photopatterned cross-linked polyacrylamide gels, Analytical Chemistry, 78(14), pp. 4976-4984, Jul. 2006.
He et al. (ed); Food microbiological inspection technology; Chapter 5: Modern food microbiological inspection technology; China Quality Inspection press; pp. 111-113; (English Translation included) Nov. 2013.
Henderson et al.; Estrogens as a cause of human cancer: The Richard and Hinda Rosenthal Foundation award lecture. Cancer Res, 48(2), pp. 246-253, Jan. 1988.
Hennequin et al.; Synthesizing microcapsules with controlled geometrical and mechanical properties with microfluidic double emulsion technology; Langmuir; 25(14); pp. 7857-7861; Jul. 2009.
Herdewijn et al.; 2'-5'-Oligoadenylates (2-5A) as Mediators of Interferon Action. Synthesis and Biological Activity of New 2-5A Analogues. E. De Clerq (ed.) Frontiers in Microbiology, 231-232, Springer, Dordrecht Jan. 1987.
Hertz et al.; Estrogen-progestogen combinations for contraception. Journal of the American Medical Association, 198(9), pp. 1000-1006, Nov. 1966.
Hong et al.; Three-dimensional digital microfluidic manipulation of droplets in oil medium; Scientific Reports; 5 (Article No. 10685); 5 pgs.; Jun. 2015.
Horn et al.; Oligonucleotides with alternating anionic and cationic phosphoramidate linkages: Synthesis and hybridization of stereo-uniform isomers; Tetrahedron Lett.; 37(6); pp. 743-746; Feb. 1996.
Hou et al.; Microfluidic devices for blood fractionation; Micromachines; 2(3); pp. 319-343; Jul. 20, 2011.
Huh et al.; Reversible Switching of High-Speed Air-Liquid Two-Phase Flows Using Electrowetting-Assisted Flow-Pattern Change, J. Am. Chem. Soc., 125, pp. 14678-14679; Dec. 2003.
Ihalainen et al.; Application of paper-supported printed gold electrodes for impedimetric immunosensor development; Biosensors; 3(1); pp. 1-17; Mar. 2013.
Jacobson et al.; High-Speed Separations on a Microchip, Anal. Chem., 66(7), pp. 1114-1118, Apr. 1994.
Jacobson et al.; Precolumn Reactions with Electrophoretic Analysis Integrated on a Microchip, Anal. Chem., 66(23), pp. 4127-4132, Dec. 1994.
Jebrail et al., Combinatorial Synthesis of Peptidomimetics Using Digital Microfluidics, J. Flow Chem., 2(3), pp. 103-107; (online) Aug. 2012.

Jebrail et al., Let's get digital: digitizing chemical biology with microfluidics, Curr. Opin. Chem. Biol., 14(5), 574-581, Oct. 2010.
Jebrail et al., Synchronized synthesis of peptide-based macrocycles by digital microfluidics, Angew. Chem. Int. Ed. Eng., 49(46), pp. 8625-8629, Nov. 2010.
Jebrail et al., World-to-digital-microfluidic interface enabling extraction and purification of RNA from human whole blood, Analytical Chemistry, 86(8), pp. 3856-3862, Apr. 2014.
Jebrail et al.; A Solvent Replenishment Solution for Managing Evaporation of Biochemical Reactions in Air-Matrix Digital Microfluidics Devices, Lab on a Chip, 15(1), pp. 151-158; Jan. 2015.
Jebrail et al.; Digital Microfluidic Method for Protein Extraction by Precipitation; Analytical Chemistry; 81(1); pp. 330-335; Jan. 2009.
Jebrail et al.; Digital Microfluidics for Automated Proteomic Processing, Journal of Visualized Experiments, 33 (e1603), 5 pgs., Nov. 2009.
Jebrail et al.; Digital microfluidics: a versatile tool for applications in chemistry, biology and medicine; Lab Chip; 12 (14); pp. 2452-2463; Jul. 2012.
Jemere et al., An integrated solid-phase extraction system for sub-picomolar detection, Electrophoresis, 23(20), pp. 3537-3544, Oct. 2002.
Jenkins et al., The biosynthesis of carbocyclic nucleosides; Chem. Soc. Rev.; 24(3); pp. 169-176; Jan. 1995.
Jessome et al.; Ion Suppression: A Major Concern in Mass Spectrometry. LC-GC North America, 24(5), pp. 498-510, May 2006.
Jia et al.; Ultrasensitive detection of microRNAs by exponential isothermal amplification; Angew. Chem. Int. Ed. Engl.; 49(32); pp. 5498-5501; Jul. 2010.
Jung et al.; Hybridization of Alternating Cationic/Anionic Oligonucleotides to RNA Segments; Nucleosides & Nucleotides; 13(6-7); pp. 1597-1605; Jul. 1994.
Kaaks et al.; Postmenopausal serum androgens, oestrogens and breast cancer risk: The European prospective investigation into cancer and nutrition. Endocrine-Related Cancer, 12(4), pp. 1071-1082, Dec. 2005.
Keng et al., Micro-chemical synthesis of molecular probes on an electronic microfluidic device,PNAS, 109(3), pp. 690-695; Jan. 2012.
Kiedrowski et al., Parabolic Growth of a Self-Replicating Hexadeoxynucleotide Bearing a 3'-5'-Phosphoamidate Linkage; Angew. Chemie Intl. Ed.; 30(4); pp. 423-426; Apr. 1991.
Kim et al.; Automated digital microfluidic sample preparation for next-generation DNA sequencing; JALA; Journal of the Association for Laboratory Automation; 16(6); pp. 405-414; Dec. 2011.
Kim et al., A Microfluidic DNA Library Preparation Platform for Next-Generation Sequencing, PLoS One, 8(7), Article ID: e68988; 9 pgs., Jul. 2013.
Kim et al.; Microfabricated Monolithic Multinozzle Emitters for Nanoelectrospray Mass Spectrometry; Anal Chem; 79(10); pp. 3703-3707; May 2007.
Koster et al.; Drop-based microfluidic devices for encapsulation of single cells; Lab on a Chip; 8(7); pp. 1110-1115; Jul. 2008.
Kralj et al.; Integrated continuous microfluidic liquid-liquid extraction. Lab on a Chip, 7(2), pp. 256-263, Feb. 2007.
Kutter et al., Solid phase extraction on microfluidic devices, Journal of Microcolumn Separations, 12(2), pp. 93-97, Jan. 2000.
Kutter et al., Solvent-Programmed Microchip Open-Channel Electrochromatography, Analytical Chemistry, 70(15), pp. 3291-3297, Aug. 1998.
Labrie et al.; Androgen glucuronides, instead of testosterone, as the new markers of androgenic activity in women. The Journal of Steroid Biochemistry and Molecular Biology, 99(4-5), pp. 182-188, Jun. 2006.
Labrie; Intracrinology. Molecular and Cellular Endocrinology, 78(3), pp. C113-C118, Jul. 1991.
Lamar et al.; Serum sex hormones and breast cancer risk factors in postmenopausal women. Cancer Epidemiol Biomarkers Prev, 12(4), pp. 380-383, Apr. 2003.
Langevin et al., A rapid and unbiased method to produce strand-specific RNA-Seq libraries from small quantities of starting materiaRNA Biol., 10(4), pp. 502-515, (online) Apr. 2013.

(56) References Cited

OTHER PUBLICATIONS

Lawyer et al.; High-level expression, purification, and enzymatic characterization of full-length Thermus aquaticus DNA polymerase and a truncated form deficient in 5' to 3' exonuclease activity; Genome Res; 2 (4); pp. 275-287; May 1993.
Lawyer et al.; Isolation, characterization, and expression in *Escherichia coli* of the DNA polymerase gene from Thermus aquaticus; J. Biol. Chem.; 264; pp. 6427-6437; Apr. 1989.
Lebrasseur et al.; Two-dimensional electrostatic actuation of droplets using a single electrode panel and development of disposable plastic film card; Sensors and Actuators A; 136(1); pp. 368-386; May 2007.
Lee et al.; Electrowetting and electrowetting-on-dielectric for microscale liquid handling, Sens. Actuators A, 95(2), pp. 259-268, Jan. 2002.
Lee et al.; Removal of bovine serum albumin using solid-phase extraction with in-situ polymerized stationary phase in a microfluidic device; Journal of Chromatography A; 1187(1-2); pp. 11-17; Apr. 2008.
Lee et al.; Surface-Tension-Driven Microactuation Based on Continuous Electrowetting; J. Microelectromechanical Systems; 9(2); pp. 171-180; Jun. 2000.
Letsinger et al., Cationic oligonucleotides, J. Am. Chem. Soc., 110(13), pp. 4470-4471, Jun. 1988.
Letsinger et al., Effects of pendant groups at phosphorus on binding properties of d-ApA analogues, Nucl. Acids Res., 14(8), pp. 3487-3499, Apr. 1986.
Letsinger et al., Phosphoramidate analogs of oligonucleotides, J. Org. Chem., 35(11), pp. 3800-3803, Nov. 1970.
Lettieri et al., A novel microfluidic concept for bioanalysis using freely moving beads trapped in recirculating flows, Lab on a Chip, 3(1), pp. 34-39, Feb. 2003.
Levy et al.; Genetic screening of newborns, Annual Review of Genomics and Human Genetics, 1, pp. 139-177, Sep. 2000.
Li et al., A perspective on paper-based microfluidics: Current status and future trends, Biomicrofluidics, 6(1), p. 011301 (13 pgs), Mar. 2012.
Li et al., Application of microfluidic devices to proteomics research: identification of trace-level protein digests and affinity capture of target peptides, Molecular & cellular Proteomics, 16(2), pp. 157-168, Feb. 2002.
Li et al., Paper-based microfluidic devices by plasma treatment, Anal. Chem., 80(23), pp. 9131-9134, Nov. 2008.
Li et al.; A Low-Cost and High resolution droplet position detector for an intelligent electrowetting on dielectric device; Journal of Lab. Automation 2015; 20(6); pp. 663-669; Dec. 2015.
Li et al.; One-step ultrasensitive detection of microRNAs with loop-mediated isothermal amplification (LAMP); Chem Commun; 47(9); pp. 2595-2597; Mar. 2011.
Li et al.; Test structure for characterizing low voltage coplanar EWOD system; IEEE Transaction on Semiconductor Manufacturing; IEEE Service Center; Piscataway, NJ.; 22(1); pp. 88-95; Feb. 4, 2009.
Liana et al.; Recent Advances in Paper-Based Sensors; Sensors; 12(9); pp. 11505-11526; Aug. 2012.
Link et al.; Electric Control of Droplets in Microfluidic Devices; Angew Chem Int Ed Engl; 45(16); pp. 2556-2560; Apr. 2006.
Liu et al., Three-dimensional paper microfluidic devices assembled using the principles of origami, JACS, 133(44), pp. 17564-17566, Nov. 2011.
Liu et al.; Attomolar ultrasensitive microRNA detection by DNA-scaffolded silver-nanocluster probe based on isothermal amplification; Anal Chem; 84(12); pp. 5165-5169; Jun. 2012.
Lizardi et al.; Mutation detection and single-molecule counting using isothermal rolling-circle amplification; Nat. Genet.; 19(3); pp. 225-232; Jul. 1998.
Locascio et al.; Surface chemistry in polymer microfluidic systems; in Lab-on-a-Chip; Elsevier Science; 1st Ed.; pp. 65-82; Oct. 2003.
Loeber; Neonatal screening in Europe; the situation in 2004, Journal of Inherited Metabolic Disease, 30(4), pp. 430-438, Aug. 2007.

Lohman et al.; Efficient DNA ligation in DNA-RNA hybrid helices by Chlorella virus DNA ligase; Nucleic Acids Research; 42(3); pp. 1831-1844; Nov. 2013.
Luk et al.; Pluronic Additives: A Solution to Sticky Problems in Digital Microfluidics, Langmuir, 24(12), pp. 6382-6389, Jun. 2008.
Luk et al.; A digital microfluidic approach to proteomic sample processing; Analytical Chemistry; 81(11); pp. 4524-4530; Jun. 2009.
Mag et al., Synthesis and selective cleavage of an oligodeoxynucleotide containing a bridged internucleotide 5'-phosphorothioate linkage, Nucleic Acids Res., 19(7), pp. 1437-1441, Apr. 1991.
Mais et al.; A solvent replenishment solution for managing evaporation of biochemical reactions in air-matrix digital microfluidics devices; Lab on a Chip; 15(1); pp. 151-158; Jan. 2015.
Makamba et al.; Surface modification of poly(dimethylsiloxane) microchannels; Electrophoresis; 24(21); pp. 3607-3619; Nov. 2003.
Malloggi et al.; Electrowetting—A versatile tool for controlling microdrop generation, Eur. Phys. J. E, 26(1), pp. 91-96, May 2008.
Mandl et al.; Newborn screening program practices in the United States: notification, research, and consent, Pediatrics, 109(2), pp. 269-273, Feb. 2002.
Maroney et al.; A Rapid, quantitative assay for direct detection of microRNAs and other small RNAs using splinted ligation; RNA; 13(6); pp. 930R936; Jun. 2007.
Maroney et al.; Direct detection of small RNAs using splinted ligation; Nat. Protocols3(2); pp. 279-287; Jan. 2008.
Marre et al.; Synthesis of micro and nanostructures in microfluidic systems; Chemical Society Reviews; 39(3); pp. 1183-1202; Mar. 2010.
Martinez et al., Simple Telemedicine for Developing Regions: Camera Phones and Paper-Based Microfluidic Devices for Real-Time, Off-Site Diagnosis, Anal. Chem., 80(10), pp. 3699-3707, May 2008.
Martinez et al., Three-dimensional microfluidic devices fabricated in layered paper and tape, PNAS, 105(50), pp. 19606-19611, Dec. 2008.
Martinez et al.; Patterned paper as a platform for inexpensive low-volume portable bioassays, Angewandte Chemie, 46(8), pp. 1318-1320, Feb. 2007.
Martinez-Sanchez et al.; MicroRNA Target Identification—Experimental Approaches; Biology; 2; pp. 189-205; Jan. 2013.
Matern et al.; Reduction of the false-positive rate in newborn screening by implementation of MS/MS-based second-tier tests: the Mayo Clinic experience (2004-2007), Journal of Inherited Metabolic Disease, 30(4), pp. 585-592, Aug. 2007.
Mauney, Thermal Considerations for Surface Mount Layouts, in Texas Instruments Portable Power Supply Design Seminar, 16 pgs., 2006.
Mega; Heterogenous ion-exchange membranes RALEX; 3 pgs.; retrieved Mar. 1, 2016 from the internet: http://www.mega.cz/heterogenous-ion-exchange-membranes-ralex.html.
Meier et al., The photochemistry of stilbenoid compounds and their role in materials technology, Chem. Int. Ed. Engl., 31(11), pp. 1399-1420, Nov. 1992.
Mellors et al.; Fully Integrated Glass Microfluidic Device for Performing High-Efficiency Capillary Electrophoresis and Electrospray Ionization Mass Spectrometry, Analytical Chemistry, 80(18), pp. 6881-6887 (Author Manuscript, 18 pgs.), Sep. 2008.
Michigan Dept. of Community Health; Specimen collection procedure from Michigan Newborn Screening Program, 37 pgs., (retrieved Feb. 9, 2017 online: http://web.archive.org/web/20100715000000*/http://www.michigan.gov/documents/Bloodco2_60773_7.pdf) Jul. 2009.
Miller et al.; A digital microfluidic approach to homogeneous enzyme assays, Anal. Chem., 80(5), pp. 1614-1619, Mar. 2008.
Millington et al.; Digital Microfluidics: A Future Technology in the Newborn Screening Laboratory?, Seminars in Perinatology, 34(2), pp. 163-169 (Author Manuscript, 14 pgs.), Apr. 2010.
Millington et al.; Digital Microfluidics: A novel platform for multiplexed detection of LSDs with potential for newborn screening (conference presentation); Oak Ridge Conference; 15 pgs.; 2009.
Millington et al.; Tandem mass spectrometry: a new method for acylcarnitine profiling with potential for neonatal screening for

(56) References Cited

OTHER PUBLICATIONS inborn errors of metabolism, Journal of Inherited Metabolic Disease, 13(3), pp. 321ý324, May 1990.
Millington et al.; The Analysis of Diagnostic Markers of Genetic Disorders in Human Blood and Urine Using Tandem Mass Spectrometry With Liquid Secondary Ion Mass Spectrometry, International Journal of Mass Spectrometry, 111, pp. 211-228, Dec. 1991.
Miralles et al.; A Review of Heating and Temperature Control in Microfluidic Systems: Techniques and Applications; Diagnostics; 3; pp. 33-67; Jan. 2013.
Mitchell et al.; Circulating microRNAs as stable blood-based markers for cancer detection; Proc Nat Acad Sci; 105(30); pp. 10513-10518; Jul. 2008.
Moon et al.; An integrated digital microfluidic chip for multiplexed proteomic sample preparation and analysis by MALDI-MS. Lab Chip, 6(9), pp. 1213-1219, Sep. 2006.
Moqadam et al.; The Hunting of Targets: Challenge in miRNA Research; Leukemia; 27(1); pp. 16-23; Jan. 2013.
Mousa et al.; Droplet-scale estrogen assays in breast tissue, blood, and serum, Science Translational Medicine, 1(1), 6 pgs., Oct. 2009.
Murran et al.; Capacitance-based droplet position estimator for digital microfluidic devices; Lab Chip; 12(11); pp. 2053-2059; May 2012.
Nakamura et al.; Simple and accurate determination of CYP2D6 gene copy number by a loop-mediated isothermal amplification method and an electrochemical DNA chip; Clinica Chimica Acta; 411(7-8); pp. 568-573; Apr. 2010.
Nelson et al., Incubated protein reduction and digestion on an EWOD digital microfluidic chip for MALDI-MS, Analytical Chemistry, 82(23), pp. 9932-9937, Dec. 2010.
Newborn Screening Ontario, The newborn screening ontario unsatisfactory sample indicator (educational resource), 3 pgs., retrieved online: https://www.newbornscreening.on.ca/en/health-care-providers/submitters/report-cards/nso_unsalisfatory_sample_indicator Jan. 2017, (web address was available to applicant(s) at least as of Jan. 2010).
Ng et al., Digital microfluidic magnetic separation for particle-based immunoassays, Anal. Chem., 84(20), 8805-8812, Oct. 2012.
Nilsson et al.; RNA-templated DNA ligation for transcript analysis; Nucl. Acid Res.; 29(2); pp. 578-581; Jan. 2001.
Njiru; Loop-Mediated Isothermal Amplification Technology: Towards Point of Care Diagnostics; PLoS; 6(6); pp. e1572 (4 pgs.); Jun. 2012.
Notomi et al.; Loop-mediated isothermal amplification of DNA; Nucleic Acid Research; 28(12); p. e63 (7 pgs.); Jun. 2000.
Okubo et al.; Liquid-liquid extraction for efficient synthesis and separation by utilizing micro spaces. Chemical Engineering Science, 63(16), pp. 4070-4077, Aug. 2008.
Oleschuk et al., Trapping of bead-based reagents within microfluidic systems: On-chip solid-phase extraction and electrochromatography, Analytical Chemistry, 72(3), pp. 585-590, Feb. 2000.
Padilla et al.; Newborn screening in the Asia Pacific region, Journal of Inherited Metabolic Disease, 30(4), pp. 490-506, Aug. 2007.
Paik et al., Coplanar digital microfluidics using standard printed circuit board processes, in Proceedings 9th Int'l Conf Miniaturized Systems for Chemistry and Life Sciences (MicroTAS 2005), Boston, MA, USA, pp. 566-568, Oct. 9-13, 2005.
Paneri et al.; Effect of change in ratio of electrode to total pitch length in EWOD based microfluidic system; InComputer Applications and Industrial Electronics (ICCAIE); 2010 International Conference; pp. 25-28; Dec. 5, 2010.
Parida et al.; Rapid detection and differentiation of Dengue virus serotypes by a real-time reverse transcription-loop-mediated isothermal amplification assay; J Clinical Microbiology: 43(6); pp. 2895-2903; Jun. 2005.
Pauwels et al., Biological-Activity of New 2-5a Analogs, Chemica Scripta, 26 (1), pp. 141-145, Mar. 1986.
Peltonen et al.; Printed electrodes on tailored paper enable electrochemical functionalization of paper; TAPPI Nanotechnology Conference; Espoo, Finland; 20 pgs.; Sep. 2010.

Peterschmitt et al.; Reduction of false negative results in screening of newborns for homocystinuria, New England Journal of Medicine, 341(21), 1572-1576, Nov. 1999.
Petersen et al., On-chip electro membrane extraction, Microfluidics and Nanofluidics, 9(4), pp. 881-888, Oct. 2010.
Pitt et al.; Hormone replacement therapy for osteoporosis. Lancet, 335 (8695), p. 978, Apr. 1990.
Pollack et al.; Electrowetting-based actuation of droplets for integrated microfluidics; Lab on a Chip; 2(2); pp. 96-101; May 2002.
Pollack et al.; Electrowetting-based actuation of liquid droplets for microfluidic applications, Appl. Phys. Lett., 77(11), pp. 1725-1726, Sep. 2000.
Provincial Health Services Authority (British Columbia Perinatal Health Program), Perinatal Services BC Neonatal Guideline 9: Newborn Screening, 29 pgs., (retrieved Feb. 9, 2017 online: http://www.perinatalservicesbc.ca/health-professionals/guidelines-standards/newborn) guideline revised: Dec. 2010.
Rahhal et al.; The impact of assay sensitivity in the assessment of diseases and disorders in children. Steroids, 73(13), pp. 1322-1327, Dec. 2008.
Rashad; Clinical applications of tandem mass spectrometry: ten years of diagnosis and screening for inherited metabolic diseases, Journal of Chromatography B: Biomedical Sciences and Applications, 756(1), pp. 27-48, Jul. 2001.
Rashed et al.; Diagnosis of inborn errors of metabolism from blood spots by acylcarnitines and amino acids profiling using automated electrospray tandem mass spectrometry, Pediatric Research, 38(3), 324-331, Sep. 1995.
Rawls, Optimistic About Antisense: Promising clinical results and chemical strategies for further improvements delight antisense drug researchers; Chemical & Engineering News; 75(22); pp. 35-39; Jun. 2, 1997.
Ren et al., Automated on-chip droplet dispensing with volume control by electro-wetting actuation and capacitance metering, Sens. Actuator B Chem., 98(2-3), pp. 319-327, Mar. 2004.
Ren et al.; Design and testing of an interpolating mixing architecture for electrowetting-based droplet-on-chip chemical dilution; 12th International Conference on Transducers, Solid-State Sensors, Actuators and Microsystems; vol. 2; Boston, MA, USA; pp. 619-622; Jun. 8-12, 2003.
Ro et al.; Poly (dimethylsiloxane) microchip for precolumn reaction and micellar electrokinetic chromatography of biogenic amines, Electrophoresis, 23(7-8), pp. 1129-1137, Apr. 2002.
Roman et al.; Fully integrated microfluidic separations systems for biochemical analysis, J. Chromatogr. A, 1168(1-2), pp. 170-188, Oct. 2007.
Roman et al.; Sampling and Electrophoretic Analysis of Segmented Flow Streams in a Microfluidic Device, Anal. Chem., 80(21), pp. 8231-8238 (author manuscript, 19 pgs.), Nov. 2008.
Sabourin et al.; Interconnection blocks: a method for providing reusable, rapid, multiple, aligned and planar microfluidic Interconnections; Journal of Micromechanics and Microengineering: 19(3): 10 pages; doi:10.1088/0960-1317/19/3/035021; Feb. 18, 2009.
Sadeghi et al.; On Chip Droplet Characterization: A Practical, High-Sensitivity Measurement of Droplet Impedance in Digital Microfluidics; Anal. Chem.; 84(4); pp. 1915-1923; Feb. 2012.
Sahai et al.; Newborn screening, Critical Reviews in Clinical Laboratory Sciences, 46(2), pp. 55-82, (online) Mar. 2009.
Samsi et al.; A Digital Microfluidic Electrochemical Immunoassay; Lab on A Chip; 14(3); pp. 547-554; Feb. 2014.
Sanghvi & Cook (Ed.); Carbohydrate Modifications in Antisense Research; Chapters 2 and 3, American Chemical Society, Washington DC; (207th National Meeting of the American Chemical Society Mar. 13-17, 1994, San Jose, CA); Dec. 1994.
Sanghvi & Cook (Ed.); Carbohydrate Modifications in Antisense Research; Chapters 6 and 7, American Chemical Society, Washington DC; (207th National Meeting of the American Chemical Society Mar. 13-17, 1994, San Jose, CA); Dec. 1994.
Santen et al.; Superiority of gas chromatography/tandem mass spectrometry assay (GC/MS/MS) for estradiol for monitoring of aromatase inhibitor therapy. Steroids. 72(8), pp. 666-671, Jul. 2007.
Sasano et al.; From Endocrinology to Intracrinology. Endocr Pathol, 9(1), pp. 9-20, Spring 1998.

(56) References Cited

OTHER PUBLICATIONS

Satoh et al.; Electrowetting-based valve for the control of the capillary flow, J. Appl. Phys., 103(3), 034903, Feb. 2008.
Satoh et al.; On-chip microfluidic transport and mixing using electrowetting and incorporation of sensing functions, Anal. Chem., 77(21), pp. 6857-6863, Nov. 2005.
Sawai et al., Synthesis and properties of oligoadenylic acids containing 2 ?- 5? phosphoramide linkage, Chem. Lett., 13(5), pp. 805-808, May 1984.
Schertzer et al.; Using capacitance measurements in EWOD devices to identify fluid composition and control droplet mixing; Sens. Actuators B; 145(1); pp. 340-347; Mar. 2010.
Scriver_Commentary; A Simple Phenylalanine Method for Detecting Phenylketonuria in Large Populations of Newborn Infants by Guthrie et al., Pediatrics, 32(3), 338-343, Sep. 1963.
Shah et al., On-demand droplet loading for automated organic chemistry on digital microfluidics, Lab Chip, 13(14), pp. 2785-2795, Jul. 2013.
Shamsi et al.; A digital microfluidic electrochemical immunoassay; Lab on a Chip; 14(3); pp. 547-554; (year of pub. sufficiently earlier than effective US filing date and any foreign priority date) 2014.
Shih et al., A feedback control system for high-fidelity digital microfluidics, Lab Chip, 11(3), pp. 535-540, Feb. 2011.
Simpson et al.; Estrogen—the Good, the Bad, and the Unexpected. Endocr Rev, 26(3), pp. 322-330; May 2005.
Sinha et al., A Versatile Automated Platform for Micro-scale Cell Stimulation Experiments, J. Vis. Exp., e50597, 8 pgs., Aug. 2013.
Sinton et al.; Electroosmotic velocity profiles in microchannels, Colloids Surf. A, 222(1-3), pp. 273-283, Jul. 2003.
Skendzel, Rubella immunity: Defining the level of protective antibody, Am. J. Clin. Pathol., 106(2), 170-174, Aug. 1996.
Smith et al.; Diagnosis and Management of Female Infertility. Journal of the American Medical Association 290(13), pp. 1767-1770, Oct. 2003.
Sooknanan et al., Nucleic Acid Sequence-Based Amplification, Ch. 12; Molecular Methods for Virus Detection (1st Ed.), Academic Press, Inc., pp. 261-285; Jan. 1995.
Sprinzl et al., Enzymatic incorporation of ATP and CTP analogues into the 3' end of tRNA, Eur. J. Biochem., 81(3), pp. 579-589, Dec. 1977.
Srinivasan et al.; An integrated digital microfluidic lab-on-a-chip for clinical diagnostics on human physiological fluids, Lab Chip, 4(4), pp. 310-315, Aug. 2004.
Stanczyk et al.; Standardization of Steroid Hormone Assays Why, How, and When?, Cancer Epidemiol Biomarkers Prev, 16(9), pp. 1713-1719, Sep. 2007.
Steckl et al.; Flexible Electrowetting and Electrowetting on Flexible Substrates; Proc. SPIE 7956; Advances in Display Technologies; and E-papers and Flexible Displays; 795607 (6 pgs.); Feb. 2011.
Stegink et al.; Plasma amino acid concentrations and amino acid ratios in normal adults and adults heterozygous for phenylketonuria ingesting a hamburger and milk shake meal, American Journal of Clinical Nutrition, 53(3), pp. 670-675, Mar. 1991.
Sun et al.; Rapid and direct microRNA quantification by an enzymatic luminescence assay; (author manuscript; 17 pgs.) Analytical Biochemistry; 429(1); pp. 11-17; Oct. 2012.
Svoboda et al.; Cation exchange membrane integrated into a microfluidic device; Microelectronic Engineering; 86; pp. 1371-1374; Apr.-Jun. 2009.
Szarewski et al.; Contraception. Current state of the art. British Medical Journal, 302(6787), pp. 1224-1226, May 1991.
Szymczak et al.; Concentration of Sex Steroids in Adipose Tissue after Menopause. Steroids, 63(5-6), pp. 319-321, May/Jun. 1998.
Tachibana et al.; Application of an enzyme chip to the microquantification of L-phenylalanine, Analytical Biochemistry, 359(1), pp. 72-78, Dec. 2006.
Tan et al.; A lab-on-a-chip for detection of nerve agent sarin in blood; Lab Chip; 8(6); pp. 885-891; Jun. 2008.
Tang et al.; Mechano-regulated surface for manipulating liquid droplets; Nature Communications; 10 pages; DOI: 10.1038/ncomms14831; ; Apr. 4, 2017.
Teh et al.; Droplet microfluidics, Lab Chip, 8(2), pp. 198-220, Feb. 2008.
Theberge et al.; Microdroplets in microfluidics: an evolving plarform for discoveries in chemistry and biology; Angewandte Chemie International Edition; 49(34); pp. 5846-5868; Aug. 2010.
Therrell et al.; Newborn screening in North America, Journal of Inherited Metabolic Disease, 30(4), pp. 447-465, Aug. 2007.
Tian et al., Printed two-dimensional micro-zone plates for chemical analysis and ELISA, Lab on a Chip, 11(17), pp. 2869-2875, Sep. 2011.
Tobjörk et al., IR-sintering of ink-jet printed metal-nanoparticles on paper, Thin Solid Films, 520(7), pp. 2949-2955, Jan. 2012.
Tomita et al.; Loop-mediated isothermal amplification (LAMP) of gene sequences and simple visual detection of products; Nature Protocols; 3(5); pp. 877-882; (online) Apr. 2008.
Torkkeli; Droplet microfluidics on a planar surface; VTT Technical Research Centre of Finland; Publications 504; 214 pages (Dissertation); Oct. 2003.
Turgeon et al.; Combined Newborn Screening for Succinylacetone, Amino Acids, and Acylcarnitines in Dried Blood Spots, Clinical Chemistry, 54(4), pp. 657-664, Apr. 2008.
Udenfriend et al.; Fluorescamine: a reagent for assay of amino acids, peptides, proteins, and primary amines in the picomole range, Science, 178(4063), pp. 871-872, Nov. 1972.
Unger et al.; Monolithic microfabricated valves and pumps by multilayer soft lithography, Science, 288(5463), pp. 113-116, Apr. 2000.
Univ. of Maryland—Baltimore Washington Medical Center; Plasma amino acids, 6 pgs., retrieved Feb. 10, 2017 from: http://www.mybwmc.org/library/1/003361, Web address available to applicant(s) at least as of Jan. 2010.
Verkman; Drug Discovery in Academia; Am J Physiol Cell Physiol; 286(3); pp. C465-C474; Feb. 2004.
Walker et al.; A Chemiluminescent DNA Probe Test Based on Strand Displacement Amplification (Chapter 15); Molecular Methods for Virus Detection (1st Ed.), Academic Press, Inc., pp. 329-349; Jan. 1995.
Walker et al.; A passive pumping method for microfluidic devices, Lab Chip, 2(3), pp. 131-134, Aug. 2002.
Wang et al.; Paper-based chemiluminescence ELISA: lab-on-paper based on chitosan modified paper device and, Biosens. Bioelectron., 31(1), pp. 212-218, Jan. 2012.
Wang et al., Simple and covalent fabrication of a paper device and its application in sensitive chemiluminescence immunoassay, Analyst, 137(16), pp. 3821-3827, Aug. 2012.
Wang et al.; An integrated microfluidic device for large-scale in situ click chemistry screening; Lab on a Chip; 9(16); 9(16); pp. 2281-2285; 9 pages (Author Manuscript); Aug. 2009.
Wang et al.; Highly sensitive detection of microRNAs based on isothermal exponential amplification-assisted generation of catalytic G-quadruplexDNAzyme; Biosensors and Bioelectronics, 42; pp. 131-135; Apr. 2013.
Washburn et al.; Large-scale analysis of the yeast proteome by multidimensional protein identification technology, Nat. Biotechnol., 19(3), pp. 242-247, Mar. 2001.
Watson et al.; Multilayer hybrid microfluidics: a digital-to-channel interface for sample processing and separations; Anal. Chem.; 82(15); pp. 6680-6686; Aug. 2010.
Wheeler et al.; Electrowetting-Based Microfluidics for Analysis of Peptides and Proteins by Matrix-Assisted Laser Desorption/Ionization Mass Spectrometry; Anal Chem; 76(16); pp. 4833-4838; Aug. 2004.
Wheeler; Chemistry. Putting electrowetting to work; Science; 322(5901); pp. 539-540; Oct. 2008.
Wlodkowic et al.; Tumors on chips: oncology meets microfluidics; Current opinion in Chemical Biology; 14(5); pp. 556-567; Oct. 2010.
Wu et al.; Design, Simulation and Fabrication of Electrowetting-Based Actuators for Integrated Digital Microfluidics; Proceedings

(56) References Cited

OTHER PUBLICATIONS of the 1st IEEE International Conference on Nano/Micro Engineered and Molecular Systems; Zhuhai, China; pp. 1097-1100; Jan. 18-21, 2006.

Wu et al.; Electrophoretic separations on microfluidic chips, J. Chromatogr. A, 1184(1-2), pp. 542-559, Mar. 2008.

Yan et al., A microfluidic origami electrochemiluminescence aptamer-device based on a porous Au-paper electrode and a phenyleneethynylene derivative, Chem. Commun. (Camb), 49(14), pp. 1383-1385, Feb. 2013.

Yan et al., Paper-based electrochemiluminescent 3D immunodevice for lab-on-paper, specific, and sensitive point-of-care testing, Chem.--Eur. J., 18(16), pp. 4938-4945, Apr. 2012.

Yi et al.; Spangler et al., Eds; Channel-to-droplet extractions for on-chip sample preparation, in Proceedings of Solid-State Sensor, Actuator and Microsystems Workshop, pp. 128-131, Jun. 2006.

Yin et al.; One-step, multiplexed fluorescence detection of microRNAs based on duplex-specific nuclease signal amplification; J. American Chem. Soc.; 134(11); pp. 5064-5067; Mar. 2012.

Yoon et al.; Preventing Biomolecular Adsorption in Electrowetting-Based Biofluidic Chips; Anal Chem; 75; pp. 5097-5102; Aug. 2003.

Yoon; Open-Surface Digital Microfluidics; The Open Biotechnology Journal; 2(1); pp. 94-100; Apr. 2008.

Young et al.; Calculation of DEP and EWOD Forces for Application in Digital Microfluidics, J. Fluids Eng., 130(8), pp. 081603-1-081603-9, Jul. 2008.

Yu et al., Monolithic porous polymer for on-chip solid-phase extraction and preconcentration prepared by photoinitiated in situ polymerization within a microfluidic device, Analytical Chemistry, 73(21), pp. 5088-5096, Nov. 2001.

Yu et al., Preparation of monolithic polymers with controlled porous properties for microfluidic chip applications using photoinitiated free-radical polymerization, Journal of Polymer Science, Part A: Polymer Chemistry, 40(6), pp. 755-769, Mar. 2002.

Yu et al.; A plate reader-compatible microchannel array for cell biology assays; Lab Chip; 7(3); pp. 388-391; Mar. 2007.

Yu et al.; Microfabrication of a digital microfluidic platform integrated with an on-chip electrochemical cell; Journal of Micromechanics and Microrngineering; 23(9); pp. 10 pages; doi: 10.1088/0960-1317/23/9/095025; Aug. 2013.

Yu et al.; Microfabrication of a digital microfluidic platform integrated with an on-chip electrochemical cell; Journal of Micromechanics and Microengineering; 23(9); doi:10.1088/0960-1317/23/9/095025, 10 pages; Aug. 28, 2013.

Yu et al.; Parallel-plate lab-on-chip electrochemical analysis; Journal of Micromechanics and Microengineering; 24(1); 7 pages; doi: 10.1088/0960-1317/24/1/015020; Dec. 16, 2013.

Yue; Undergraduate Chemistry experiment (11); Hunan Normal University Press; First Edition; p. 96; (Machine Translation included); Oct. 2008.

Yung et al.; Micromagnetic-microfluidic blood cleansing devices; Lab on a Chip; 9(9); pp. 1171-1177; May 2009.

Zaffanello et al.; Multiple positive results during a neonatal screening program: a retrospective analysis of incidence, clinical implications and outcomes, Journal of Perinatal Medicine, 33(3), pp. 246-251, May 2005.

Zhang et al.; Multiplexed detection of microRNAs by tuning DNA-scaffolded silver nanoclusters; Analyst; 138(17); pp. 4812-4817; Sep. 2013.

Zhang et al.; The permeability characteristics of silicone rubber; In Proceedings of 2006 SAMPE Fall Technical Conference; 10 pages; Nov. 6, 2006.

Zhao et al., Lab on Paper, Lab Chip, 8(12), pp. 1988-1991, Dec. 2008.

Znidarsic-Plazl et al.; Steroid extraction in a microchannel system—mathematical modelling and experiments. Lab Chip, 7(7), pp. 883-889, Jul. 2007.

Zuker; Mfold Web Server for Nucleic Acid Folding and Hybridization Prediction; Nucleic Acid Research ; 31(13); pp. 3406-3415; Jul. 2003.

Zytkovicz et al.; Tandem mass spectrometric analysis for amino, organic, and fatty acid disorders in newborn dried blood spots: a two-year summary from the New England Newborn Screening Program, Clinical Chemistry, 47(11), pp. 1945-1955, Nov. 2001.

Tecan; Freedom EVO; 16 pages; retrieved from the internet: https(//instruments.cz/wp-content/uploads/2018/04/EVO.pdf) Oct. 4, 2023.

Jebrail et al.; U.S. Appl. No. 18/451,828 entitled "Methods of mechanical microfluidic manipulation," filed Aug. 17, 2023.

Soto-Moreno et al.; U.S. Appl. No. 18/457,325 entitled "Multi-cartridge digital microfluidics apparatuses and methods of use," filed Aug. 28, 2023.

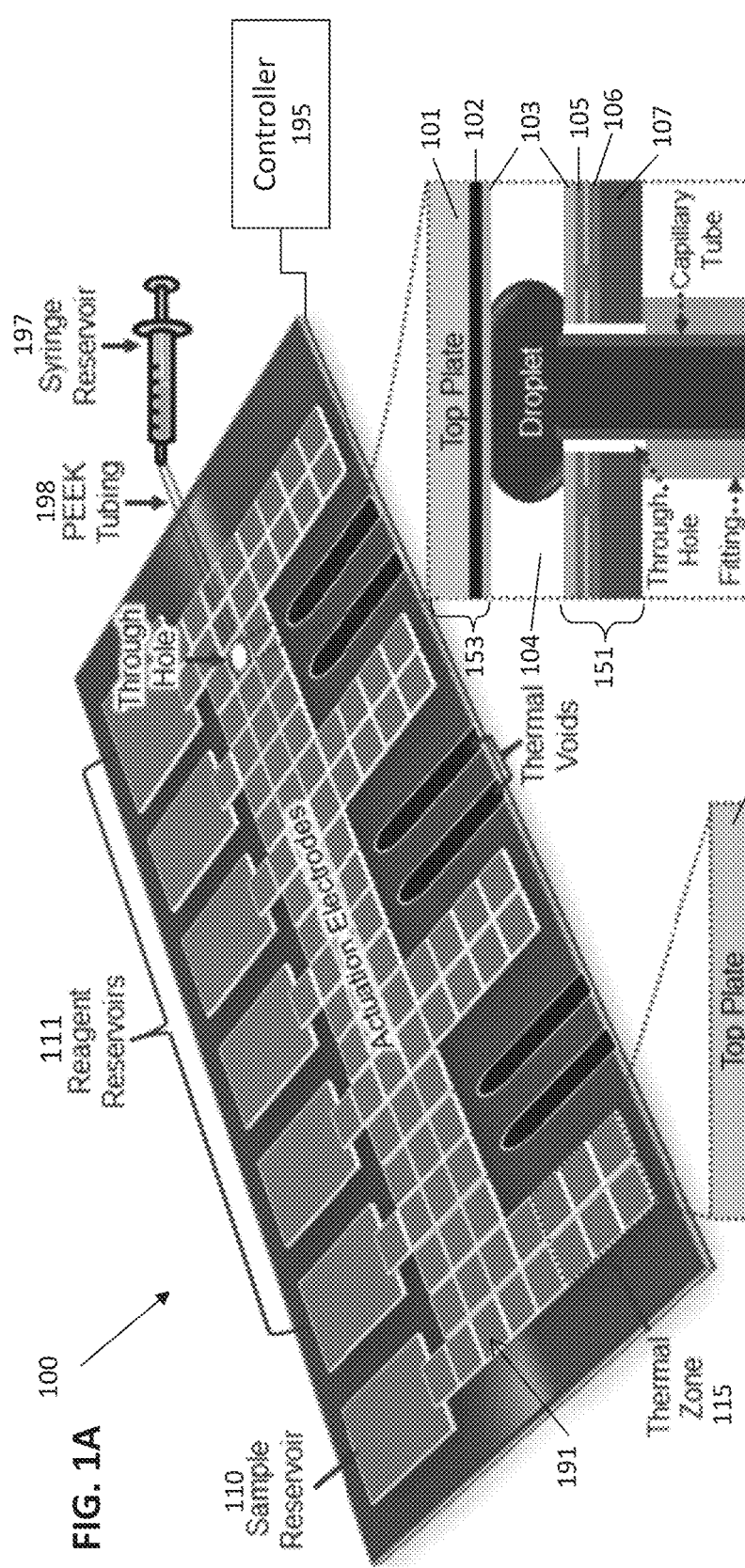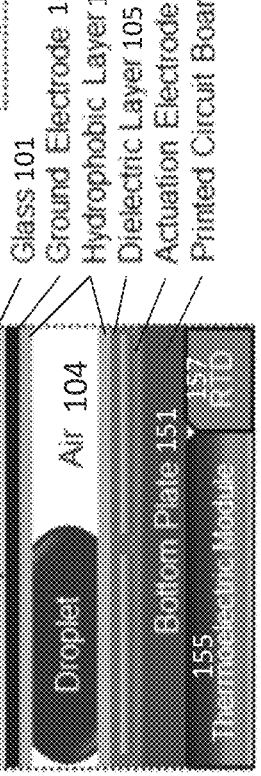

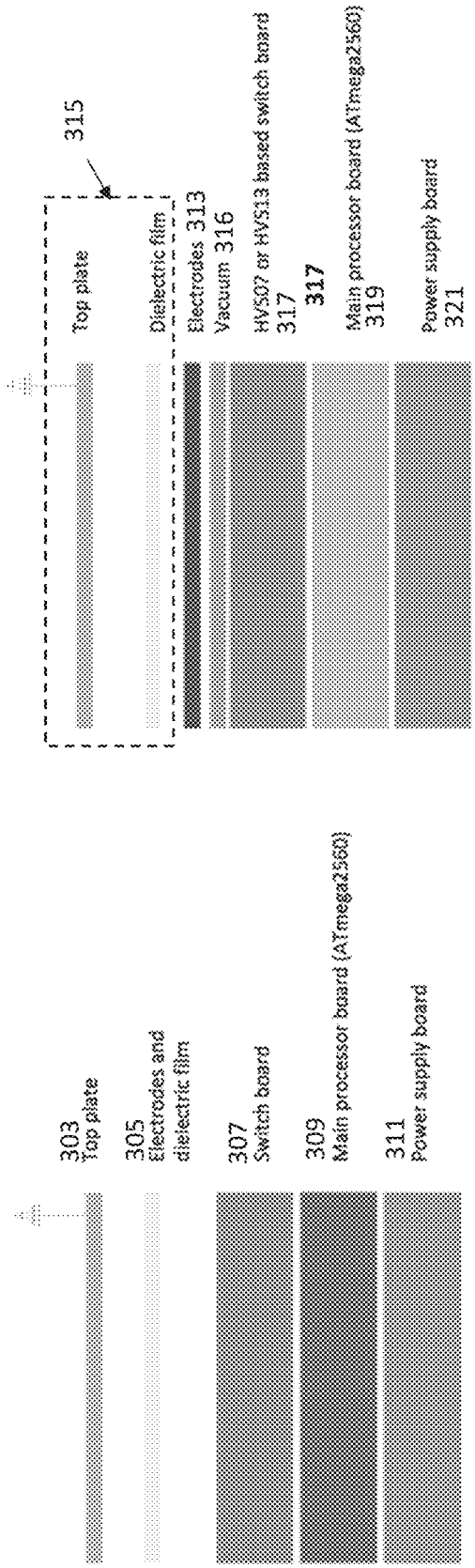

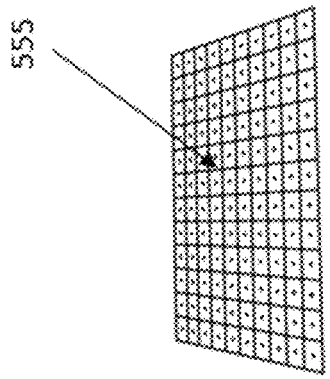
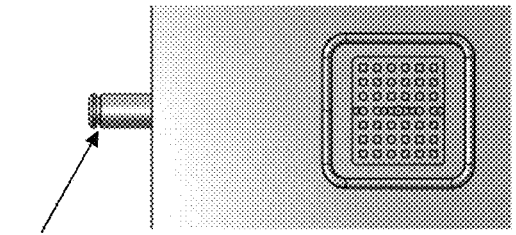
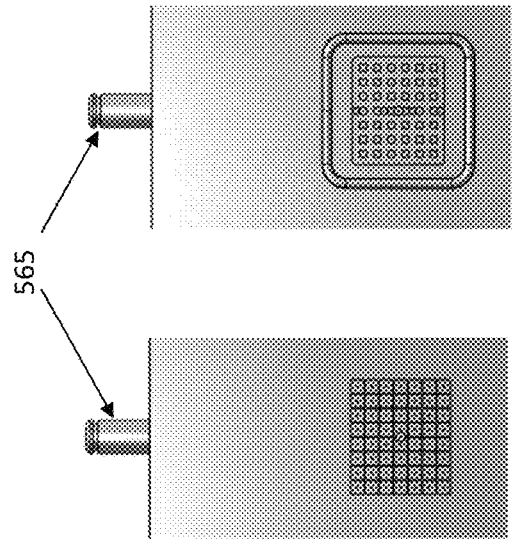
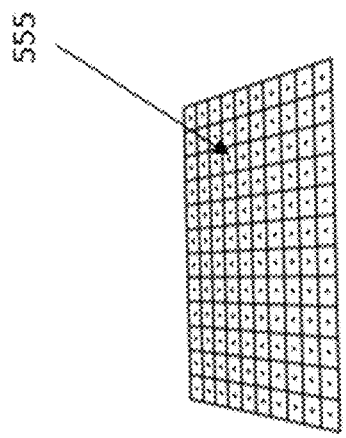
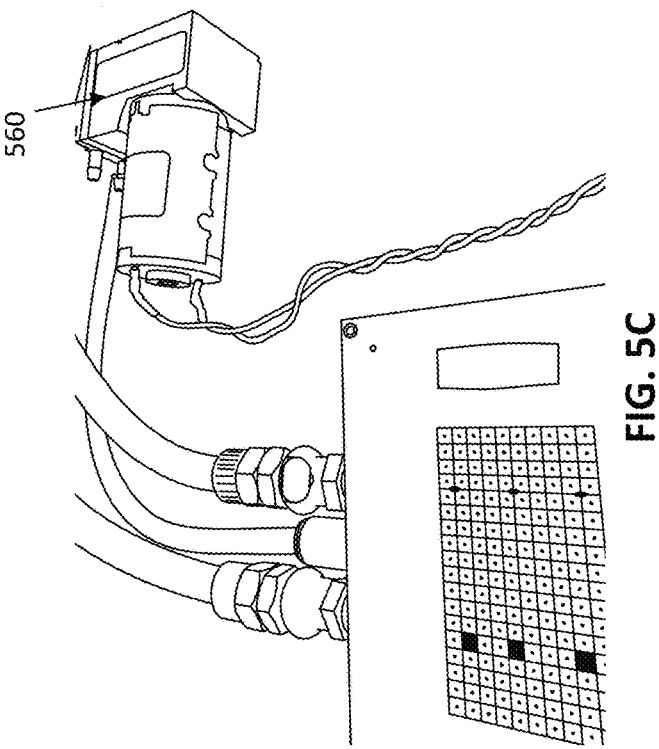

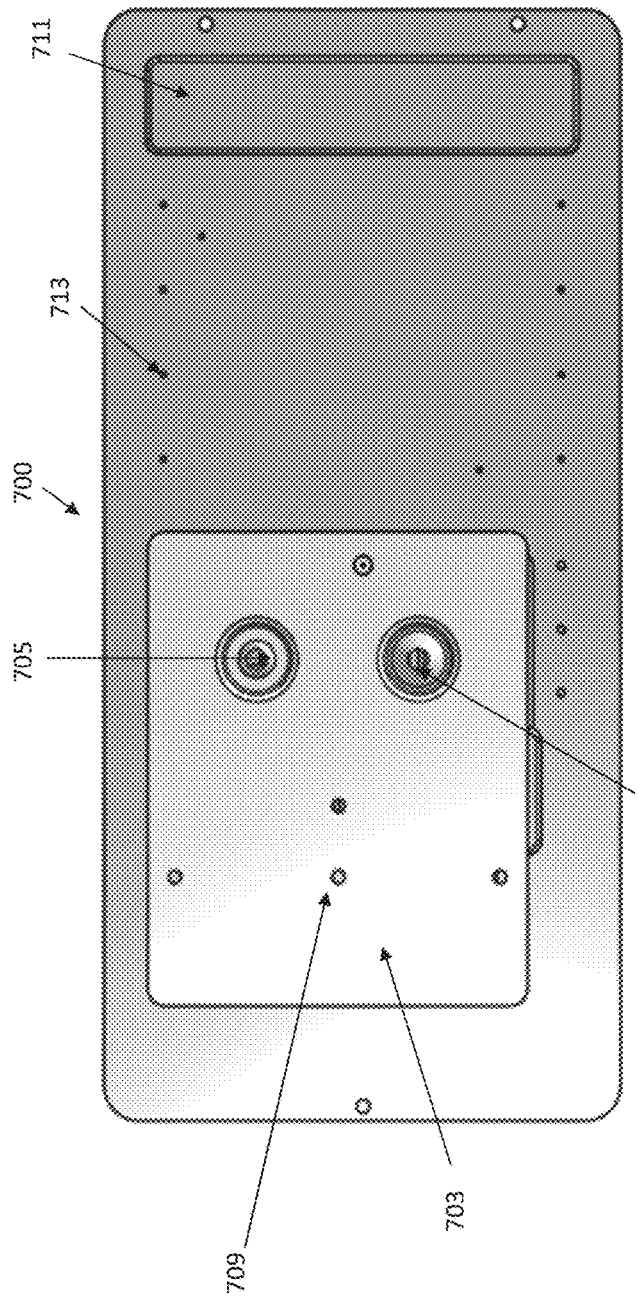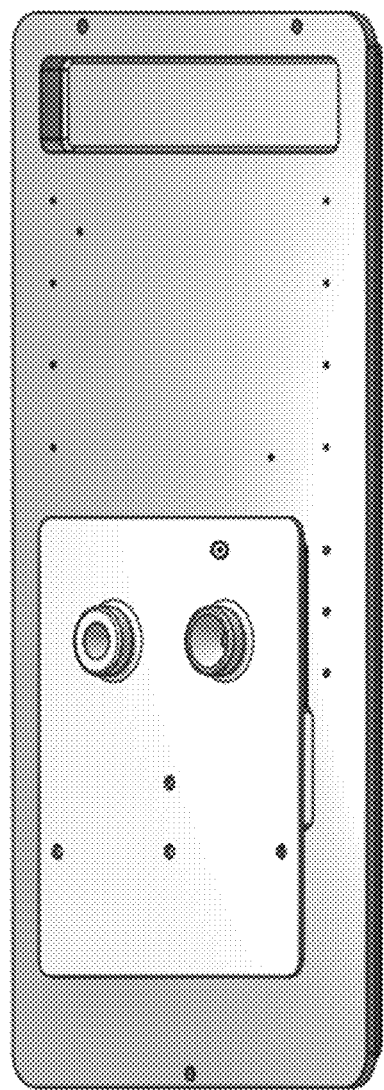
FIG. 7A
FIG. 7B

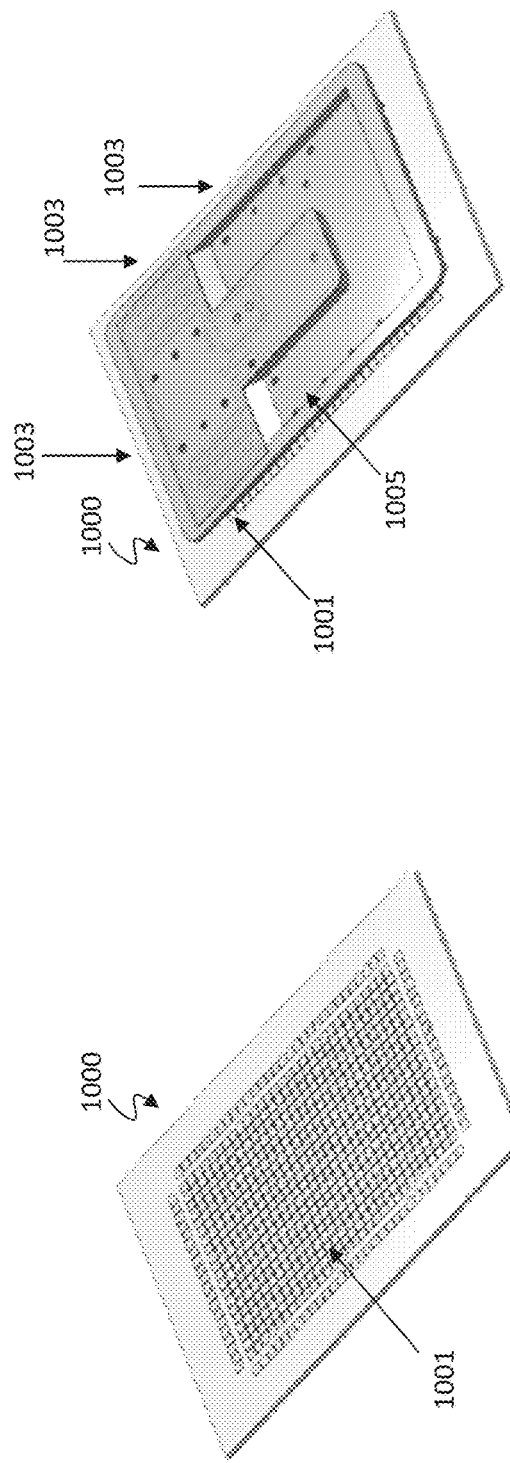
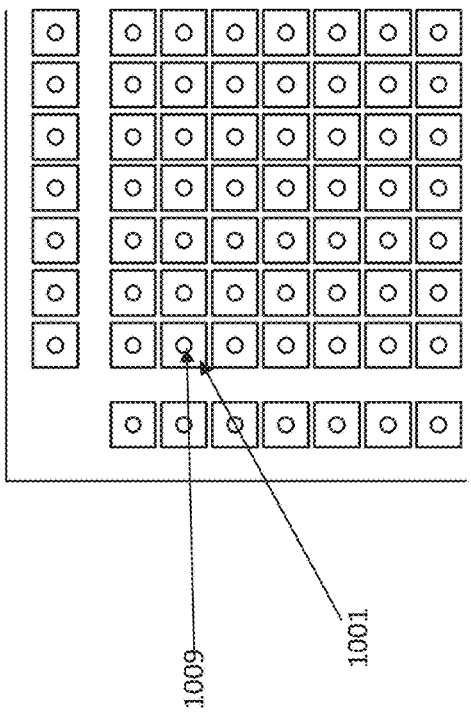
FIG. 11
FIG. 12
FIG. 10

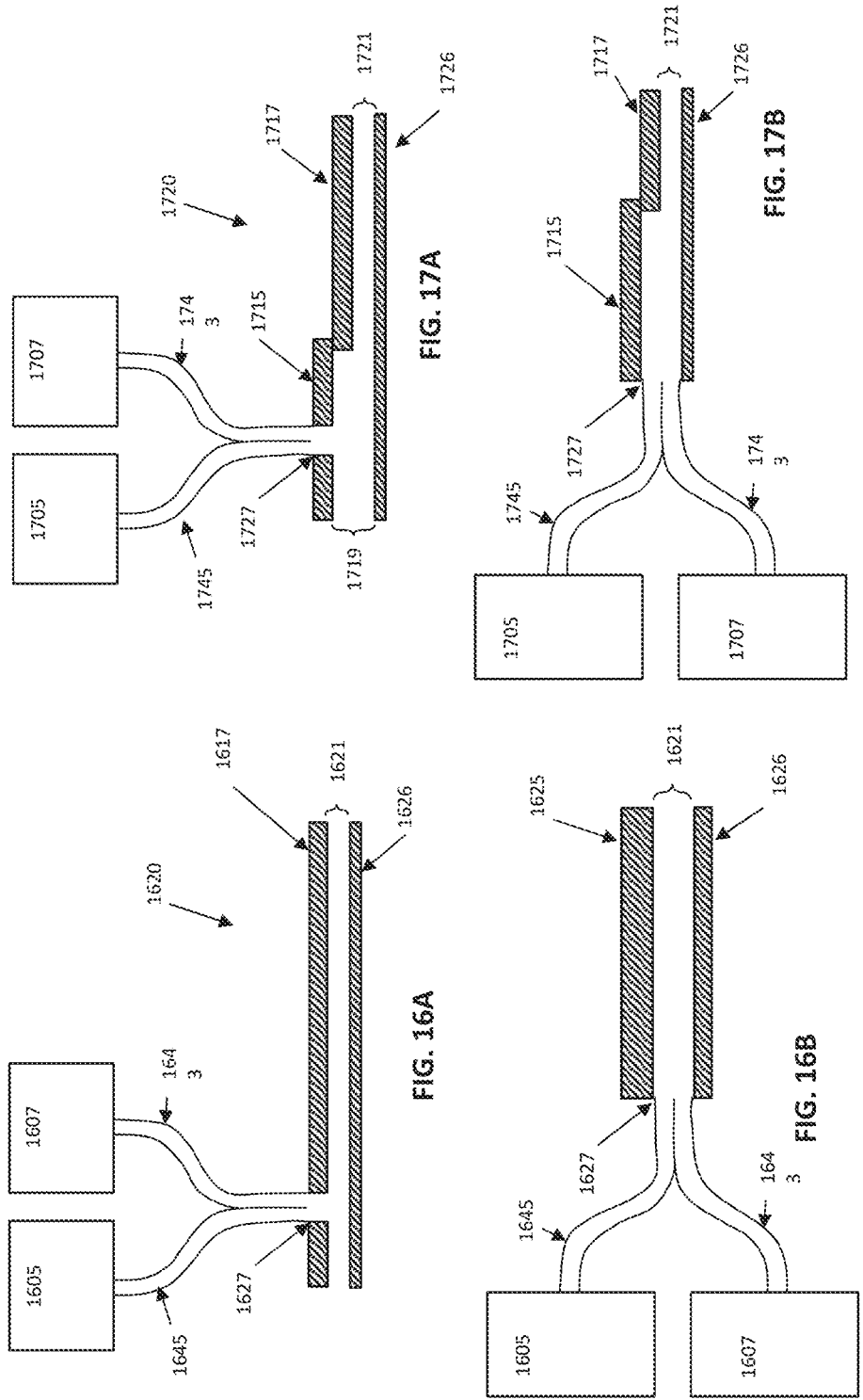

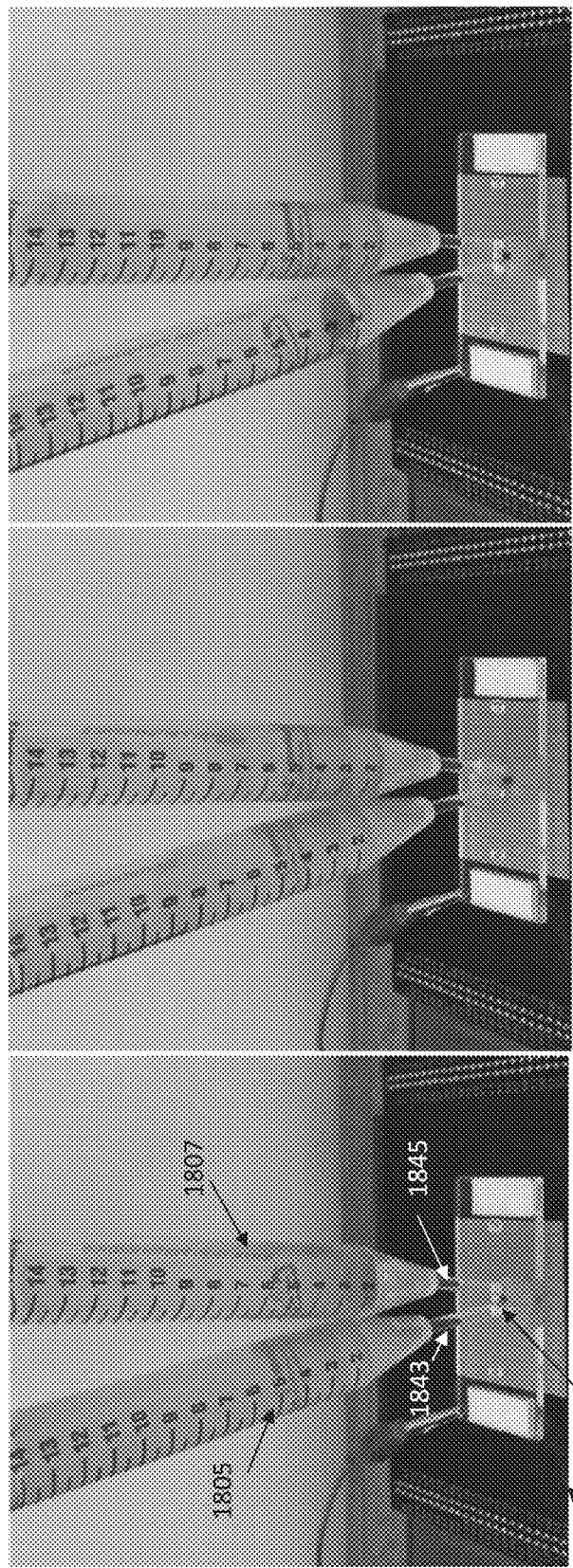

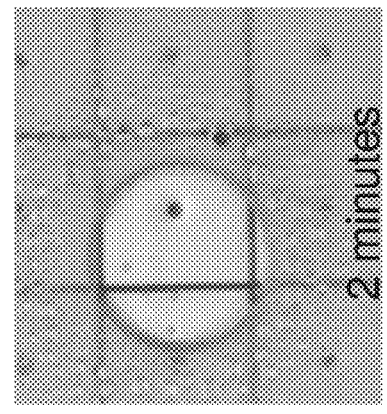
FIG. 19A 0 minutes
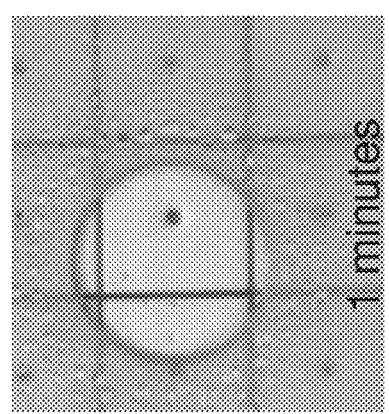
FIG. 19B 1 minutes
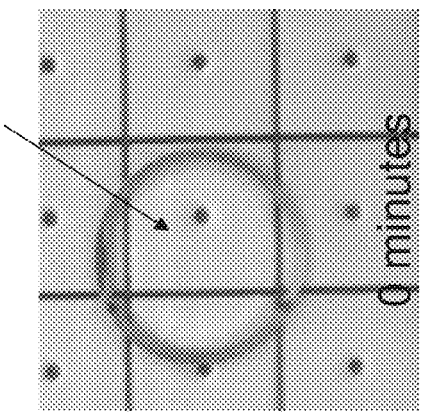
FIG. 19C 2 minutes
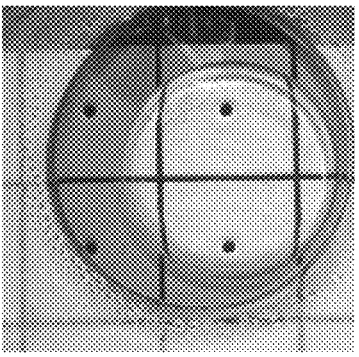
FIG. 20A 0 minutes
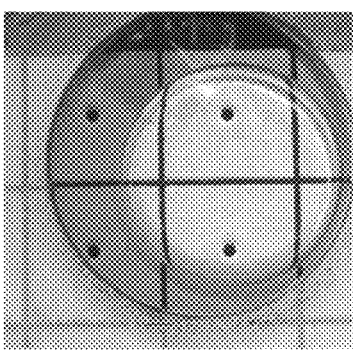
FIG. 20B 60 minutes
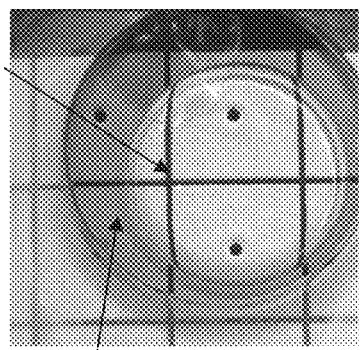
FIG. 20C 120 minutes

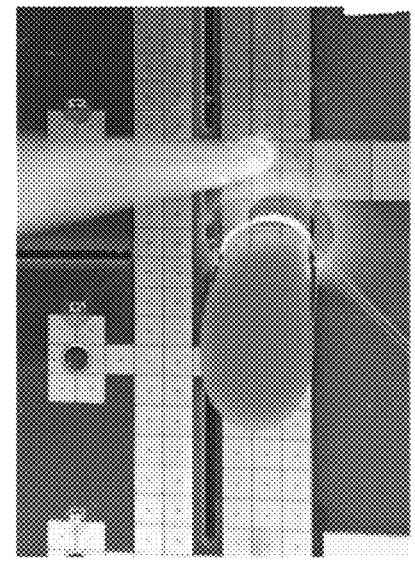
FIG. 21E
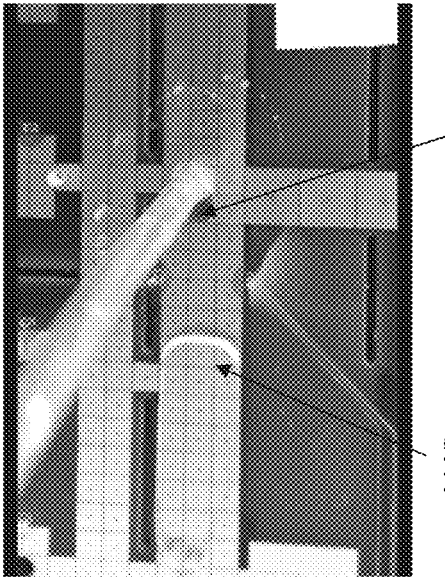
FIG. 21F
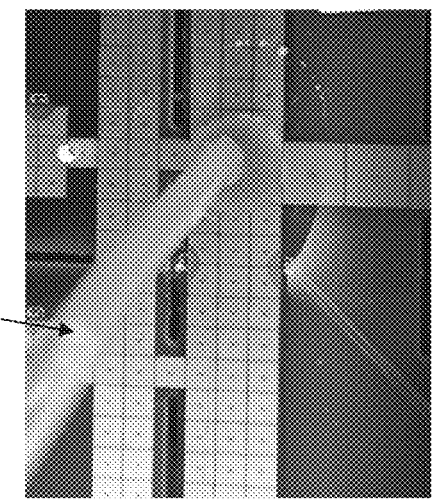
FIG. 21H
FIG. 21G
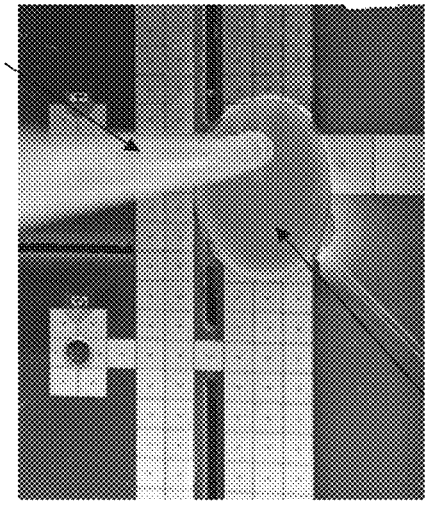
FIG. 21I

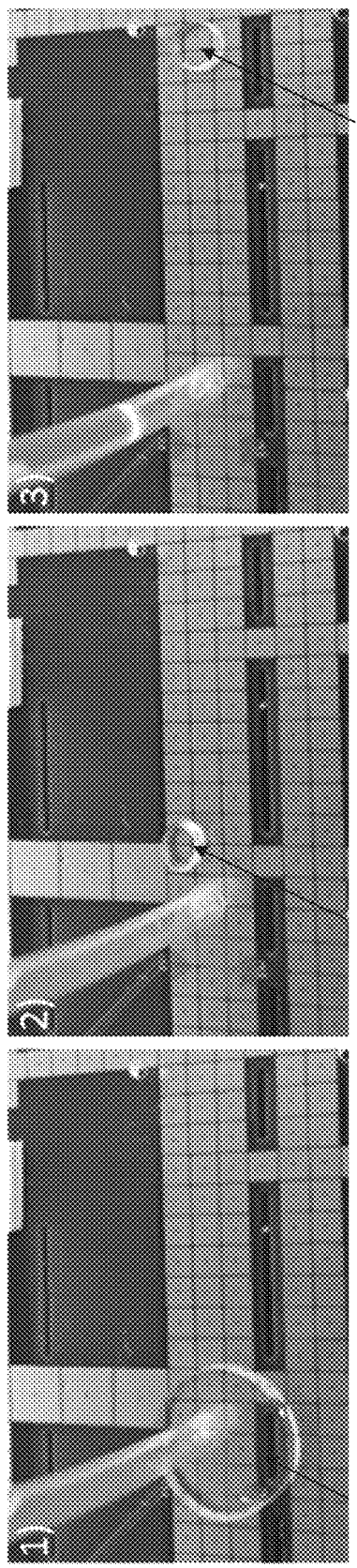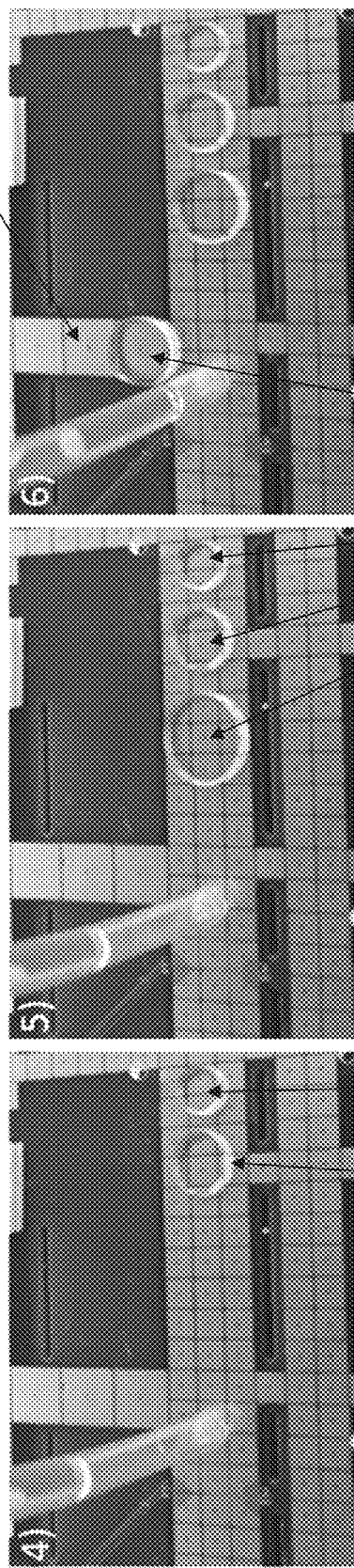
FIG. 23A  FIG. 23B  FIG. 23C
FIG. 23D  FIG. 23E  FIG. 23F

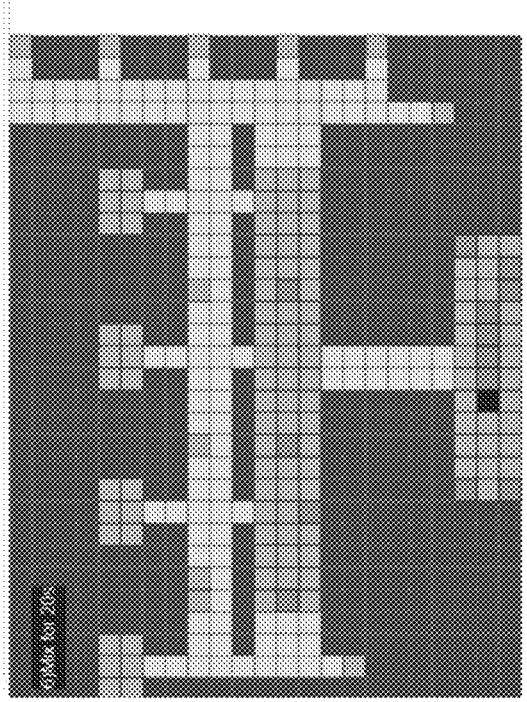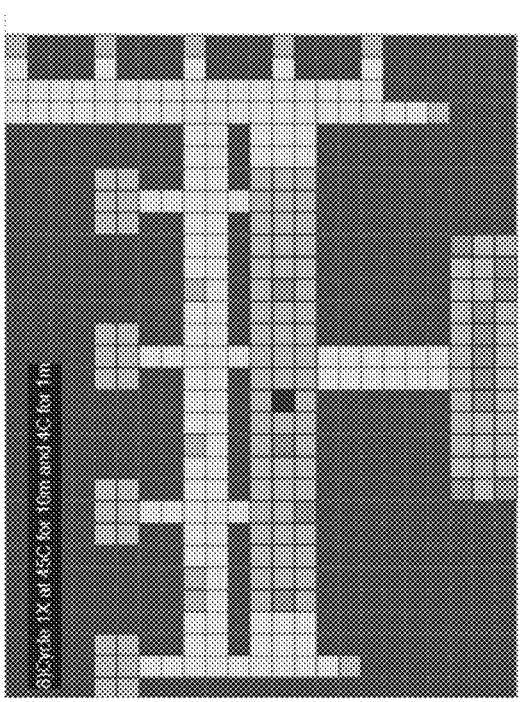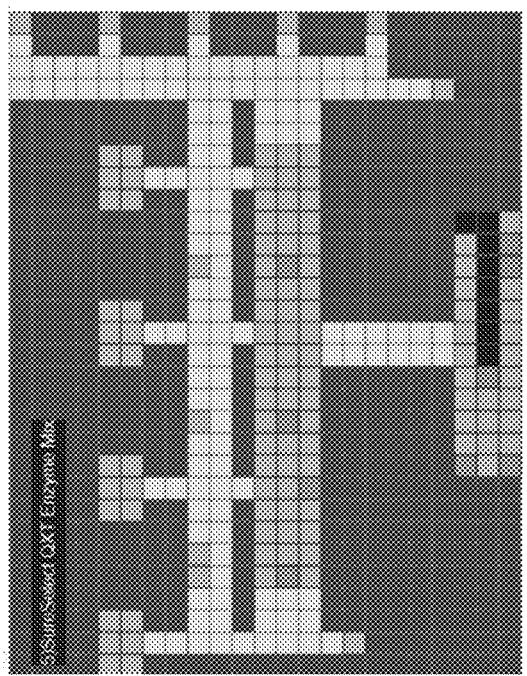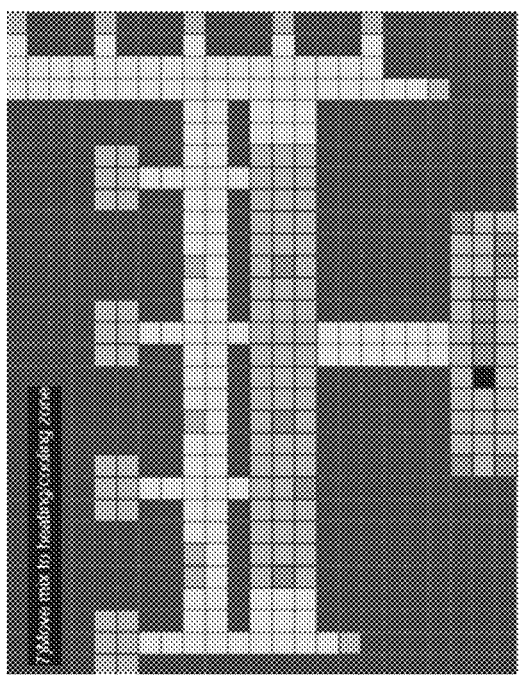

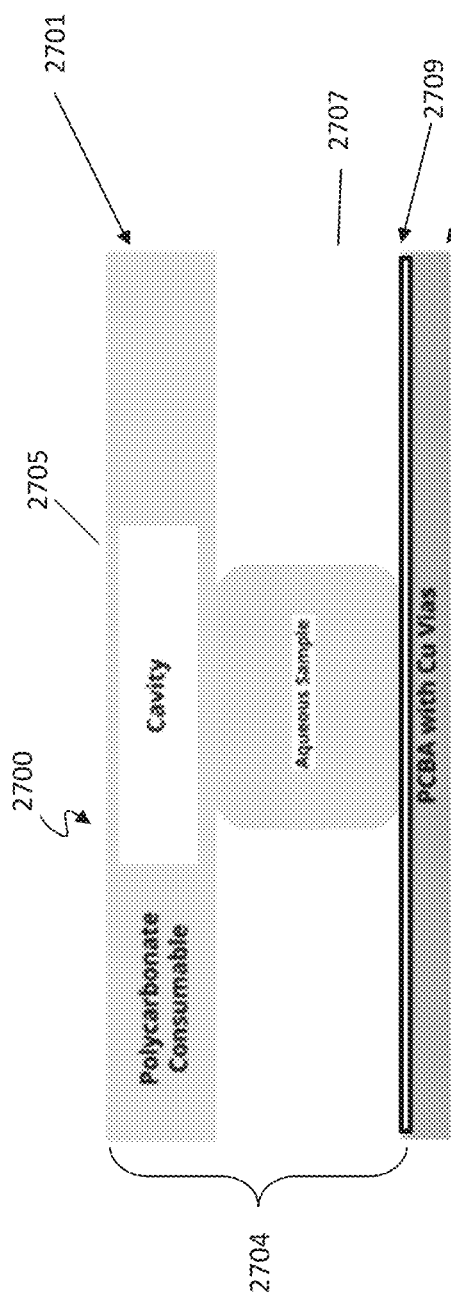
FIG. 27
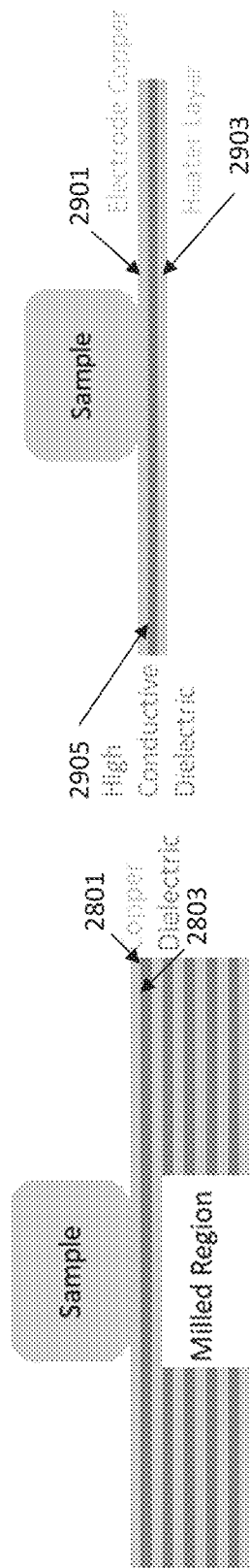
FIG. 29
FIG. 28

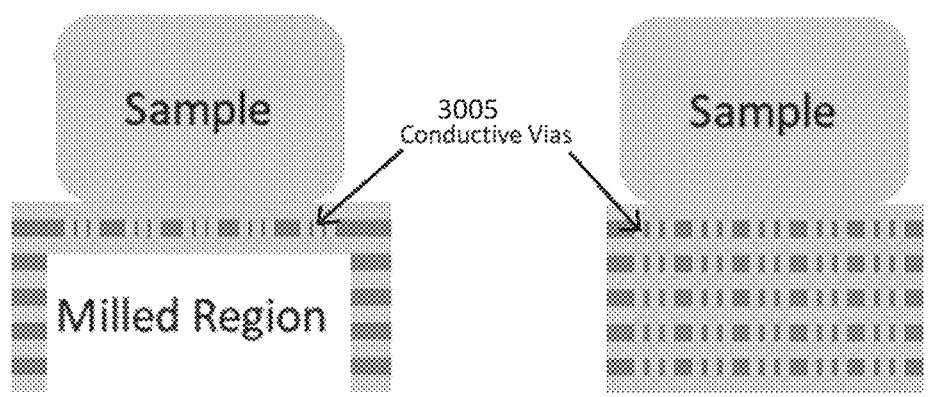
FIG. 30A  FIG. 30B
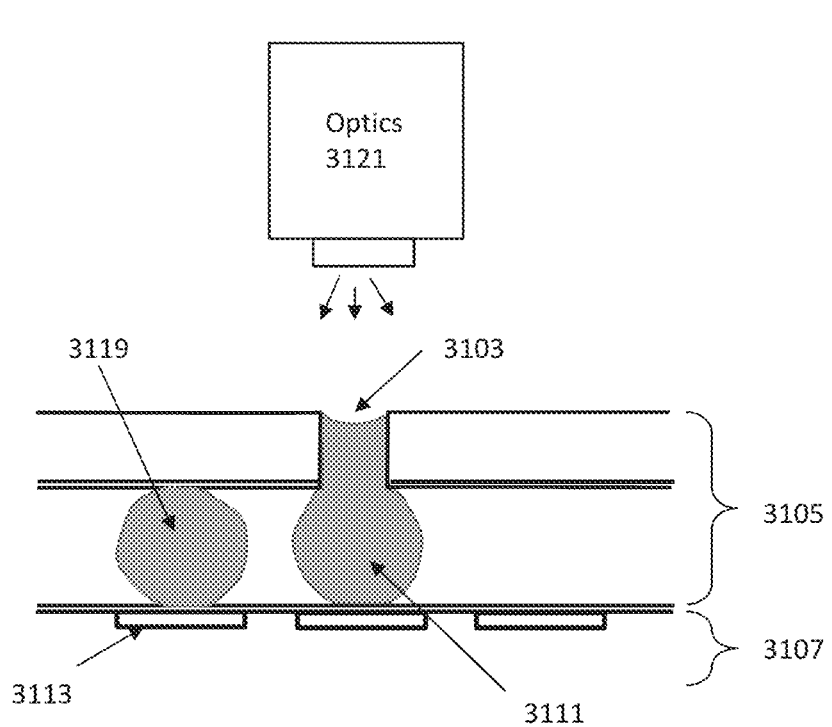
FIG. 31

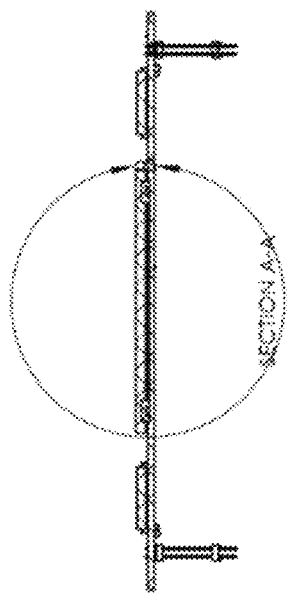
FIG. 36A
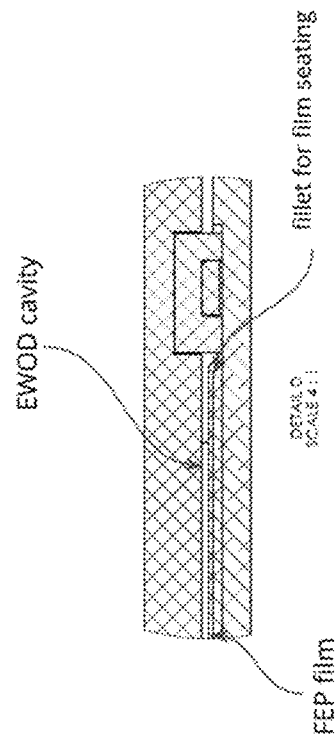
FIG. 36B
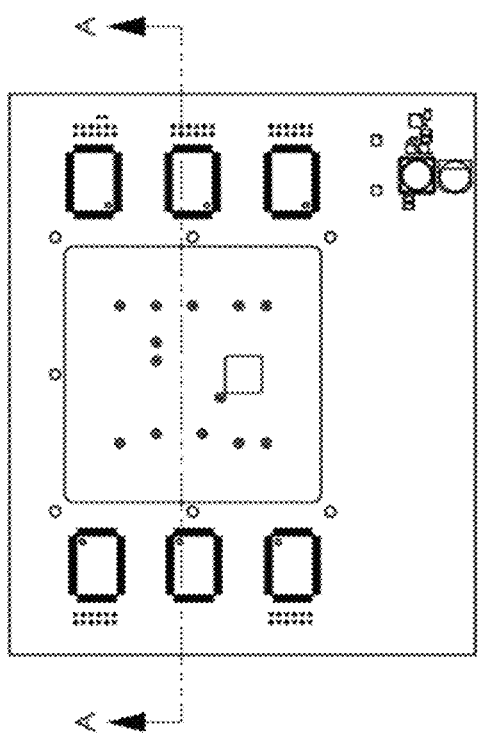
FIG. 36C
FIG. 36D

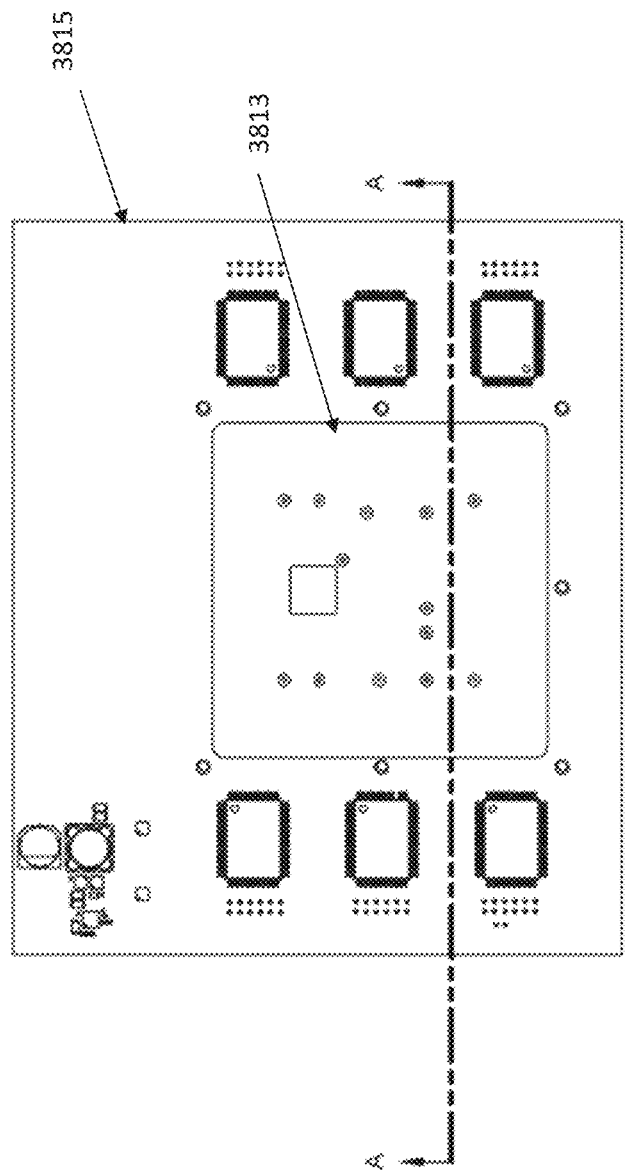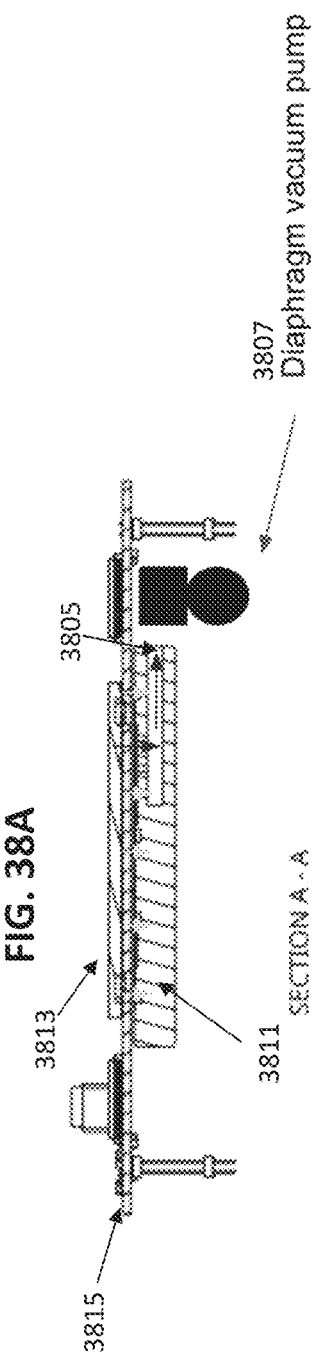
FIG. 38A
FIG. 38B

SECTION A-A

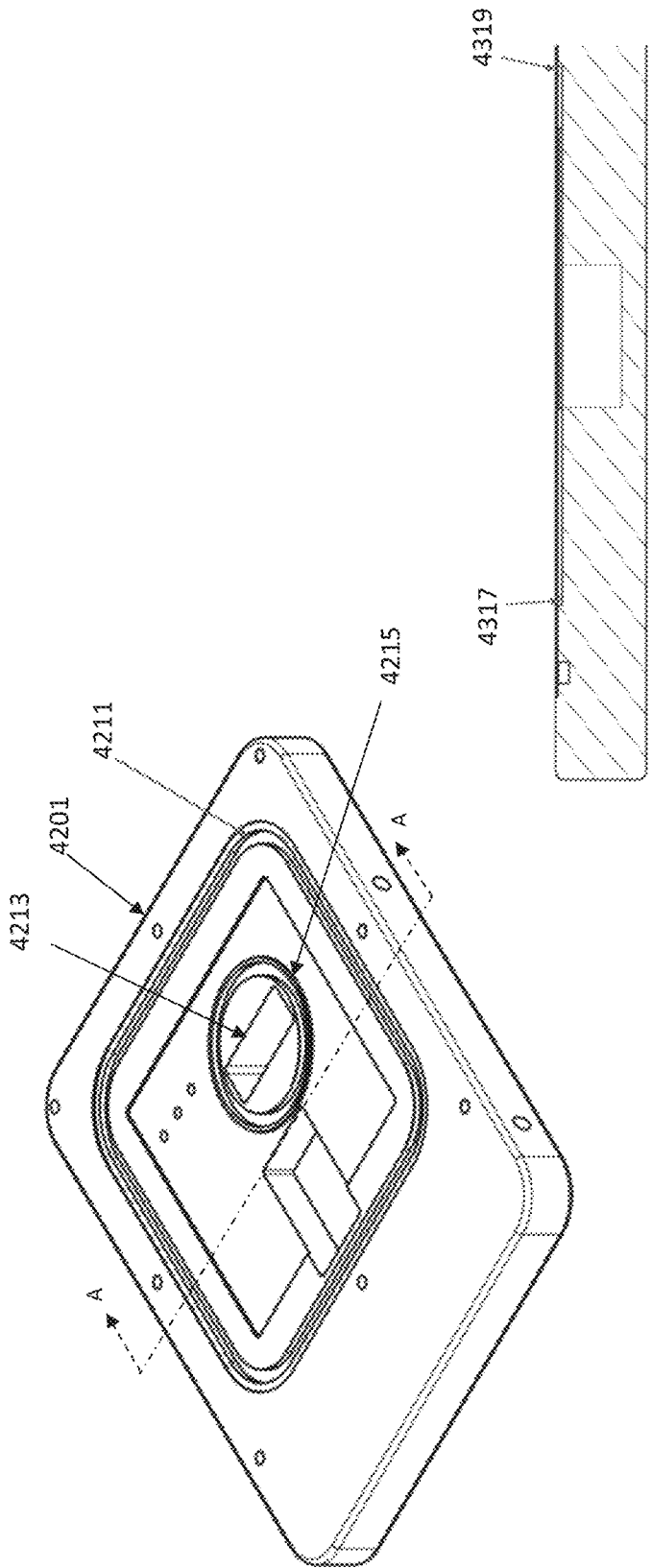

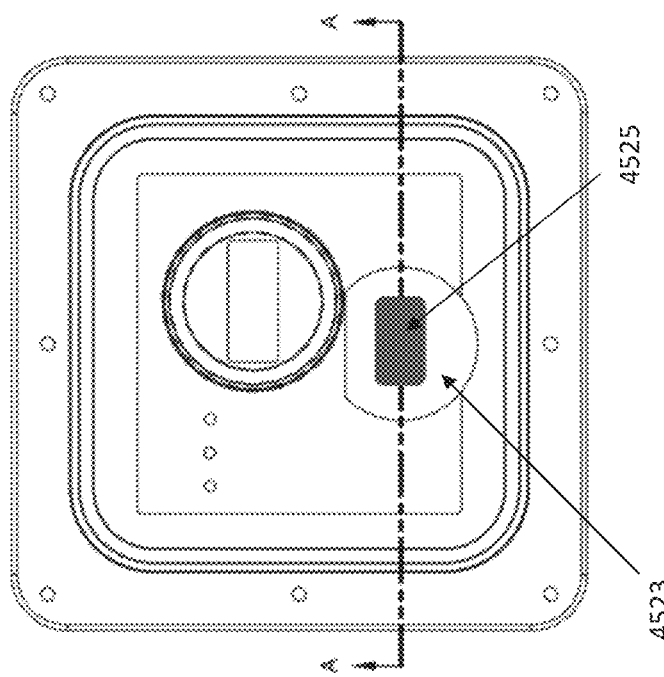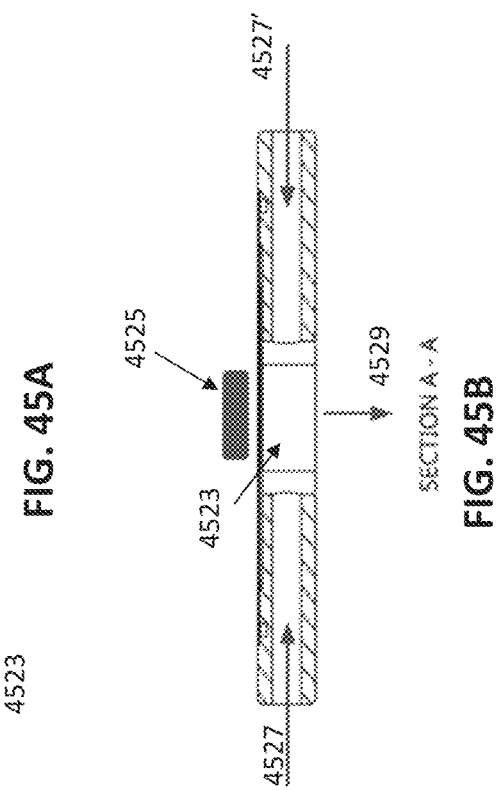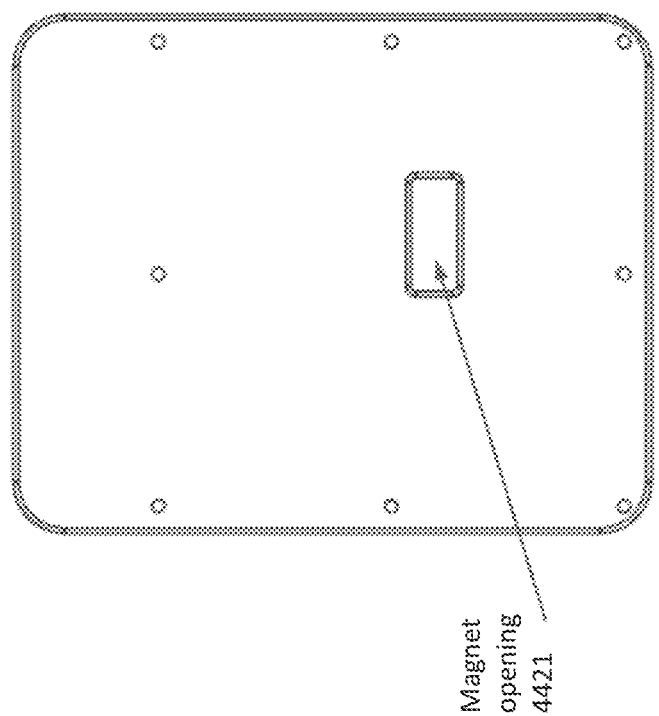

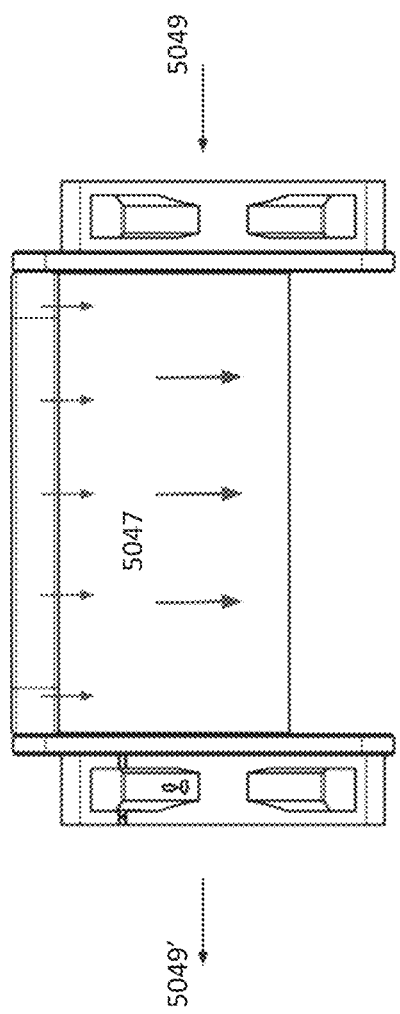
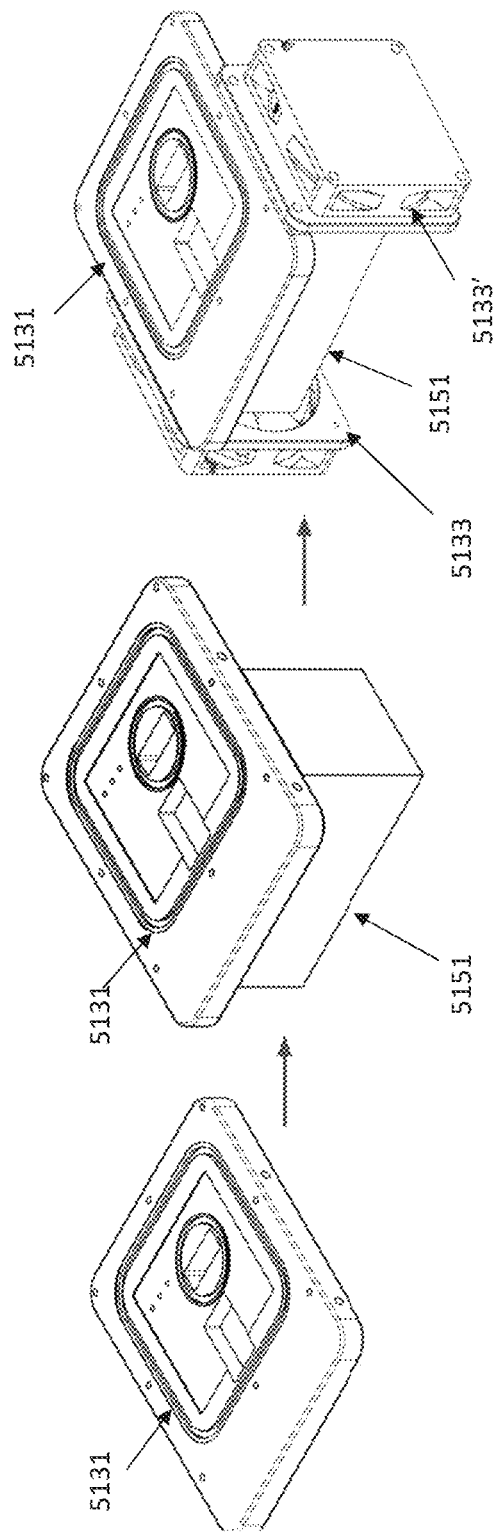
FIG. 50
FIG. 51A  FIG. 51B  FIG. 51C

A: POWER SUPPLY CONDITIONING
B: ISOTHERMAL HEATER POWER SUPPLY
C: THERMISTOR AMPS, TEC & HEATER PROTECTION LOGIC
D: DROPLET DETECTION
E: PRESSURE SENSOR
F: DIGITAL AND ANALOG ISOLATION CIRCUITRY
G: VIBE MOTOR
H: TEC POWER SUPPLY
I: SOLID STATE RELAYS
J: HVPS REGULATION CIRCUITRY

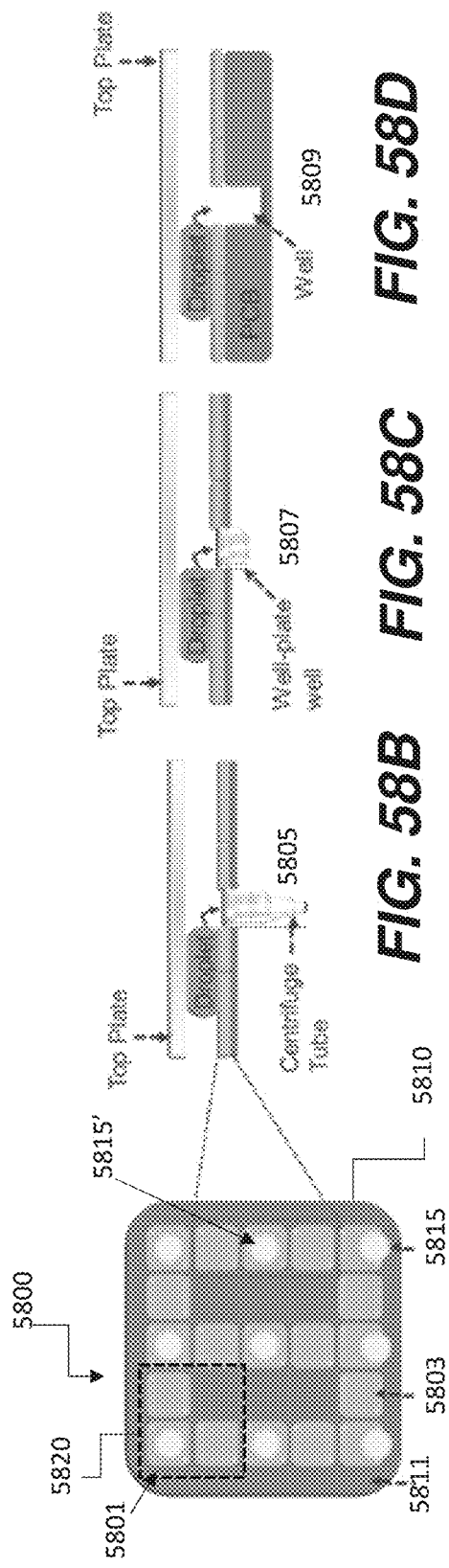
FIG. 58A FIG. 58B FIG. 58C FIG. 58D
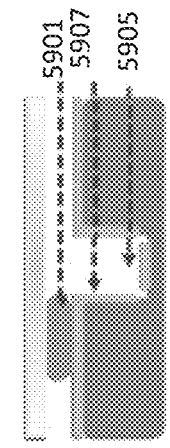
FIG. 59A
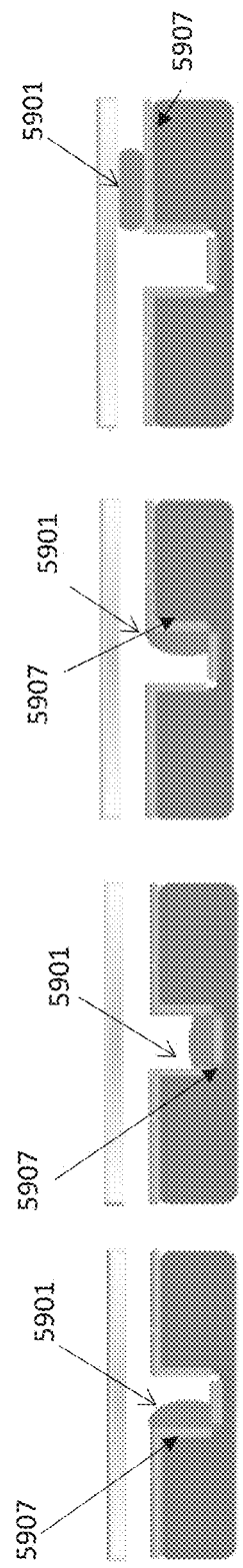
FIG. 59B FIG. 59C FIG. 59D FIG. 59E

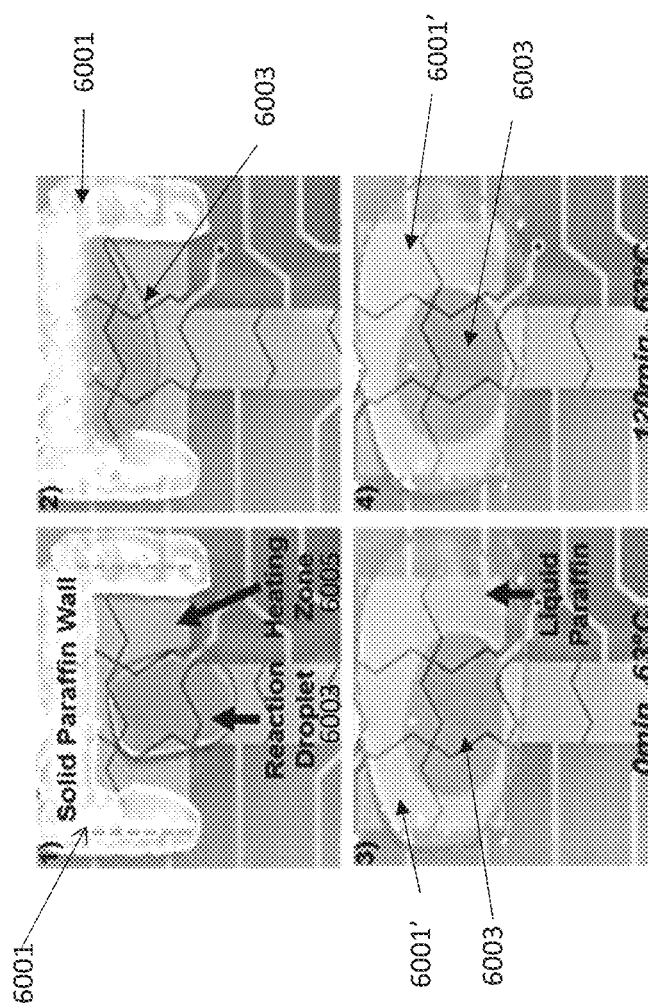
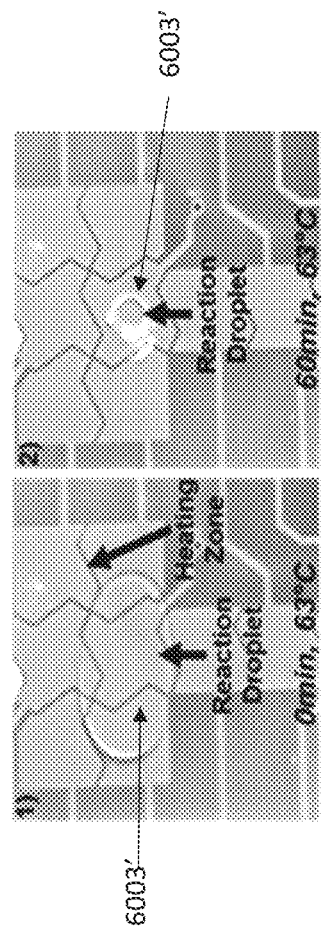
FIG. 60A
FIG. 60B

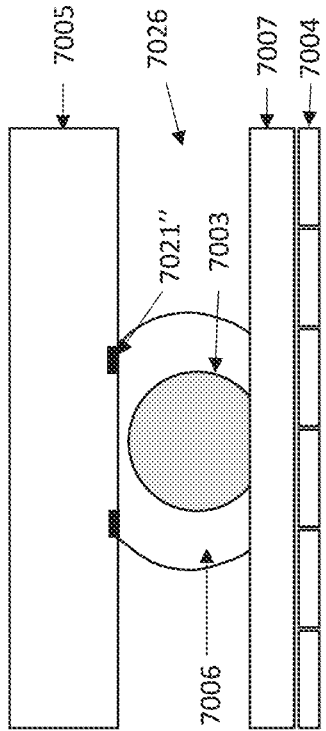
FIG. 71B
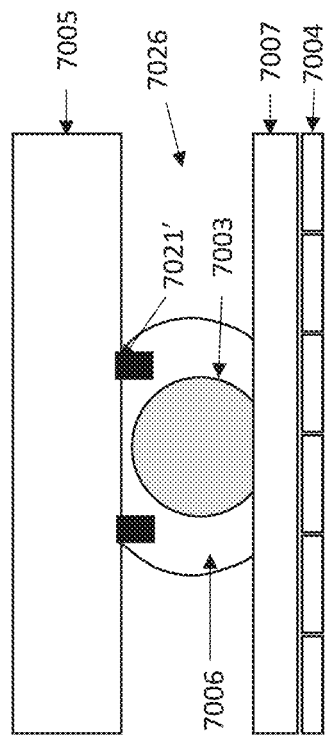
FIG. 71C
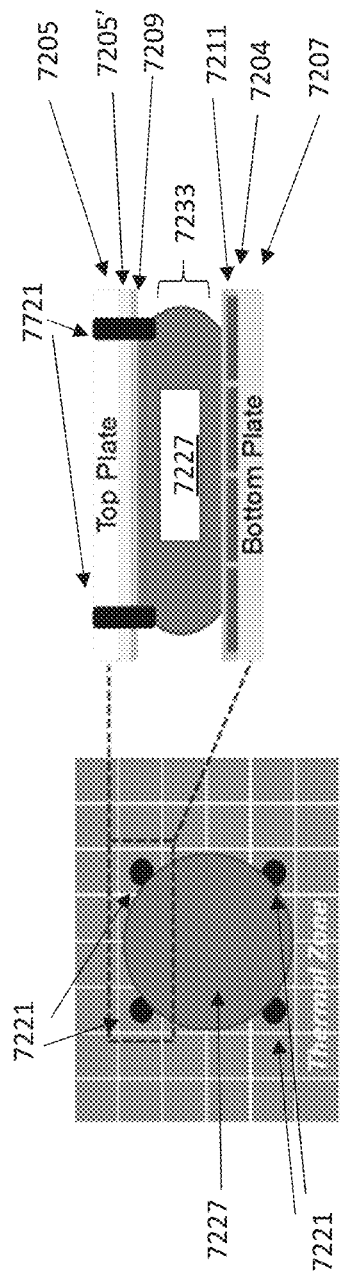
FIG. 72A
FIG. 72B

CONTROL OF EVAPORATION IN DIGITAL MICROFLUIDICS

CROSS REFERENCE TO RELATED APPLICATIONS

This application is a continuation of International Patent Application No. PCT/US2019/033794, filed May 23, 2019, titled "CONTROL OF EVAPORATION IN DIGITAL MICROFLUIDICS," now International Patent Publication No. WO 2019/226919, which claims priority to U.S. Provisional Patent Application No. 62/675,749, filed May 23, 2018, titled "CONTROL OF EVAPORATION IN DIGITAL MICROFLUIDICS, the disclosures of each are herein incorporated by reference in its entirety.

In the United States, some of the material in this patent application may be related as a continuation-in-part of U.S. patent application Ser. No. 15/579,455 (titled "AIR-MATRIX DIGITAL MICROFLUIDICS APPARATUSES AND METHODS FOR LIMITING EVAPORATION AND SURFACE FOULING") which claims priority as a 35 U.S.C. § 371 national phase application of International Application No. PCT/US2016/036015, titled "AIR-MATRIX DIGITAL MICROFLUIDICS APPARATUSES AND METHODS FOR LIMITING EVAPORATION AND SURFACE FOULING," filed on Jun. 6, 2016, and/or as a continuation-in-part of U.S. patent application Ser. No. 15/579,239 (titled "EVAPORATION MANAGEMENT IN DIGITAL MICROFLUIDIC DEVICES") claims priority as a 35 U.S.C. § 371 national phase application of International Application No. PCTUS2016036022, filed on Jun. 6, 2016.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

Air-matrix digital microfluidic (DMF) apparatuses and methods for manipulating and processing droplets while reducing evaporation or the effect of evaporation are described herein.

BACKGROUND

Microfluidics has transformed the way traditional procedures in molecular biology, medical diagnostics, and drug discovery are performed. Lab-on-a-chip and biochip type devices have drawn much interest in both scientific research applications as well as potentially for point-of-care applications because they carry out highly repetitive reaction steps within a small reaction volume, saving both materials and time. Traditional biochip-type devices utilize micro- or nano-sized channels and typically require corresponding micropumps, microvalves, and microchannels coupled to the biochip to manipulate the reaction steps. As a result, these additional components greatly increase cost and complexity of biochip-type microfluidic devices.

Digital microfluidics (DMF) has emerged as a powerful preparative technique for a broad range of biological and chemical applications. DMF enables real-time, precise, and highly flexible control over multiple samples and reagents, including solids, liquids, and even harsh chemicals, without need for pumps, valves, or complex arrays of tubing. In DMF, discrete droplets of nanoliter to microliter volumes are dispensed from onto a planar surface coated with a hydrophobic insulator, where they are manipulated (transported, split, merged, mixed, heated, cooled) by applying a series of electrical potentials to an embedded array of electrodes. Complex reaction steps can be carried out using DMF alone, or using hybrid systems in which DMF is integrated with channel-based microfluidics.

Despite significant advances, both evaporation, particularly in air-matrix DMF, and surface fouling remain issues. Surface fouling occur when components from the reaction mixture irreversibly adhere to surfaces of the microfluidic or DMF device after contacting these surfaces. Surface fouling is a particularly acute problem when operating at higher (e.g., greater than 37° C.) temperatures. Various strategies have been proposed to prevent surface fouling, such as using polymers, glass, and metals to fabricate the device or modifying the material surfaces chemically. However, these strategies have had limited success, particularly in the context of DMF, despite efforts to test and fabricate surfaces and surface coatings that are resistant to surface fouling. In some instances, a coating intended to prevent surface fouling may cause undesirable interactions and result in secondary reactions with the reaction mixture and/or reagents used. In general, it would be desirable to have a simple solution to minimizing surface fouling in microfluidic and DMF devices.

Evaporation is also a concern when performing reactions in an air-matrix DMF device. In general, an air-matrix DMF apparatus may refer to any non-liquid interface of the DMF apparatus in which the liquid droplet being manipulated by the DMF apparatus is surrounded by air (or any other gas). As used herein, an air-matrix may also and interchangeably be referred to as a "gas-matrix" DMF apparatus; the gas does not have to be air, though it may be. Evaporation may be especially problematic in air-matrix DMF methods and that heat for a sustained period of time (e.g., greater than 30 seconds). Evaporation limits the utility of air-matrix DMF, because enzymatic reactions are often highly sensitive to changes in reactant concentration. Largely for this reason, others have attempted to use oil-matrix DMF for biochemical applications, despite numerous drawbacks including: the added complexity of incorporating gaskets or fabricated structures to contain the oil; unwanted liquid-liquid extraction of reactants into the surrounding oil; incompatibility with oil-miscible liquids (e.g., organic solvents such as alcohols); and efficient dissipation of heat, which undermines localized heating and often confounds temperature-sensitive reactions. Another strategy for addressing evaporation has been to place the air-matrix DMF device in a closed humidified chamber, but this may not be sufficient, may add expense and/or may result in undesirable effects.

Thus, there exists a need for air-matrix DMF apparatuses and methods that may prevent or limit evaporation and/or prevent or limit surface fouling. Described herein are apparatuses and methods that may address this need.

SUMMARY OF THE DISCLOSURE

A DMF apparatus (e.g., system, device, etc.) may include or may operate (e.g., as part of a removable/replaceable cartridge) within an air gap formed by at least two surfaces that are separated by the air gap. The surfaces may be parallel. These surfaces may be referred to for convenience herein as "plates" although it should be understood that one or both surfaces (plates) may be formed of a membrane or sheet of material, such as a dielectric material. Thus, the plates do not have to be rigid. The DMF apparatus may also include an array of individually controllable actuation electrodes, which may be high-voltage electrodes, may be on (or in) one of the plates (typically the bottom plate), or may be separable from, but configured to be placed into electrical contact with one of the plates (e.g., the bottom plate). One or more ground electrodes may be on (or in) the opposite plate (e.g., the top plate), or configured to be placed in electrical contact with one of the plates. Alternatively, the one or more ground electrode(s) can be provided on or in the same side as the actuating electrodes. The surfaces of the plates in the air gap may include a hydrophobic material which may be dielectric or in some variations an additional dielectric layer may form at least part of the plate. The hydrophobic and/or dielectric layer(s) may decrease the wettability of the surface and add capacitance between the droplet and the control electrode. Droplets may be moved or otherwise manipulated while in the air gap space between the plates. The air gap may be divided up into regions, and some regions of the air gap may be thermally regulated by one or more heating/cooling elements (e.g., resistive heating, thermoelectric heating/cooling, fluid heat exchange heating/cooling, etc.). In some variations the system may include a thermal regulator (e.g., a Peltier device, a resistive heating device, a convective heating/cooling device, etc.) that is in thermal contact with the region, and may be localized to that region. For example, the seating surface onto which the cartridge (e.g., the plates forming the air gap) may be held may include regions that are thermally regulated by the system. Reactions performed on with the air-matrix DMF apparatus may be detected, including imaging or other sensor-based detection, electrical (e.g., resistive, capacitive, etc.) detection, and, and may be performed at one or more localized regions or over all or over a majority of the air gap space of the air-matrix DMF apparatus.

As mentioned, the air gap may be formed as a part of a cartridge that is removable from a reusable base unit; in some variations the electrodes (e.g., the array of drive electrodes and/or the ground electrode(s) and/or the thermal control may be part of the reusable base unit and the dielectric forming all or part of the plates may in the separate cartridge.

Described herein are methods and apparatuses (including DMF apparatuses, cartridges, etc.) that reduce or eliminate evaporation and/or surface fouling. For example, in some variations, a shell or coating of a hydrophobic material (e.g., liquid wax, oils, etc.) may be used. The liquid coating may be a conductive (e.g., ionic) hydrophobic layer, such as a conductive liquid wax. In some variations a barrier or chamber formed of a hydrophobic material (e.g., wax, e.g., paraffin, and/or polymers including a wax, such as parafilm) may be used. In some variations a combination of a liquid hydrophobic coating and solid hydrophobic material may be used. In some variations, adjacent droplets of aqueous material may be used to form local (e.g., a subset of the air matrix) humidification regions surrounding an aqueous droplet. In any of these variations, the dimensions of the air matrix may be modified (e.g., enlarged) to retain the droplet and any shell or coating of liquid hydrophobic material (e.g., liquid wax) within the air gap.

In general, the methods and apparatuses described herein may be configured to prevent evaporation and to maintain the local position of the aqueous droplet within the air gap of the DMF apparatus. This may be beneficial in variations in which the droplet, particularly when using a liquid shell coating of a hydrophobic material (e.g., liquid wax) that may otherwise permit the droplet to unintentionally move (e.g., roll) within the air gap. In some variations anchoring aqueous droplets may be positioned adjacent to the droplet coated with hydrophobic (e.g., liquid wax) material. In some variations a chamber made of inert hydrophobic material (e.g., a paraffin containing polymer or mixture) may be used. For example, described herein are methods and apparatuses including a combination of liquid wax and solid wax (e.g., paraffin or a plastic paraffin film, such as mixtures of polyolefins and paraffin waxes, commercially available as "parafilm" or "parafilm M") may be used in an air-matrix device to prevent or limit evaporation.

For example, an air-matrix DMF apparatus as described herein may include an oil droplet or wax within the reaction chamber that may be used to protect an aqueous droplet within the air gap. For example, a wax material may be included in the air gap even if a separate reaction chamber apparatus is included. The wax may be present in or adjacent to a thermal zone (e.g., a thermally controlled sub-region of the air gap) as a solid (e.g., a wall, channel, cave, or other structure of wax) all or some of which can be melted to form a wax liquid and combined with a reaction droplet. The liquid wax, upon mixing together with the reaction droplet, will typically form a coating over and around the liquid droplet, protecting it from evaporation. In some variations, the coating (hydrophobic coating) may be a coating of material that is liquid before any treatment.

In some variations, described herein are air-matrix DMF apparatuses that include a wax material in a solid state at room temperature and below, but may selectively and controllably combined with a reaction droplet within the air gap when the wax structure is heated. For example, described herein are air-matrix digital microfluidic (DMF) apparatuses configured to prevent evaporation. The apparatus may include a first plate having a first hydrophobic layer; a second plate having a second hydrophobic layer; an air gap formed between the first and second hydrophobic layers; a plurality of actuation electrodes adjacent to the first hydrophobic layer, wherein each actuation electrode defines a unit cell within the air gap; one or more ground electrodes adjacent to actuation electrode of the plurality of actuation electrodes; a thermal regulator arranged to heat a thermal zone portion of the air gap wherein a plurality of unit cells are adjacent to the thermal zone; a wax body within the thermal zone of the air gap; and a controller configured to regulate the temperature of the thermal zone to melt the wax body and to apply energy to actuation electrodes of the plurality of actuation electrode to move a droplet through the air gap.

The wax body may span one or more (e.g., a plurality of adjacent) unit cells. The wax body may comprise a wall of wax within the air gap. In some variations the wax body forms a channel or vessel within the air gap. For example, the wax body may form a concave shape in the air gap, which may help it combine with a reaction droplet when heated. The wax body may be melted immediately before combining with the reaction droplet. In some variations the wax body may itself be a droplet (wax droplet) that is moved into position by the air-matrix DMF apparatus so that it can combine with the reaction droplet.

In some variations, the wax body may be formed of any appropriate wax that is typically solid at room temperature, such as, e.g., paraffin wax. Other waxes may generally include hydrophobic, malleable solids near ambient temperatures such as higher alkanes and lipids, typically with melting points above about 40° C. (104° F.) that may melt to give low viscosity liquids. Examples of waxes include natural waxes (beeswax, plant waxes, petroleum waxes, etc.). Liquid waxes (e.g., wax materials that are liquid at lower temperatures (e.g., liquid at and below 25° C., below 20° C., below 18° C., below 17° C., below 15° C., etc.) may be used, alternatively or in addition to the wax bodies described herein.

Any of these apparatuses may include features such as those described above, e.g., at least one temperature sensor in thermal communication with the thermal regulator. The plurality of actuation electrodes may be in electrical communication with a portion of the first plate. The one or more ground electrodes may be adjacent to the second hydrophobic layer, across the air gap from the first plate. The apparatus may also include a dielectric between the first hydrophobic layer and the plurality of actuation electrodes (or in some variations the dielectric layer is the hydrophobic layer, as some hydrophobic layers are also dielectric materials). As mentioned above, a thermal regulator may be a thermoelectric heater.

Any of the method described herein may optionally include: introducing a reaction droplet into an air gap of the air-matrix DMF apparatus which is formed between a first plate and a second plate of the air-matrix DMF apparatus; melting a wax body within the air gap of the air-matrix DMF; combining the reaction droplet with the melted wax body to protect the reaction droplet from evaporation; and allowing a reaction to proceed within the reaction droplet.

Melting the wax body typically comprises increasing the temperature of a portion of the air gap comprising a thermal zone to a temperature above the melting point of the wax forming the wax body. In some variations, melting the wax body comprises melting a solid wax body formed into a wall or open chamber within the air gap.

Introducing the reaction droplet into an air gap may comprise combing multiple droplets to form a reaction droplet within the air gap. The first plate may comprise a plurality of adjacent actuation electrodes, and wherein combing the reaction droplet with the melted wax body comprises applying energy to a subset of the actuation electrodes of the plurality of adjacent actuation electrodes to move the reaction droplet in contact with the wax body prior to melting the wax body.

The first plate may comprise a plurality of adjacent actuation electrodes, wherein combing the reaction droplet with the melted wax body may comprise applying energy to a subset of the actuation electrodes of the plurality of adjacent actuation electrodes to move the reaction droplet in contact with the melted wax body.

Allowing a reaction to proceed may comprise heating portion of the air gap containing the reaction droplet. As mentioned, any of these methods may include detecting a product within the reaction droplet.

Although the majority of the devices described herein are air-matrix DMF apparatuses that include two parallel plates forming the air gap, any of the techniques (methods and apparatuses) may be adapted for operation as part of a one-plate air-matrix DMF apparatus. In this case, the apparatus includes a single plate and may be open to the air above the single (e.g., first) plate; the "air gap" may correspond to the region above the plate in which one or more droplet may travel while on the single plate. The ground electrode(s) may be positioned adjacent to (e.g., next to) each actuation electrode, e.g., in, on, or below the single plate. The plate may be coated with the hydrophobic layer (and an additional dielectric layer maybe positioned between the hydrophobic layer and the dielectric layer, or the same layer may be both dielectric and hydrophobic). The methods and apparatuses for correcting for evaporation may be particularly well suited for such single-plate air-matrix DMF apparatuses.

In some embodiments, an air-matrix digital microfluidic (DMF) apparatus configured to prevent evaporation is provided. The apparatus includes a first plate having a first hydrophobic layer; a second plate having a second hydrophobic layer; and an air gap formed between the first and second hydrophobic layers. The apparatus may further include a plurality of actuation electrodes adjacent to the first hydrophobic layer; a thermal regulator arranged to heat a portion of the air gap configured as a thermal zone; a wax body within the thermal zone of the air gap; and a controller. The controller is programmed to actuate the plurality of actuation electrodes to transport an aqueous reaction droplet through the air gap, e.g., to the thermal zone; regulate the temperature of the thermal zone.

In variations including a wax body, the thermal zone may be regulated to melt the wax body into a liquid wax that may encapsulate the aqueous reaction droplet. The temperature of the thermal zone may be regulated to perform a reaction protocol within the droplet, which may be encapsulated with the melted wax body and/or a liquid wax encapsulating the aqueous reaction droplet. The apparatus may actuate the plurality of actuation electrodes to transport the aqueous reaction droplet away from the thermal zone. In some variations the apparatus (or a method using it) may be configured to actuate the plurality of actuation electrodes to bring a carrier droplet comprising an oil or an organic solvent coated aqueous droplet to the aqueous reaction droplet; and merge the carrier droplet with the aqueous reaction droplet.

In variations including a wax body, the wax body may spans a plurality of adjacent actuation electrodes of the plurality of actuation electrodes. In some embodiments, the wax body comprises a wall of wax within the air gap (or a plurality of walls, e.g. forming a channel or chamber, which may be bound by the upper and lower surface); for example, in some variations the wax body forms a channel or vessel within the air gap. In some embodiments, the wax body comprises paraffin wax.

The apparatus may include at least one temperature sensor in thermal communication with the thermal regulator.

The plurality of actuation electrodes may form a portion of the first plate, or may be part of a seating region into which a cartridge is seated, placing the bottom plate (e.g., a dielectric material) in electrical communication with the actuation electrodes. As mentioned, the first plate or the second plate may be part of a removable cartridge.

In some embodiments, the thermal regulator comprises a thermoelectric heater.

In some embodiments, the carrier droplet comprises beads. In some embodiments, the beads are magnetic. In some embodiments, the beads are configured to bind to a molecule selected from the group consisting of DNA, RNA, and proteins.

In some embodiments, the carrier droplet comprises a reagent, a primer, a dilution buffer, an enzyme, a protein, a nanopore, a wash buffer, an alcohol, formamide, or a detergent.

In some embodiments, introducing the aqueous reaction droplet into an air gap comprises combining multiple droplets to form the aqueous reaction droplet within the air gap.

Any of the methods described herein may include detecting a product within the aqueous reaction droplet, and/or mixing the reaction droplet with a plurality of beads after the carrier droplet has been merged with the aqueous reaction droplet. Any of these methods may include immobilizing the beads after the carrier droplet has been merged with the aqueous reaction droplet, and/or moving the merged carrier droplet and aqueous reaction droplet away from the immobilized beads and/or re-suspending the immobilized beads with an aqueous droplet.

In particular, described herein are methods and apparatuses for "pinning" a droplet within a DMF apparatus (device, system, including in some variations a cartridge) Pinning may include securing the droplet and/or a shell (e.g., a liquid wax shell) around the droplet within a sub-region of the air gap. In variations in which a shell is used around the aqueous droplet (e.g., a liquid wax shell to limit or prevent evaporation), pinning may help hold the shell uniformly distributed around the droplet, particularly when processing (e.g., heating, mixing, reacting materials within, etc.) the droplet Pinning may also limit the movement of the droplet so that, although the droplet may be effectively moved by electrowetting, the droplet may be prevented from spilling due to movement of the device or system (including the cartridge), such as when transporting the cartridge or device, or when adding materials (e.g., pipetting, etc.) to/removing from the cartridge or device, and/or when vibration is otherwise applied (e.g., for mixing, etc.). The pinned droplet may be less likely to move due to small movements of the system or cartridge, but may the droplets may still be intentionally moved, e.g., by electrowetting. Thus, described herein are various methods and apparatuses for pinning a droplet (and in particular, pinning a shell of material, such as liquid wax, around a droplet. The apparatuses configured to pin droplet(s) in the air gap may be cartridges, devices, etc. that include one or more (e.g., two or more, three or more, etc.) "pins" in the air gap region that is configured to pin the droplet without interfering with the electrowetting. The pins may be projections that extend partially into the air gap, or they may be non-polar regions (that may interact with the non-polar shell on the droplet) that are either flush with the upper surface (upper plate) or extend into the air gap from the upper plate. In general, the terms upper and lower are in reference to the location of the actuation electrodes, which are typically in electrical commination with the lower plate.

For example, a digital microfluidics method as described herein may include: driving a droplet within an air gap of an air-matrix digital microfluidic (DMF) apparatus to a sub-region of the air gap by electrowetting; pinning the droplet within the sub-region by contacting the droplet with two or more pins (e.g., three or more pins) extending from or on an upper surface of the air gap into the air gap, where the two or more pins extend only partially into the air gap, if at all; and performing one or more manipulations on the pinned droplet. The pins may be protrusions, as will be described in greater detail herein. The method may further include coating the aqueous reaction droplet with a liquid wax, where pinning the droplet includes pinning at least the liquid wax coating.

Any appropriate manipulation may be performed, such as heating, cooling, mixing (adding another droplet, applying a vibrations force/sonicating, etc.), applying a magnetic field (e.g., to move one or more magnetic beads in the droplet), applying an electric field (e.g., to provide an electrochemical reaction, to electroporate, etc.), applying light, etc., including any combination of these. In some variations, performing one or more manipulations may include heating the sub-region of the air gap including the droplet. In some variations, the method may further include driving the droplet away from the sub-region and off of the protrusions by electrowetting.

Alternatively or additionally, a droplet (or droplets) may be pinned in the air gap before moving the air gap (e.g., moving a cartridge including the air gap). Alternatively or additionally, a droplet (or droplets) may be pinned in the air gap prior to imaging the droplet (holding it secure), etc.

In some variations of the method, performing one or more manipulations may include performing at least one of: vortexing a plurality of magnetic beads within the pinned droplet, cooling the sub-region of the air gap including the pinned droplet, detecting the pinned droplet; driving the pinned droplet to a channel hole within the sub-region of the air gap; aspirating the droplet into a channel of the channel hole; and driving the droplet from the sub-region by electrowetting.

In any of these methods, the two or more pins (e.g., protrusions) may include two to ten pins. The two or more pins may include four pins. The pins may be arranged at the perimeter of the pinning region within the air gap. In some variations, each of the two or more pins may have a cylindrical or rectangular shape.

In some variations of the method, each of the two or more pins may have a lateral dimension on the upper surface of the air gap between 0.5 mm to 2.8 mm. In some variations, each of the two or more pins may have a lateral dimension on the upper surface of the air gap between 0.8 mm and 1.2 mm. In some variations, each of the two or more pins may have a maximum vertical dimension extending into the air gap of between 0.1% to 99% of a vertical dimension of the air gap, e.g., between the upper and lower surfaces forming the air gap (e.g., between 0.1% and 80%, between 0.1% and 75%, between 0.1% and 70%, between 0.1% and 60%, between 0.1% and 50%, between 0.1% and 40%, between 0.1% and 30%, between 0.1% and 25%, etc., including 80% or less, 75% or less, 60% or less, 50% or less, 40% or less, 30% or less, 25% or less, 20% or less, 15% or less, 10% or less, etc.). In some variations, each of the two or more pins may have a vertical dimension extending into the air gap of 0.1% to 20% of a vertical dimension of the air gap.

An air-matrix digital microfluidic (DMF) apparatus as described herein, configured for pinning droplet (or a shell of a droplet) may include: a first surface having a first hydrophobic layer; a second surface having a second hydrophobic layer; and an air gap formed between the first and second hydrophobic layer. The air-matrix digital microfluidic (DMF) apparatus (e.g., system) may further include a plurality of actuation electrodes adjacent to the first hydrophobic layer; a thermal regulator arranged to heat a thermal zone portion of the air gap. As mentioned, the air gap (including the upper and lower surfaces) may be formed as a removable cartridge with the apparatus configured to seat the lower (e.g., dielectric) surface on the plurality of actuation electrodes. Alternatively in some variations the system may include an integrated air gap in which the actuation electrodes are integrated into the lower plate/surface.

Any of the air-matrix digital microfluidic (DMF) apparatuses described herein may further includes a plurality of pins (e.g., protrusions) facing the air gap in the thermal zone portion of the air gap, where each pin is disposed adjacent to or extending from the second hydrophobic layer and partially into the air gap, but does not extend completely across the air gap. The device may also include a controller configured to apply energy to the actuation electrodes to move a droplet in the air gap.

The device may include one or more pinning regions (e.g., 2 or more, 3 or more, 4 or more, 5 or more, between 1-10, between 1-7, etc.) including a set of pins (e.g., protrusions). The pins may form the perimeter of the pinning region where the droplet is pinned. The number of the pins in each pinning region may be, e.g., between two and 10, e.g., between 2 and 5, between 2 and 4, between 2 and 3, etc. The pins may be the same dimensions or different dimensions.

The pins may be formed of any appropriate material. For example, the pins may be formed of a hydrophobic, oleophilic or hydrophilic material. In some variations, the pins are formed of a silicone rubber. The pins may be protrusions formed of a silicone rubber that extends, e.g., 50% or less into the air gap (e.g., 30% or less, 20% or less, etc.). The material may be a material that reduce or prevent air bubbles from forming. For example, in some variations the surface of the pin may be porous.

The plurality of pins, e.g., protrusions, may each have a vertical dimension extending between 0.01 mm to 1 mm into the air gap. In some variations, the plurality of pins may each have a vertical dimension extending between about 0.1% to 80% into a vertical dimension of the air gap. In some variations, the plurality of protrusions may each have a vertical dimension extending less than 40% or less than 30%, etc., into a vertical dimension of the air gap. For example, the plurality of protrusions may each have a vertical dimension extending between 0.01 mm to 0.2 mm into the air gap. In some variations, the plurality of protrusions may each have a vertical dimension extending between 0.1% to 20% into a vertical dimension of the air gap.

In some variations of the apparatus, a vertical dimension of the air gap between a surface facing the air gap of the first hydrophobic layer and a surface facing the air gap of the second hydrophobic layer may be between 0.8 mm and 2.5 mm (e.g., between about 0.8 mm and 2 mm, between 0.8 mm and 1.8 mm, between 0.8 and 1.5 mm, etc., 0.75 mm or greater, 0.8 mm or greater, 0.9 mm or greater, 1 mm or greater, etc.).

Each of the pins may have a lateral dimension on the surface of the second hydrophobic layer of between 0.1 mm to 2.8 mm (e.g., between 0.5 mm and 2.5 mm, between 0.5 mm and 2.4 mm, etc.). In some variations, each of the plurality of pins may have a lateral dimension on the surface of the second hydrophobic layer of between 0.8 mm and 1.2 mm. The lateral dimension may be a diameter of the each of the plurality of pins. In some variations, each of the plurality of pins may have a polygonal shape on the surface of the second hydrophobic layer, and the lateral dimension is a dimension spanning a largest horizontal dimension of the polygonal shape.

As mentioned, the plurality of pins may be disposed at a perimeter of a region on the surface of the second hydrophobic layer having an area of between about 1 $mm^2$ and 625 $mm^2$. In some variations, each of the plurality of pins may be disposed at a perimeter of the thermal zone portion of the air gap.

As mentioned, the first plate may be a bottom plate of a cartridge configured to be seated on a seating surface of the DMF apparatus including the plurality of actuation electrodes. This plate may be a dielectric membrane (which may be held taut by a frame).

The apparatus may include a plurality of regions having a plurality of pins facing the air gap in a plurality of thermal zone portions of the air gap, where each pin is disposed adjacent to or extending from the second hydrophobic layer and partially into the air gap, further where each pin does not extend completely across the air gap.

The second hydrophobic layer may be disposed on a first side of the second plate and the second plate may include a channel extending from the surface facing the air gap through the second plate to a second side of the second plate. The channel may be disposed opposite to a perimeter of the thermal zone.

Also described herein are cartridges for use with a DMF apparatus (e.g., system, device, etc.) that include an air gap having one or more pinning regions formed by a plurality of pins as described herein. For example, a cartridge for a digital microfluidics (DMF) apparatus may have a bottom and a top, the cartridge including: a sheet of dielectric material having a first side and a second side, the first side forming an exposed bottom surface on the bottom of the cartridge, where at least the second side of the sheet of dielectric material includes a first hydrophobic surface; a top plate having a first side and a second side and a thickness therebetween; a second hydrophobic surface on the first side of the top plate; an air gap separating the first hydrophobic layer and the second hydrophobic layer; and a plurality of pins facing the air gap, where each pin (e.g., protrusion) does not extend completely across the air gap, further where the plurality of pins are configured to pin a droplet within a region of the air gap. In some variations of the cartridge, the cartridge may further include a tensioning frame holding the sheet of dielectric material in tension so that it is substantially flat.

Any appropriate number of pins may be included forming each (of the one or more) pinning region in the air gap. For example, the plurality of pins facing the air gap may include between 2 and 10, between 2 and 7 between 2 and 5, between 2 and 4, etc.). Different pinning regions may have different arrangements and/or numbers of pins. As mentioned, the pins may be formed of a hydrophobic, oleophilic or hydrophilic material. For example, the pins may be formed of silicone rubber.

Thus, a cartridge may include a plurality of pins (e.g., protrusions) that may be disposed adjacent to or extending from the second hydrophobic surface.

Each of the plurality of pins may have a vertical dimension extending between 0.01% and 90% (e.g., between 0.01% and 80%, between 0.01% and 60%, between 0.01% and 50%, between 0.01% and 40%, between 0.01% and 30%, between 0.01% and 25%, 50% or less, 40% or less, 30% or less, 25% or less, 20% or less, etc.) into the air gap. For example, each of the plurality of protrusions may have a vertical dimension extending from 0.01 mm to 0.2 mm into the air gap.

As mentioned, each of the protrusions of the plurality of pins may have a lateral dimension on the surface facing the air gap from 0.5 mm to 2.8 mm Each of the plurality of pins may have a lateral dimension on the surface facing the air gap of between 0.8 mm and 1.2 mm. The lateral dimension may be a diameter of each protrusion of the plurality of pins. In some variations, each of the plurality of pins may have a polygonal shape on the surface facing the air gap, and the lateral dimension is a dimension spanning a largest horizontal dimension of the polygonal shape. In some variations, each of the plurality of pins may be disposed at a perimeter of a region (e.g., pinning region) on the surface facing the air gap having an area of between 1 $mm^2$ and 625 $mm^2$. Each of the plurality of pins may be disposed at a perimeter of the thermal zone portion of the air gap (or a portion of a thermal zone, or encompassing a thermal zone). Thus a pinning region may overlap with a thermal zone and/or may be concurrent with a thermal zone.

An apparatus may include a plurality of pinning regions each having a plurality of pins facing the air gap in a plurality of thermal zone portions of the air gap, where each pin (e.g., protrusion) does not extend completely across the air gap, further where the plurality of pins are configured to pin a droplet within a region of the air gap.

The second hydrophobic layer may be disposed on a first side of the second plate and the second plate further includes a channel extending from the surface facing the air gap through the second plate to a second side of the second plate.

A method of heating an aqueous reaction droplet in an air-matrix digital microfluidic (DMF) apparatus is also described herein. Any of the methods described herein may include pinning the droplet (and/or the coating layer of the droplet). For example, a method may include: coating the aqueous reaction droplet with a liquid wax material within an air gap formed between a first hydrophobic layer of a first plate and a second hydrophobic layer of a second plate of the DMF apparatus; pinning the liquid wax coating of the aqueous reaction droplet to at least two protrusions within a sub-region of the air gap, thereby distributing the liquid wax around the reaction droplet; and heating at least the sub-region of the air gap including the coated aqueous reaction droplet, whereby the liquid wax coating limits or prevents evaporation from the aqueous reaction droplet.

In some variations, pinning may include pinning the liquid wax coating to the at least two pins disposed adjacent to the second hydrophobic layer of the second plate.

In any of the methods described herein, the method may further include moving a coated aqueous reaction droplet away from the sub-region of the air gap after heating. Moving may include driving the coated aqueous reaction droplet by energizing a sub-set of a plurality of driving electrodes adjacent to the first hydrophobic layer of the first plate of the DMF apparatus. Moving may further include withdrawing at least a portion of the coated aqueous reaction droplet from a surface of the air gap of the DMF apparatus before energizing the sub-set of the plurality of driving electrodes; and reintroducing the at least portion of the coated aqueous reaction droplet back to the surface of the air gap of the DMF apparatus as a front of the aqueous reaction droplet exits the sub-region. In some variations, withdrawing may include withdrawing the at least portion of the coated reaction droplet via a channel from a surface of the second hydrophobic layer of the second plate to at least partially through the second plate.

The aqueous reaction droplet may be driven to the sub-region (e.g., pinning region) using a sub-set of a plurality of driving electrodes adjacent to the first hydrophobic layer of the first plate of the DMF apparatus.

Also described herein are methods and apparatuses (e.g., systems, devices, cartridges, etc.) for removing a shell material (e.g., liquid wax) on a droplet as described herein. Wicking may be used to selectively remove the coating/shell material from the aqueous droplet. For example, an air-matrix digital microfluidic (DMF) apparatus may be configured to separate a liquid oil or wax from an encapsulated aqueous droplet and may include: an air gap, e.g., between a first and second hydrophobic layer; the first layer may be configured to be seated next to a plurality of actuation electrodes to produce electrowetting in the air gap (e.g., the first layer may be a dielectric membrane that is held taut by a frame); alternatively the first layer may be integrated with all or some of the drive electrodes. Any of these apparatuses may include a wick configured to absorb the coating/shell material on the droplet, such as an oil absorbent wick, disposed within the air gap. The oil absorbent wick may be configured to selectively separate the liquid oil or wax from the encapsulated aqueous droplet. The apparatus may also include a controller programmed to actuate a first subset of the plurality of actuation electrodes to transport the encapsulated aqueous droplet through the air gap to make contact with the oil absorbent wick, and to actuate a second subset of the plurality of actuation electrodes to transport the aqueous reaction droplet away from the oil absorbent wick after the liquid oil or wax has been separated from the aqueous droplet. In some variation the wick may be configured as a wicking region that at least partially surrounds (or is immediately adjacent to) a drive region (e.g., a region of the air gap overlying one or more actuating electrodes).

The wick (e.g., an oil absorbent wick) may be hydrophobic. In some variations, the wick may include a tip. The tip may terminate in a point or a series of points (e.g., serrations). The tip may have a width less than the diameter of the encapsulated aqueous droplet.

The controller may be programmed to actuate a first subset of the plurality of actuation electrodes to transport the encapsulated aqueous droplet through the air gap to make contact with the wick, including with a tip of the wick. The plurality of actuation electrodes may form a portion of the first plate and/or may be separate from a removable cartridge forming the air gap. The first plate or the second plate may be part of a removable cartridge, as mentioned above.

For example, described herein are methods method of separating a liquid oil or wax from an encapsulated aqueous droplet within an air-matrix digital microfluidic (DMF) apparatus. Any of these methods may include: transporting the encapsulated aqueous droplet to wick (e.g., an oil absorbent wick) by actuating a first subset of electrodes of the DMF apparatus; transferring the shell/coating material (e.g., liquid oil or wax) surrounding the aqueous droplet to the wick; and transporting the aqueous droplet away from the wick after the shell/coating material has been substantially transferred to the wick, by actuating a second subset of electrodes of the DMF apparatus. All, some or most of the shell/coating material may be removed in this way (e.g., greater than 50%, greater than 60%, greater than 70%, greater than 75%, greater than 80%, greater than 85%, greater than 90%, greater than 95%, etc.). Multiple exposures to the wick may be provided, including repeatedly contacting the droplet with the wick material. The wick may be porous. In some variations multiple wicks may be used.

As mentioned, the wick may have a tip and the encapsulated aqueous droplet may be transported to the tip of the wick. The aqueous droplet may not be substantially transferred to the wick. The wick may be hydrophobic.

Also described herein are air-matrix digital microfluidic (DMF) apparatuses configured to prevent or limit evaporation is provided that include both a paraffin (higher melting point) wax material as well as a coating/shell material of liquid wax (lower melting point). Any of these apparatuses may include: an air gap between a first layer and a second layer; a plurality of actuation electrodes adjacent or configured to be placed adjacent to the first layer; a barrier within the air gap including a paraffin material forming an open enclosure having an area of between 1 $mm^2$ and 625 $mm^2$; and a droplet of liquid wax configured to form a coating over an aqueous droplet within the air gap when combined with the aqueous droplet.

An air-matrix digital microfluidic (DMF) apparatus may be configured to prevent or limit evaporation. For example, a DMF apparatus may include: an air gap between a first layer and a second layer; a plurality of actuation electrodes adjacent or configured to be placed adjacent to the first layer; a barrier within the air gap including a paraffin material forming an open enclosure having an area of between 1 $mm^2$ and 625 $mm^2$; and a droplet of liquid wax configured to form a coating over an aqueous droplet within the air gap when combined with the aqueous droplet.

In some variations, the droplet of liquid wax may be within the barrier. In some variations, the barrier may include one or more walls extending at least partially between the top layer and the bottom layer. In some variations, the barrier may include a pair of parallel fences. In some variations, the barrier may have three sides. The apparatus may further include a heater adjacent to the barrier configured to heat the air gap region including the open enclosure.

The apparatuses described herein may further include a plurality of air vias through the second layer over the open enclosure formed by the barrier.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 1A is a schematic of one example of an air-matrix digital microfluidic (DMF) apparatus, from a top perspective view.

FIG. 1B shows an enlarged view through a section through a portion of the air-matrix DMF apparatus shown in FIG. 1A, taken through a thermally regulated region (thermal zone).

FIG. 1C shows an enlarged view through a second section of a region of the air-matrix DMF apparatus of FIG. 1A; this region includes an aperture through the bottom plate and an actuation electrode, and is configured so that a replenishing droplet may be delivered into the air gap of the air-matrix DMF apparatus from the aperture (which connects to the reservoir of solvent, in this example shown as an attached syringe).

FIG. 3A shows an example of a typical DMF arrangement, e.g., using a rigid cartridge; FIG. 3B shows an example of a DMF configuration in which the cartridge 315 is a disposable portion that does not include the electrodes but that is held onto the reusable electrodes by a plurality of localized vacuum ports (adjacent to or passing through the electrodes).

In FIG. 4A, 18 rows and 10 columns are shown; larger or smaller arrays may be used.

In FIG. 4B, a temperature sensor (e.g., thermistor) is shown.

FIG. 5C shows another view of a PCB with the electrodes similar to that shown in FIGS. 4A-4C, connected to a vacuum pump as well as the liquid coolant (input and output).

FIGS. 5D and 5E illustrate the application of vacuum to secure a cartridge (shown here as a proof of concept by just the dielectric material. In FIG. 5D the vacuum is off, and the dielectric is not secured against the electrodes. The dielectric may wrinkle, and may include regions of poor contact, including poor electrical contact. By comparison, FIG. 5E shows the dielectric held against the electrodes by a plurality of openings through the electrodes, which holds the dielectric uniformly against the electrodes, and results in surprisingly uniform electrical properties between the removable cartridge and the electrodes.

FIG. 5F shows an example of a top view of a PCB showing a small electrode array with holes formed through the central region of each electrode.

FIG. 5G shows a portion of the PCB of FIG. 5F below the electrodes (over which the other layers may be formed), showing the holes through the PCB forming that may be connected to the vacuum pump.

In FIG. 6, the removable cartridge has been made transparent (a microfluidics region above the top plate, air-gap and dielectric forming the DMF portion of the cartridge has been made transparent). The different regions are indicated by different boxes, and may be distributed in a particular arrangement over the array. For example, in FIG. 6, seven of the electrodes are configured as magnetic regions 605, which can apply a local (to that electrode) magnetic force to retain a magnetic bead or particle within a droplet on the electrode. Eight of the peripheral regions (each spanning six electrodes) are configured as cooling zones 607, which may be in thermal contact with a Peltier device or other thermal cooling region. In addition, in FIG. 6, six 16-electrode regions on the left side are configured as cooling zones 607 which may also be in thermal contact with the same or different Peltier device (e.g., holding them below 10 deg. C.). Two central heating zones (one spanning five electrodes, the other spanning 32 electrodes) are also included, and may be thermally cycled over the entire zone or over regions of the zone(s). Four optically read zones 608 (each spanning four electrodes) are spaced apart from each other on the right side perimeter of the device. In general, the heating and/or thermally cycling regions are centrally located, apart from the peripheral cooling/storage regions. There may be overlap between the zones, such as the magnetic zones and the heating/cooling zones.

FIG. 6 also shows, in a transparent view, a microfluidics portion that may be formed above (and in the top plate, as described) the air gap. For example, in FIG. 6, the microfluidics portion 611 includes a pair of serpentine microfluidics channels 615, 616 that each connect to an opening (which may be regulated by a valve) into the air gap. The microfluidics portion may also include valves. In FIG. 6, the microfluidics channel also includes a pair of ports 617, 618 through which positive and/or negative pressure may be applied to modulate (along with any valves) the movement of fluid in the microfluidics region and (in some variations) into or out of the air gap. The microfluidics portion may also include one or more waste chambers 621, FIG. 7A is a top view of an exemplary cartridge as described herein. In this example the cartridge includes a DMF portion, including a top plate and dielectric, separated by an air gap, and a microfluidics portion that connects to the air gap, and may externally connect to a channel input and/or output. Fluid may be applied into the cartridge through one or more openings into the air gap (shown as small openings) and/or through the channel input/outputs. The right side of the cartridge includes a window region, allowing optical viewing through the cartridge.

FIG. 7B shows a top perspective view of the cartridge of FIG. 7A.

FIG. 10 shows an example of an open array of electrodes under a disposable plastic top plate and a dielectric.

FIG. 11 shows a two-plate cartridge over the open array, held in place by a vacuum to keep it rigidly attached over the electrodes.

FIG. 12 illustrates the use of openings through the electrode array; these openings may be used to apply suction (e.g., vacuum) sufficient to hold the cartridge (e.g., the bottom, dielectric layer) aligned and secured to the apparatus. Positive pressure may be applied to release the cartridge.

In FIG. 13, the microfluidics portion of a cartridge is shown as a pair of channels each connected to an inlet/outlet, and each ending in a bridging region forming an opening into the air gap of the DMF portion of the cartridge (in this example, below the microfluidics portion). Fluid may be removed, added, washed, etc. into/out of the air gap of the DMF portion. In FIGS. 14 and 15, fluid washed through the bridging droplet and into the air gap by alternating and applying suction between the inlet/outlet, as shown. In this example, external fluidic components (e.g., tubing and reservoirs) are integrated into the top plate of the DMF portion, allowing a compact form factor. The microfluidics channels may be used for adding/removing reagent (e.g., removing waste, washing, etc.). The bridging droplet may be an electrode or group of electrodes and the size of the droplet may be regulated by DMF.

FIGS. 16A and 16B illustrate extraction and mixing of fluid in a DMF apparatus (e.g., cartridge) as described herein, using a fluid application and extraction technique that includes a bifurcated channel, allowing a large volume of fluid to be exchanged between two reservoirs. In FIG. 16A, the fluid application and extraction device is connected through the top plate. In FIG. 16B, the fluid application and extraction device is connected from the side plate.

FIG. 17A is another example of a DMF cartridge configured for mixing, extraction, adding, etc. fluid with one or more droplets in the air gap of the DMF cartridge. In FIG. 17A, the interface 1127 for the fluid lines, which may be microfluidic channels, including microfluidic channels formed in part by the top plate 1117, interfaces through the top plate, and (unlike FIG. 16A) the air gap in this interface region may be larger than the air gap in other portions of the DMF cartridge.

In FIG. 17B, the interface 1127 for the fluid line(s) is at the edge of the air gap, similar to FIG. 17B; in FIG. 17B, the air gap region is larger than in other regions of the cartridge.

In any of the FIGS. 16A-16B, 17A-17B, the fluid lines (e.g., 1143, 1145) and reservoirs (1105, 1107) may form part of the DMF apparatus, and may interface with a port on the cartridge, e.g., the top surface of the cartridge, and/or one or more valves.

FIGS. 18A-18C illustrate operation of a fluid application and extraction device similar to the one shown in FIG. 17A.

FIGS. 19A-19C illustrates the effect of evaporation on a droplet over 2 minutes in an air-gap DMF apparatus held at 95 degrees C., showing substantial evaporation.

FIGS. 20A-20C show the resistance to evaporation when using a jacketing of nonpolar material (e.g., liquid paraffin) after one hour (FIG. 20B) and two hours (FIG. 20C), showing little or no evaporation.

Figure 21A:
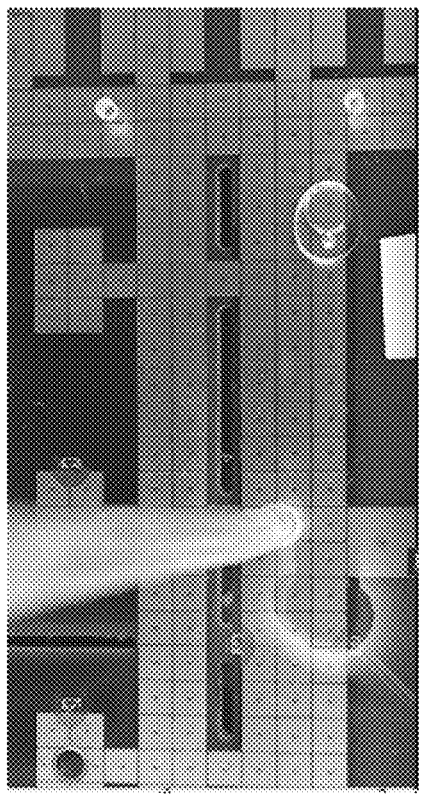
Figure 21B:
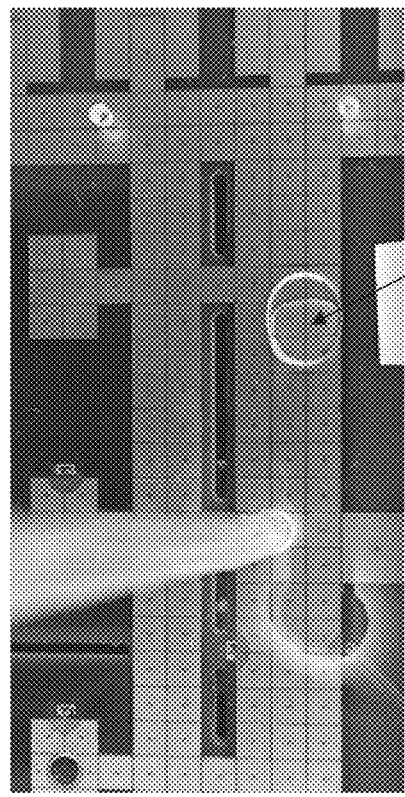
Figure 21C:
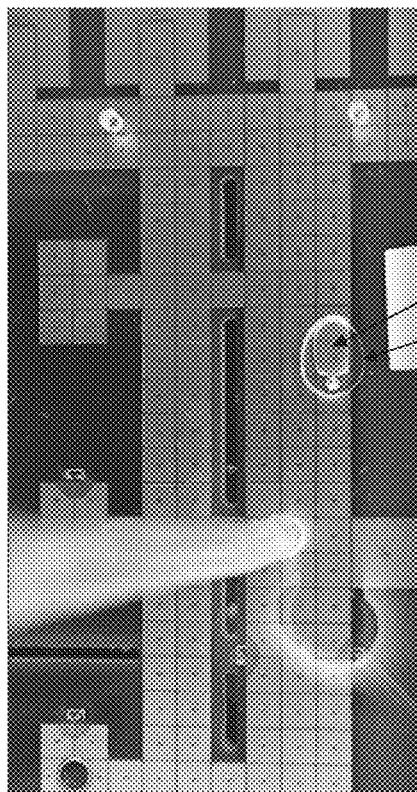
Figure 21D:
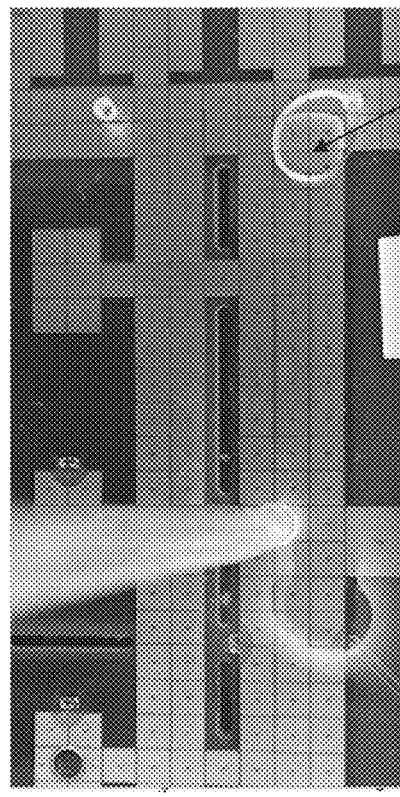

FIGS. 21A-21D illustrate the use of a non-polar jacketing material in an air-matrix DMF apparatus. FIGS. 21A-21B show the movement of the aqueous (polar) droplet while coated with a non-polar jacketing material that is moved along with the droplet. FIGS. 21C-21D illustrate additional polar material to the droplet, which expands to include the additional polar material. FIG. 21E-21I illustrate adding a large sample to a jacketing material, and mixing the sample.

Figure 22A:
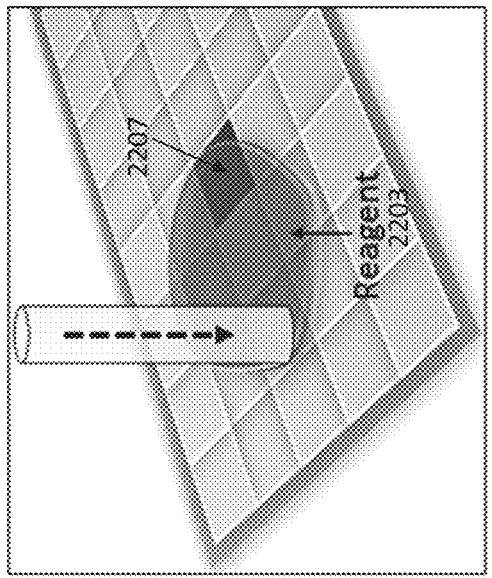
Figure 22B:
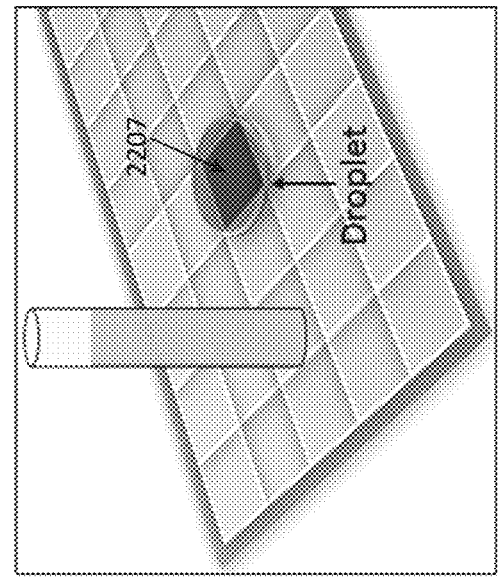
Figure 22C:
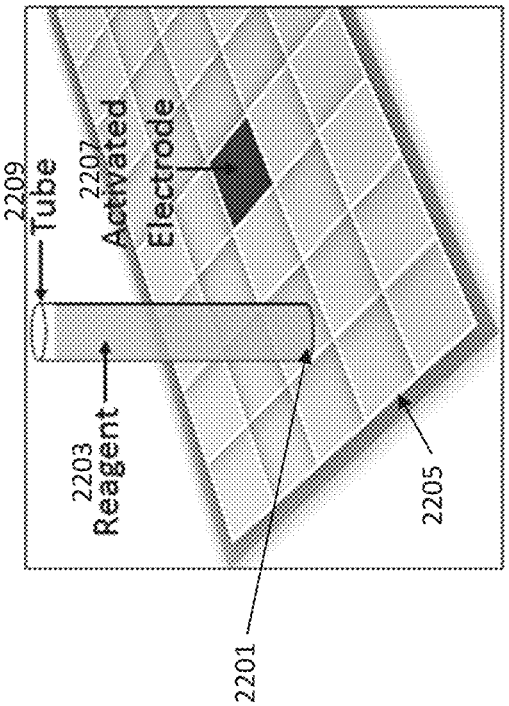
Figure 22D:
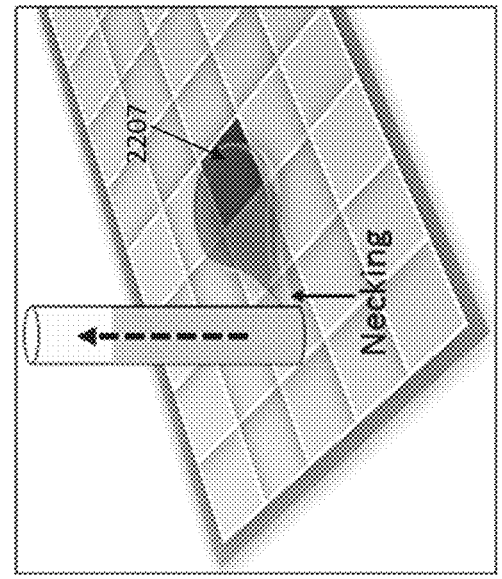

FIGS. 22A-22D illustrate the control of droplet volume when dispensing droplets (e.g., reagents) into an air-gap of a DMF apparatus. In particular, the air-gaps described herein may be large air-gaps (e.g., greater than 280 micrometers, greater than 300 micrometers, >400 micrometers, >500 micrometers, >600 micrometers, etc. separation between the top and bottom dielectrics). In such cases, the electrowetting forces alone may not be sufficient to dispense droplets of a predetermined volume. As shown in FIGS. 22A-22D, droplet break off from a large volume may be used to dispense a predetermined volume. In FIG. 22A, a dispensing electrode is activated, spaced from the dispensing port (tube). In FIG. 22B, the reagent to be dispensed is applied into the air gap, flooding the region including the dispensing electrode that is separated from the dispensing port by at least one electrode. In FIG. 22C the reagent is then sucked back into the dispensing port, while the dispensing electrode(s) is/are active, but the electrode(s) between the dispensing port and the dispensing electrode(s) is/are not active, forming a neck, which (as shown in FIG. 22D) eventually breaks off, leaving the droplet of a predetermined volume on the dispensing electrode(s).

FIGS. 23A-23F illustrate example of dispensing droplets of predefined volumes using the technique described in FIGS. 22A-22D, above.

Figure 24:
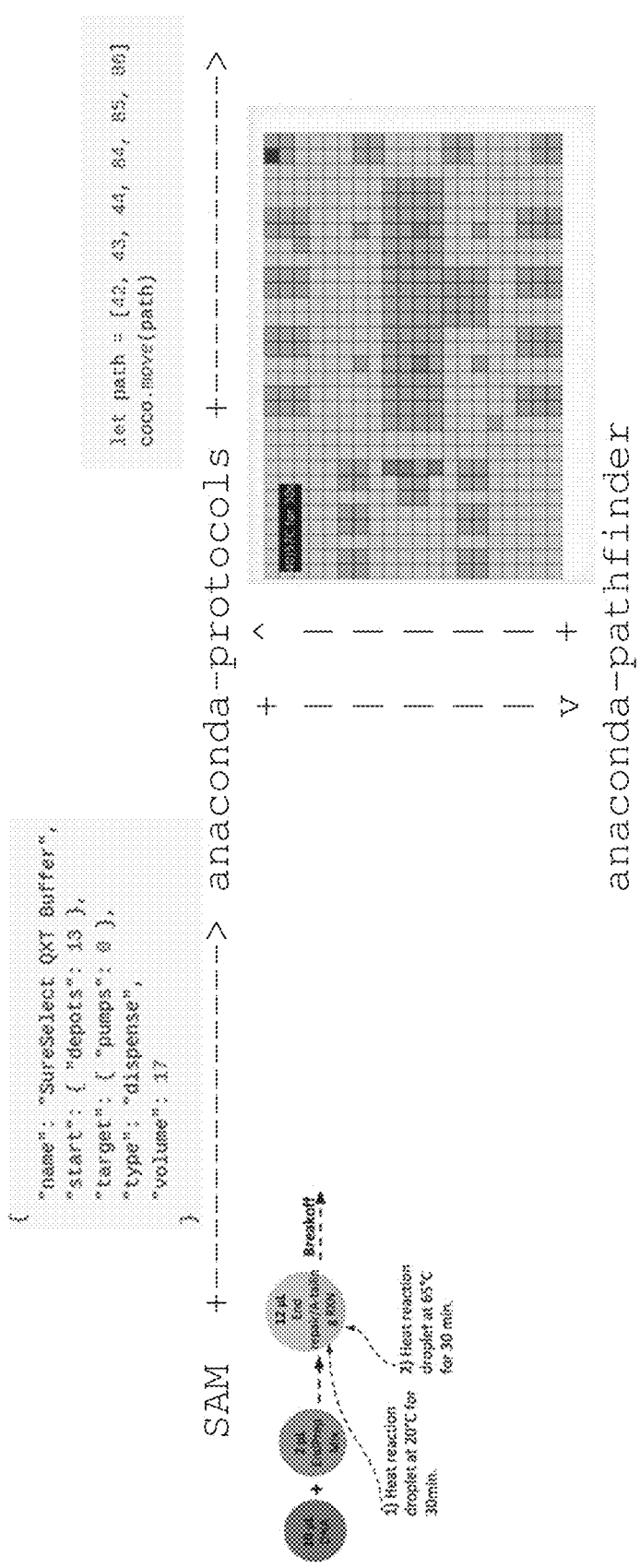

FIG. 24 shows an example of a method of controlling a DMF apparatus as described herein, including programming the apparatus using a graphical user interface.

Figure 25A:
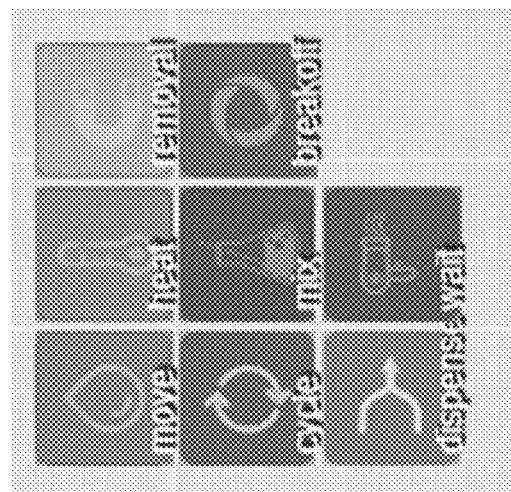
Figure 25B:
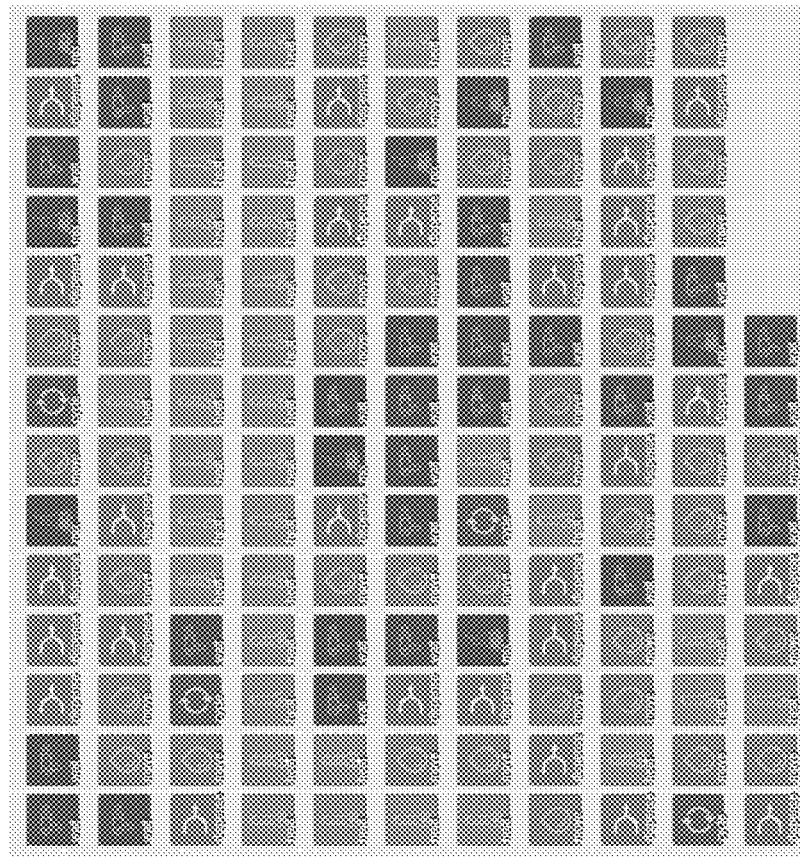

FIG. 25A-25B illustrates an example of visual controls or commands (FIG. 25A) and a protocol describes using these visual controls/commands (FIG. 25B).

FIGS. 26A-26H illustrate an example of a user interface for controlling a DMF apparatus as described herein.

FIG. 27 illustrates an example of a portion of a cartridge showing a thermally controlled region.

FIG. 28 is an example of a portion of an apparatus (e.g., cartridge seat portion) having a reduced thermal mass to enhance the rate of temperature regulation of cartridge held on the seat portion.

FIG. 29 is another example of a portion of an apparatus (e.g., cartridge seat portion) having a reduced thermal mass to enhance the rate of temperature regulation of cartridge held on the seat portion.

FIGS. 30A and 30B illustrate examples of apparatuses include thermal vias for helping control the temperature of a cartridge (e.g., of one or more cells of an air gap of a cartridge).

FIG. 31 is an example of a cartridge including an opening in the top plate for sampling or adding fluid to a droplet in the cartridge.

Figure 32A:
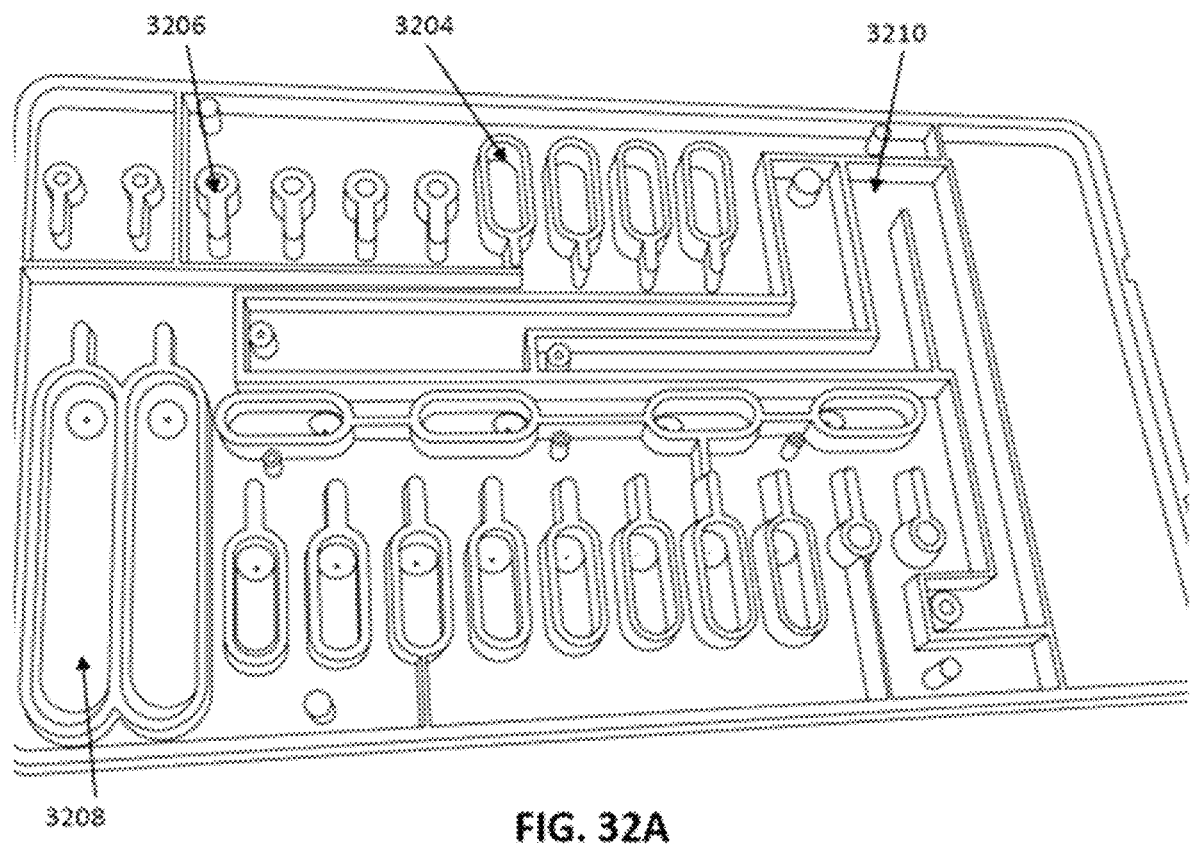
Figure 32B:
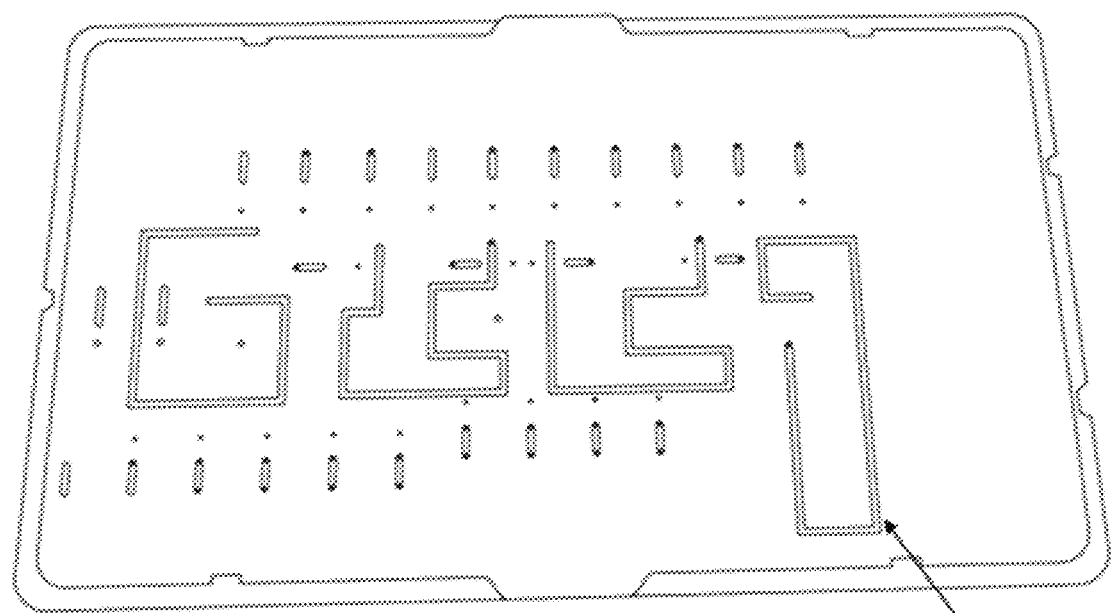

FIGS. 32A and 32B illustrate top and bottom perspective views, respectively of one example of a top portion of digital microfluidics cartridge as described herein.

Figure 33B:
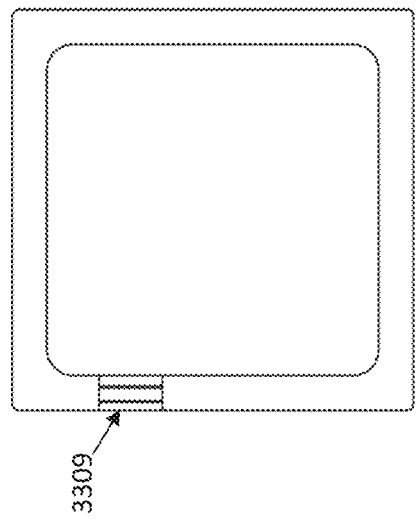
Figure 33D:
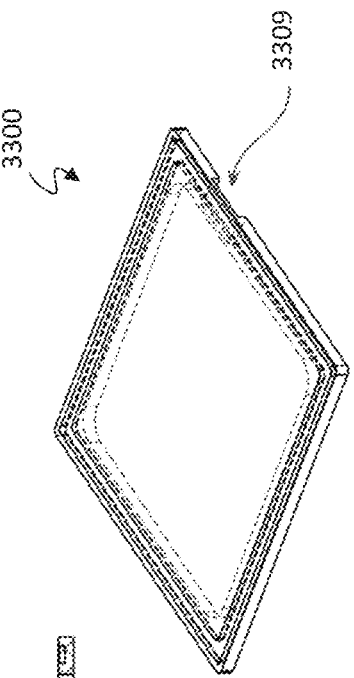
Figure 33A:
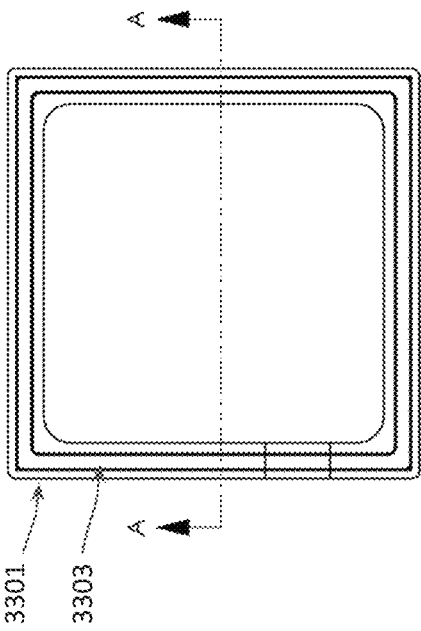

FIGS. 33A and 33B illustrate a tensioning frame and a film frame, respectively, for securing and holding smooth a film (e.g., dielectric film) that may form the bottom of a cartridge.

Figure 33C:
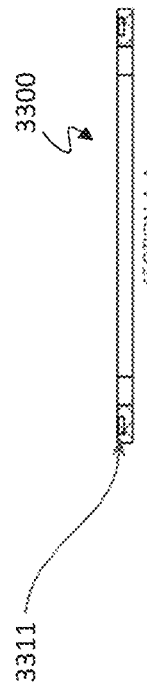

FIG. 33C is a side view of an assembled tensioning frame.

FIG. 33D is a perspective view of an assembled tensioning frame.

Figure 34:
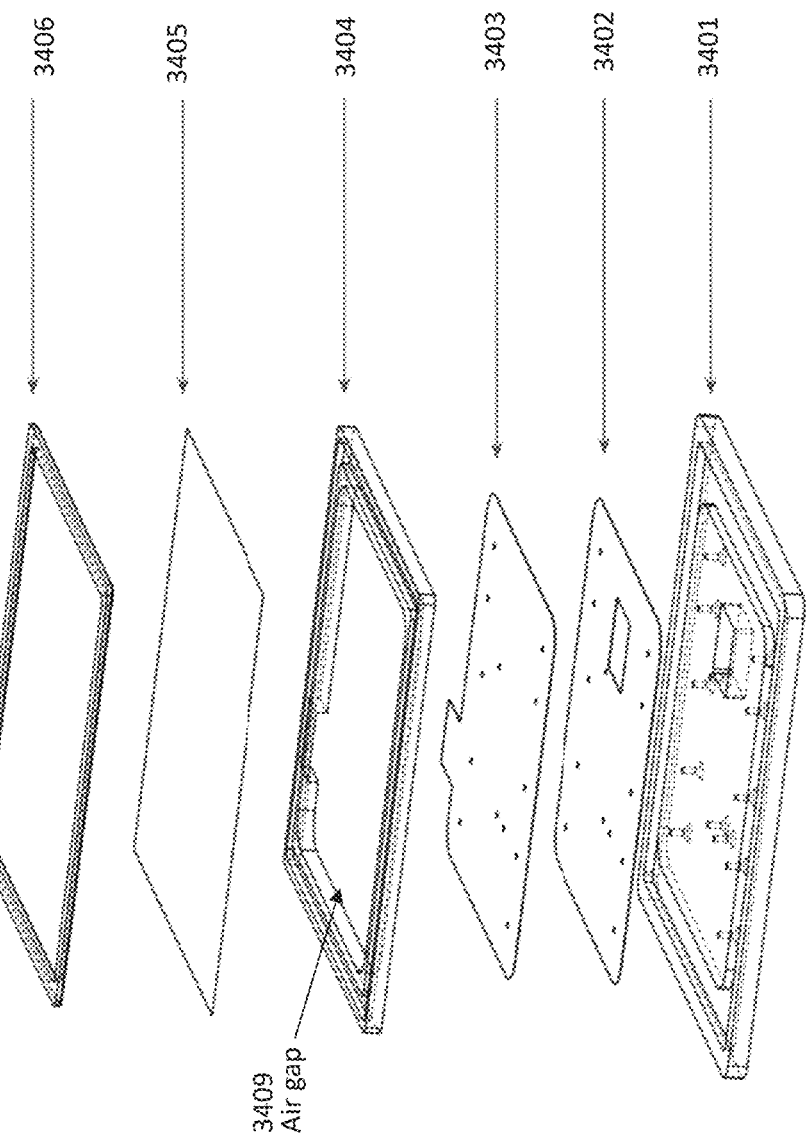

FIG. 34 is an example of an exploded view of a two-plate cartridge.

Figure 35:
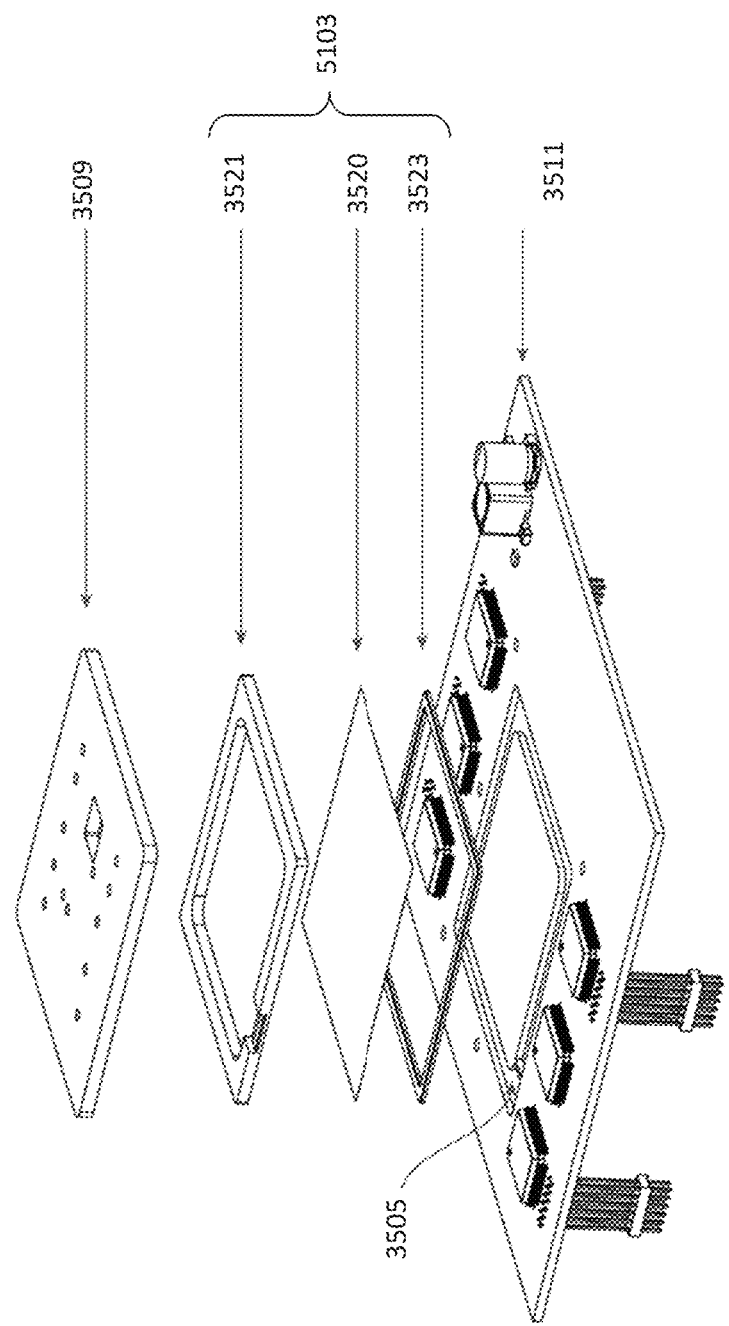

FIG. 35 is an exploded view of an example of a cartridge and a cartridge seating portion of an apparatus.

FIG. 36A is a top view of a PCB of an apparatus to which a cartridge may be seated on.

FIG. 36B is a side view of the PCB portion shown in FIG. 36A.

FIG. 36C is an example of a side view of a cartridge shown on a seating surface of an apparatus.

FIG. 36D is an enlarged view from FIG. 36C.

Figure 37:
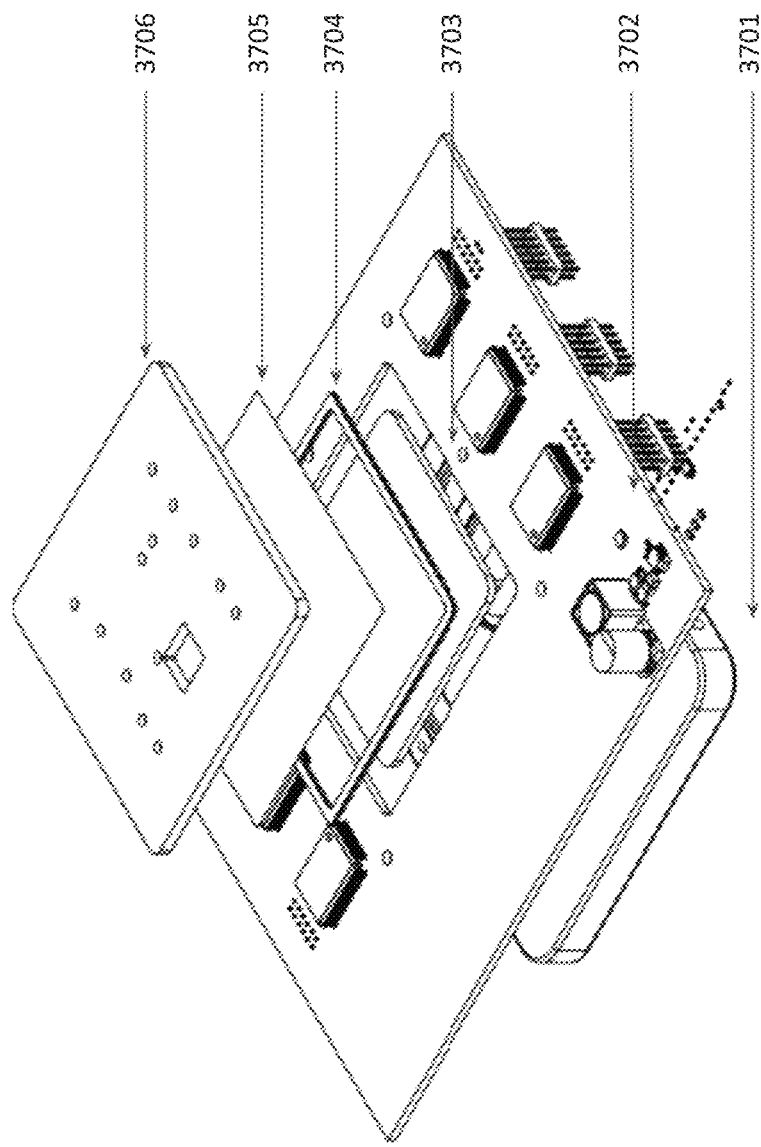

FIG. 37 is an exploded view of a cartridge and seating surface/region of an apparatus.

FIG. 38A is a top view of a PCB (that may form the seating surface) of an apparatus.

FIG. 38B is a side sectional view through the portion of the apparatus shown in FIG. 38A.

Figure 39A:
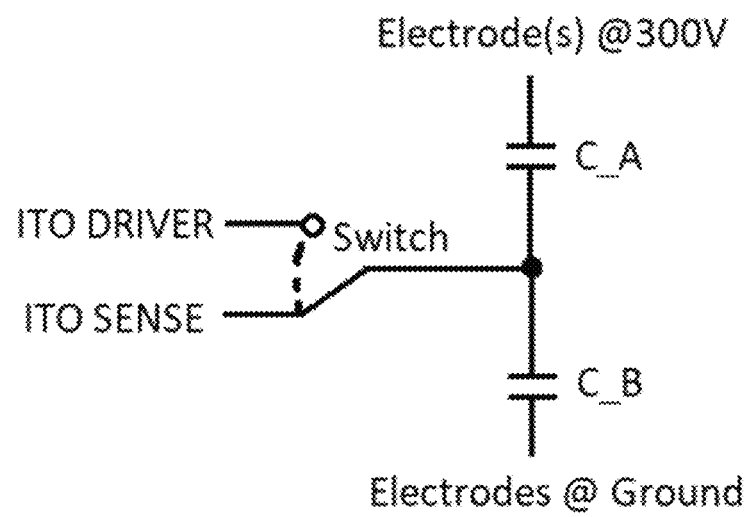

FIG. 39A shows an ITO sensing circuit with a switch.

Figure 39B:
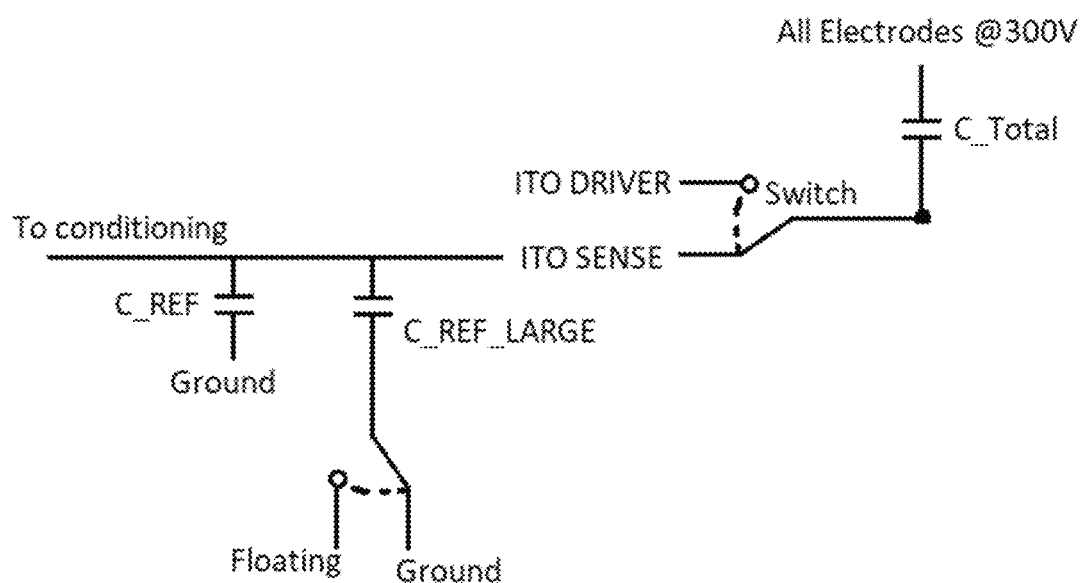

FIG. 39B illustrates another example of a capacitive sensing circuit that includes multiple reference capacitors.

Figure 40A:
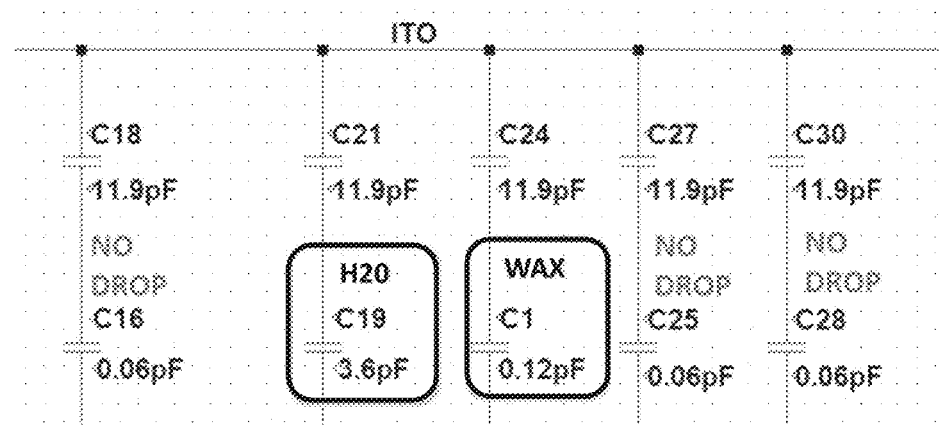
Figure 40B:
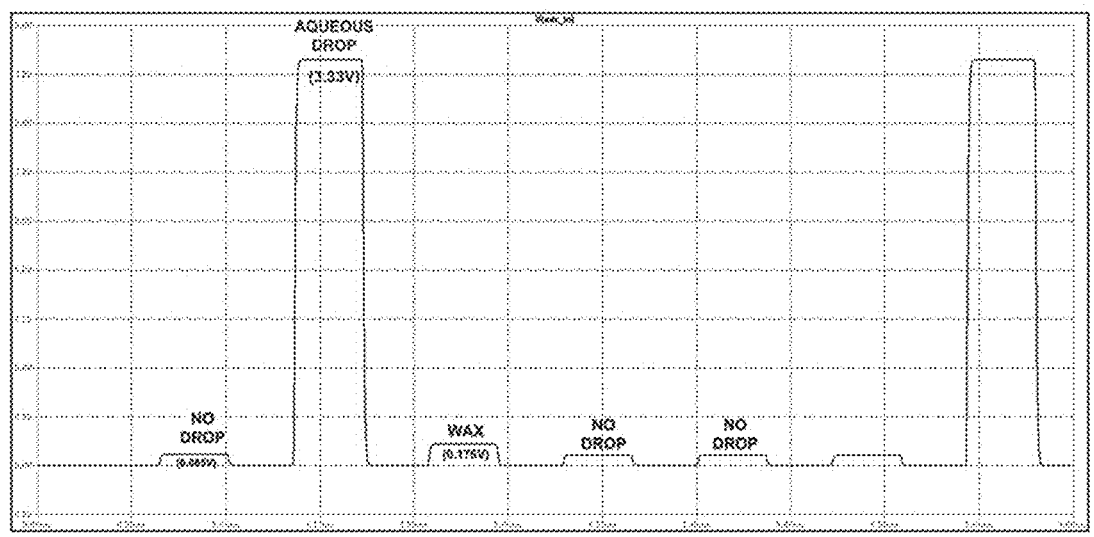
Figure 40C:
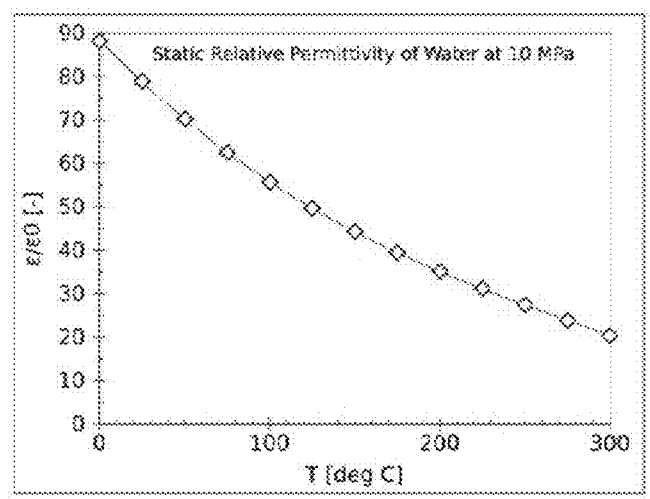

FIGS. 40A-40C illustrate one method of identifying and/or locating a droplet in the air gap as described herein. FIG. 40A shows one example of a range of capacitances corresponding to the presence or absence of various materials (e.g., aqueous droplet, wax, etc.) in the air gap at a particular cell. FIG. 40B is a graph showing exemplary voltage measurements from the sensing electrode (top electrode). FIG. 40C is a graph showing an example of the change in electrical permittivity of water as a function of temperature.

Figure 41A:
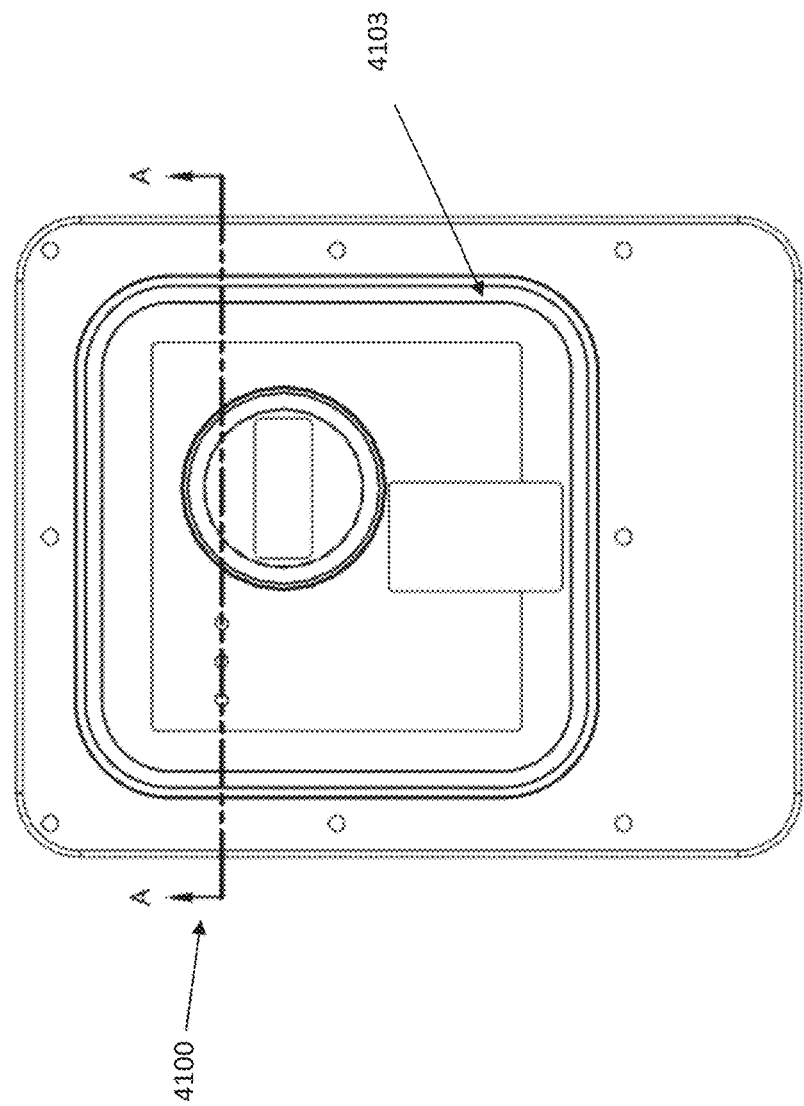

FIG. 41A is a top view of one example of a vacuum chuck.

Figure 41B:
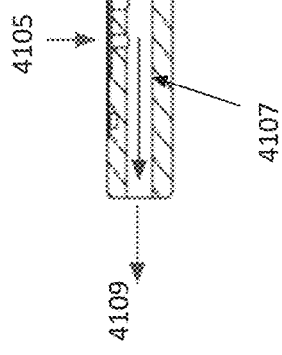

FIG. 41B is a cross sectional view of the vacuum chuck of FIG. 41A.

FIG. 42 shows an isometric view of the chuck shown in FIGS. 35A-35B.

FIG. 43 shows a cross sectional and zoomed-in view of this chuck.

FIG. 44 shows a bottom view of a chuck similar to that shown in FIGS. 41A-41B.

FIG. 45A shows one example of a heat dissipation system that may be included in any of the apparatuses described herein.

FIG. 45B is a sectional view through the chuck of FIG. 41A.

Figure 46:
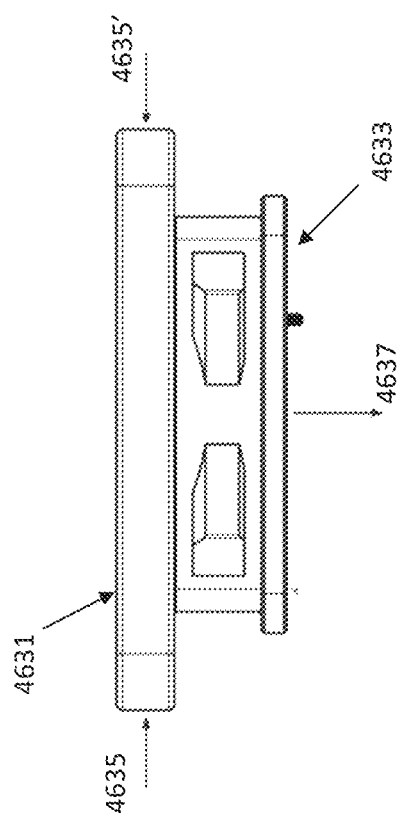

FIG. 46 shows a front view of a chuck and a fan.

Figure 47:
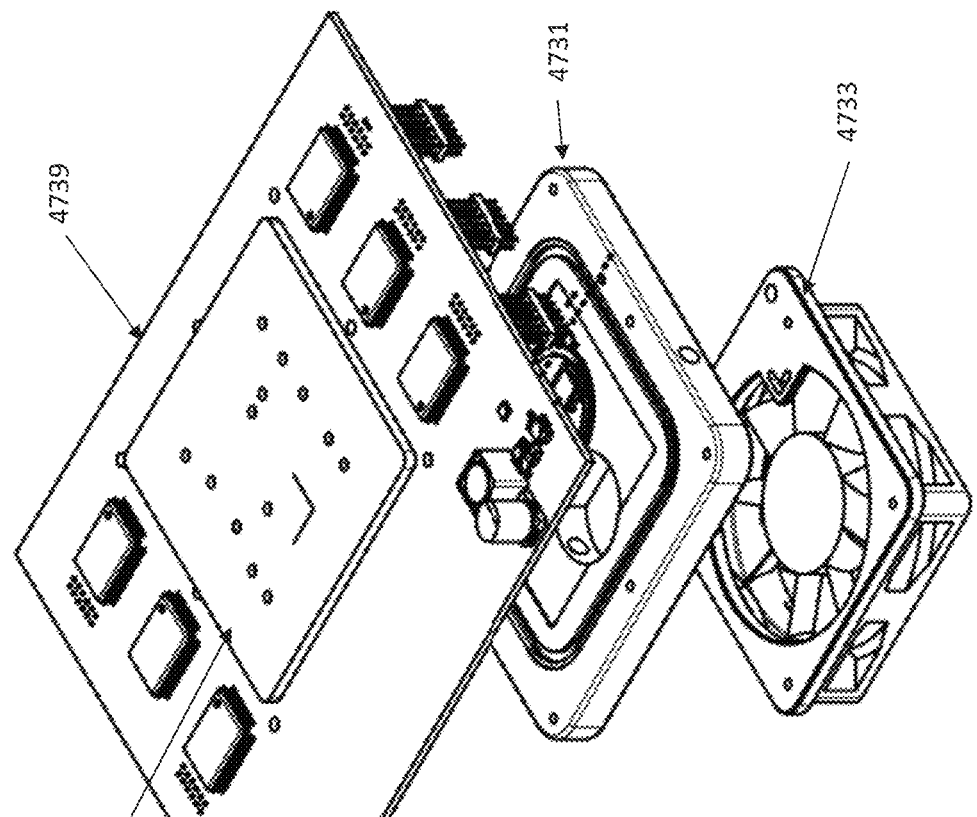

FIG. 47 shows an example of an arrangement of a chuck, a fan and a PCB (part of a seating surface).

Figure 48:
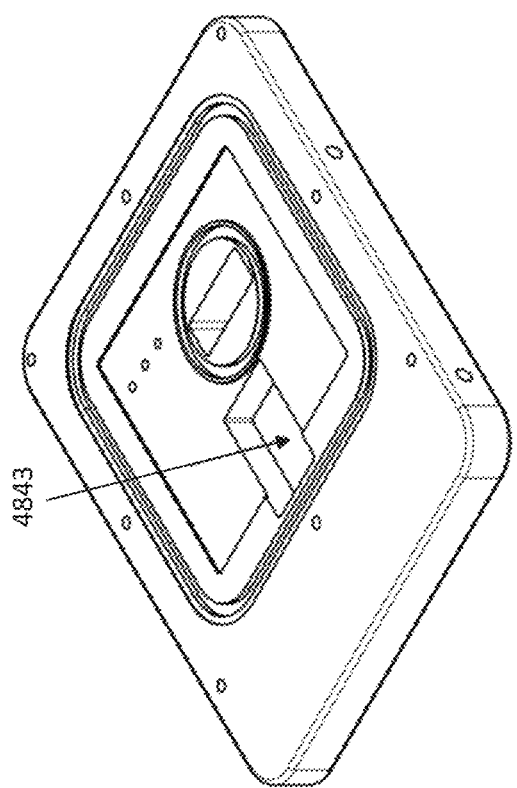

FIG. 48 is an isometric view of a chuck that may include a thermal (e.g., heat) dissipation system for regulating temperature of a cartridge.

Figure 49A:
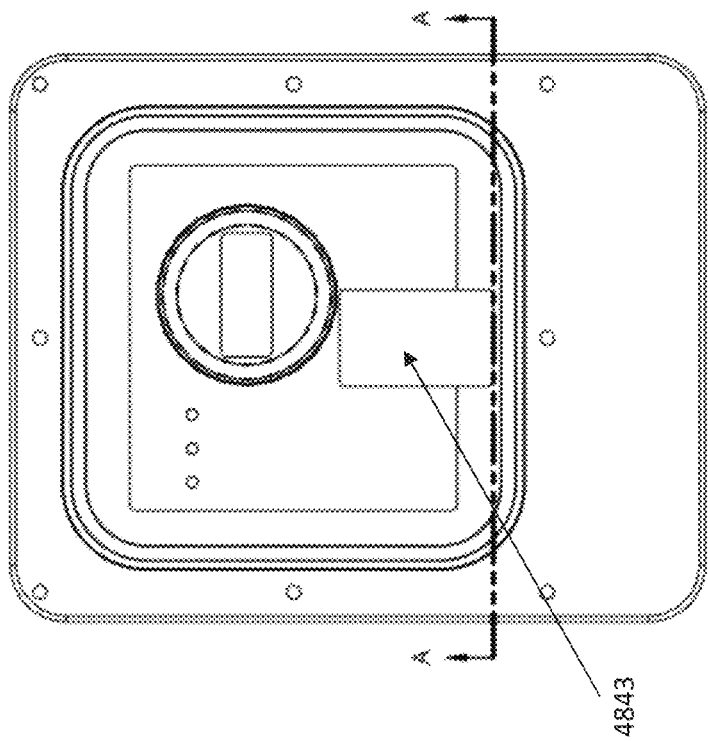

FIG. 49A is a top view of the chuck of FIG. 44.

Figure 49B:

FIG. 49B is a sectional view through the chuck of FIG. 45A.

FIG. 50 shows a side view of an assembly of a chuck, a heat sink and a pair of cooling fans, with arrows indicating the flow of temperature (cooling the chuck and therefore the cartridge when loaded onto the apparatus).

FIGS. 51A-51C illustrate the assembly of a vacuum chuck and cooling subsystem (e.g., heat sink block and cooling fans).

Figure 52:
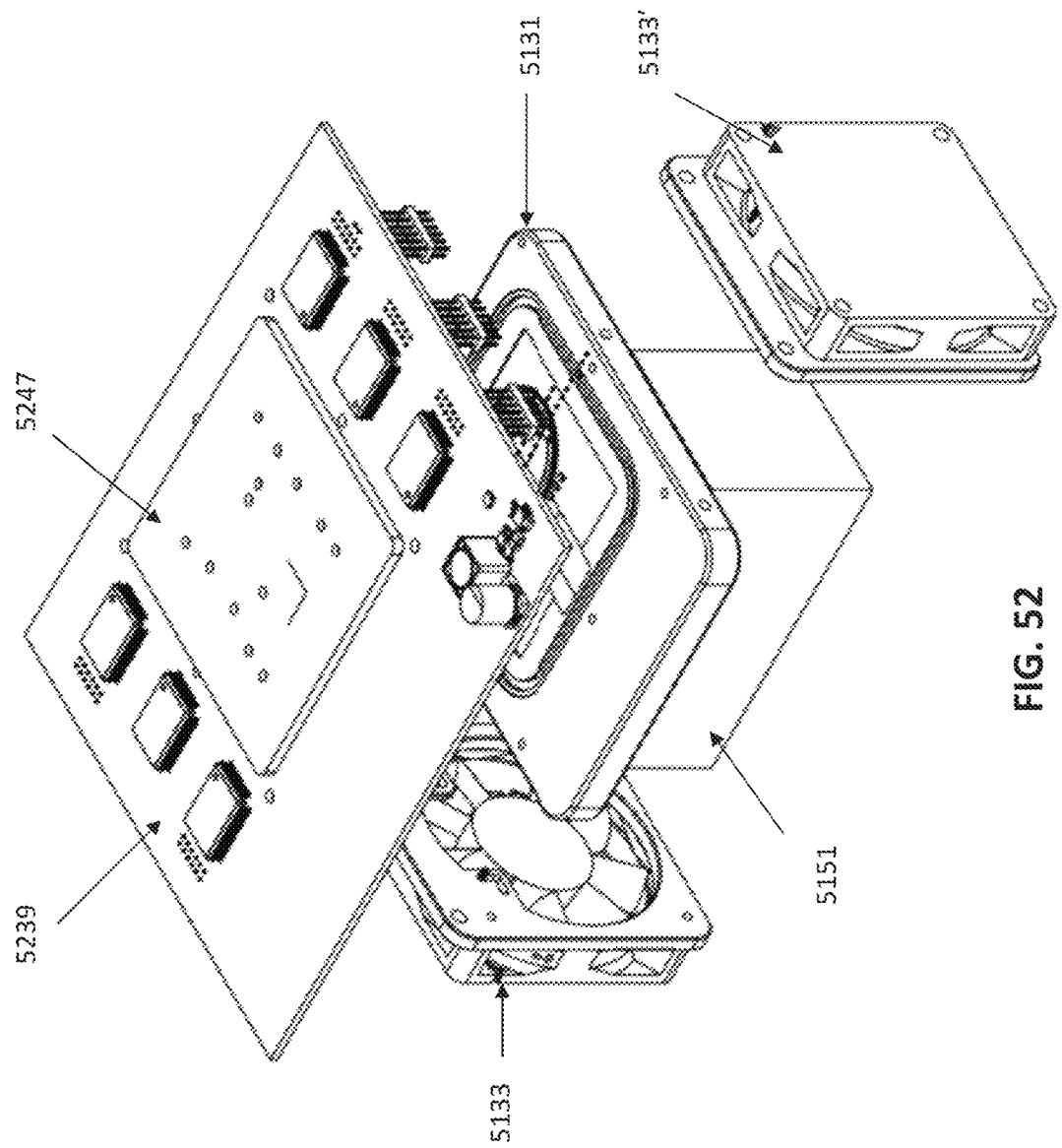

FIG. 52 illustrates one example of an assembly for an apparatus including a PCB with an array of electrodes for applying DMF to a cartridge (not shown), a vacuum block for holding the cartridge bottom onto the PCB and a thermal regulator subsystem including a heat sink/heat block and a pair of cooling fans.

Figure 53A:
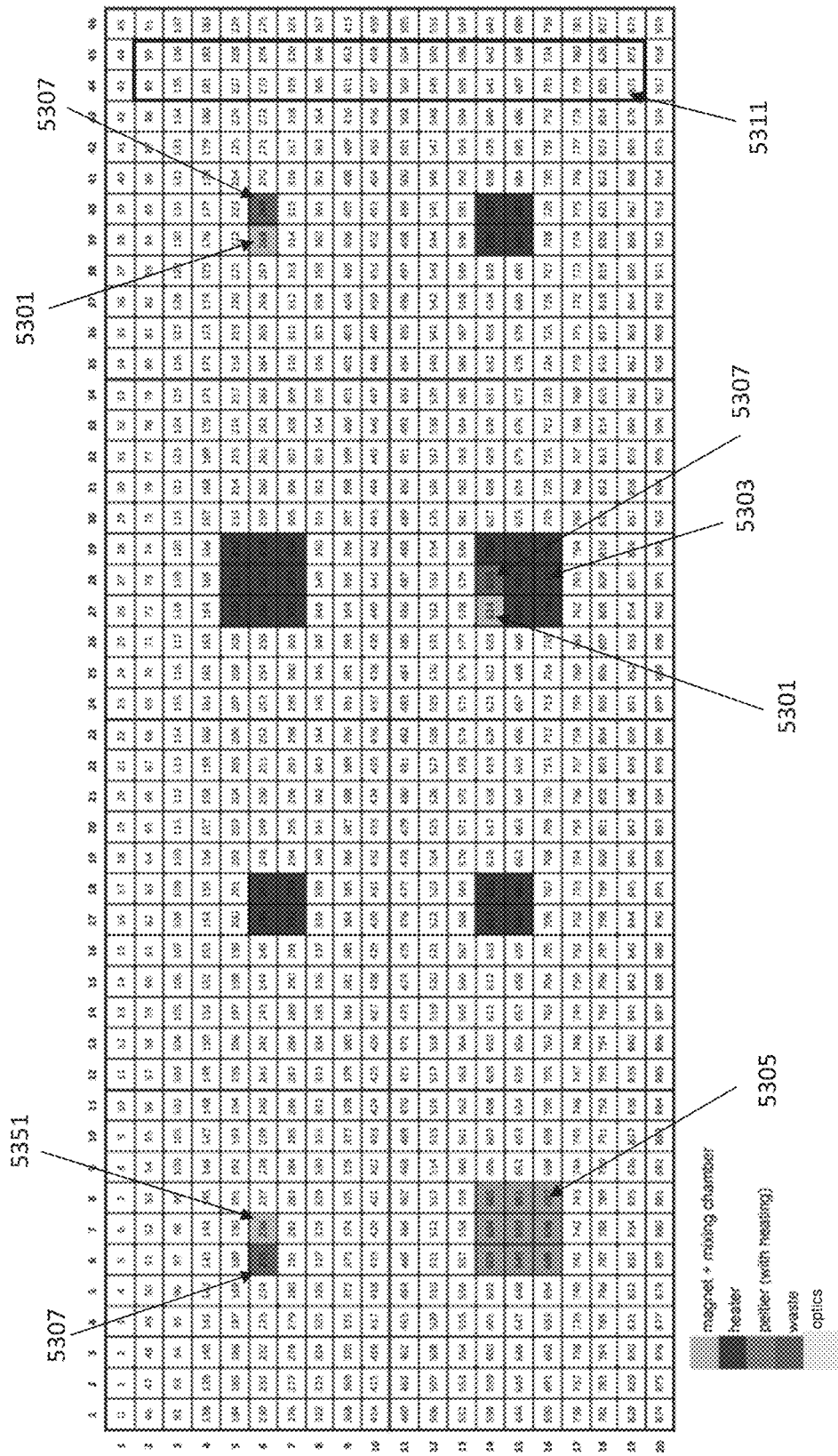

FIG. 53A shows an example of an electrode grid setup with independent action zones.

Figure 53B:
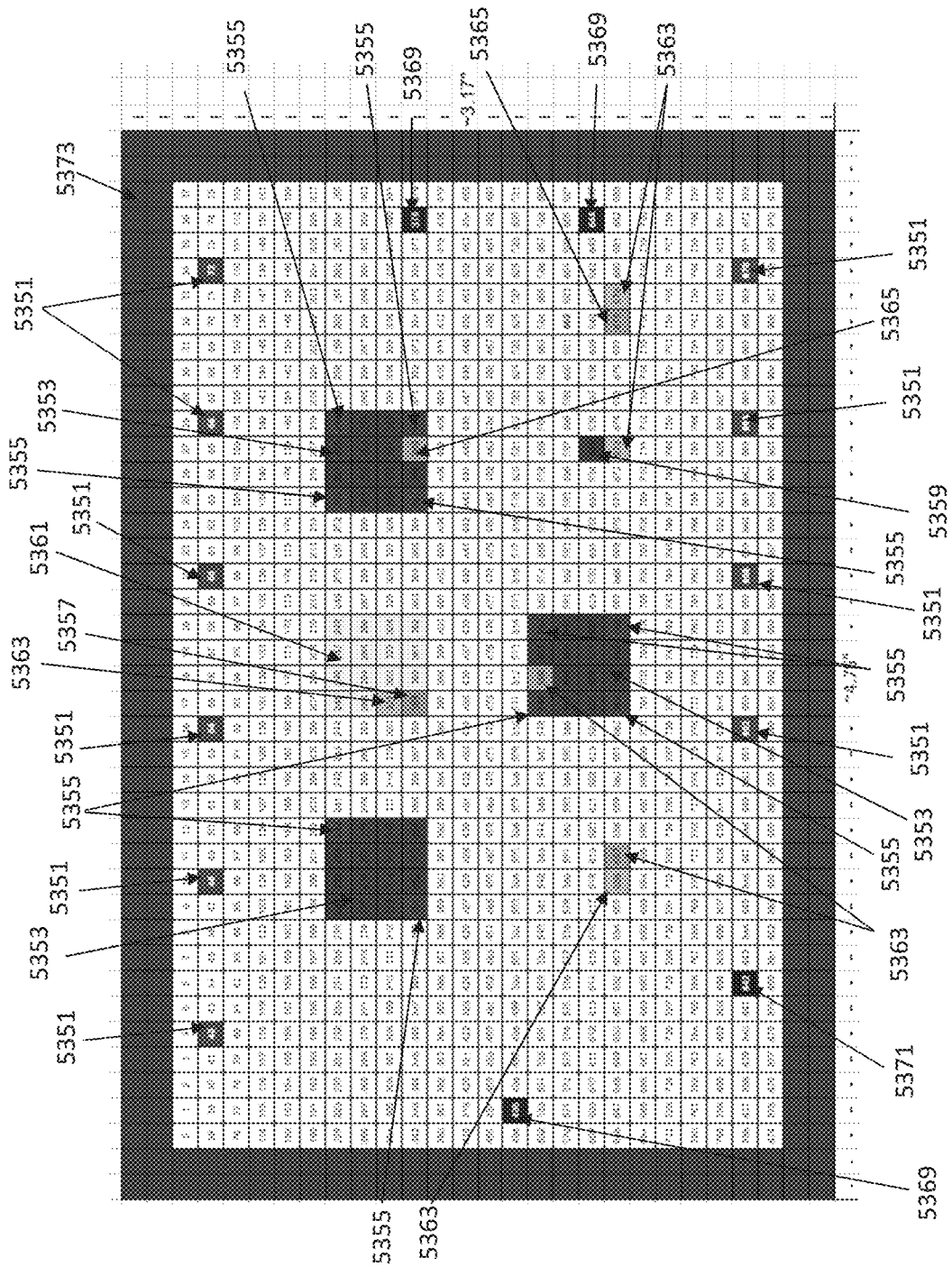

FIG. 53B shows another example of an electrode grid setup with independent action.

FIGS. 54A-54D illustrate examples of a thermal regulation subsystem of an apparatus as described herein.

Figure 55A:
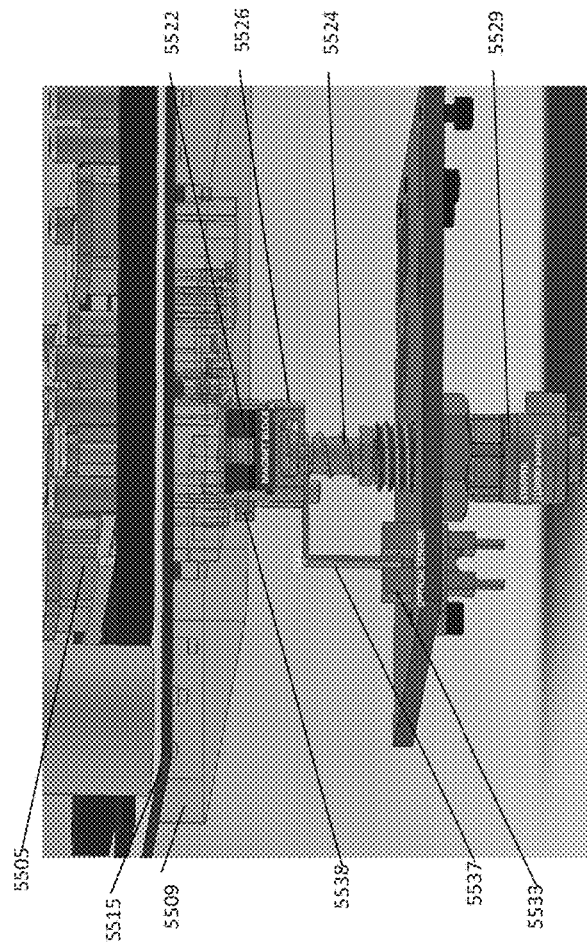
Figure 55B:
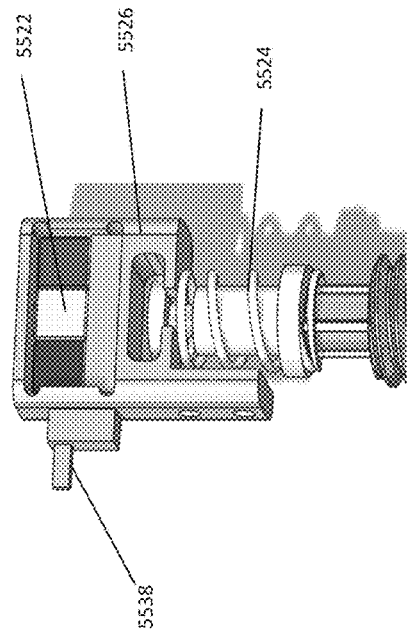

FIGS. 55A-55B illustrate examples of a magnetic subsystem of an apparatus as described herein.

Figure 56A:
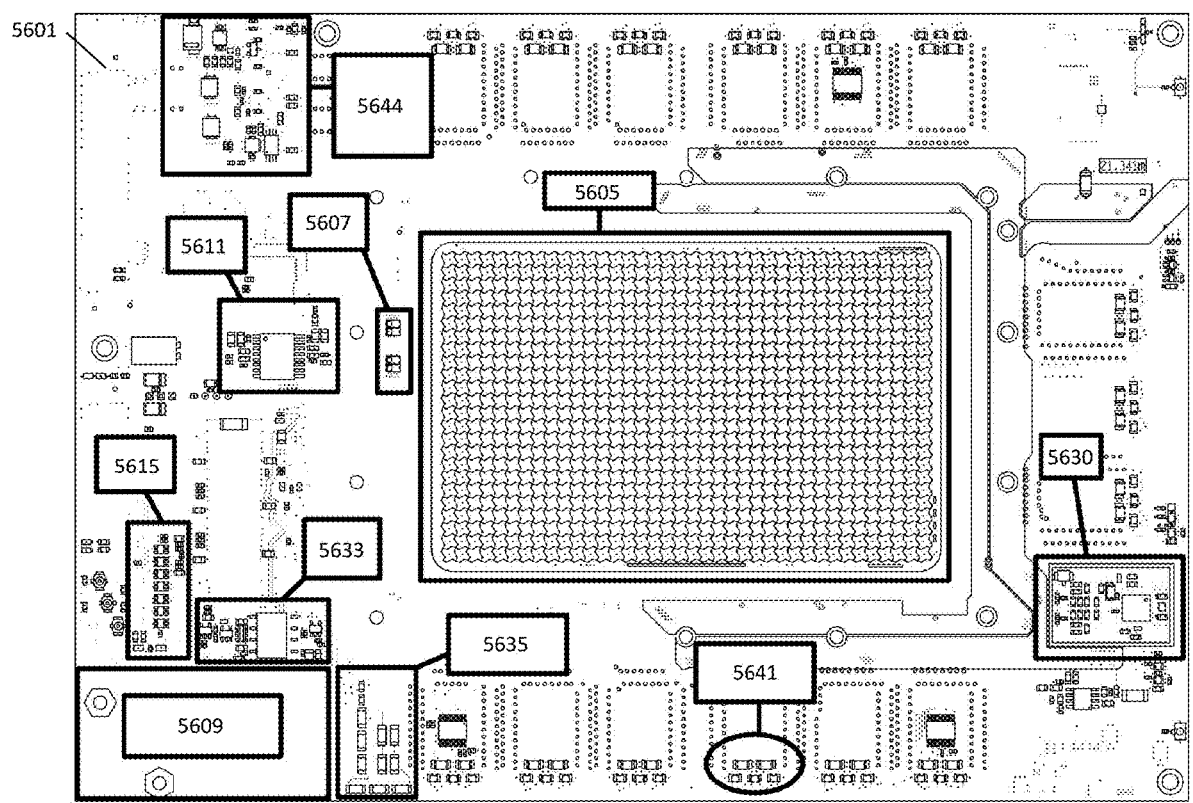
Figure 56B:
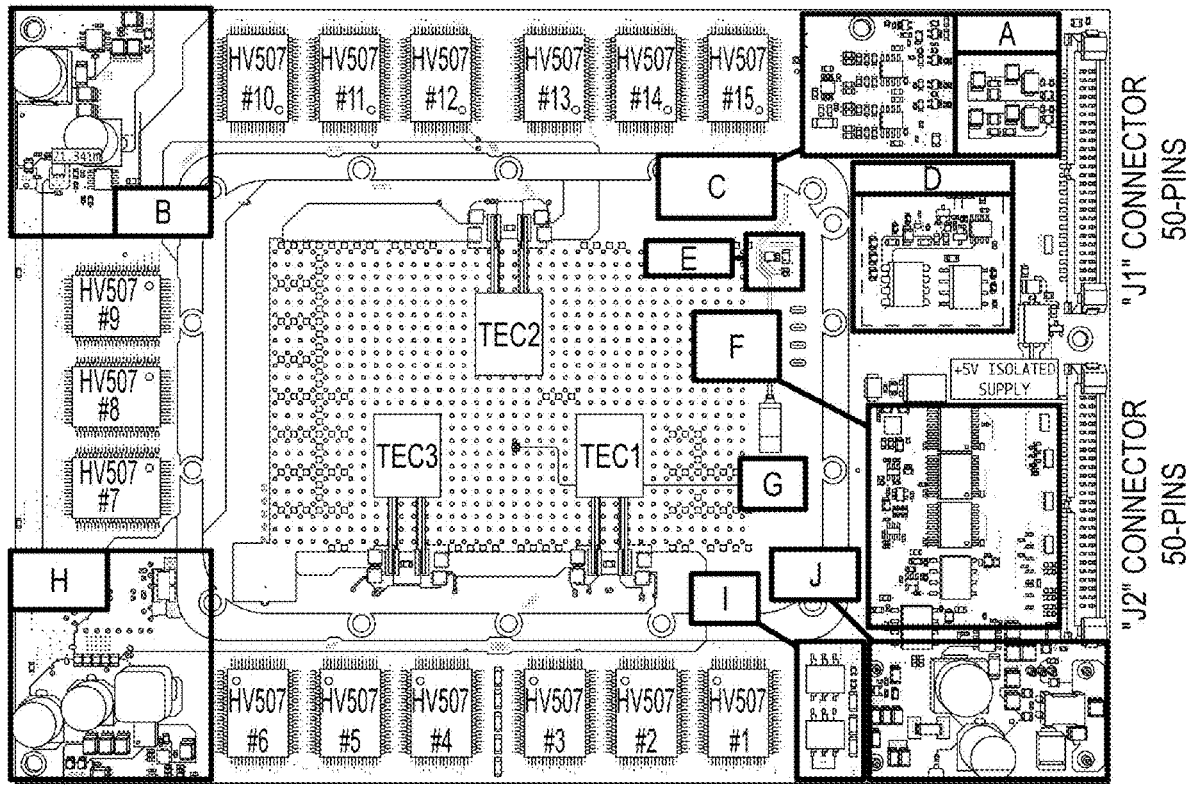

FIGS. 56A-56B illustrate an example of an electrode subsystem of an apparatus as described herein.

Figure 57:
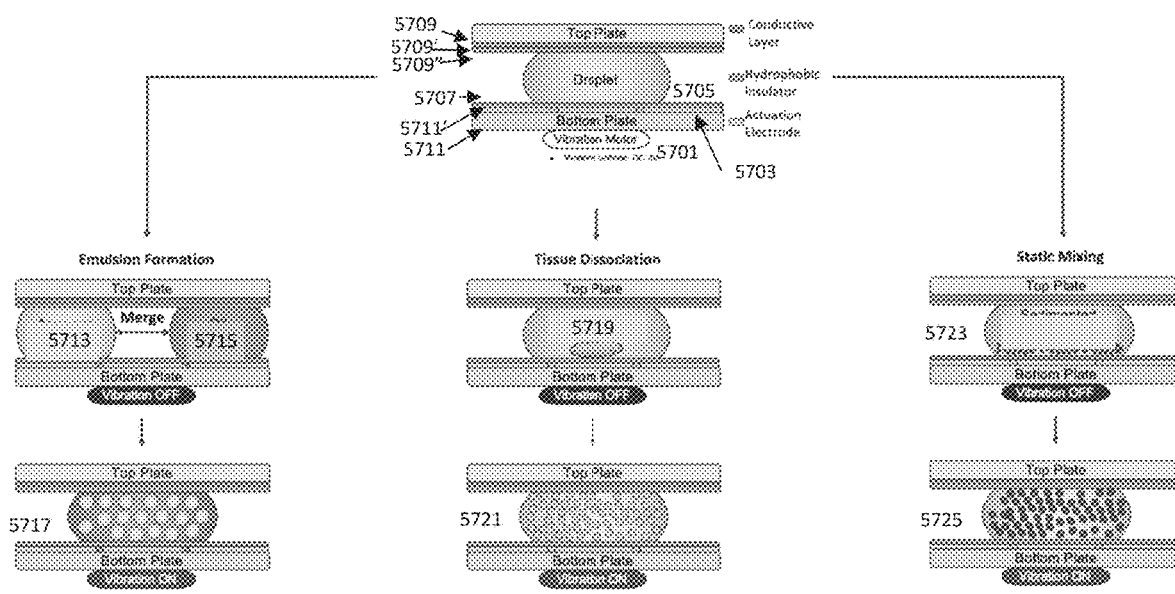

FIG. 57 is a schematic representation of an example of an apparatus including a vortex (mechanical vibration) subassembly and methods of use thereof.

FIG. 58A is a top view of an example of a portion of an air-matrix DMF apparatus, showing a plurality of unit cells (defined by the underlying actuating electrode 5813) and reaction chamber openings 5815 (access holes).

FIGS. 58B-58D show side views of variations of reaction chamber wells that may be used in an air-matrix DMF apparatus. In FIG. 58B the reaction chamber well comprises a centrifuge tube; in FIG. 58C the reaction chamber well comprises a well plate (which may be part of a multi-well plate); and in FIG. 58D the reaction chamber well is formed as part of the pate of the air-matrix DMF apparatus.

FIGS. 59A to 59E illustrate movement (e.g., controlled by a controller of an air-matrix DMF apparatus) into and then out of a reaction chamber, as described herein. In this example, the reaction chamber well is shown in a side view of the air-matrix DMF apparatus and the reaction chamber is integrally formed into a plate (e.g., a first or lower plate) of the air-matrix DMF apparatus which includes actuation electrodes (reaction well actuation electrodes) therein.

FIG. 60A shows a time series of photos of an air matrix DMF apparatus including a wax (in this example, paraffin) body which is melted and covers a reaction droplet.

Figure 4A:
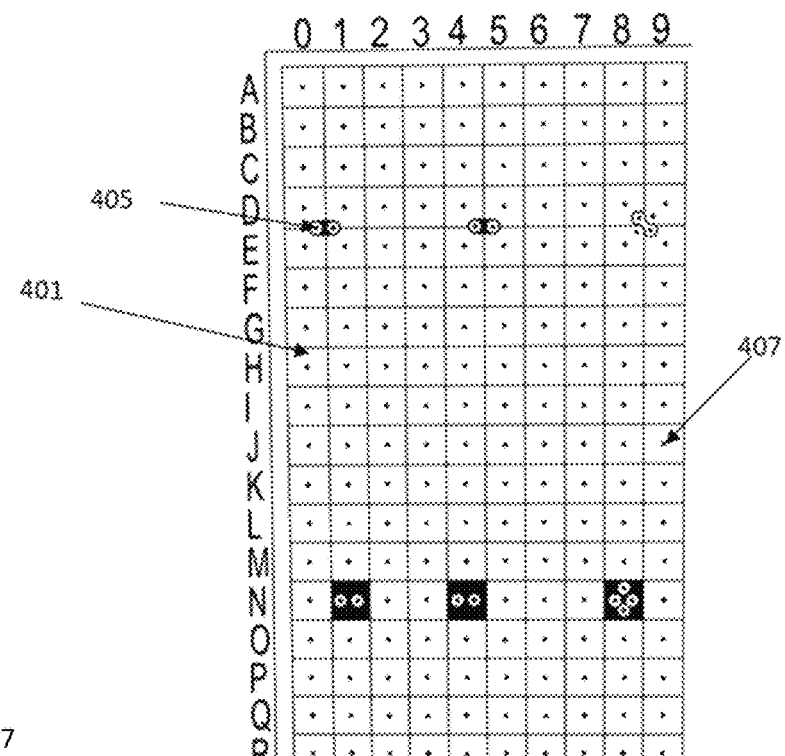
FIG. 4A shows a top view of the electrodes (e.g., electrode array) formed as part of the apparatus. The electrodes may include a plurality of vacuum openings through them, as shown. The electrodes may define different regions, including thermally controlled regions (e.g., regions having a thermistor and/or cooling and/or heating.

FIG. 60B is an example of a time series similar to that shown in FIGS. 4A(3) and 4A(4), without using a wax body to cover the reaction droplet, showing significant evaporation.

Figure 61A:
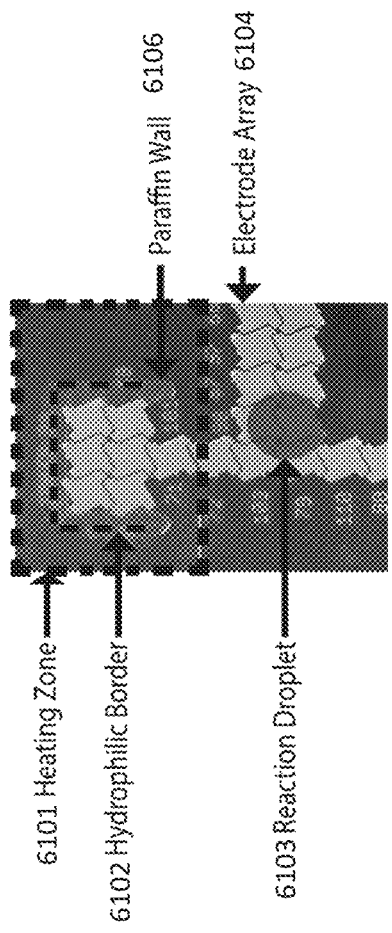
Figure 61B:
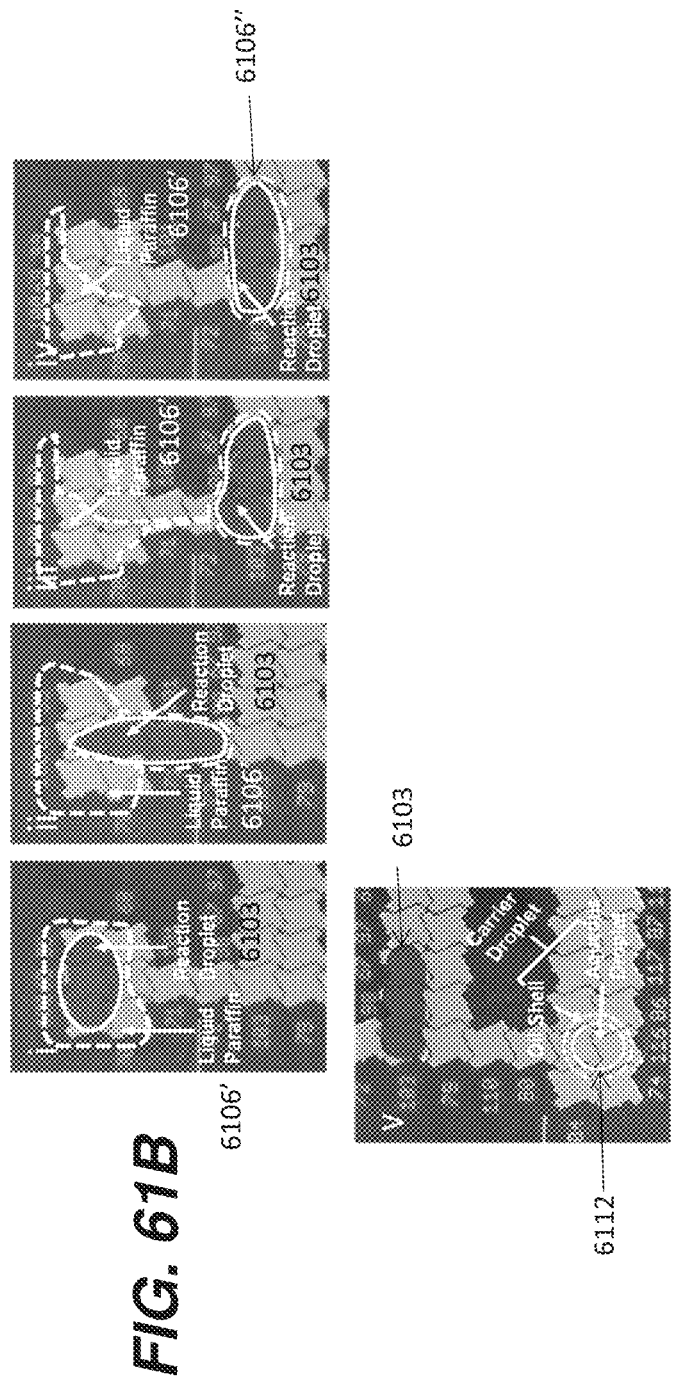

FIGS. 61A and 61B show the encapsulation of a droplet within wax in a thermal zone and the subsequent separation of the droplet from the liquid wax.

Figure 62A:
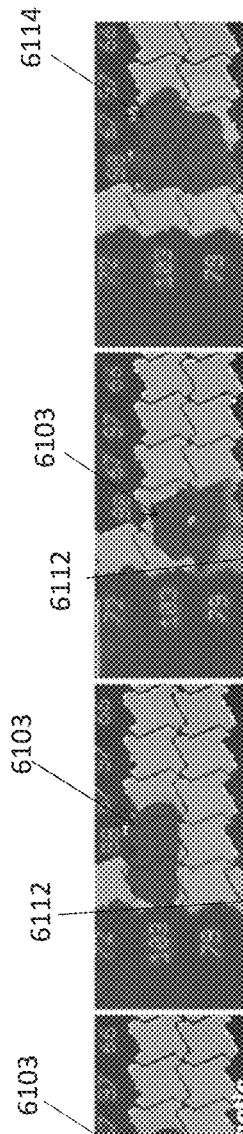
Figure 62B:
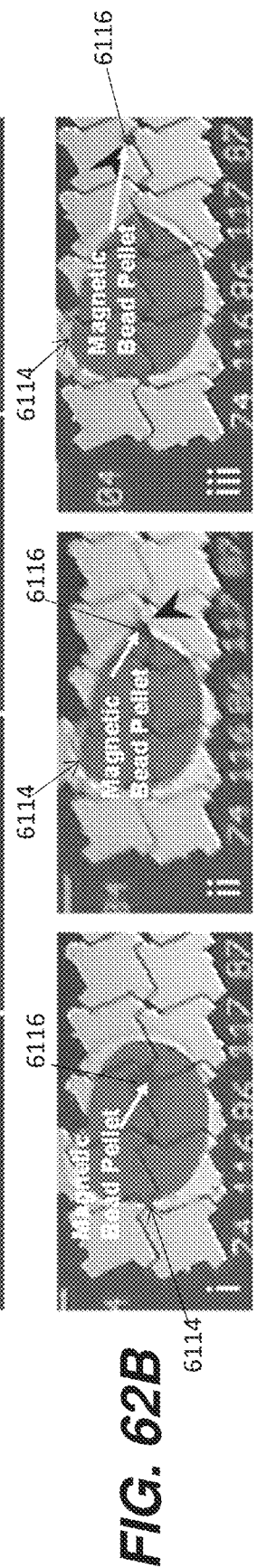
Figure 62C:
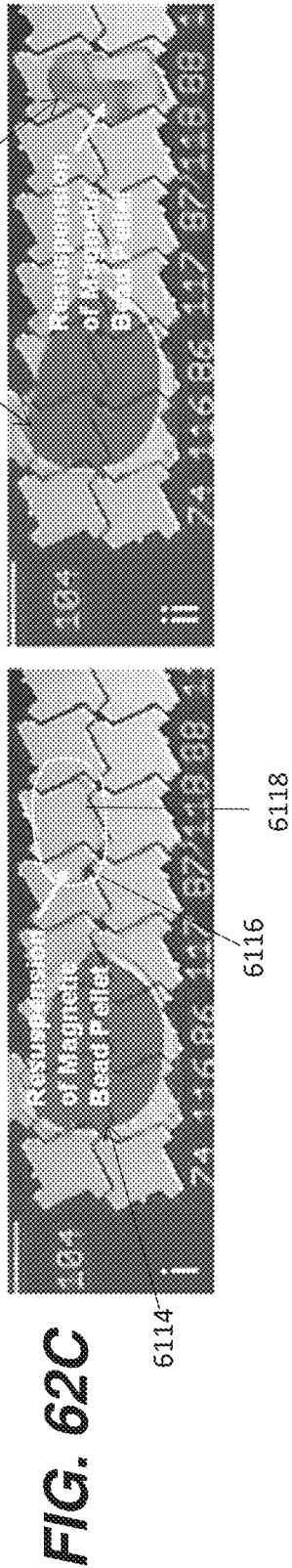

FIGS. 62A to 62C show the merging of a carrier droplet with beads with the droplet from FIGS. 61A and 61B and the subsequent separation and re-suspension of the beads.

Figure 63:
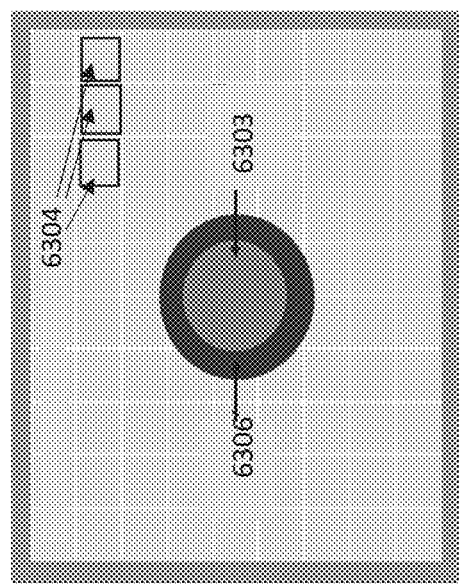

FIG. 63 is an example of an air-matrix DMF apparatus in which a liquid wax shell or coating is used to reduce or eliminate evaporation, particularly during heating.

Figure 64:
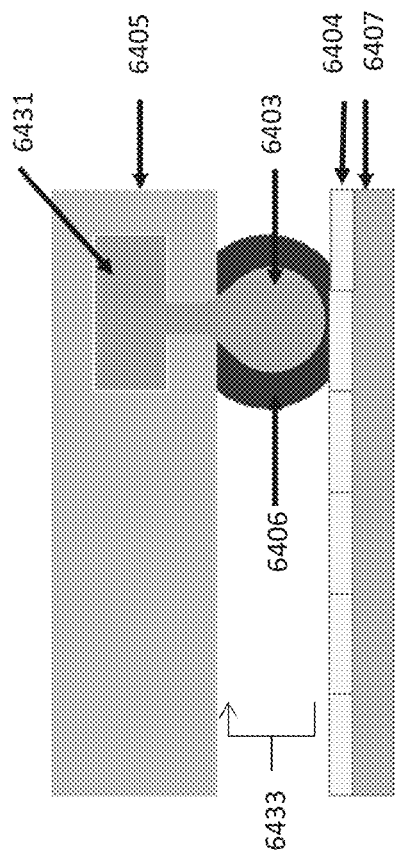

FIG. 64 is a profile view of one example of an air-matrix DMF apparatus in which a conductive liquid wax shell is used.

Figure 65:
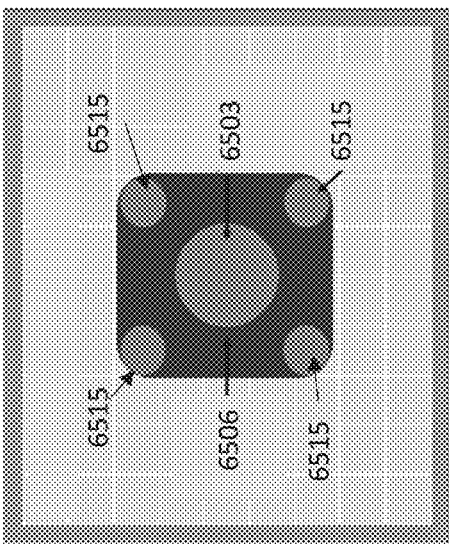

FIG. 65 is an example of a method of pinning a liquid wax material within an air matrix DMF apparatus, in which the air matrix DMF apparatus is kept stationary and/or uniformly surrounded by the liquid wax material.

Figure 66:
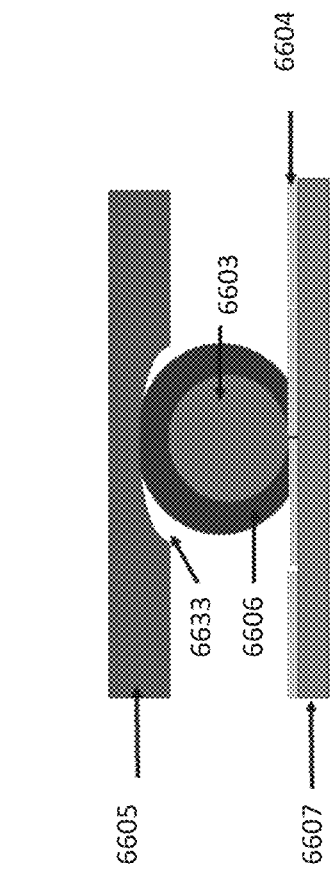

FIG. 66 is an example of an air matrix DMF apparatus in which the gap is locally larger, forming a chamber that may passively retain and/or help keep the aqueous droplet uniformly surrounded by a liquid wax material.

Figure 67:
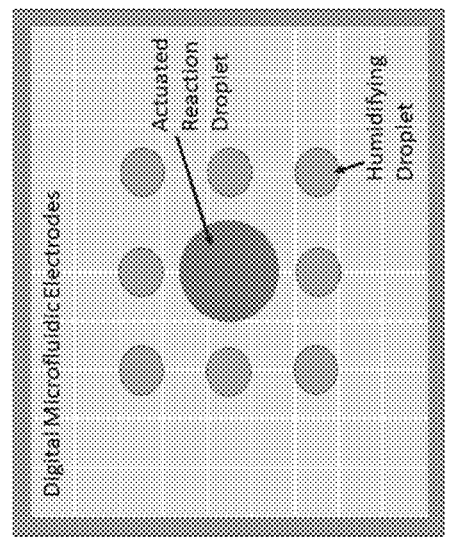

FIG. 67 is an example of a microhumidifcation chamber formed within an air matrix DMF apparatus by surrounding the aqueous reaction droplet with additional aqueous droplets to form a local region of higher humidity; the surrounding droplets may be heated (e.g., to a temperature that is greater than the temperature of the reaction droplet or to the same temperature as the reaction droplet).

Figure 68:
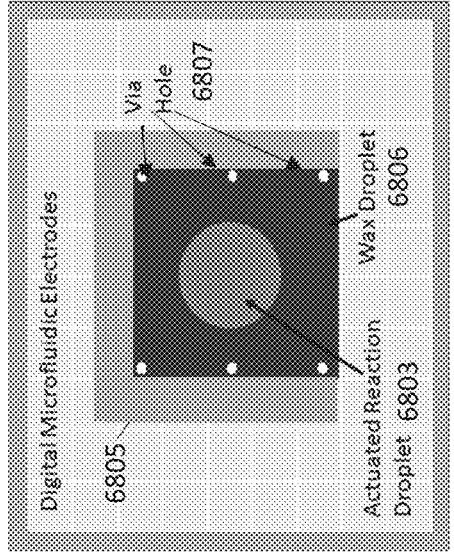

FIG. 68 is an example of an air-matrix DMF apparatus in which the droplet is pinned within the air gap of the DMF apparatus by a barrier or fence (which may be formed of a hydrophobic, oleophilic and/or hydrophilic material). The barrier may extend partially or completely across the gap.

Figure 69:
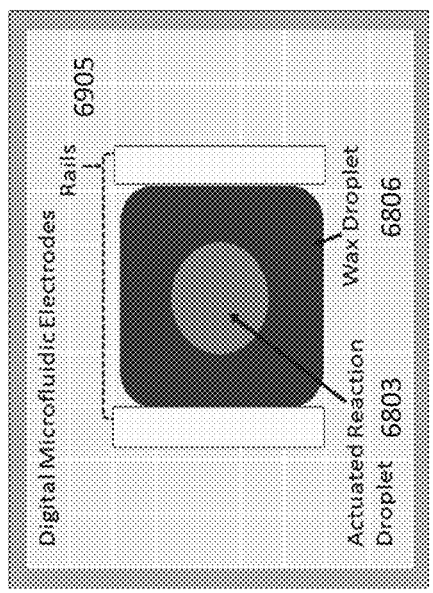

FIG. 69 is another example of an air-matrix DMF apparatus in which the droplet is pinned within the air gap of the DMF apparatus by a partial barrier or fence, similar to that shown in FIG. 68 (but open on two sides). The barrier may extend partially or completely across the gap.

Figure 70:
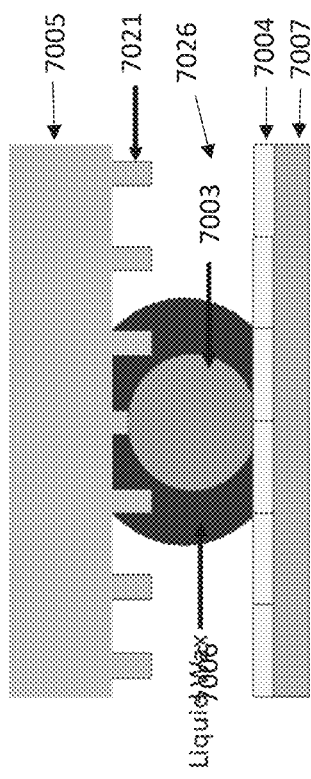

FIG. 70 illustrate another example of an air matrix DMF apparatus in which the droplet is pinned within the air gap of the DMF apparatus by a plurality of pins (e.g., protrusions, pillars, etc.) within the air gap, which may be formed of a hydrophobic, oleophilic and/or hydrophilic material. In FIG. 70, the pins extend partially from the upper plate into the air gap and extend over a plurality of active regions (e.g., regions formed in part by a drive electrode).

Figure 71A:
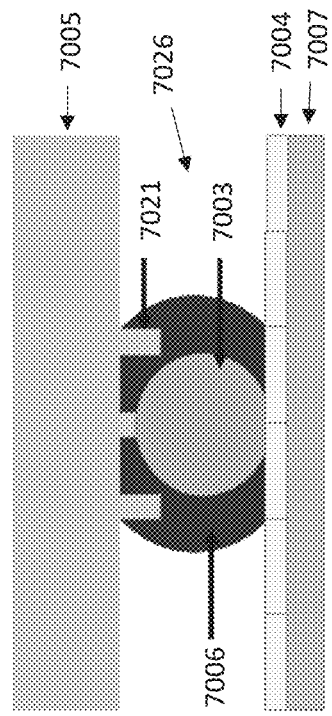

FIG. 71A shows a portion of an air gap having a limited number of pins; the pins extend over a smaller number of active electrodes regions (e.g., 2-3 active regions, 2-5 active regions, 2-7 active regions, etc.) and may form a pinning region.

FIG. 71B shows another example in which the pinning region includes pins at the outer boundary (periphery) of the pinning region. The air gap may be formed as part of a cartrdige including the lower (e.g. dielectric sheet) plate that is configured to seat on an array of actuation electrodes, as shown.

FIG. 71C illustrates an example in which the pinning region is formed by a plurality of pins that are flush with the upper surface, as shown.

FIG. 72A is a top view of a droplet within an exemplary pinning region forming a reaction chamber having pins (e g, pinning pillar features) within the air gap of an air-matrix DMF apparatus according to one embodiment of the disclosure.

FIG. 72B is a side view of a portion of the droplet within a pinning region of the air gap (e.g., a reaction chamber) showing the droplet being held in place by the pins as described herein.

Figures 73A, 73B, 73C:
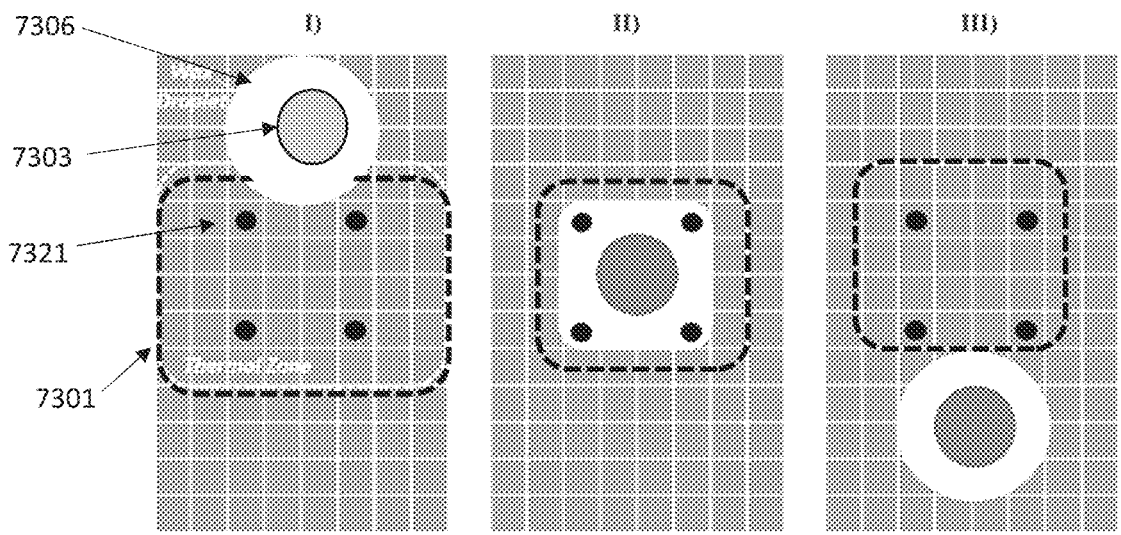

FIGS. 73A to 73C illustrate a method of moving a droplet having a liquid wax coating or shell using actuation electrodes, into a reaction chamber formed within the air gap and having four pinning features; retaining the droplet within the reaction chamber while heating by pinning with the four pinning features; and driving the droplet out of the reaction chamber using actuation electrodes.

Figures 74A, 74B, 74C:
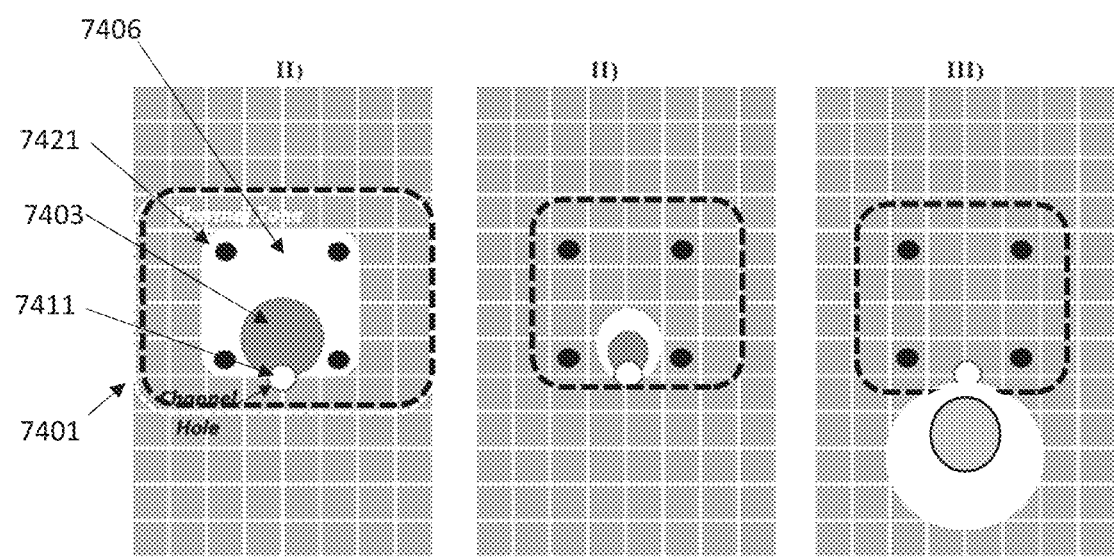

FIGS. 74A to 74C illustrate a method of moving a droplet out of a reaction chamber formed within the air gap, which has four pinning features and a channel hole in a top plate of the air-matrix DMF apparatus, and driving the droplet out of the reaction chamber using actuation electrodes in combination with withdrawing at least a portion of the droplet having a liquid wax coating or shell up into the channel hole.

Figure 75A:
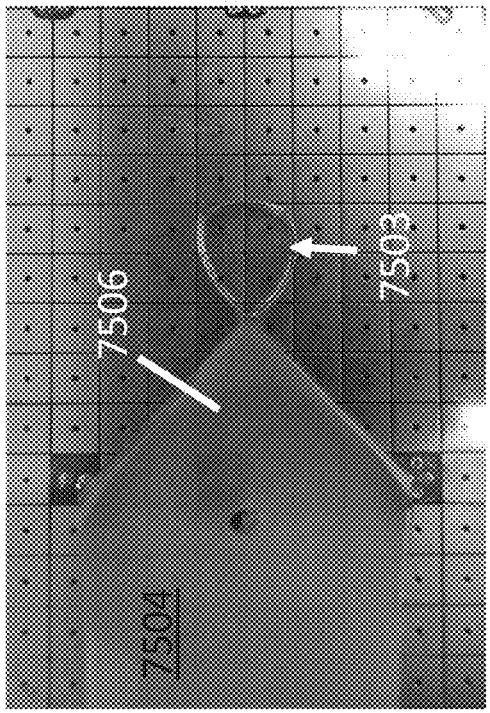
Figure 75B:
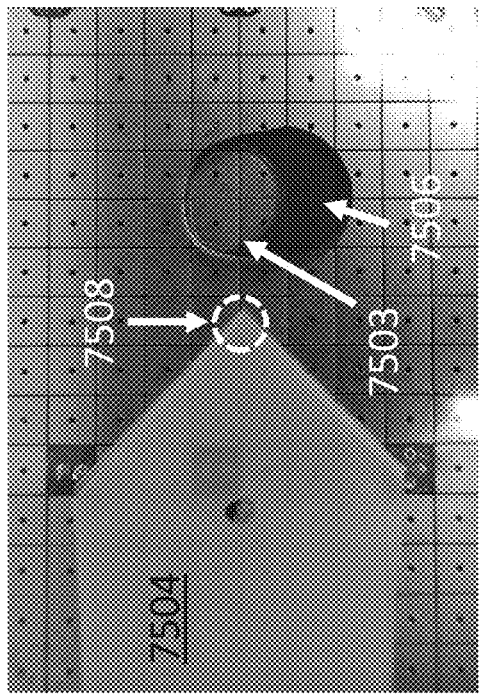
Figure 75C:
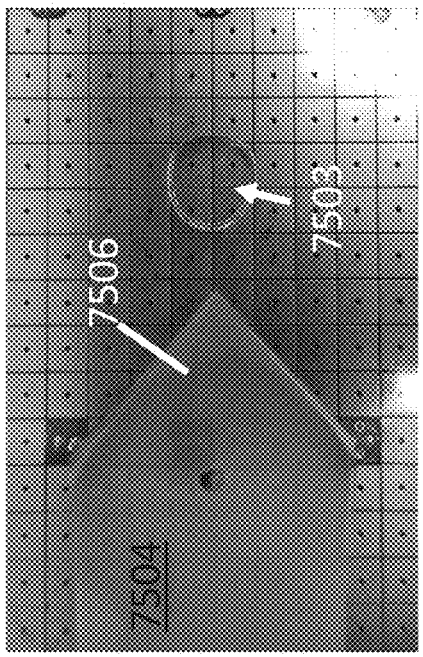

FIGS. 75A to 75C illustrate one method of separation of a liquid wax coating/shell material from an encapsulated droplet by using a wick (e.g., an oil absorbent wick) as described herein.

Figure 76:
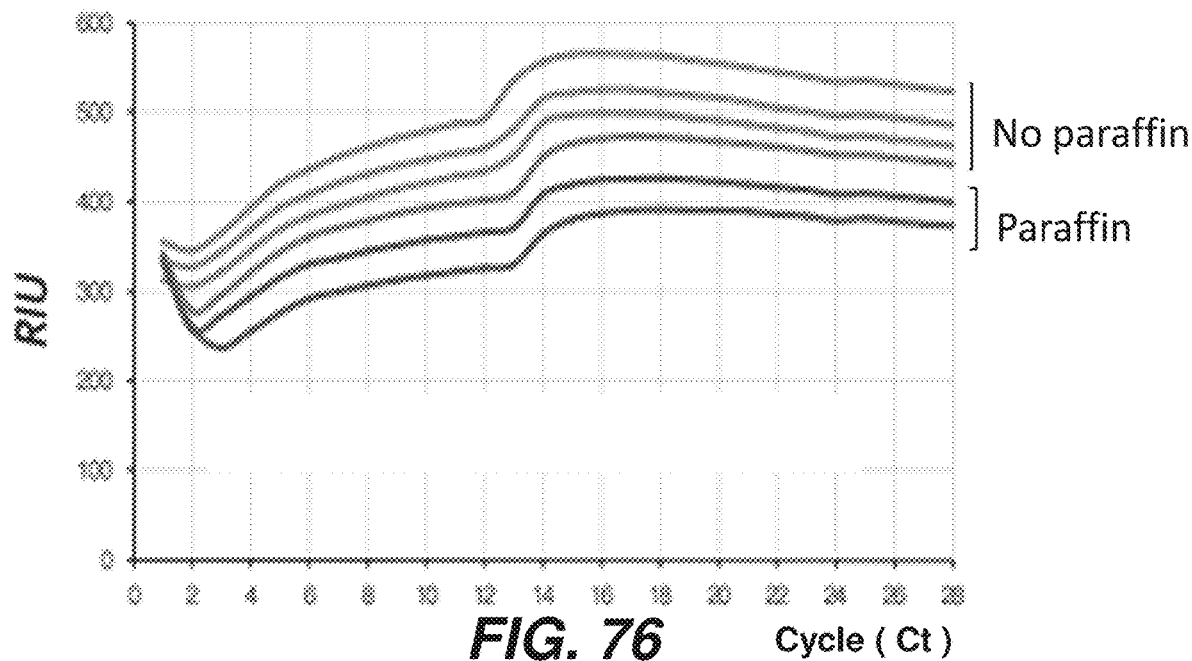

FIG. 76 is a graph comparing an amplification reaction by LAMP with and without a wax covering as described herein, protecting the reaction droplet from evaporation.

Figure 77A:
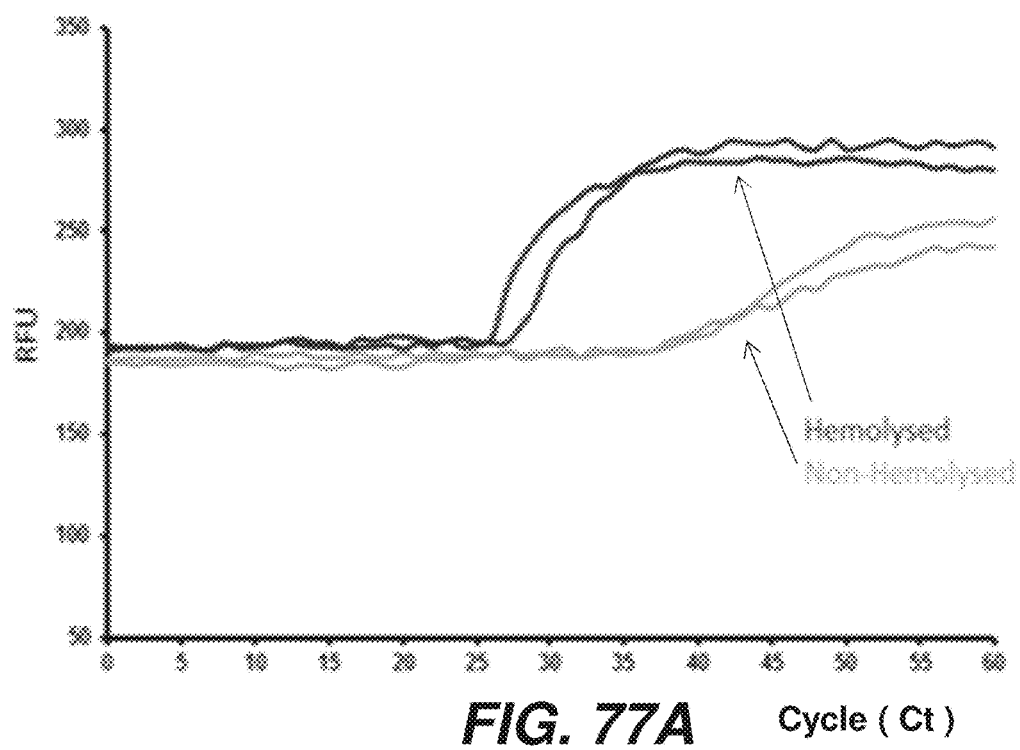
Figure 77B:
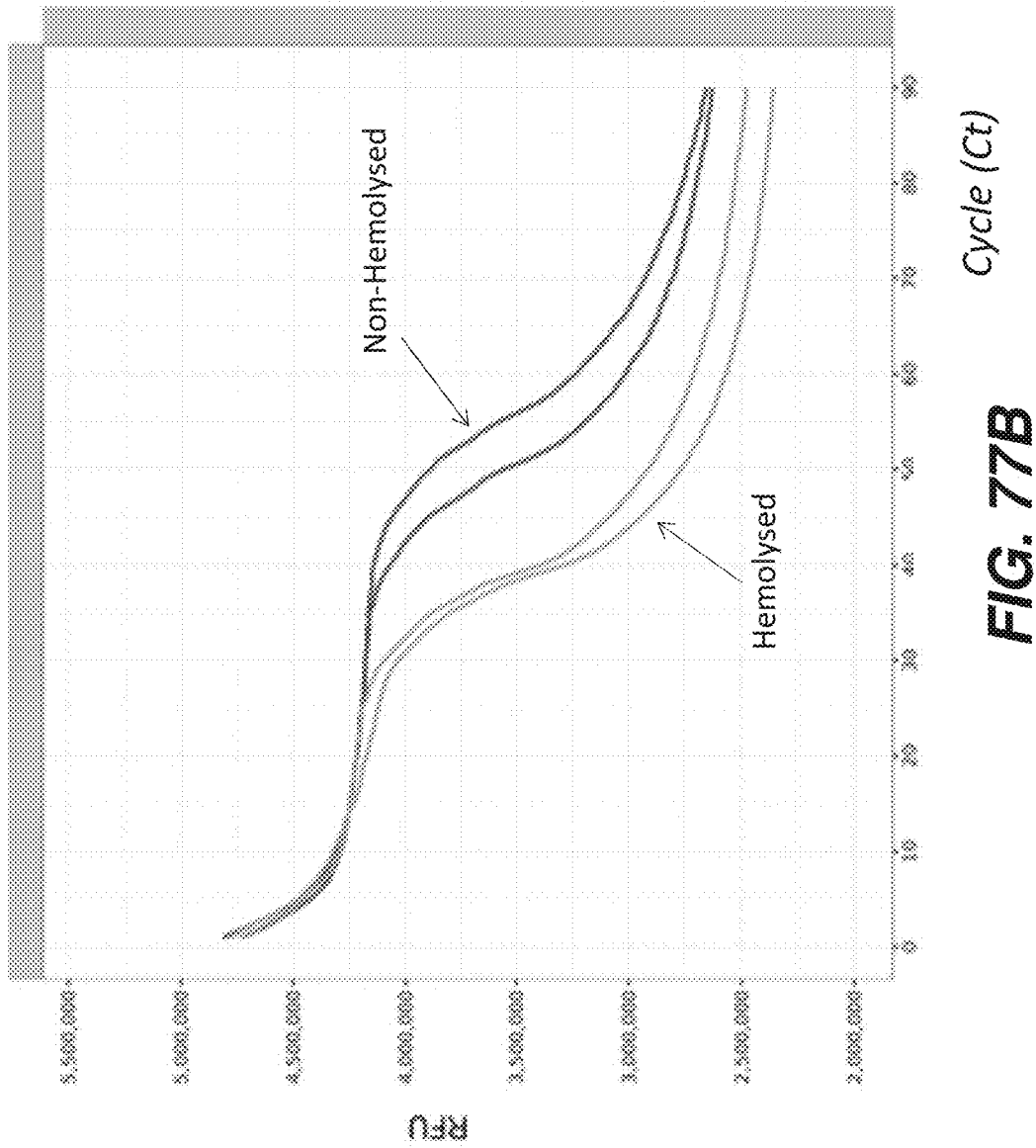

FIG. 77A shows graphical results of LAMP using paraffin-mediated methods; this may be qualitatively compared to the graph of FIG. 77B showing graphical results of LAMP using conventional methods.

DETAILED DESCRIPTION

Described herein are air-matrix digital microfluidics (DMF) methods and apparatuses that may minimize the effect of surface fouling and/or evaporation and may be particularly helpful for stabilizing (e.g., pinning) a droplet within the air gap of an air-matrix DMF apparatus. Also described herein are methods of removing a coating or shell material (such as a liquid wax). The methods and apparatuses described herein may be particularly useful when heating the reaction droplets being processed.

As used herein, the term "surface fouling" may refer to accumulation of unwanted materials on solid surfaces, including with the air gap of the air matrix DMF apparatus (e.g., upper and/or lower plate surfaces). Surface fouling materials can consist of either living organisms (biofouling) or a non-living substance (inorganic or organic). Surface fouling is usually distinguished from other surface-growth phenomena in that it occurs on a surface of a component, or system and that the fouling process impedes or interferes with function.

Generally, the air-matrix DMF apparatuses described herein may include at least one hydrophobic surface and may include a plurality of activation electrodes (e.g., "drive electrodes") adjacent to the surface, or may be configured to be held adjacent to the activation electrodes. The hydrophobic surface may also be a dielectric material or an additional dielectric material/layer may be positioned between the actuation electrodes and the hydrophobic surface. For example, in some variations, the air-matrix DMF includes a series of layers on a printed circuit board (PCB) forming a first or bottom plate. The outer (top) surface of this plate is the hydrophobic layer. Above this layer is the air gap (air gap region) along which a reaction droplet may be manipulated. In some variations a second plate may be positioned opposite from the first plate, forming the air gap region between the two. The second plate may also include a hydrophobic coating and in some variations may also include a ground electrode or multiple ground electrodes opposite the actuation electrodes. The actuation electrodes may be configured for moving droplets from one region to another within the DMF device, and may be electrically coupled to a controller (e.g., control circuitry) for applying energy to drive movement of the droplets in the air gap. As mentioned, this plate may also include a dielectric layer for increasing the capacitance between the reaction droplet and the actuation electrodes. The reaction starting materials and reagents, as well as additional additive reagents may be in reservoirs that may be dispensed into the air gap, where the reaction mixture is typically held during the reaction. In some instances the starting materials, reagents, and components needed in subsequent steps may be stored in separate areas of the air gap layer such that their proximity from each other prevents them from prematurely mixing with each other. In other instances, the air gap layer may include features that are able to compartmentalize different reaction mixtures such that they may be close in proximity to each other but separated by a physical barrier.

In some variations, the apparatus includes a cartridge that is removable from a base unit. The base unit may include the drive electrodes and the cartridge may include a dielectric layer with a hydrophobic coating that may sit on the drive electrodes to control movement of one or more droplets within the air gap formed by the cartridge. The cartridge may be secured onto the drive electrodes by applying a vacuum force as is described below in more detail.

The air gap DMF apparatuses described herein may also include other sub-systems or components for providing the needed reaction conditions. For instance, the air gap DMF apparatuses may include one or more thermal regulators (e.g., heating or cooling element such as thermoelectric modules) for heating and cooling all or a region (thermal zone) of the air gap. In other instances, heating or cooling may be provided by controlling endothermic or exothermic reactions to regulate temperature. The air gap DMF apparatuses may also include temperature detectors (e.g., resistive temperature detector) for monitoring the temperature during a reaction run. In addition, the DMF apparatuses may also include one or more magnets that can be used to manipulate magnetic beads in an on demand fashion. For example, the magnet(s) can be an electromagnet that is controlled by a controller to generate a magnetic field that can agitate or immobilize magnetic beads.

Thus, the air gap DMF apparatuses described herein may include one or more thermal zones. Thermal zones are regions within the air gap of air-matrix DMF apparatuses that may be heated or cooled, where the thermal zones may transfer the heating or cooling to a droplet within the thermal zone through one or more surfaces in contact with the air gap region in the zone (e.g., the first plate). Heating and cooling may be controlled through a thermal regulator such as a thermoelectric module or other type of temperature-modulating component. The temperature of one or many thermal zones may be monitored through a temperature detector or sensor, where the temperature information may be communicated to a computer or other telecommunication device. The temperature may be regulated between 4° C. and 100° C., as when these apparatuses are configured to perform one or more reactions such as, but not limited to: nucleic acid amplifications, like LAMP, PCR, molecular assays, cDNA synthesis, organic synthesis, etc.

An air gap DMF apparatus may also include one or more thermal voids. Thermal voids may be disposed adjacent to the different thermal zones. The thermal voids are typically regions in which heat conduction is limited, e.g., by removing part of the plate (e.g., first plate) (forming the "void"). These voids may be strategically placed to isolate one thermal zone from another which allows the correct temperatures to be maintained within each thermal zone.

In some variations, any of the air-matrix DMF apparatuses described herein may include a separate reaction chamber that is separate or separable from the air gap of the apparatus, but may be accessed through the air gap region. The reaction chamber typically includes a reaction chamber opening that is continuous with the lower surface of the air gap (e.g., the first plate), and a reaction chamber well that forms a cup-like region in which a droplet may be controllably placed (and in some variations, removed) by the apparatus to perform a reaction when covered. The cover may be a mechanical cover (e.g., a cover the seals or partially seals the reaction chamber opening, or a cover that encapsulates, encloses or otherwise surrounds the reaction droplet, such as an oil or wax material that mixes with (then separates from and surrounds) the reaction droplet when the two are combined in the reaction chamber. In some other variations, one or more reaction chambers may be formed within the air gap itself. In these variations, a well or other receptacle passing through the plane of the electrodes and/or through a PCB forming a lower substrate of the air-matrix DMF apparatus is not required.

In general, the reaction chamber opening may be any shape or size (e.g., round, square, rectangular, hexagonal, octagonal, etc.) and may pass through the first (e.g., lower) plate, and into the reaction chamber well. In some variations, the reaction chamber opening passes through one or more actuation electrodes; in particular, the reaction chamber opening may be completely or partially surrounded by an actuation electrode.

More extensive description of air-matrix DMF apparatuses and other components and sub-systems is provided below. Any of the features described throughout this disclosure may be used in any combination for the methods and specific apparatuses described herein.

FIG. 58A shows a top view of an exemplary air-matrix DMF apparatus 5800. As shown, the DMF device may include a series of paths defined by actuation electrodes. The actuation electrodes 5803 are shown in FIG. 58A as a series of squares, each defining a unit cell. These actuation electrodes may have any appropriate shape and size, and are not limited to squares. For example, the unit cells formed by the actuation electrodes in the first layer may be round, hexagonal, triangular, rectangular, octagonal, parallelogram-shaped, etc. In the example of FIG. 58A, the squares representing the unit cells may indicate the physical location of the actuation electrodes in the DMF device or may indicate the area where the actuation electrode has an effect (e.g., an effective area such that when a droplet is situated over the denoted area, the corresponding actuation electrode may affect the droplet's movement or other physical property). The actuation electrodes 5803 may be placed in any pattern. In some examples, actuation electrodes may span the entire corresponding bottom or top surface of the air gap of the DMF apparatus. The actuation electrodes may be in electrical contact with starting sample chambers (not shown) as well as reagent chambers (not shown) for moving different droplets to different regions within the air gap to be mixed with reagent droplets or heated.

In the air-matrix apparatuses described herein, the first (lower) plate may also include one or more reaction chamber openings (access holes) 5815, 5815' which pass through the plane of the electrodes 5803 and through the PCB 5811 on which the electrodes are disposed. Access to the reaction chamber wells may allow reaction droplets to be initially introduced or for allowing reagent droplets to be added later. In particular, one or more reaction droplets may be manipulated in the air gap (moved, mixed, heated, etc.) and temporarily or permanently moved out of the air gap and into a reaction chamber well though a reaction chamber opening. As shown, some of the reaction chamber openings 5805'5815' pass through an actuation electrode. As will be shown in greater detail herein, the reaction chamber may itself include additional actuation electrodes that may be used to move a reaction chamber droplet into/out of the reaction chamber well. In some variations one or more actuation electrodes may be continued (out of the plane of the air gap) into the reaction chamber well.

In general, one or more additional reagents may be subsequently introduced either manually or by automated means in the air gap. In some instances, the access holes may be actual access ports that may couple to outside reservoirs of reagents or reaction components through tubing for introducing additional reaction components or reagents at a later time. As mentioned, the access holes (including reaction chamber openings) may be located in close proximity to a DMF actuation electrode(s). Access holes may also be disposed on the side or the bottom of the DMF apparatus. In general, the apparatus may include a controller 5810 for controlling operation of the actuation electrodes, including moving droplets into and/or out of reaction chambers. The controller may be in electrical communication with the electrodes and it may apply power in a controlled manner to coordinate movement of droplets within the air gap and into/out of the reaction chambers. The controller may also be electrically connected to the one or more temperature regulators (thermal regulators 5820) to regulate temperature in the thermal zones 5801, which may encompass one or more unit cells and may further encompass reaction chamber 5815, 5815'. One or more sensors (e.g., video sensors, electrical sensors, temperature sensors, etc.) may also be included (not shown) and may provide input to the controller which may use the input from these one or more sensors to control motion and temperature.

As indicated above, surface fouling is an issue that has plagued microfluidics, including DMF devices. Surface fouling occurs when certain constituents of a reaction mixture irreversibly adsorbs onto a surface that the reaction mixture is in contact with. Surface fouling also appears more prevalent in samples containing proteins and other biological molecules. Increases in temperature may also contribute to surface fouling. The DMF apparatuses and methods described herein aim to minimize the effects of surface fouling. One such way is to perform the bulk of the reaction steps in a reaction chamber that is in fluid communication with the air gap layer. The reaction chamber may be an insert that fits into an aperture of the DMF device as shown in FIGS. 58B and 58C. FIG. 58B shows the floor (which may be the first plate) of an air gap region coupled to a centrifuge (e.g., Eppendorf) tube 5805 while FIG. 58C incorporates a well-plate 5807 (e.g., of a single or multi-well plate) into the floor of the air gap region. A built-in well 5809 may also be specifically fabricated to be included in the air-matrix DMF apparatus as shown in FIG. 58D. When a separate or separable tube or plate is used, the tubes may be coupled to the DMF device using any suitable coupling or bonding means (e.g., snap-fit, friction fit, threading, adhesive such as glue, resin, etc., or the like).

Having a dedicated reaction chamber within the DMF device may minimize surface fouling especially when the reaction is heated. Thus, while surface fouling may still occur within the reaction chamber, it may be mainly constrained to within the reaction chamber. This allows the majority of the air gap region floor to remain minimally contaminated by surface fouling and clear for use in subsequent transfer of reagents or additional reaction materials if needed, thus allowing for multi-step or more complex reactions to be performed. When the reaction step or in some instances, the entire reaction is completed, the droplet containing the product may be moved out of the reaction chamber to be analyzed. In some examples, the product droplet may be analyzed directly within the reaction chamber.

In order to bring the droplet(s) containing the starting materials and the reagent droplets into the reaction chamber, additional actuation electrodes, which may also be covered/coated with a dielectric and a hydrophobic layer (or a combined hydrophobic/dielectric layer), may be used. FIGS. 59A-59E shows a series of drawings depicting droplet 5901 movement into and out of an integrated well 5905. As this series of drawings show, in addition to lining the floor of the air gap layer, additional actuation electrodes 5907 line the sides and the bottom of the well. In some variations, the same actuation electrode in the air gap may be extended into the reaction chamber opening. The actuation electrodes 5907 (e.g., the reaction chamber actuation electrodes) may be embedded into or present on the sides and bottom of the well for driving the movement of the droplets into/out of the reaction chamber well. Actuation electrodes may also cover the opening of the reaction chamber. In FIG. 59A, a droplet 5901 (e.g., reaction droplet) in the air gap layer may be moved (using DMF) to the reaction chamber opening. The actuation electrodes 5907 along the edge of the well and the sides of the well maintain contact with the droplet as it moved down the well walls to the bottom of the well (shown in FIGS. 59B and 59C). Once in the reaction chamber well, the droplet may be covered (as described in more detail below, either by placing a cover (e.g., lid, cap, etc.) over the reaction chamber opening and/or by mixing the droplet with a covering (e.g., encapsulating) material such as an oil or wax (e.g., when the droplet is aqueous). In general, the droplet may be allowed to react further within the well, and may be temperature-regulated (e.g., heated, cooled, etc.), additional material may be added (not shown) and/or it may be observed (to detect reaction product). Alternatively or additionally, the droplet may be moved out of the well using the actuation electrode 5907 of FIG. 59E; if a mechanical cover (e.g., lid) has been used, it may be removed first. If an encapsulating material has been used it may be left on.

In some variations contacts may penetrate the surfaces of the reaction chamber. For example, there may be at least ten electrical insertion points in order to provide sufficient electrical contact between the actuation electrodes and the interior of the reaction chamber. In other examples there may need to be at least 20, 30, or even 40 electrical insertion points to provide sufficient contact for all the interior surfaces of the reaction chamber. The interior of the reaction chamber may be hydrophobic or hydrophilic (e.g., to assist in accepting the droplet). As mentioned, an electrode (actuation electrode) may apply a potential to move the droplets into and/or out of the well.

In general, the actuation electrodes may bring the droplet into the well in a controlled manner that minimizes dispersion of the droplet as it is moved into the well and thus maintaining as cohesive a sample droplet as possible. FIGS. 59D and 59E show the droplet being moved up the wall of the well and then out of the reaction chamber. This may be useful for performing additional subsequent steps or for detecting or analyzing the product of interest within the droplet, although these steps may also or alternatively be performed within the well. Actuation electrodes may be on the bottom surface, the sides and the lip of the well in contact with the air gap layer; some actuation electrodes may also or alternatively be present on the upper (top) layer.

In instances where the reaction compartment is an independent structure integrated with the DMF devices as those shown in FIGS. 58A and 58B, the thickness of the substrate (e.g., PCB 5811) may be similar to what is commonly used in DMF fabrication. When the reaction compartment is an integrated well structure fabricated in the bottom plate of the DMF device as shown in FIG. 58D, the thickness of the substrate may be equivalent to the depth of the well.

In another embodiment, the electrodes embedded in the reaction compartments can include electrodes for the electrical detection of the reaction outputs. Electrical detection methods include but are not limited to electrochemistry. In some instances, using the changes in electrical properties of the electrodes when the electrodes contact the reaction droplet, reagent droplet, or additional reaction component to obtain information about the reaction (e.g., changes in resistance correlated with position of a droplet).

The apparatuses described herein may also prevent evaporation. Evaporation may result in concentrating the reaction mixture, which may be detrimental as a loss of reagents in the reaction mixture may alter the concentration of the reaction mixture and result in mismatched concentration between the intermediate reaction droplet with subsequent addition of other reaction materials of a given concentration. In some variations, such as with enzymatic reactions, enzymes are highly sensitive to changes in reaction environment and loss of reagent may alter the effectiveness of certain enzymes. Evaporation is especially problematic when the reaction mixture has to be heated to above ambient temperature for an extended period of time. In many instances, microfluidics and DMF devices utilizes an oil-matrix for performing biochemical type reactions in microfluidic and DMF devices to address unwanted evaporation. One major drawback of using an oil matrix in the DMF reaction is the added complexity of incorporating additional structures to contain the oil.

The methods and apparatuses described herein may prevent or reduce evaporation, including by the use of a liquid wax shell (e.g., a wax having a melting temperature that is below 25 degrees C. (e.g., below 20 degrees C., below 18 degrees C., below 15 degrees C., etc.). Also described herein are methods and apparatuses that use a wax (e.g., paraffin) having a melting point that is greater than 25 degrees C., which may be useful for forming chambers that may help in minimizing evaporation during a reaction. A wax substance may include substances that are composed of long alkyl chains. Some waxes are solids at ambient temperatures and have a melting point of between approximately 46° C. to approximately 68° C. depending upon the amount of substitution within the hydrocarbon chain. However, low melting point paraffins can have a melting point as low as about 37° C., and some high melting point waxes can have melting points lower than about 70-80° C. In some instances higher melting point waxes may be purifying crude wax mixtures.

As mentioned, wax is one type of sealing material that may be used as a cover (e.g., within a reaction chamber that is separate from the plane of the air gap). In some variations, wax may be used within the air gap. In particular, the wax may be beneficially kept solid until it is desired to mix it with the reaction droplet so that it may coat and protect the reaction droplet. Typically the wax material (or other coating material) may be mixed with the reaction droplet and enclose (e.g., encapsulate, surround, etc.) the aqueous reaction droplet. The inventions described herein may use wax as a pin (or post, etc.), including forming a wall or chamber that may be used in conjunction with a coating or shell material, referred to herein as a liquid wax, that may prevent evaporation.

When a reaction droplet is maintained within a paraffin coating, not only is evaporation minimized, but the paraffin may also insulate the reaction droplet from other potentially reaction interfering factors. In some instances, a solid piece of paraffin or other wax substance may be placed within a thermal zone of the air gap layer of the DMF device. For example, to perform a reaction, actuation electrodes may move a reaction droplet to a wax (e.g., paraffin) body which forms a reaction chamber within the air gap. The actuation electrodes may move the reaction droplet into the reaction chamber thus formed, and may contact the reaction droplet with a wall formed by the wax body. Optionally, upon heating to a temperature above the melting point of the wax, the wax body may melt and cover or surround the reaction droplet. The reaction then may be performed by heating for an extended period of time (including at elevated temperatures) without needing to replenish the reaction solvents and preventing loss by evaporation. For example, a wax-encapsulated droplet may be held and/or moved to a thermal zone to control the temperature. The temperature may be decreased or increased (allowing control of the phase of the wax as well, as the wax is typically inert in the reactions being performed in the reaction droplet). The temperature at that particular thermal zone may be further increased to melt the paraffin and/or release the reaction droplet. The reaction droplet may be analyzed for the desired product when encapsulated by the liquid or solid wax, or it may be moved to another region of the DMF device for further reaction steps after removing it from the wax covering. Paraffins or other wax materials having the desired qualities (e.g. melting point above or below the reaction temperature, as needed) may be used. For example, paraffins typically have melting points between 50 and 70 degrees Celsius, but their melting points may be increased with increasing longer and heavier alkanes.

Figure 4B:
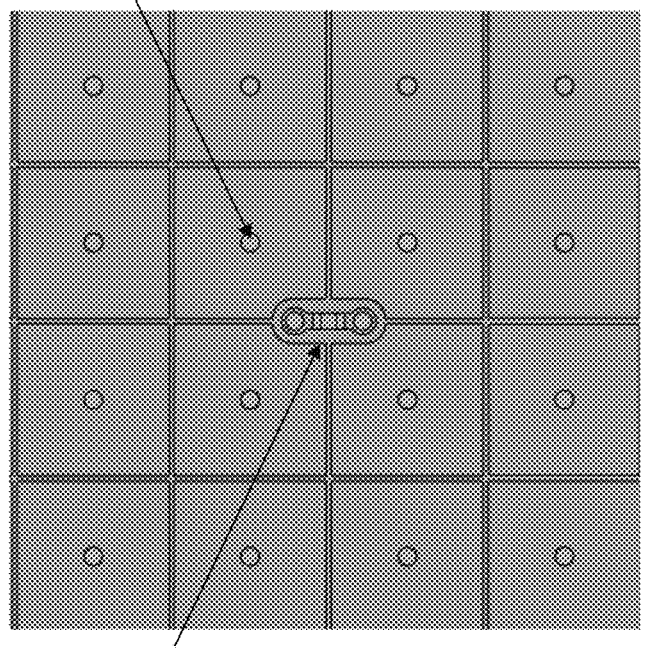
FIG. 4B shows an enlarged region of the electrodes, forming the upper electrode layer, showing the vacuum openings through most (e.g., >50%, 55%, 60%, 65%, 70%, 75%, 80%, 85%, 90%, 95%, etc.) or all of the electrodes. Although square electrodes are shown (with centered vacuum openings), other electrode shapes, e.g., interlocking, rectangular, circular, etc., or vacuum opening locations (off-centered, etc.) through the electrodes may be used.

FIG. 60A shows a time-sequence images (numbered 1-4) taken from an example using a wax body within the air matrix as discussed above, showing profound reduction in evaporation as compared to a control without wax (shown in FIG. 60B, images 1-2). In FIG. 60A, in image no. 1, shows an 8 µL reaction droplet 6003 that has been moved by DMF in the air matrix apparatus to a thermal zone 6005 ("heating zone") containing a solid wax body (e.g., paraffin wall 6001). Once in position, the reaction droplet may be merged with a solid paraffin wall (e.g., thermally printed onto DMF), as shown in image 2 of FIG. 60A, or the wax material may be melted first (not shown). In FIG. 60A image 3, the thermal zone is heated (63° C.) to or above the melting point of the wax material thereby melting the paraffin around the reaction droplet, and the reaction droplet is surrounded/ encapsulated by the wax material 6001', thus preventing the droplet from evaporation as shown in FIG. 60A images 3 and 4. Using this approach, in the example shown in FIG. 60A image 4, the volume of reaction droplets was maintained roughly constant at 63° C. for an incubation time approximately two hours long (120 min). An equivalent experiment without the paraffin wall was performed, and shown in FIG. 60B. The left picture (image 1) in FIG. 4B shows the reaction droplet 6003' at time zero at 63° C. and the right picture of FIG. 4B shows the reaction droplet 6003' after 60 minutes at 63° C. As shown, the reaction droplet almost completely evaporated within approximately one hour at 63° C.

Through this approach of enclosing a droplet in a shell of liquid wax, the reaction volume and temperature are maintained constant without the use of oil, a humidified chamber, off-chip heating, or droplet replenishment methods. Waxes other than paraffin can be used to prevent droplet evaporation as long as their melting temperature is higher than the ambient temperature, but lower or equal to the reaction temperature. Examples of such waxes include paraffin, bees and palm waxes. The wax-like solids can be thermally printed on the DMF device surface by screen-, 2D- or 3D-printing. This wax-mediated evaporation prevention solution is an important advancement in developing air-matrix DMF devices for a wide variety of new high-impact applications.

As mentioned, the wax-based evaporation methods described may be used in conjunction with the DMF devices having a separate reaction chamber feature (e.g., formed below the plane of the electrodes, or they may be used within reaction chambers formed within the air gap. When used within a separate reaction chamber, the wax may be present in the reaction chamber and the reaction droplet may be moved to the reaction chamber below the plane of the electrodes, where wax is disposed therein, for performing the reaction steps requiring heating. Once the heating step has completed, the reaction droplet may be removed from the separate reaction chamber for detection or to perform subsequent reaction steps within the air gap layer of the DMF device. If the reaction is performed within a reaction chamber formed within the air gap, detection may be performed while the reaction droplet is within the reaction chamber or the reaction droplet may be moved to other regions of the DMF apparatus for further processing.

The methods and apparatuses described herein may be used for preventing evaporation in air-matrix DMF devices and may enable facile and reliable execution of any chemistry protocols on DMF with the requirement for a temperature higher than the ambient temperature. Such protocols include, but are not limited to, DNA/RNA digestion/fragmentation, cDNA synthesis, PCR, RT-PCR, isothermal reactions (LAMP, rolling circle amplification-RCA, Strand Displacement Amplification-SDA, Helicase Dependent Amplification-HDA, Nicking Enzyme Amplification reaction-NEAR, Nucleic acid sequence-based amplification-NASBA, Single primer isothermal amplification-SPIA, cross-priming amplification-CPA, Polymerase Spiral Reaction-PSR, Rolling circle replication-RCR), as well as ligation-based detection and amplification techniques (ligase chain reaction-LCR, ligation combined with reverse transcription polymerase chain reaction-RT PCR, ligation-mediated polymerase chain reaction-LMPCR, polymerase chain reaction/ligation detection reaction-PCR/LDR, ligation-dependent polymerase chain reaction-LD-PCR, oligonucleotide ligation assay-OLA, ligation-during-amplification-LDA, ligation of padlock probes, open circle probes, and other circularizable probes, and iterative gap ligation-IGL, ligase chain reaction-LCR, over a range of temperatures (37-100° C.) and incubation times (>2 hr). Additional protocols that can be executed using the systems and methods described herein include hybridization procedures such as for hybrid capture and target enrichment applications in library preparation for next generation sequencing such as, but not limited to massively parallel sequencing protocols used by Illumina, Pacific Biosciences, 10×, Ion Torrent and Oxford Nanopore. For these types of applications, hybridization can last up to about 3 days (72 h). Other protocols include end-repair, which can be done, for example, with some or a combination of the following enzymes: DNA Polymerase I, Large (Klenow) Fragment (active at 25° C. for 15 minutes), T4 DNA Polymerase (active at 15° C. for 12 minutes), and T4 Polynucleotide Kinase (active at 37° C. for 30 minutes). Another protocol includes A-Tailing, which can be done with some or a combination of the following enzymes: Taq Polymerase (active at 72° C. for 20 minutes), and Klenow Fragment (3'→5' exo-) (active at 37° C. for 30 minutes). Yet another protocol is ligation by DNA or RNA ligases.

Manipulation and Processing of Encapsulated Droplets. Although the encapsulation of droplets in wax may prevent or reduce evaporation while executing chemistry protocols at elevated temperatures, after protocol completion, it has been discovered that when the droplet is removed and separated from the wax, e.g., by driving the droplet using the electrodes of the DMF apparatus, a small amount of liquid wax may remain with the droplet as a coating even when the aqueous droplet is moved away from the wax, and that this wax coating may prevent or interfere with subsequent processing and analysis of the reaction droplet, particularly as the droplet cools, where the wax may solidify around the droplet after the droplet is moved out of the heating zone. Therefore, in some embodiments, the wax encapsulated reaction droplet can be accessed through the wax coating using the systems and methods described herein, which enables facile and reliable execution of downstream biochemical processes.

To access the reaction droplet through the wax coating after the reaction droplet has been separated from the bulk liquid wax in the heating zone, an additional hydrophobic (e.g., oil, liquid wax, etc.) material may be added to the reaction droplet to help dissolve the solidified wax encapsulated the reaction droplet. For example, a carrier droplet (i.e., an aqueous droplet enclosed in a thin layer of oil) can be merged with the encapsulated reaction droplet. The carrier droplet gains access to the reaction droplet by having the oil from the carrier droplet dissolve and/or merge with the thin wax layer encapsulating the reaction droplet. Other materials other than oil may be used by the carrier droplet to break through the wax layer encapsulating the reaction droplet. For example, materials that are immiscible with aqueous reaction droplet and are capable of dissolving wax may be used, such as carbon tetrachloride, chloroform, cyclohexane, 1,2-dichloroethane, dichloromethane, diethyl ether, dimethyl formamide, ethyl acetate, heptane, hexane, methyl-tert-butyl ether, pentane, toluene, 2,2,4-trimethylpentane, and other organic solvents. Other materials that may be used to break through the wax layer include ionic detergents such as cetyltrimethylammonium bromide, Sodium deoxycholate, n-lauroylsarcosine sodium salt, sodium n-dodecyl Sulfate, sodium taurochenodeoxycholic; and non-ionic detergents such as dimethyldecylphosphine oxide (APO-10), dimethyldodecylphosphine oxide (APO-12), n-Dodecyl-β-D-maltoside (ULTROL®), n-dodecanoylsucrose, ELUGENT™ Detergent, GENAPOL® C-100, HECAMEG®, n-Heptyl β-D-glucopyranoside, n-Hexyl-b-D-glucopyranoside, n-Nonyl-b-D-glucopyranoside, NP-40 Alternative, n-Octanoylsucrose, n-Octyl-b-D-glucopyranoside, n-Octyl-b-D-thioglucopyranoside, PLURONIC® F-127, Saponin, TRITON® X-100, TRITON® X-114, TWEEN® 20, TWEEN® 80, Tetronic 90R4. At temperatures where a wax remains liquid, a carrier droplet encapsulated with wax may also be used to break through the wax encapsulating the reaction droplet. However, for lower temperatures where the wax solidifies, a carrier droplet coated with wax is generally not used since solid wax can prevent droplet movement.

For example, FIG. 61A illustrates a configuration of an air matrix DMF apparatus that is similar or the same as that shown in FIG. 60A. The setup includes a DMF device interfaced to a heating element placed below or within the bottom DMF substrate, hence generating discrete heating zones 6101 on the bottom DMF substrate. Alternatively, the heating element can be placed above or within the top substrate to form a heating zone on the top substrate. However, forming the heating zone on the bottom substrate allows visual access. On the bottom substrate, a hydrophilic region 6102 is printed or otherwise formed or disposed around the actuating electrodes in the electrode array 6104 that are in the heating zone 900. One or more wax walls 6106 or wax structures, which can be solid at room temperature, can be assembled on the top substrate by, for example, thermal printing to overlay a portion of the hydrophilic region 6102 adjacent to the electrodes in the heating zone 6101 on the bottom plate when the DMF device is assembled. Alternatively, the wax walls 6106 or wax structures can be formed directly on the bottom plate around the electrodes in the heating zone 6101. In yet another variation, the wax walls 6106 can be placed on a removable sheet that can be removably attached to either the top plate or the bottom plate. The removable sheet can have a hydrophobic surface on one side for interacting with the droplet and an adhesive on the other side for adhering to the top or bottom plate. Alternatively, the removable sheet having a hydrophobic surface on one side for interacting with the droplet may have no adhesive on the other side, and is removably attached to a seating surface of the DMF substrate containing the electrode array by other mechanisms. These non-adhesive attachment mechanism may include, but are not limited to vacuum forces pulling down on the removable sheet, thereby seating the removable sheet onto the seating surface. Reagents and other materials can also be placed on the removable sheet to interact with the droplets. In some embodiments, the top plate, the bottom plate, or both, can be part of a removable cartridge that is onto the seating surface of the DMF device, as described in more detail below, where the wax walls 6106, or structure, may be printed onto one of the two plates of the removable cartridge. A hydrophilic region 6102 may also be printed or disposed around the wax walls 6106, on the plate of the removable cartridge, similarly as described above for introduction to a substrate having an electrode array.

As described herein, a reaction droplet 6103 can be transported to the heating zone 6101 along a path of actuating electrodes, which may be a relatively narrow path formed by a single line of actuating electrodes to the heating zone 6101, as shown in FIG. 61A. Then the heating zone 6101 is heated, and the wax wall 6106, surrounding the heating zone 6101 and reaction droplet 6103, melts to encapsulate the reaction droplet 6103 in liquid wax 6106' as shown in FIG. 61B (frame i), thereby preventing or reducing evaporation from the reaction droplet 6103 during the reaction protocol. The hydrophilic region 6102 surrounding the heating zone 6101 functions to pin or localize the liquid wax 6106' in place in the heating zone 6101 and allows the reaction droplet 6103 to break away as described below.

As shown in FIG. 61B (frames ii-iv), the process of breaking away or separating the encapsulated reaction droplet 6103 from liquid wax 6106' can be accomplished by driving the aqueous reaction droplet 6103 away from the heating zone 6101 and the large mass of liquid wax 6106' by actuating the actuating electrodes in the heating zone and path. As the aqueous reaction droplet 6103 is actuated away from the heating zone 6101 the hydrophilic region 6102 surrounding the liquid wax 6106' helps hold the liquid wax 6106' in place as the reaction droplet 6103 moves away from the heating zone 6101 which causes the liquid wax 6106' encasing the droplet 6103 to begin to neck and eventually break off from the droplet 6103, thereby leaving trace or small quantities of liquid wax 6106" surrounding the separated reaction droplet 6103. The heating zone 6101 may be configured for single use only to avoid cross-contamination. However, in situations where cross-contamination is not an issue, the heating zone 6101 may be reused by heating and melting the wax within the heating zone and then moving the next droplet into the reheated liquid wax 6106'.

Because the reaction droplet may be surrounded by a thin layer of liquid wax 6106" after separation from the heating zone 6101, it may be difficult to merge the reaction droplet 6103 with another aqueous droplet since the liquid wax 6106" coating may act as a barrier. In addition, the liquid paraffin wax 6106' may solidify as the droplet cools to form a physical barrier that impedes merger with another droplet. Therefore, to facilitate merging of a liquid wax 6106" coated reaction droplet 6103 or a cooled reaction droplet 6103 with a solid wax coating with another droplet, a carrier droplet 6112 can be used to merge with the reaction droplet 908 as shown in FIG. 61B (frame v). The carrier droplet 912 can be an aqueous droplet that is coated with a thin layer of oil or another organic solvent as described above. The aqueous portion of the carrier droplet 6112 can include additional reagents, beads coated (or not) with DNA/RNA probes or antibodies or antigens for performing separations, uncoated beads, magnetic beads, beads coated with a binding moiety, solid phase reversible immobilization (SPRI) beads, water for dilution of the reaction droplet, enzymes or other proteins, nanopores, wash buffers, ethanol or other alcohols, formamide, detergents, and/or other moieties for facilitating further processing of the reaction droplet 6103. As shown in FIG. 62A (frames i-iv), when the carrier droplet 6112 and the reaction droplet 6103 are moved by the actuating electrodes to the same location, the thin layer of oil surrounding the carrier droplet 6112 can merge with the thin layer of liquid wax (not marked here for clarity) surrounding the reaction droplet 6103, thereby facilitating the merger of the aqueous portions of the two droplets 6103, 6112 to form a combined droplet 6114.

After the carrier droplet 6112 has been merged with the reaction droplet 6103, further processing of the combined droplet 6114 can proceed, such as extracting an analyte from the combined droplet 6114 and/or perform other steps such as hybridizing capture probes, digesting the reaction product using an enzyme, amplifying the reaction product with a set of primers, and the like. For example, the carrier droplet 6112 can be carrying beads for extracting the analyte, e.g., DNA or RNA or proteins. When the droplets are merged, the beads, which can be magnetic, can be used to mix the combined droplet 6114 by application of a magnetic field.

The target analyte binds to the beads, which can be immobilized against the substrate by the magnetic field to form a bead pellet 6116, as shown in FIG. 62B (frame i). Next, the combined droplet 6114 can be moved away from the immobilized bead pellet 916, leaving the bead pellet 6116 with bound analyte on the substrate, as shown in FIG. 62B (frames ii-iii). The combined droplet 6114 can be moved away from the immobilized bead pellet 6116 by actuating the electrodes. Alternatively, the combined droplet 6114 can be held in place while the bead pellet 6116 is moved away from the combined droplet 6114. The bead pellet 6116 can be moved away and separated from the combined droplet 6114 by, for example, moving the magnetic field (e.g., by moving the magnet generating the magnetic field) that is engaging the bead pellet 6116 away from the combined droplet 6114. In some embodiments, the combined droplet 6114 can be actively immobilized through actuation of the electrodes in contact with the droplet and/or surrounding the droplet. Alternatively or in addition, the droplet 6114 can be passively immobilized through natural adhesive forces between the droplet and substrate on which the droplet is contacting, as well as physical structures, such as retaining walls that partially surround the combined droplet 6114 while having an opening for passing the bead pellet 6116. As shown in FIG. 61C (frames i and ii), an aqueous droplet 6118 can be moved over the bead pellet 6116 to resuspend the beads with the bound analyte. See Example 3 described below for an embodiment of this procedure used for miRNA purification.

Liquid Hydrophobic Shells

In addition to the examples provided above, in some variations evaporation of an aqueous reaction droplet in an air-matrix DMF apparatus may include the use of a liquid material that forms a protective shell or layer over the aqueous droplet at temperatures below 37 degrees (e.g., at temperatures of about 4 degrees C. and above, e.g., 10 degrees C. and above, 15 degrees C. and above, 20 degrees C. and above, 25 degrees C. and above, etc. including nonpolar material that is liquid at 25 degrees C. and below, 22 degrees C. and below, 20 degrees C. and below, 18 degrees C. and below, 15 degrees C. and below, etc.). In any of these variations, the hydrophobic (and in some variations, polar) liquid material may be a "liquid wax" (e.g., such as a paraffin wax having a low melting point).

The liquid wax encapsulates or surrounds a reaction droplet and may include one or more non-polar compounds comprising hydrocarbon oils, silicone oils, fluorinated oils, plant-based oils, or any combination thereof. In some embodiments, the liquid wax may be liquid paraffin oil, mineral oil or a linear hydrocarbon molecule having more than 10 backbone carbons (e.g., hexadecane). In yet other embodiments, the liquid wax may be liquid paraffin oil and/or mineral oil. In some further embodiments, the liquid wax may be liquid paraffin oil.

In various embodiments of the composition, the liquid wax may have a density from about 0.75 g/ml to about 0.90 g/ml at 20° C. In some embodiments, the liquid wax may have a density of about 0.77 g/ml. In various embodiments of the composition, the liquid wax may have a contact angle from about 20 to about 65 degrees. In some embodiments, the liquid wax may have a contact angle of about 30 to about 35 degrees.

In some embodiments, a shell or coating of wax, which may be a liquid wax, may further include a non-ionic surfactant. In some embodiments, the non-ionic surfactant may be Brij 93, Span 20, Span 40, Span 60, Span 65, Span 80, Span 85, 1-Stearoyl-rac-glycerol, phosphatidylcholine (lecithin), Sorbitan sesquioleate, Tetronic 90R4, Tetronic 701, Pluronic® L-31, Pluronic® L-61, Pluronic® L-81, Pluronic® L-121, Pluronic® 31R1, Brij 52, MERPOL® A, or any combination thereof. In some embodiments, the lipophilic mobilizing component may be Brij 93.

The composition may include a non-ionic surfactant present in a concentration (v/v %) from about 0.001% to about 10%; about 0.001% to about 1.0%; about 0.001% to about 0.10%; about 0.01% to about 10%; about 0.01% to about 1.0%; about 0.01% to about 0.10%, or any value therebetween. In some embodiments, the non-ionic surfactant may be present in a concentration (v/v %) from about 0.01% to about 0.10%.

As mentioned above, digital microfluidics (DMF) enables real-time, precise, and highly flexible control over multiple samples and reagents, including solids, liquids, and harsh chemicals, without need for pumps, valves, or complex arrays of tubing. In DMF, discrete droplets of nanoliter to microliter volumes are dispensed from reservoirs onto a planar surface coated with a hydrophobic insulator, where they are manipulated (transported, split, merged, mixed) by applying a series of electrical potentials to an embedded array of electrodes. For many applications it is most convenient to carry out DMF on an open surface, such that the matrix surrounding the droplets is ambient air. However, use of the air-matrix format necessitates accounting for droplet evaporation, especially when the droplets are subjected to high temperatures for long periods of time. In some instances, evaporation is considered a desirable feature, as it can facilitate concentration and isolation of solutes of interest.

In biochemical contexts, however, evaporation may otherwise limits the utility of air-matrix DMF, because enzymatic reactions are often highly sensitive to changes in reactant concentration. To counteract evaporation, described herein are multiple methods and systems (including those discussed above) by which the (typically aqueous) biochemical reaction droplet is maintained over a range of temperatures (e.g., 37-100° C.) and incubation times (>2 hr).

In some variations, the methods and apparatuses include encapsulating a reaction droplet in a droplet of liquid wax while keeping the reaction droplet stationary within the digital microfluidics air gap. The liquid wax may be added to the aqueous droplet by combining it (e.g., by actuating the DMF apparatus to move the aqueous droplet into contact with a droplet of liquid wax (or other immiscible liquid; the immiscible liquid may have a vapor point that is above that of water, and/or above the temperature applied to the droplet). For example, FIG. 63 shows one example of an aqueous reaction droplet 6303 that is actuated by the DMF apparatus to move within the air gap. The droplet may be combined with a (e.g., stationary) droplet of liquid wax 6306' within the air gap. The digital microfluidic electrodes (selected individual electrodes 6304 of the entire grid (not shown) in FIG. 63) may underlie the DMF air gap, beneath the dielectric and hydrophobic layer(s). In FIG. 63, the liquid wax may more generically be any fluid that is immiscible and nonreactive with the aqueous fluid in the reaction droplet and preferably has a vapor point above the aqueous fluid (including hydrophobic materials); for convenience it may be referred to herein as "liquid wax".

The liquid wax may form a shell, layer, coating, etc. over the aqueous droplet. The shell or layer may be uniform around the aqueous droplet, or non-uniform. In some variations, the reaction droplet and the liquid wax shell or layer may kept substantially fixed in position within the air gap of the DMF apparatus, including a thermal control region (e.g., when thermally cycling or otherwise modifying the temperature of the aqueous reaction droplet). This may keep the liquid wax layer at approximately a uniform thickens around the perimeter of the aqueous reaction droplet.

In some variations, it may be beneficial to use a conductive material as the liquid wax coating. For example, described herein are conductive liquid wax coatings that may be moved by DMF within the air gap. Conductive (including ionic) liquid wax materials may enable pinning and/or controlling of the liquid wax droplet around the aqueous reaction droplet by electrowetting forces. This may allow the reaction droplets coated with a liquid wax material to be continuously actuated to ensure positioning.

A conductive liquid wax may made conductive (and therefore moveable by DMF) by infusion with one or more ions (e.g., by infusion with one or more ionic liquids), such as, for example, 0.001-50% v/v (e.g., between 0.01-40% v/v) of one or more of: Methyl-trioctylammonium bis(trifluoromethylsulfonyl)imide, 1-Hexyl-3-methylimidazolium hexafluorophosphate, Trihexyltetradecylphosphonium bis (2,4,4-trimethylpentyl)phosphinate, Trihexyltetradecylphosphonium decanoate, Trihexyltetradecylphosphonium bromide, Trihexyltetradecylphosphonium chloride, Trihexyltetradecylphosphonium bis(trifluoromethylsulfonyl)amide, 1-Butyl-1-methylpiperidinium bis(trifluoromethylsulfonyl)imide, 1-Hexyl-3-methylimidazolium tris (pentafluoroethyl)trifluorophosphate]. Alternatively or additionally, the liquid wax material may be made conductive by infusion with one or more of (including between 0.001-50% v/v, e.g., between 0.01-40% v/v): conductive nanoparticles (carbon nanotubes, silver, gold, aluminum, copper, indium tin oxide, chromium), etc. The conductivity of the liquid wax relative to the aqueous reaction droplet can be modified (by varying the type and/or amount of ionic/conductive materials included, e.g., from the list above or others) to allow precise control of reaction droplet versus wax droplet.

A conductive liquid wax material may serve as a droplet carrier to avoid contamination by surface fouling (e.g., in case a reagent is fouling the surface). In some variations the liquid wax material may be shuttled underneath a reservoir's dispensing zone so that dispensed reagent gets sheathed by the conductive liquid wax instead of contacting the hydrophobic surface directly; movement of the aqueous droplet within the air gap may be continuously protected by the shell of conductive liquid wax.

For example, FIG. 64 illustrates dispensing an aqueous droplet 6403 directly in contact with a conductive liquid wax 6406 so that the aqueous droplet is protected on the bottom (and potentially on all sides, including between the top and/or bottom surfaces of the layers forming the air gap). An aqueous droplet is dispensed form a reagent reservoir 6431, which may be disposed within or on the upper plate 6405 of the DMF apparatus or cartridge for a DMF apparatus into the air gap 6433 and onto a conductive liquid wax 6406. Once the dispensed droplet 6403 is coated, both the reaction droplet 6403 and the shell of conductive liquid wax (e.g., immiscible liquid) 6406 may be moved by DMF, e.g., actuating driving electrodes 6404 of the bottom plate 6407 within the air gap. In some variations, differences in the conductivity may be used to separately drive the aqueous droplet relative to the shell of conductive liquid wax, allowing separation of the two (see also, the removal of the liquid wax shell, described below in reference to FIGS. 75A-75C).

In any of these variations it may be beneficial to hold or pin the shell of liquid wax around the aqueous reaction droplet. For example, FIGS. 65 and 66 illustrate methods of holding a liquid wax shell around an aqueous reaction droplet on the surface of a DMF apparatus having actuation electrodes or a cartridge disposed thereupon (not shown). This may be referred to herein as pinning the liquid wax shell around the reaction droplet. In FIG. 65, a plurality of adjacent droplets (water and/or ionic liquid) may be used to pin the liquid wax around the reaction droplet. For example, the liquid wax may be pinned around the reaction droplet, housing the reaction droplet in a droplet of liquid wax, by pinning the liquid wax droplet 6506 at three or more positions around the stationary aqueous reaction droplet. In FIG. 65, four pinning (aqueous) droplets 6515 are used at each of the four corners within the shell of the liquid wax 6506, holding the liquid wax more uniformly around the central aqueous reaction droplet 6503. In this example, two or more (e.g., four) pinning droplets 6515 of water and/or ionic liquids droplets that are immiscible with the liquid wax shell help hold the position of the liquid wax relative to the reaction droplet 6503. This may help ensure the liquid wax droplet stays stationary and completely surrounds the reaction droplet.

Alternatively or additionally, FIG. 66 illustrates an example of a liquid wax coated reaction droplet that is held with in a sub region 6633 of the air gap, between upper plate 6605 and lower plate 6607, having actuation electrodes 6604, where the sub region 6633 has a greater height than the adjacent regions of the air gap, forming a chamber that may hold the coated droplet stationary. In FIG. 66, the reaction droplet 6603 is coated by a liquid wax 6606 and held within the chamber (formed by the dome region 6633) having a greater local spacing within the air gap (formed by a recess within the upper plate of the DMF apparatus/cartridge). This variation may include a dome or rectangular or triangular structure (e.g., a 1×1 to 25×25 mm region) in the top plate may help pin the reaction droplet that is coated with the liquid wax material.

FIGS. 68 and 69 illustrate other examples of an apparatus and method for pinning a droplet coated by a liquid wax material. In these examples, the reaction droplet 6803 is shown coated with a liquid wax material 6806. However, the droplet maybe further retained and protected by including a barrier (e.g., a fence, wall, stop, etc.) formed of a hydrophobic, oleolophilic, hydrophilic, etc., material at least partially surrounding the encapsulated (coated) reaction droplet. The barrier may form a chamber that is open on one or more sides. The barrier may extend from the top to the bottom of the air gap, or partially into the air gap. For example, the barrier may be formed of a material including a wax (e.g. paraffin) such as a polymeric material mixed with a paraffin. In FIG. 68, a chamber in the air matrix is formed by the barrier; the chamber may be any appropriate size, e.g., 1×1 to 25×25 mm. In FIG. 68, the chamber is formed by a fence of a hydrophobic, oleophilic and/or hydrophilic fence. For example, the barrier may be formed, e.g., of a material such as an acrylic, polycarbonate, Parafilm®, DuraSeal™, high melting temperature fluorowaxes/solid ski waxes, etc. The barrier may be formed as part of the top or bottom plate. In use, the barrier may pin the wax droplet around the reaction droplet. As shown in FIG. 68, the wax droplet 6806 surrounds the aqueous reaction droplet 6803 and is held within the open chamber in the air gap formed by the barrier 6805. One or more (e.g., a plurality of) air holes 6807 through the top of bottom plates opening in to the air gap may be included. The via holes may be formed in the top plate to release air bubbles (that can otherwise displace the reaction droplet) that may form during heating/incubation.

FIG. 69 illustrates another option in which a two-membered barrier (e.g., fence, rails, etc.) 6905 (optionally without via holes) is shown retaining the liquid wax 6806 encapsulating a reaction droplet 6803. In this example, air bubbles may readily vent on the ends of rails. This example may be used with a conductive liquid wax. For example, a conductive liquid wax can be shuttled to the reaction in order to ensure the aqueous droplet does not come in contact with air and evaporates.

Pinning Features.

The solid wax walls shown in FIGS. 68 and 69 may also be used to pin the liquid shell/coating material on the aqueous droplet (e.g., the liquid wax) so that it both helps retain the droplet in a predetermined position, but may also center or maintain the shell/coating over the droplet, as shown. In general, any of the devices described herein may include one or more (or two or more, etc.) pinning region that include two or more (e.g., 3 or more, 4 or more, etc.) pins, typically at the perimeter of the pinning region, that extend into the air gap to help retain the material within the pinning region. These pins may be formed of a hydrophobic and/or nonionic material that engages with the coating material (e.g., the liquid wax). The pins may be on just one side of the air gap (e.g., the top) or may extend from just one side (e.g., just from the top). Pins may be protrusions that protrude into the air gap for a limited distance (e.g., less than 50%, less than 40%, less than 30%, less than 25%, less than 20%, less than 15%, less than 10%, etc.) into the air gap. The pins may permit the droplet to move under or around the pin. In some variations the pins may be formed flush with the top surface (or in some cases, the bottom surface) of the air gap, as discrete regions of an oleophilic and/or hydrophilic material (or a nonionic material) that preferentially engages with the shell (e.g., liquid wax) material. In some variations the pin is a cylindrical, spherical or pyramidal protrusion into the air gap.

For example, in FIGS. 70 and 71A-71C illustrate examples of a pinning region including a plurality of pins (which may be referred to as partial barriers) that may pin the encapsulated droplet (and particularly the liquid wax encapsulating the reaction droplet). In FIG. 70, the top of the air gap includes a plurality of pins (configured as protrusions) 7021 extending into the air gap (e.g., pillars, posts, tabs, etc.), directed towards the actuation electrodes 7004 disposed adjacent to the substrate or bottom plate 7007. The protrusions 7021 may be formed of a hydrophobic, oleophilic and/or hydrophilic material. The protrusions may be disposed on the inner surface of the upper plate 7005. In some variations, the protrusions are formed as part of the top plate 7005. The protrusions may help pin the liquid wax around the reaction droplet. In FIG. 70, the majority of the air gap region may include the protrusions 7021. Alternatively in some variations only one or more local regions (pinning regions) may include protrusions. For example, in FIG. 71A, only a sub-region of the air gap includes the pins (protrusions 7021). (e.g., a selected region of top plate of the air gap includes protrusions).

FIG. 71B shows an example of a portion of an air gap in a cartridge including pins (configured as protrusions 7021') extending from the upper plate 7005 into the air gap 7026. FIG. 71C is a similar embodiment in which the upper plate 7005 includes a plurality of pins 7021" formed flush (or substantially flush) against the upper plate, as shown. The surfaces of the pins may engage with the shell (e.g. coating of liquid wax 7006) on the aqueous droplet 7003 and weakly hold the shell region in place. This may prevent unintentional movement of the droplet and/or may help center the aqueous droplet in the shell. The droplet and shell may be readily moved away from the pins by electrowetting.

Pins (e.g., protrusions) may be formed from materials inserted through part of an upper plate of a DMF apparatus or a cartridge for use therein, as shown in FIGS. 72A-72B. FIG. 72A is a top view down, showing the placement of the protrusions 7221, which is designed to keep a droplet 7227 in place within the thermal zone. For droplet 7227, the liquid wax shell or coating encapsulating an aqueous reaction droplet is not shown, for clarity, but is present. The protrusions may be present at the perimeter of a thermal zone within the air gap in order to maintain the droplet within the thermal zone while heating continues. FIG. 72B shows a lateral projection through the region including two of the protrusions 7221, contacting the edge of the liquid wax encapsulated droplet 7227 between the two plates of the DMF apparatus or two plates of a cartridge as described herein for use within an air-matrix DMF apparatus. Accordingly, as shown in FIG. 72B, the pins (protrusions 7221) may be inserted to pass through the top plate 7205, having a conductive layer 7205' and a hydrophobic layer 7209, which may be part of the top plate or may be part of a removable cartridge that may operate within the DMF apparatus. Alternatively, the protrusions may be formed upon the inner surface of the hydrophobic layer 7209, and extend into the air gap. The droplet 7227 contacts the hydrophobic layer 7209 forming the upper inner surface of the air gap 7233. The droplet 7227 is disposed upon a second hydrophobic layer 7211 which is the inner surface of a lower layer forming the bottom of the air gap 7233. Hydrophobic layer 7211 may be part of the lower plate of the DMF apparatus having a plurality of actuation electrodes 7204 disposed upon a lower substrate 7207 or hydrophobic layer 7211 may be a lower portion of a removable cartridge as described in more detail herein. Each protrusion is disposed adjacent to or extending from the hydrophobic layer 7209, and partially into the air gap, and each protrusion does not extend completely across the air gap.

As mentioned, protrusions may alternatively be deposited or formed on the inner surface of the upper plate forming the air gap.

While only one thermal zone is illustrated in FIGS. 72A-72B, a DMF apparatus or a removable cartridge for use therein, may have a plurality of thermal zones each having a plurality of pins arranged therein. In each thermal zone, the plurality of pins may include 2, 3, 4, 5, 6, 7, 8, 9, 10 or more pins. In some variations, there may be between two to five pins within a thermal zone. In some other variations, there may be between two to four pins.

The pins may be made or formed from hydrophobic, oleophilic or hydrophilic material. Such materials include but are not limited to silicone rubbers, fluorosilicones, nitrile rubber, natural rubber, low density polyethylene, butyl rubber, polystyrene, nylons, perfluorinated polymers such as Teflon™, and the like. In some variations, the plurality of protrusions may include silicone rubber. Any of these pins may be configured to prevent or reduce nucleation of air bubbles within the droplet.

For example, in some variations, the protrusions may be made of a conformable or soft material such as silicone rubber. The conformability of a polymer such as silicone rubber will permit the protrusion to completely fill a through-hole through which the material protrudes through an upper plate of a DMF apparatus or a cartridge for a DMF apparatus. When the conformable protrusion (which may be formed like a pillar or have any other suitable shape as described herein) completely fills a through hole, less nucleation of bubbles occurs at the protrusion pinning the droplet while incubations at elevated temperatures are conducted. This reduction of nucleation limits displacement forces acting to eject the droplet from the thermal zone.

The plurality of protrusions may each have a vertical dimension extending between about 0.1% to 99% (e.g., less than 80%, less than 75%, less than 70%, less than 60%, less than 50%, less than 40%, less than 30%, less than 25%, less than 20%, less than 10%, etc., such as between 0.01% and 50%, between 0.01% and 40%, between 0.01% and 30%, etc.) into a vertical dimension of the air gap. In other variations, the plurality of protrusions may each have a vertical dimension extending less than about 80%, less than about 70%, less than about 60%, less than about 50%, less than about 40%, less than about 30%, less than about 20%, less than about 10%, less than about 5%, less than about 4%, less than about 3%, less than about 2%, less than about 1%, or less than about 0.5% into the vertical dimension of the air gap. In other variations, the plurality of protrusions may each have a vertical dimension extending about 0.1% to about 20%; about 0.5% to about 15%, or about 0.1% to about 12% into the vertical dimension of the air gap.

It may be useful to limit the extension of the protrusions into the air gap to reduce the amount of force needed to drive the reaction droplet away from the thermal zone after heating is completed. It may be useful to limit the amount of force needed to drive the reaction droplet away for efficient automation of processes within the DMF apparatus. However, in other variations, increased extension of the protrusions into the air gap can provide increased pinning capability. Driving the reaction droplet to exit after such use can be accomplished as described below.

In some variations of the apparatus or removable cartridge for use therein, a vertical dimension of the air gap between a surface facing the air gap of the first hydrophobic layer and a surface facing the air gap of the second hydrophobic layer may be between about 0.5 mm to about 3 mm; about 0.7 mm to about 2 mm, about 0.8 mm to about 1.5 mm or about 0.9 mm to about 1.2 mm.

In some variations of the apparatus, the plurality of protrusions may each have a vertical dimension extending between 0.01 mm to 1 mm into the air gap, for example, for DMF apparatuses and/or removable cartridges having an air gap of about 0.9 mm, about 1.0 mm, about 1.1 mm, or about 1.2 mm, for use therein. The plurality of protrusions, in some variations, can nearly, but not entirely reach to the opposite side of the air gap. The protrusions may extend from the surface of the plate on which or through which the protrusions are formed, and have a vertical dimension from that surface of about 0.01 mm about 0.05 mm, about 0.1 mm, about 0.2 mm, about 0.3 mm, about 0.4 mm, about 0.5 mm, about 0.6 mm, about 0.7 mm, about 0.8 mm, about 0.9 mm, or about 1.0 mm. In some other variations, the plurality of protrusions may each have a vertical dimension extending between about 0.01 mm to about 0.3 mm; about 0.01 mm to about 0.2 mm; about 0.03 mm to about 0.2 mm; about 0.03 mm to about 0.1 mm or about 0.05 mm to about 0.2 mm into the vertical dimension of the air gap.

In some variations of the apparatus, each of the plurality of protrusions may have a lateral dimension on the surface where the protrusions are formed thereupon or protrude therethrough of between about 0.2 mm to about 3.0 mm, about 0.5 mm to 2.8 mm, about 0.6 mm to about 2.5 mm, about 0.7 mm to about 2.0 mm, about 0.8 mm to about 1.2 mm or about 0.9 mm to about 1.1 mm. In some variations, each of the plurality of protrusions may have a lateral dimension on the surface of between 0.8 mm and 1.2 mm.

The protrusions may have any suitable shape. In some variations, the lateral dimension may be a diameter of each of the plurality of protrusions (e.g., the protrusion has a round or oval cross section). In some variations, each of the plurality of protrusions may have a polygonal shape on the surface of the second hydrophobic layer, including but not limited to square, rectangular, pentagonal and the like, and the lateral dimension is a dimension spanning a largest horizontal dimension of the polygonal shape. Alternatively, the protrusion may have a many sided or irregular cross-sectional form. The vertical elevation of the protrusion may be a columnar or pillar shape, having any number of angles to the column or pillar. In other variations, the protrusion may have a conical or spherical shape, or any kind of irregular shape.

In some variations, each of the plurality of protrusions may be disposed at a perimeter of a region on the surface of the DMF apparatus, or a removable cartridge designed for use therein, having an area of between about 1 $mm^2$ to about 625 $mm^2$; about 1 $mm^2$ to about 500 $mm^2$; about 1 $mm^2$ to about 400 $mm^2$; about 1 $mm^2$ to about 300 $mm^2$; about 1 $mm^2$ to about 200 $mm^2$; about 1 $mm^2$ to about 100 $mm^2$; about 1 $mm^2$ to about 50 $mm^2$; or any value therebetween. In some variations, each of the plurality of protrusions may be disposed about or at a perimeter of the thermal zone portion of the air gap, e.g., the protrusions are not located in the center of the thermal zone portion of the air gap. Each of the protrusions may be disposed such that a combined reaction droplet and a liquid wax shell surrounding it may enter between the protrusions or can pass through a gap between the protrusions to enter and exit a thermal zone.

Thus, an air-matrix digital microfluidic (DMF) apparatus is provided, the apparatus including: a first plate having a first hydrophobic layer; a second plate having a second hydrophobic layer; and an air gap formed between the first and second hydrophobic layer. The air-matrix digital microfluidic (DMF) apparatus further includes a plurality of actuation electrodes adjacent to the first hydrophobic layer; a thermal regulator arranged to heat a thermal zone portion of the air gap. The air-matrix digital microfluidic (DMF) apparatus further includes a plurality of protrusions facing the air gap in the thermal zone portion of the air gap, where each protrusion is disposed adjacent to or extending from the second hydrophobic layer and partially into the air gap, further where each protrusion does not extend completely across the air gap; and a controller configured to apply energy to the actuation electrodes to move a droplet in the air gap.

Additionally, a cartridge for a digital microfluidics (DMF) apparatus is provided, the cartridge having a bottom and a top, the cartridge including: a sheet of dielectric material having a first side and a second side, the first side forming an exposed bottom surface on the bottom of the cartridge, where at least the second side of the sheet of dielectric material includes a first hydrophobic surface; a top plate having a first side and a second side and a thickness therebetween; a second hydrophobic surface on the first side of the top plate; an air gap separating the first hydrophobic layer and the second hydrophobic layer; and a plurality of protrusions facing the air gap, where each protrusion does not extend completely across the air gap, further where the plurality of protrusions are configured to pin a droplet within a region of the air gap. In some variations of the cartridge, the cartridge may further include a tensioning frame holding the sheet of dielectric material in tension so that it is substantially flat. In some variations of the cartridge, each of the plurality of protrusions may be disposed adjacent to or extending from the second hydrophobic surface.

In some variations of the apparatus or cartridge, the second hydrophobic layer may be disposed on a first side of the second plate and the second plate further includes a channel extending from the surface facing the air gap through the second plate to a second side of the second plate, and where the channel is disposed opposite to a perimeter of the thermal zone. The DMF apparatus and/or cartridge may have any combination of features as described above.

Turning to FIGS. 73A-C and 74A-C, methods for using the protrusions may be described. In FIGS. 73A-73C, a method is shown for moving a reaction droplet 7303, having a liquid wax shell 7306 surrounding it to a thermal zone 7301 by DMF, as shown in FIG. 73A. The wax shell 6306 is pinned to the protrusions 7321, which have shapes or distribution on the surface like any protrusion described above. The protrusions 7321 may have a vertical dimension extending into the air gap of less than about 40%, less than about 30%, less than about 20%, less than about 10%, less than about 5% or less than about 1% of the vertical dimension of the air gap Pinning permits incubation at elevated temperatures to be performed without displacing the reaction droplet 7303, as shown in FIG. 73B. As mentioned above, protrusions that do not propagate bubbles are helpful in keeping the reaction droplet in contact with the thermal zone as desired. When the incubation is complete, the combined reaction droplet 7303/wax shell 7306 may be driven out of the thermal zone using DMF actuation. The protrusions, while sufficiently extended into the air gap to pin and retain the reaction droplet/wax shell within the thermal zone, do not extend sufficiently to prevent the DMF forces from moving the combined droplet. This is especially helpful for automation of the moving, incubating and exiting process of the method.

In other variations, such as shown in FIGS. 74A-74C, the DMF apparatus or a removable cartridge for use therein, has a channel hole 7411 in the upper plate of the apparatus or cartridge at the edge of the thermal zone 7401. After incubation is completed, the reaction droplet 7403 with its liquid wax shell 7406 is driven to the channel hole 7411 within the thermal zone 7401. A portion of the reaction droplet/wax shell is pulled up into the channel 7411, until a small portion of the original volume of the combined droplet/wax shell remains on the surface of the apparatus or cartridge. Driving electrodes are turned on, to begin to drive the remnant volume out of the thermal zone. As the leading edge of the combined droplet exits the thermal zone, the remainder of the combined droplet/wax shell is re-introduced to the DMF/cartridge surface. In this pump-assisted method of exiting, additional pinning can be used during the incubation, while still affording exit from the thermal zone at the completion of the protocol.

For this variation, a DMF apparatus or a removable cartridge for use therein is employed that has a channel hole 7411 in the upper plate of the apparatus or cartridge. The protrusions may extending more than about 20-30% into the air gap, and may extend more than about 30%, more than about 40%, more than about 50%, more than about 60%, more than about 70%, more than about 80%, or more than about 90% into the vertical dimension of the air gap. The reaction droplet 7403/wax shell 7406 is moved into the thermal zone 7401 and pinned to the protrusions 7421 as described above for FIGS. 73A-73B. After incubation is completed, the reaction droplet 7403 with its liquid wax shell 7406 is driven to the channel hole 7411 within the thermal zone 7401. A portion of the reaction droplet/wax shell is pulled up into the channel 7411, and breaks the contact of the wax shell 7406 with the protrusions 7421. A small portion of the original volume of the combined droplet/wax shell remains on the surface of the apparatus or cartridge. Driving electrodes are turned on, to begin to drive the remaining volume out of the thermal zone 7401. As the leading edge of the combined droplet exits the thermal zone, the remainder of the combined droplet/wax shell is re-introduced to the DMF/cartridge surface from the channel 7411, and total volume of the reaction droplet 7403/wax shell 7406 is driven out of the thermal zone 7411. In this pump-assisted method of exiting, additional pinning can be used during the incubation, while still affording exit from the thermal zone at the completion of the protocol.

Thus, a digital microfluidics method is provided, the method including: driving a droplet within an air gap of an air-matrix digital microfluidic (DMF) apparatus to a sub-region of the air gap by electrowetting; pinning the droplet within the sub-region by contacting the droplet with two or more protrusions extending from an upper surface of the air gap into the air gap, where the two or more protrusions extend only partially into the air gap; and performing one or more manipulations on the pinned droplet. The method may further include coating the aqueous reaction droplet with a liquid wax, where pinning the droplet includes pinning at least the liquid wax coating.

In some variations, performing one or more manipulations may include heating the sub-region of the air gap including the droplet. In some variations, the method may further include driving the droplet away from the sub-region and off of the protrusions by electrowetting. In some variations of the method, the two or more protrusions may include two to ten protrusions. In some variations, the two or more protrusions may include four protrusions. In some variations, each of the two or more protrusions may have a cylindrical or rectangular shape.

In some variations of the method, each of the two or more protrusions may have a lateral dimension on the upper surface of the air gap between 0.5 mm to 2.8 mm. In some variations, each of the two or more protrusions may have a lateral dimension on the upper surface of the air gap between 0.8 mm and 1.2 mm. In some variations, each of the two or more protrusions may have a vertical dimension extending into the air gap of 0.1% to 99% of a vertical dimension of the air gap. In some variations, each of the two or more protrusions may have a vertical dimension extending into the air gap of 0.1% to 20% of a vertical dimension of the air gap.

In some variations of the method, performing one or more manipulations may include performing at least one of: vortexing a plurality of magnetic beads within the pinned droplet, cooling the sub-region of the air gap including the pinned droplet, detecting the pinned droplet; driving the pinned droplet to a channel hole within the sub-region of the air gap; aspirating the droplet into a channel of the channel hole; and driving the droplet from the sub-region by electrowetting.

In another aspect, a method of heating an aqueous reaction droplet in an air-matrix digital microfluidic (DMF) apparatus is provided, the method including: coating the aqueous reaction droplet with a liquid wax material within an air gap formed between a first hydrophobic layer of a first plate and a second hydrophobic layer of a second plate of the DMF apparatus; pinning the liquid wax coating of the aqueous reaction droplet to at least two protrusions within a sub-region of the air gap, thereby distributing the liquid wax around the reaction droplet; and heating at least the sub-region of the air gap including the coated aqueous reaction droplet, whereby the liquid wax coating limits or prevents evaporation from the aqueous reaction droplet.

In some variations, pinning may include pinning the liquid wax coating to the at least two protrusions disposed adjacent to the second hydrophobic layer of the second plate.

In some variations, the at least two protrusions may include two to ten protrusions. In some variations, the at least two protrusions may include four protrusions. In some variations, each of the at least two protrusions may have a cylindrical or rectangular shape. In some variations, each of the at least two protrusions may have a lateral dimension between 0.5 mm to 2.8 mm. In some variations, each of the at least two protrusions may have a lateral dimension between 0.8 mm and 1.2 mm. In some variations, each of the at least two protrusions may have a vertical dimension extending into the air gap of 0.1% to 99% of a vertical dimension of the air gap. In some variations, each of the at least two protrusions may have a vertical dimension into the air gap extending less than 40% or less than 30% of a vertical dimension of the air gap. In some variations, each of the two or more protrusions may have a vertical dimension extending into the air gap from 0.1% to 20% of a vertical dimension of the air gap.

In some variations, the method may further include vortexing a plurality of magnetic beads within the coated reaction droplet within the thermal zone.

In some variations, the method may further include moving the coated aqueous reaction droplet away from the sub-region of the air gap after completing heating. In some variations, moving may include driving the coated aqueous reaction droplet by energizing a sub-set of a plurality of driving electrodes adjacent to the first hydrophobic layer of the first plate of the DMF apparatus. In some variations, moving may further include withdrawing at least a portion of the coated aqueous reaction droplet from a surface of the air gap of the DMF apparatus before energizing the sub-set of the plurality of driving electrodes; and reintroducing the at least portion of the coated aqueous reaction droplet back to the surface of the air gap of the DMF apparatus as a front of the aqueous reaction droplet exits the sub-region. In some variations, withdrawing may include withdrawing the at least portion of the coated reaction droplet via a channel from a surface of the second hydrophobic layer of the second plate to at least partially through the second plate.

In some variations, the aqueous reaction droplet may be driven to the sub-region using a sub-set of a plurality of driving electrodes adjacent to the first hydrophobic layer of the first plate of the DMF apparatus.

In some variations, the first plate may include a bottom plate of a cartridge configured to be seated on a seating surface of the DMF apparatus including the plurality of actuation electrodes. In some variations, the second plate may include a top plate of the cartridge.

Local Humidification

In any of the variations described herein local humidity may be controlled within the air gap (that is otherwise open) by including one or more regions in which the reaction droplet may be surrounded by additional humidifying droplets. Thus, the reaction droplet may be surrounded with multiple neat droplets of water to humidify reaction droplet during heating/incubation. In some variations the surrounding droplets may be heated to the same temperature or to a higher temperature than the reaction droplet. In some variations, the region in which the reaction droplets is being heated may be partially enclosed within the air gap (e.g., by a barrier region, which may enhance the local humidity.

Oil/Wax Removal from Encapsulated Droplet

In any of the variations described herein in which an encapsulating fluid (e.g., liquid wax) material is used, the encapsulating fluid may be removed. The removal may include wicking the material (e.g., liquid wax) off of the reaction droplet. For example, as shown in FIGS. 75A-75C, in some embodiments, the liquid wax or oil 7506 that encapsulates the aqueous droplet 7503, can be separated from the aqueous portion of the droplet by using an oil absorbent wick 7504. The wick 7504 can be made of a hydrophobic material that selectively wicks away the liquid wax or oil 7506 while leaving the aqueous droplet 7503 behind. To help promote wicking, in some embodiments the wick 7504 can be also made from a porous and/or fibrous material that can be fabricated into a sponge-like structure. In other embodiments, the wick 7504 can be made of a nonporous material that simply adsorbs the oil onto its surface. In some embodiments, the wick 7504 can be made of two or more layers of material separated by a small gap(s), and the oil wicks into the gap. In some embodiments, the wick 7504 can be made of parafilm M, which is made primarily from polyolefins and paraffin waxes. Other hydrophobic polymers can be used to fabricate the wick.

The shape of the wick 7504 can vary. In some embodiments, the wick 7504 has tip 7508 that tapers into a point, corner, or other narrow tipped structure. In some variations the wick has a flat edge. In some embodiments, the tip 7508 has a width that is less than 0.1, 0.2, 0.3, 0.4, 0.5, 0.6, 0.7, 0.8, 0.9, or 1.0 of the diameter of the encapsulated droplet. In some embodiments, the wick has an edge or side with a plurality of tips that can be used to simultaneously separate the oil from a plurality of encapsulated droplets. The size of the wick, which may include the size of the gaps between the layers of wick, the surface area of the wick, and/or the volume of the wick, determines the volume of liquid oil or wax that can be absorbed. In some embodiments, the wick 7504 can be heated (i.e., above the melting point of the oil or wax) to ensure that the liquid oil or wax does not solidify in the wick during the wicking process.

The wick 7504 can be located within the air gap of the DMF device, such as between the top and bottom substrates (i.e., top plate and bottom plate of reusable device or between film and plate of disposable cartridge), so that the encapsulated droplet can be manipulated by the DMF device to make contact with the wick 7504. In some embodiments, the wick 7504 can be removable and replaceable from the DMF device, such as through a port or opening in the top or bottom substrate. In some variations, the wick may be movable within the air gap to make contact with the coated droplet. For example, a cartridge may automatically move a wick into (and/or out of) the air gap.

To separate the liquid oil or wax 7506 from the encapsulated aqueous droplet 7503, the aqueous/oil droplet is connected with wick tip 7508 by sequentially activating a path of electrodes to move the droplet towards the wick tip 7508, as shown in FIG. 75A. When the liquid oil or wax 7506 layer surrounding the aqueous droplet 7503 makes contact with the wick tip 7508, the liquid oil/wax phase is separated from aqueous droplet 7503 by adsorption into the wick 7508, as shown in FIG. 75B. When all or substantially all (i.e., at least 90%, 95%, 99%, or 100%) of the oil/wax has been absorbed into the wick 7508, the electrodes can be sequentially turned on to drive the remaining aqueous droplet 7503 away from the wick 7508, free of oil/wax. In some embodiments, the aqueous droplet loses less than 10, 5, 4, 3, 2, or 1 percent of its volume during the oil separation process.

Example 1: Device Fabrication and Assembly. DMF apparatuses that include embedded centrifuge tubes and/or well-plate wells (e.g., FIGS. 58B, 58C) were constructed by drilling 5.5 mm diameter holes into 3 mm thick PCB substrates, bearing copper (43 µm thick) plated with nickel (185 µm) and gold (3.6 µm) for electrodes and conductive traces. Tubes and wells were then inserted into holes. DMF devices with embedded wells (e.g., FIG. 58D) were fabricated with holes (5 mm diameter, 10 mm depth) drilled in 15 mm thick PCB substrates. Actuation electrodes (each 10 mm×10 mm) were formed by conventional photolithography and etching, and were coated with soldermask (~15 µm) as the dielectric. As shown in FIGS. 59A-59E, some of the electrodes were formed around and adjacent to the hole which served as the access point to reaction compartments. The electrical contact pads were masked with polyimide tape (DuPont; Hayward, CA), and the substrate was spin-coated with a 50 nm layer of Teflon-AF (1% wt/wt in Fluorinert FC-40, 1500 rpm for 30 sec) and then baked at 100° C. for 3 h. The top plate of the DMF device, consisting of a glass substrate coated uniformly with unpatterned indium tin oxide (ITO) (Delta Technologies Ltd; Stillwater, MN) with 5.5 mm diameter PDMS plugs was spin-coated with 50 nm of Teflon-AF, as described above.

Prototype devices fabricated as described above performed better than or as well as air-gap DMF apparatuses without reaction chambers.

Example 2: Quantifying evaporation prevention using waxes. To qualitatively evaluate the effect of wax bodies to prevent evaporation in our assays, loop mediated amplification (LAMP) reactions were executed while covered in liquid paraffin wax in tubes on the benchtop using a real-time PCR Machine. As shown in FIG. 76, the LAMP assay amplified miR-451, and the Ct values with and without paraffin were comparable (~13 cycles), indicating no significant effect on the assay. For LAMP on DMF, the reaction droplet (8 µL) was driven to a heating zone (as shown in FIG. 60A), and driven to location within the open chamber formed by a solid wax body. There, the droplet wet the solid paraffin wax wall which under subsequent conditional heating at 63° C. melted into liquid wax encircling the reaction volume. The encapsulated reaction droplet was maintained intact throughout the incubation time at 63° C. FIG. 77A shows a LAMP assay using paraffin-mediated methods, while FIG. 77B shows a LAMP assay using conventional methods. In FIG. 77A, the two upper traces are for a hemolyzed sampled while the two lower traces are for a non-hemolyzed sample. The two traces of each are to show repeatability of the runs using wax-mediated air matrix DMF. In FIG. 77B, the conventional LAMP assay for a hemolyzed sample are shown in upper two traces while the non-hemolyzed LAMP runs are shown in lower two traces. Again, the two upper and two lower traces each are to show result repeatability. The wax-mediated approach on DMF generated results comparable in Ct values to those generated by conventional LAMP in tubes as shown in FIGS. 77A and 77B.

Example 3: miRNA purification. Human Panel A beads from the TaqMan® miRNA ABC Purification Kit (Thermo Fisher Scientific). Aliquots of miRNA (4 ul), or "reaction droplets", were loaded onto the DMF platform and brought to an array of electrodes overlaying the heating zone such that the droplet came into contact with the paraffin wall. The heating zone was then heated (65° C., 2 min) to melt the paraffin around the droplet. Once the paraffin melted, the reaction droplets were driven away from the heating zone and merged with miRNA Binding Beads (4×10⁶ beads; FIG. 62A) in 2 ul of mineral oil (i.e., carrier droplet). After mixing, the droplets were incubated (30° C., 30 min) to allow miRNA to bind to the miRNA Binding Beads. Beads were captured by engaging an external magnet positioned below the bottom plate. Once a pellet was formed, the beads were recovered from solution by moving the magnet laterally along the bottom plate while simultaneously actuating the electrodes positioned below the reaction droplet (FIG. 62B). The miRNA Binding Beads were then re-suspended in water (4 ul) using the DMF platform and transferred to a centrifuge tube for elution of miRNA (70° C., 3 min; FIG. 62C). The efficiency of miRNA recovery from paraffin-encased miRNA droplets was evaluated against recovery from miRNA droplets without paraffin, but only in oil. RT-qPCR analysis of miRNA prepared by the system from samples with and without paraffin encasement generated comparable Ct values.

Example 4: PCR Reaction. Returning to FIG. 73A-73C, an aqueous reaction (RXN) droplet 7303 is surrounded by liquid wax droplet 7306 (e.g., n-hexadecane with 0.06% Brij) and is driven into a thermal zone 7301, that also includes a pinning region or zone (formed by four peripheral pins 7321) as shown in FIG. 73A. The wax-coated droplet (7303 within 7306) is pinned to the pillars, 7321 by contact with the silicone rubber of the pillars (see FIG. 73B). The protrusions (pinning pillars, extending from the inner surface of the plate forming the air gap) extend up to about 20% into the vertical dimension of the air gap. The aqueous reaction is maintained centered within the thermal zone by activating DMF electrodes. The reaction droplet undergoes thermocycling and the droplet detection feedback system described herein verifies the presence of the droplet at every PCR cycle (every 30 sec-1 min) at its centered position inside the thermal zone, still surrounded by the liquid wax shell (n-hexadecane with 0.06% Brij). After completion of the desired numbers of thermocycling, heat is withdrawn from the thermal zone. The reaction droplet still surrounded by the liquid wax shell is driven away from the thermal zone by DMF (See FIG. 73C). The use of protrusions extending less than about 20-30% into the air gap of the DMF apparatus or removable cartridge therein, provides for smooth automation of the introduction of the droplet to the thermal zone, incubation at elevated temperatures, and exit from the thermal zone, which may be employed in a wide variety of reaction protocols.

In some further examples of this method, the protrusions extend even less into the air gap, and may extend into about 0.1% of the vertical dimension of the air gap, providing enhanced movability away from the pinning protrusions. The extent of silicone rubber pillars protrusion could vary from 0-1 mm and the closest to 0 (between 100 µm to 0 µm) is ideal for the smooth automation of PCR entrance, incubation and exit.

A further variation of this experiment may include the use of protrusions extending more than about 20-30% into the air gap as illustrated in FIGS. 74A-C. For this variation, a DMF apparatus or a removable cartridge for use therein is employed that has a channel hole 7411 in the upper plate of the apparatus or cartridge. After incubation is completed, the reaction droplet 7403 with its liquid wax shell 7406 is driven to the channel hole 7411 within the thermal zone 7401. A portion of the reaction droplet/wax shell is pulled up into the channel 7411, and pump assisted exit is performed, as described above. In this pump-assisted method of exiting, additional pinning can be used during the incubation, while still affording exit from the thermal zone at the completion of the protocol.

Air-Matrix DMF Apparatus and Sub-Systems.

For many applications it can be most convenient to carry out DMF on an open surface, such that the matrix surrounding the droplets is ambient air. FIG. 1A illustrates one example of an air-matrix DMF apparatus. In general, the air-matrix DMF apparatus such as the one shown in FIG. 1A includes a plurality of unit cells 191 that are adjacent to each other and defined by having a single actuation electrode 106 opposite from a ground electrode 102; each unit cell may any appropriate shape, but may generally have the same approximate surface area. In FIG. 1A, the unit cells are rectangular. One or more droplets to be manipulated by the actuation electrodes may be isolated from the electrodes by a hydrophobic insulator. When an electrical potential is applied, charge accumulates on either side of the insulator, a phenomenon that can be exploited to make droplets move, merge, mix, split, and dispense.

In FIGS. 1A-1C, droplets (e.g., reaction droplets) fit within the air gap between the first 153 and second 151 plates (shown in FIGS. 1A-1C as top and bottom plates). The overall air-matrix DMF apparatus 100 may have any appropriate shape, and thickness. FIG. 1B is an enlarged view of a section through a thermal zone 115 of the air-matrix DMF shown in FIG. 1A, showing layers of the DMF device (e.g., layers forming the bottom plate). In general, the DMF device (e.g., bottom plate) includes several layers, which may include layers formed on printed circuit board (PCB) material; these layers may include protective covering layers, insulating layers, and/or support layers (e.g., glass layer, ground electrode layer, hydrophobic layer; hydrophobic layer, dielectric layer, actuation electrode layer, PCB, thermal control layer, etc.). Any of these surfaces may be rigid (e.g., glass, PCB, polymeric materials, etc.). The air-matrix DMF apparatuses described herein also include both sample and reagent reservoirs, as well as a mechanism for replenishing reagents.

In the example shown in FIGS. 1A-1C, a top plate 101, in this case a glass material (although plastic/polymeric materials, including PCB, may be used) provides support and protects the layers beneath from outside particulates as well as providing some amount of insulation for the reaction occurring within the DMF device. The top plate may therefore confine/sandwich a droplet between the plates, which may strengthen the electrical field when compared to an open air-matrix DMF apparatus (without a plate). The upper plate (first plate in this example) may include the ground electrode and may be transparent or translucent; for example, the substrate of the first plate may be formed of glass and/or clear plastic. However, although it is transparent, it may be coated with a conductive material and/or may include a ground electrode adjacent to and beneath the substrate for the DMF circuitry (ground electrode layer 102). In some instances, the ground electrode is a continuous coating; alternatively multiple, e.g., adjacent, ground electrodes may be used. Beneath the grounding electrode layer is a hydrophobic layer 103. The hydrophobic layer 103 acts to reduce the wetting of the surfaces and aids with maintaining the reaction droplet in one cohesive unit.

The second plate, shown as a lower or bottom plate 151 in FIGS. 1A-1C, may include the actuation electrodes defining the unit cells. In this example, as with the first plate, the outermost layer facing the air gap 104 between the plates also includes a hydrophobic layer 103. The material forming the hydrophobic layer may be the same on both plates, or it may be a different hydrophobic material.

The air gap 104 provides the space in which the reaction droplet is initially contained within a sample reservoir and moved for running the reaction step or steps as well as for maintaining various reagents for the various reaction steps. The air gap 104 formed between the inner surface (or lower surface) of the hydrophobic layer 103 of the upper plate (e.g., facing the air gap) and the inner surface (or upper surface) of the hydrophobic layer 103 of the lower plate (e.g., facing the air gap) may have a height (vertical dimension) of about 0.250 mm or greater (e.g., about 0.260 mm or greater, about 0.280 mm or greater, about 0.3 mm or greater, about 0.4 mm or greater, about 0.5 mm or greater, about 0.6 mm or greater, about 0.7 mm or greater, about 0.8 mm or greater, about 0.9 mm or greater, about 1 mm or greater, about 1.1 mm or greater, about 1.3 mm or greater, about 1.5 mm or greater, about 1.7 mm or greater, about 1.9 mm or greater, about 2 mm or greater, about 2.5 mm or greater, about 3 mm or greater, about 3.5 mm or greater, about 4 mm or greater, about 4.5 mm or greater, or about 5 mm or greater. In some variations, the height of the air gap may be between about 0.3 mm to about 5 mm, between about 0.5 mm to about 5 mm, between about 0.5 mm to about 4.5 mm, between about 0.5 mm to about 4 mm, between about 0.5 mm to about 3.5 mm, between about 0.5 mm to about 3 mm, between about 0.5 mm to about 2.5 mm, between about 0.5 mm to about 2 mm, between about 0.5 mm to about 1.5 mm, between about 0.5 mm to about 1 mm, between about 0.6 mm to about 5 mm, between about 0.6 mm to about 4 mm, between about 0.6 mm to about 3 mm, between about 0.6 mm to about 2 mm, between about 0.6 mm to about 1.3 mm, or any height therebetween.

Adjacent to the hydrophobic layer 103 on the second plate is a dielectric layer 105 that may increase the capacitance between droplets and electrodes. Adjacent to and beneath the dielectric layer 105 is a PCB layer containing actuation electrodes (actuation electrodes layer 106). The actuation electrodes may form each unit cell. The actuation electrodes may be energized to move the droplets within the DMF device to different regions so that various reaction steps may be carried out under different conditions (e.g., temperature, combining with different reagents, magnetic regions, pump inlet regions, etc.). A support substrate 107 (e.g., PCB) may be adjacent to and beneath (in FIGS. 1B and 1C) the actuation electrode layer 106 to provide support and electrical connection for these components, including the actuation electrodes, traces connecting them (which may be insulated), and/or additional control elements, including the thermal regulator 155 (shown as a TEC), temperature sensors, optical sensor(s), magnets, pumps, etc. One or more controllers 195 for controlling operation of the actuation electrodes and/or controlling the application of replenishing droplets to reaction droplets may be connected but separate from the first 153 and second plates 151, or it may be formed on and/or supported by the second plate. In FIGS. 1A-1C the first plate is shown as a top plate and the second plate is a bottom plate; this orientation may be reversed. A source or reservoir 197 of solvent (replenishing fluid) is also shown connected to an aperture in the second plate by tubing 198.

As mentioned, the air gap 104 provides the space where the reaction steps may occur, providing areas where reagents may be held and may be treated, e.g., by mixing, heating/cooling, combining with reagents (enzymes, labels, etc.). In FIG. 1A the air gap 104 includes a sample reservoir 110 and a series of reagent reservoirs 111. The sample reservoir may further include a sample loading feature for introducing the initial reaction droplet into the DMF device. Sample loading may be loaded from above, from below, or from the side and may be unique based on the needs of the reaction being performed. The sample DMF device shown in FIG. 1A includes six sample reagent reservoirs where each includes an opening or port for introducing each reagent into the respective reservoirs. The number of reagent reservoirs may be variable depending on the reaction being performed. The sample reservoir 110 and the reagent reservoirs 111 are in fluid communication through a reaction zone. The reaction zone 112 is in electrical communication with actuation electrode layer 106 where the actuation electrode layer 106 site beneath the reaction zone 112.

The actuation electrodes 106 are depicted in FIG. 1A as a grid or unit cells. In other examples, the actuation electrodes may be in an entirely different pattern or arrangement based on the needs of the reaction. The actuation electrodes are configured to move droplets from one region to another region or regions of the DMF device. The motion and to some degree the shape of the droplets may be controlled by switching the voltage of the actuation electrodes. One or more droplets may be moved along the path of actuation electrodes by sequentially energizing and de-energizing the electrodes in a controlled manner. In the example of the DMF apparatus shown, a hundred actuation electrodes (forming approximately a hundred unit cells) are connected with the seven reservoirs (one sample and six reagent reservoirs). Actuation electrodes may be fabricated from any appropriate conductive material, such as copper, nickel, gold, or a combination thereof.

In the example device shown in FIGS. 1A-1C, the DMF apparatus is typically integrated so that the electrodes (e.g., actuation electrodes and ground electrode(s)) are part of the same structure that may be loaded with sample and/or fluid. The electrode may be part of a cartridge, which may be removable. Although cartridges have been described (see, e.g., US20130134040), such cartridges have proven difficult to use, particularly when imaging through the device and when operating in an air-matrix apparatus.

In general, described herein are digital microfluidics apparatuses and methods. In particular, described herein are air-matrix digital microfluidics apparatuses, including systems and devices, and methods of operating them to process fluid samples. For example, a DMF apparatus may include a compact DMF driver/apparatus that is configured to work with a removable/disposable cartridge. The DMF driver/apparatus may include an array of drive electrodes that are adapted to align and secure a cartridge in position by applying negative and/or positive pressure at multiple points, and specifically at the electrode-contact points, on the cartridge. The cartridge may include an air gap that is open to the environment (e.g., to the air) via openings such as side (lateral) openings and/or top openings. The air gap may be formed between two dielectric layers. An upper, top, region may include one or more ground electrodes. The ground electrode may be advantageously formed of a non-transparent material that is patterned to include one or more windows that allow imaging through the top. These windows may be arranged over the electrode, so that the ground region extends opposite the drive electrodes and around and/or between the drive electrodes.

Any of the apparatuses described herein may also include a fluid application and extraction component (e.g., a fluid application and/or extraction device) that is connected through the top, or through the side of the cartridge, into the air gap. Any of the apparatuses described herein may include or use a non-polar jacketing material (e.g., a non-polar liquid such as a room temperature wax) that forms a protective jacket around the aqueous droplet(s) in the apparatus, and may be moved with the droplet. Also described herein are user interfaces for interacting with the apparatus, including user interfaces for controlling the apparatus to move, mix, combine, wash, magnetically concentrate, heat, cool, etc. These user interfaces may allow manual, automatic or semi-automatic entering, control and/or execution of a protocol.

Figure 2:
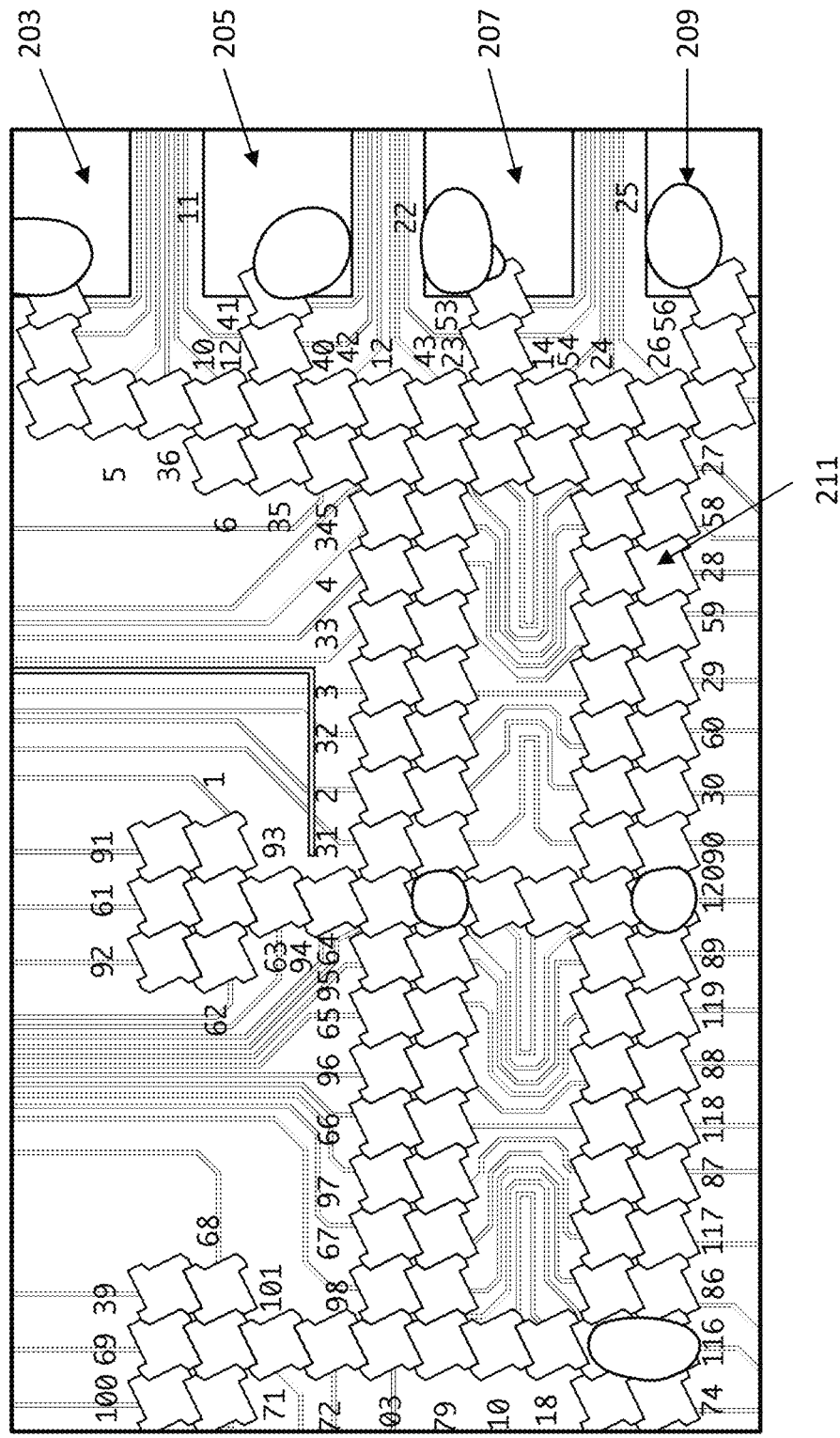
FIG. 2 is an example of a DMF surface using a rigid cartridge including the electrodes and an air-gap region, similar to that shown in FIGS. 1A-1C.

FIG. 2 illustrates an example of a DMF apparatus that is similar to the one shown in FIGS. 1A-1C. In FIG. 2, the DMF apparatus includes a plurality of drive electrodes 201 (which are shaped into non-square/non-rectangular shapes and positioned adjacent to each other in rows or lines. In FIG. 2, four reservoir regions 203, 205, 207, 209 are positioned on the right side, and may be preloaded or otherwise hold droplets of materials to be added during operation of the DMF apparatus. Some or all of the electrodes may be heated or cooled.

In the apparatus of FIG. 2, the DMF driving electrodes 211 are solid, planar electrodes. The application of energy between the driving electrodes and the ground or reference electrode result in movement of an aqueous (e.g. polar) droplet. In FIG. 2, the ground or reference electrode is formed as a conductive, transparent coating (e.g., ITO) on the upper plate, which is also clear (transparent). This allows the device to be monitored, including monitoring any of the cells, e.g., unit cells, from above the air matrix/air gap.

However, it would be beneficial to provide DMF apparatus apparatuses (e.g., devices, systems, etc.) that may be used with disposable cartridges that do not include the drive electrodes. FIGS. 3A and 3B show the different configurations of a DMF system that includes integrated drive electrodes (FIG. 3A) and a system in which the drive electrodes are part of the apparatus, but the cartridge includes only the ground electrodes (e.g., top plate), air gap and the dielectric bottom. For example, in FIG. 3A, the air gap is formed between the grounded top plate 303, and the drive electrodes and dielectric film 305 (e.g., a Teflon film). The drive electrodes and dielectric film may be part of a cartridge that includes the top plate, and may be separately attached onto the substrate (switch board 307) that connects to a main processor 309 and a power supply board 311.

In contrast, in FIG. 3B, the cartridge does not include the drive electrodes 313, but instead may include the top plate/ground electrode, dielectric and an air gap between them 315. As will be described in greater detail herein, a vacuum 316 (e.g., vacuum manifold) may be positioned beneath the electrodes 313 to apply pressure (e.g., between 50 kPa and 250 kPa, 50 kPa or greater, 60 kPa or greater, 70 kPa or greater, 80 kPa or greater, 90 kPa or greater, 100 kPa or greater, 110 kPa or greater, etc.) to fully secure the dielectric, and therefore the rest of the cartridge, to the apparatus. The electrodes may be supported on a substrate, such as a printed circuit board or switch board 317, which may also be connected to the main processor 319 and power supply 321. As shown in FIG. 3B, the dielectric film may also be hydrophobic (e.g., a Teflon film may be used) or may be treated, coated, sprayed, dipped into, etc., a hydrophobic material to make at least the side facing the air gap hydrophobic.

The seating surface of an exemplary DMF apparatus is shown in greater detail in FIGS. 4A-4C and FIGS. 10-12. In FIG. 4A, the seating surface includes an array of driving electrodes 401 (labeled in rows 0-9 and columns A-R). Each of these driving electrodes includes a central hole or opening through the electrode, through which a vacuum can be applied to hold the dielectric of a removable cartridge, which may be like any removable cartridge described herein, against the drive electrodes. In FIG. 4A, the seating surface also includes temperature sensors (thermistors 405) positioned between the electrodes in different orientations. FIG. 4B shows a slightly enlarged view of the seating surface, including the driving electrodes, showing a thermistor 405 between the driving electrodes. The vacuum openings 407 are more clearly visible in FIG. 4B. Any shape and size of driving electrodes may be used, including interlocking driving electrodes. In addition, the pattern of driving electrodes may be formed that is not monolithic; for example the electrode pattern may include open regions that do not include driving electrodes (e.g., regions surrounding driving electrodes, etc.) as shown in FIGS. 1A and 2.

Figure 4C:
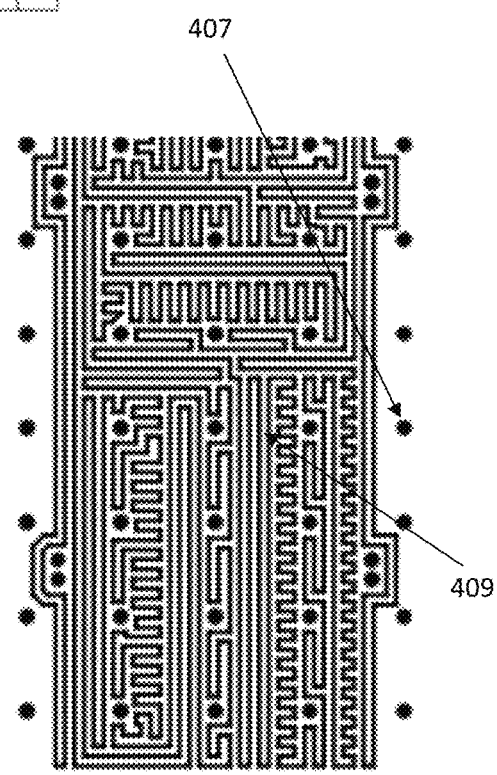
FIG. 4C illustrates a resistive heating layer that may be present beneath the electrode layer (such as is shown in FIG. 4B). One continuous, or multiple separate, trace(s) of resistive material may be used beneath the array. The black dots indicate the vacuum manifold (forming the plurality of vacuum openings through the electrodes. The resistive heating layer may be electrically isolated from the electrodes above them; the current applied through the resistive heating layer may be regionally controlled, by a controller. The controller may include PID control.

FIG. 4C shows an example of a heater that may be positioned underneath some of the drive electrodes, such as the sub-set of drive electrodes shown in FIG. 4B. In this example, resistive heating circuitry 409 may underlie the drive electrodes (e.g., embedded at any layer of the PCB forming the seating surface). In general, resistive heating and thermistors may be embedded at any layer of the electrode PCB board. The heater may be part of the PCB with the electrodes and thermistor, as shown in FIGS. 4A-4C. The current, and therefore the temperature of the driving electrodes and/or the adjacent dielectric (and therefore any droplet on the cell under the dielectric/driving electrode) may be regulated, e.g., by a PID control loop, in combination with the thermistor. To cool down the dielectric (and the entire seating surface), a liquid cooler may be circulated through the substrate, e.g., on the bottom of the seating surface. In the example of FIG. 4C, the resistive heater is shown as a continuous trace of low-resistive material (e.g., having a resistance between about 10-15 ohms).

Any appropriate temperature regulating technique may be employed. For example, stirring (e.g., magnetic stirring) may be used. Even a small-volume droplet may contain a range of local temperatures, so the temperature distribution may have a standard deviation. This can be reduced by stirring, e.g., via magnetic beads. With enough stirring, the droplet may be brought close to isothermal. In any of these variations, the top plate may be used to help regulate the temperature. For example, the top plate may be used for heatsinking A thermal conductor (e.g., a steel block) on top of the top plate may greatly speed up the time it takes for the top plate to cool down. If the top plate has a large thermal mass, or a mass is added to it, this may reduce the time needed for a set number of thermal cycles.

Differences in temperature between the top plate and a bottom heater (e.g., a buried heater) may help determine the temperature standard deviation. Heating the top plate in tandem with the electrode may reduce the time necessary to raise the temperature. For example, the top plate may include a local resistive heater, similar to that shown in FIG. 4C. The heated/cooled top plate may be achieved separately from the cartridge by including a top thermal mass that engages with the top of the cartridge when it is on the seating surface. For example, a heated and/or cooled top thermal mass may be a manifold that is pressed down onto the cartridge.

As mentioned, a liquid coolant may be applied to the bottom and/or the top of the cartridge. In particular, a circulating liquid coolant may be used. In some variations, the entire bottom of the cartridge may be cooled (e.g., to within 3-5 degrees of room temperature, e.g., between 15-35 degrees C.). In FIG. 5A, an example of a seating surface 501 is shown removed from the device to illustrate a liquid coolant coupled to the substrate of the seating surface so that coolant may be pumped into 503 and out of 505 through the seating surface 501.

Figure 5B:
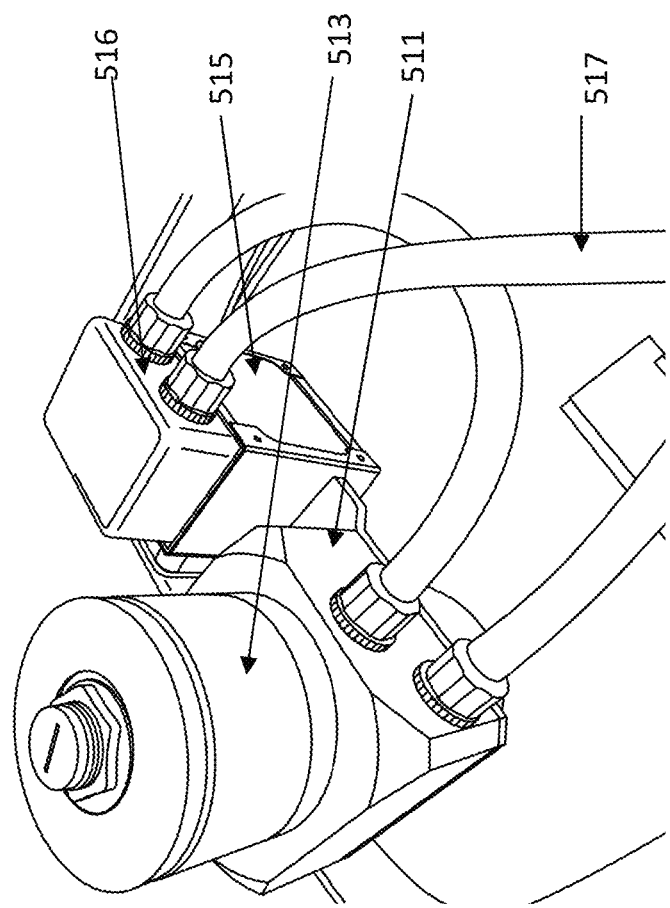
FIG. 5B shows an example of a fan and heatsink, reservoir and pump that may be used for the liquid coolant of the cartridge-contacting surface(s), including the electrodes. The pump, tubing, fan, heatsink and reservoir may be used to move water or liquid coolant below the electrodes so that the coolant can absorb the heat while passing below the electrodes, where it may then be re-circulated after being cooled again while passing through the fan and heatsink.
Figure 5A:
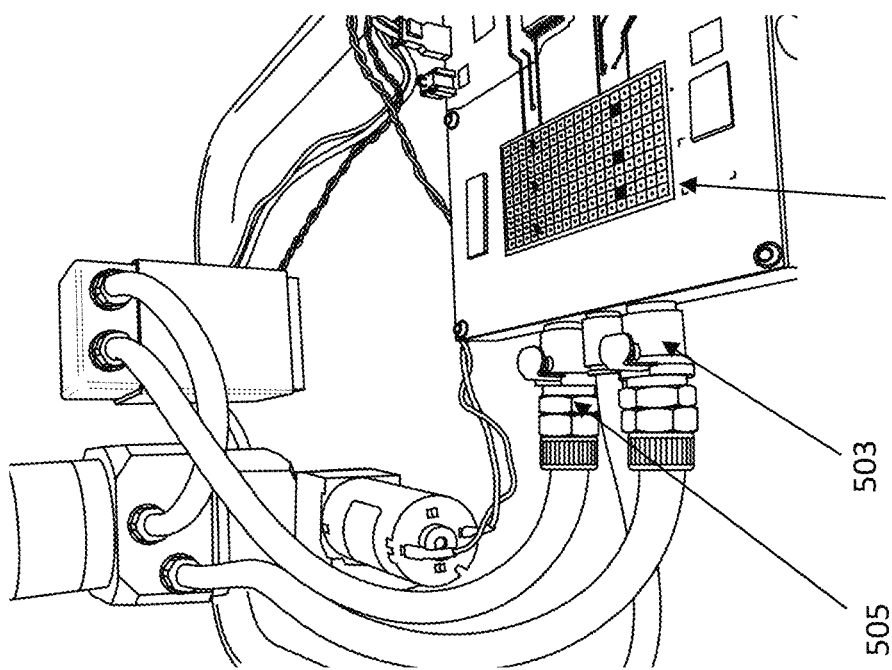
FIG. 5A shows a partially dis-assembled view of the apparatus, showing connections that may be made between the electrode-containing PCB, a liquid coolant, and the vacuum for securing the cartridge dielectric onto the electrodes.

FIG. 5B illustrates a pump 511, tubing 517, fan 515, heatsink 516 and a reservoir 513 are used to move water or liquid coolant below the electrodes. The coolant absorbs the heat while passing below the electrodes and is cooled again while passing through the fan and heatsink.

As mentioned above, the vacuum applied by the device through the openings in the electrodes permits the dielectric of the cartridge to be securely and releasably held. Openings that do not pass through the electrodes do not hold the dielectric smoothly on the seating surface. However, when the vacuum is applied through all of the driving electrodes that may be activated, the dielectric is held flat against the driving electrodes and a consistently lower energy may be applied. For example, FIGS. 5D and 5E illustrate securing a dielectric (shown unattached to a cartridge, for illustration purposes) onto a seating surface having electrodes with openings through which a vacuum is applied. In FIG. 5D the vacuum is off, and the dielectric 555 is loosely resting on the seating surface, with numerous wrinkles. In FIG. 5E, the vacuum is applied through the electrodes.

The use of a vacuum in this way allows for a reduced dielectric thickness, and thus lower power (e.g., voltage) requirements. Compared to the use of adhesive, or the use of a vacuum applied external to the electrodes, the configuration shown in FIGS. 5A-5E resulted in a reduction of the power requirements for DMF being halved. In the examples shown, the thickness of the dielectric may be between 7-13 microns. When an adhesive is used, the dielectric may be almost twice as thick (e.g., 25 microns).

In FIG. 5C, a pump 560 is shown connected via tubing to a vacuum manifold that is configured to pull air through the holes in the electrodes. The dielectric film sits on top and stays rigid as long as the pump is pulling air. In addition, any projection in the surface of the dielectric (particularly those that are around or slightly smaller than the width of the air gap of the cartridge) will not interfere with the seal, but will form enclosures, channels, barriers, or other structures within the air gap, which may help partition the air gap.

FIGS. 5F and 5G illustrate the upper and an intermediate layer of the seating surface, showing the connection between the vacuum source (via connector 565), though a mechanical and/or tubing manifold (FIG. 5G) and out of the openings through the electrodes (FIG. 5F).

FIGS. 10 to 12 illustrate an example of a seating surface 1000 onto which the cartridge may be held by the vacuum ports through the electrodes. In FIG. 10, the seating surface 1000 is formed on a substrate (e.g., a PCB or other electrically insulated surface), and includes an array of electrode 1001, shown in this example as quadrilateral (e.g., square) shapes. Any other appropriate shape may be used. The drive electrodes 1001 are thin conductive surfaces that may be flush or substantially flush with the seating surface, or may project slightly above the seating surface. In FIG. 11, a cartridge 1005 is shown placed atop the array of drive electrodes 1001 on the seating surface 1000. This cartridge may be placed on the seating surface by a drawer (as shown in FIGS. 3E and 3F, above. Once on the seating surface, a vacuum, where the direction 1003 of vacuum application is as indicated, may be applied through all or a subset of the drive electrodes (e.g., those over which a fluid will be transported in the air gap) to hold the dielectric (and therefore the cartridge) in position. As mentioned above, without the vacuum being applied through the electrodes themselves, more energy may be required to drive fluid within the air gap reliably, and the dielectric must be thicker. FIG. 12 shows an enlarged view of a portion of the seating surface 1000, showing electrodes 1001 having a central opening 1009 into the vacuum manifold.

The seating surface of the apparatus may be divided up into functional regions, controlling the location and operation of different portions, including heating, magnetic bead control, washing, adding solution(s), cooling, imaging/detecting, etc. These regions may be defined in the DMF apparatus. For example, returning now to FIG. 6, FIG. 6 illustrates different functional regions that are defined based on the connections within and/or beneath (or in some variations, above) the seating surface. For example, in FIG. 6, solution may be dispensed through the top of the cartridge (e.g., the top plate), via one or more holes. The drive electrodes under the secured dielectric may therefore form a plurality of unit cells (one drive electrode per unit cell), and each cell or region of cells (multiple cells) may be controlled to perform a specified function. For example, in FIG. 6, the DMF apparatus includes an arrangement of zones or unit cells such as cooling zones (e.g., cooling via underlying Peltier zone) 605 that are arranged around the periphery of the cartridge. These regions may also be used to store solution, and may be held at between 3 degrees C. and 20 degrees C. (e.g., below 10 degrees C., between about 2 degrees C. and 25 degrees C.). The central heating zone(s) 609 may be used for heating a droplet. One or more magnetic zones 603 may be used for turning on/off magnetic fields that may be useful to immobilize a magnetic particle (e.g., for removing a material, etc.). Any of the zones may overlap. For example, at least one unit cell in the heating zone may also be a magnetic zone. Other functional zones may include imaging/optical zones. In this case, the dual functions may be possible because the magnet may be positioned right under the heating zone when using resistive heating.

Figure 6:
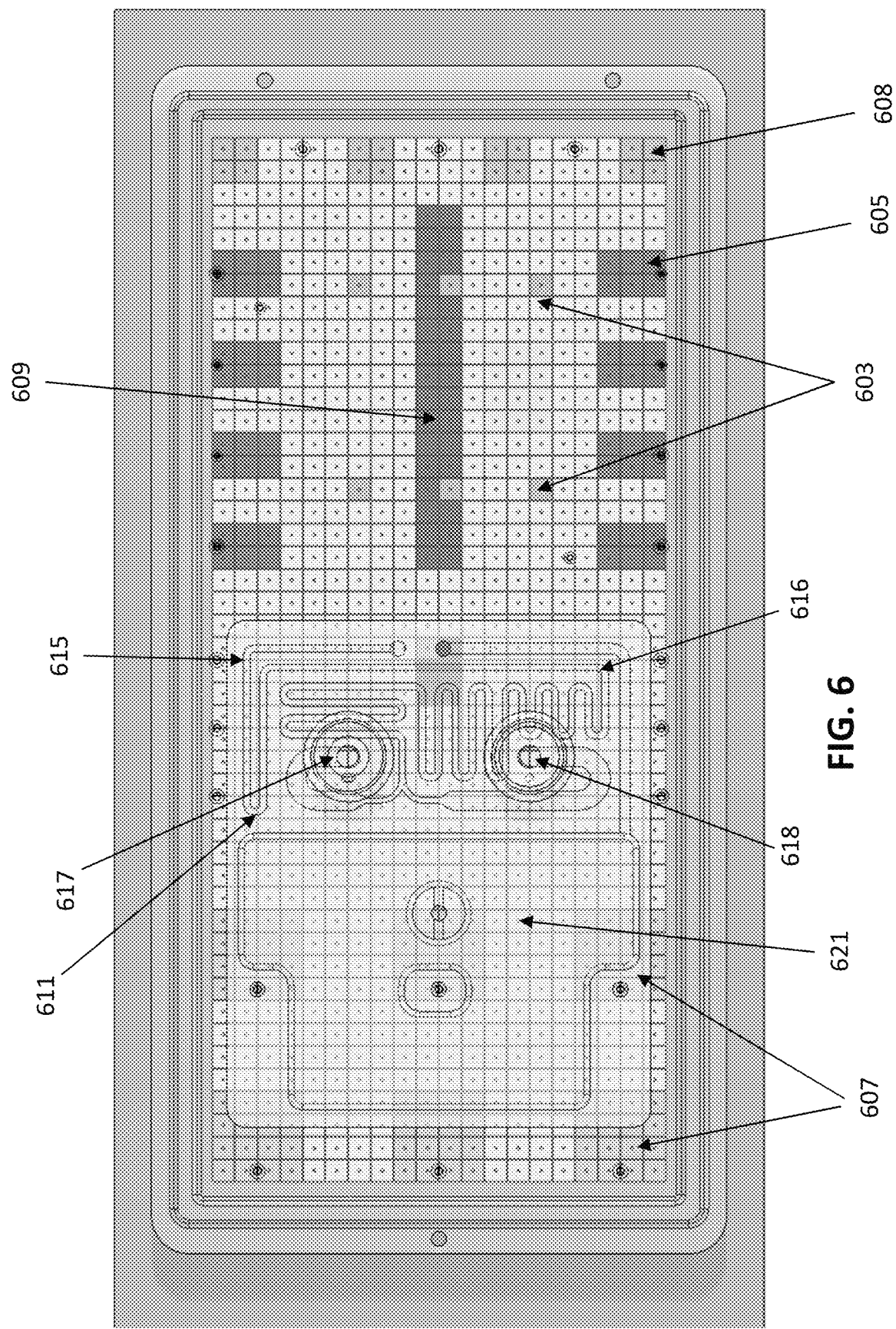
FIG. 6 illustrates the different functional regions that may be formed by the electrode array and/or removable cartridge.

In addition to the zones formed by the configuration of the seating surface of the DMF apparatus, functional zones for providing an aliquot of solution, mixing a solution, and/or removing solutions may be formed into the cartridge, e.g., by cutting into the top plate to provide intimate access the air gap. In FIG. 6, the upper (top plate) microfluidics region has been made transparent. In general, a micro channel may be used for mixing, dispensing and taking to waste on top plate from the air gap region. In addition, any of these cartridges may also include a reagent reservoir in the top plate. The microfluidics may be controlled by one or more valves (e.g., valve control) for dispensing and mixing and taking to waste.

Cartridges. In general a two-plate cartridge as described herein may include a dielectric of a bottom (or first) plate, a first hydrophobic coating on the dielectric, and a second hydrophobic coating on a top (or second) plate. In some variations, a ground electrode is incorporated within the top plate of the cartridge, and is disposed between the hydrophobic coating and the top plate. In other variations, a two-plate cartridge may not include the ground electrode. The hydrophobic coating may be a Teflon coating, for example. The cartridge may also include one or more microfluidic channels, particularly those formed directly into the top plate with controlled access into the air gap.

The two plate cartridge may have an air gap formed between inner surfaces of the hydrophobic layers of the top and bottom plates, where the air gap has a height (vertical dimension) that is similar to the air gap of the DMF apparatuses described above. That is, the air gap of a two plate cartridge may have a height of about 0.250 mm or greater (e.g., about 0.260 mm or greater, about 0.280 mm or greater, about 0.3 mm or greater, about 0.4 mm or greater, about 0.5 mm or greater, about 0.6 mm or greater, about 0.7 mm or greater, about 0.8 mm or greater, about 0.9 mm or greater, about 1 mm or greater, about 1.1 mm or greater, about 1.3 mm or greater, about 1.5 mm or greater, about 1.7 mm or greater, about 1.9 mm or greater, about 2 mm or greater, about 2.5 mm or greater, about 3 mm or greater, about 3.5 mm or greater, about 4 mm or greater, about 4.5 mm or greater, or about 5 mm or greater. In some variations, the height of the air gap may be between about 0.3 mm to about 5 mm, between about 0.5 mm to about 5 mm, between about 0.5 mm to about 4.5 mm, between about 0.5 mm to about 4 mm, between about 0.5 mm to about 3.5 mm, between about 0.5 mm to about 3 mm, between about 0.5 mm to about 2.5 mm, between about 0.5 mm to about 2 mm, between about 0.5 mm to about 1.5 mm, between about 0.5 mm to about 1 mm, between about 0.6 mm to about 5 mm, between about 0.6 mm to about 4 mm, between about 0.6 mm to about 3 mm, between about 0.6 mm to about 2 mm, between about 0.6 mm to about 1.3 mm, or any height therebetween.

For example, FIGS. 7A-7D illustrate one example of a two-plate cartridge 700 including a microfluidics region (not visible) on the upper surface, covered by a cover 703 having one or more access ports 705, 707 for accessing the microfluidics portion of the device. The cover 703 may also include one or more valves and/or one or more openings 709 that may be used for delivering removing fluid and/or gas (e.g., air). The cartridge may also include openings through the top plate 713, including openings that connect the microfluidics channel to the air gap region within the channel.

Any of the cartridges described herein may also include one or more transparent window regions 711 for optically imaging one or more regions (readout regions) within the air gap. Alternatively, the two-plate cartridge may have a top plate that is transparent, translucent or substantially transparent or substantially translucent. In embodiments where a one-plate cartridge is used, the lack of a top plate can provide full access to any point within the inner surface of the one-plate cartridge.

Figure 7C:
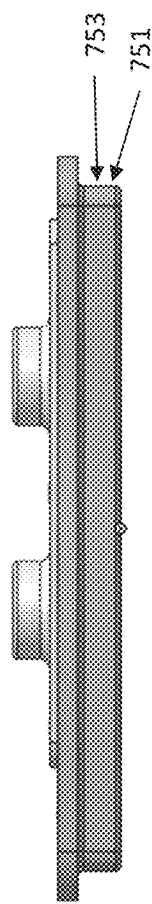
FIG. 7C is an end or side view from the left side of the cartridge of FIGS. 7A and 7B, showing the upper microfluidics channels and the lower DMF portion (showing the spacing between the top, ground, plate and the dielectric, forming the air gap.
Figure 7D:
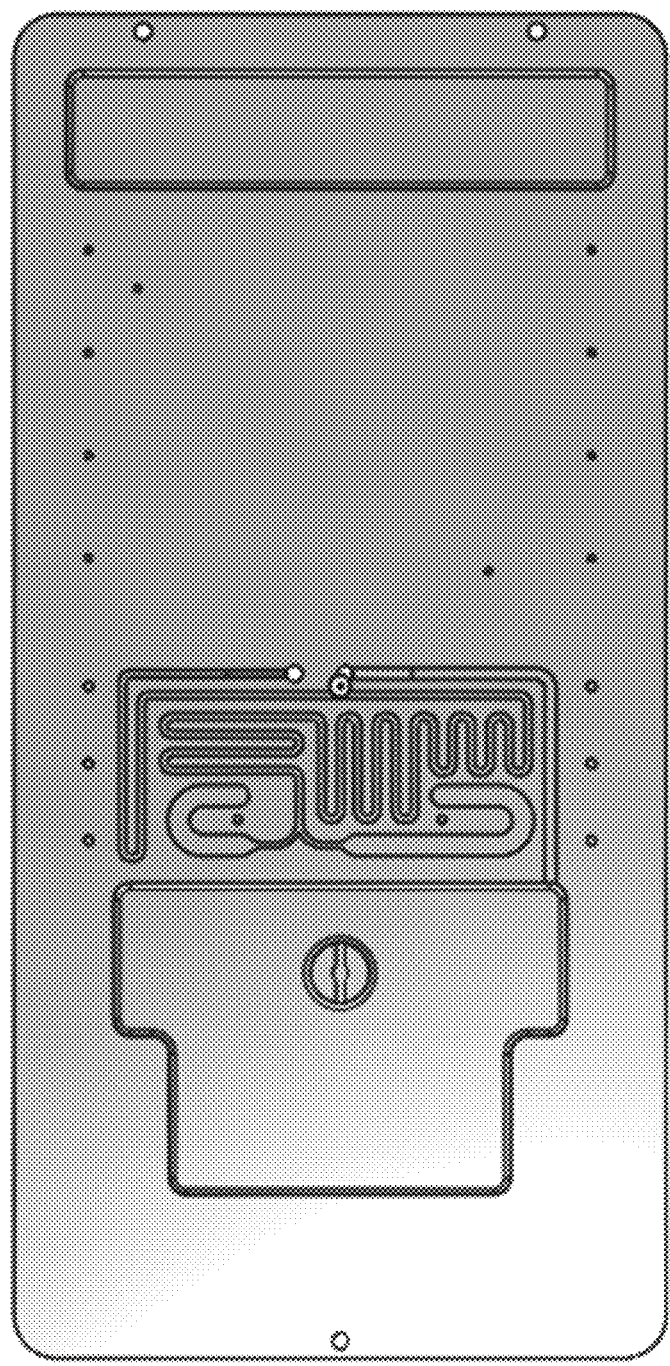
FIG. 7D is a top view of the cartridge of FIGS. 7A-7C, with the cover for the microfluidics channels removed, showing the channels.

FIG. 7B is a top perspective view of the cartridge of FIG. 7A. FIG. 7C shows a side view of the cartridge, showing the lowest bottom dielectric film 751 material. The air gap is not visible in FIG. 7C, but may refer to the spacing 753 between the dielectric and the ground electrodes. FIG. 7D shows the top plate with the cover removed. Comparing FIG. 7A to FIG. 7D, with the top removed, both the first and the second microfluidics channels are shown, each with an opening from the microfluidics channel into the air gap. In FIG. 7D, the two channels may be simultaneously used by pushing/pulling fluid through one channel into the cell underlying them for rinsing, mixing, removing waste, etc. In FIGS. 7A-7D, there are via holes through the top plate into the air gap. Although the top plate may be thicker, in some variations it may be beneficial to include more reagents, including freeze-dried reagents that may be rehydrated.

Figure 9:
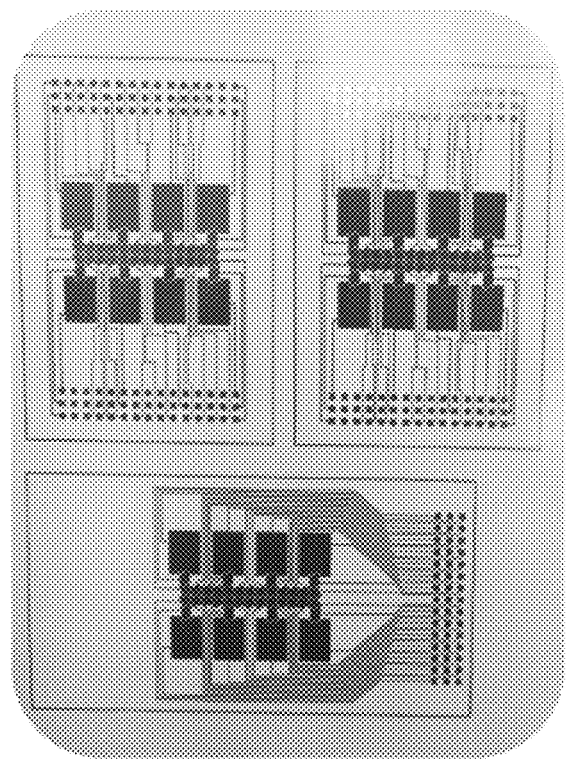
FIG. 9 shows paper digital microfluidics that may be used as part of a cartridge.
Figure 8:
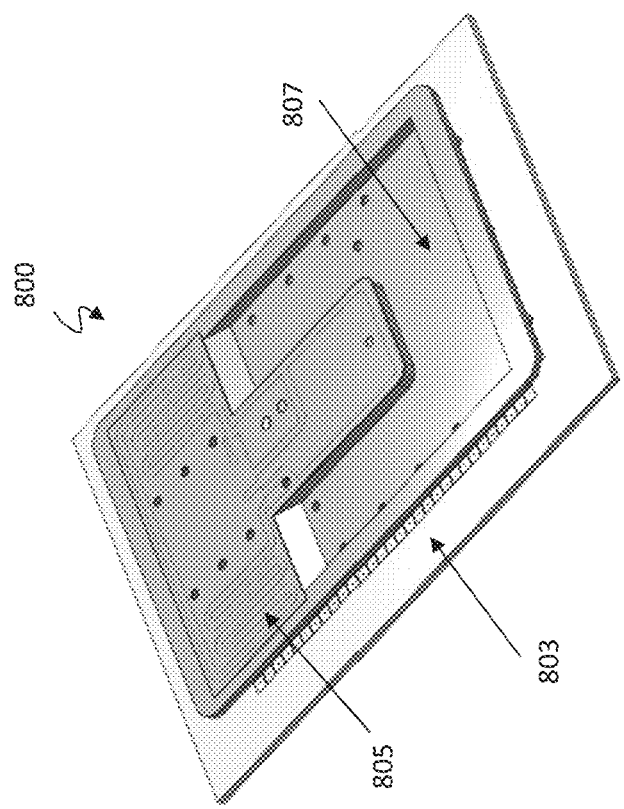
FIG. 8 is an example of a disposable cartridge, including a plastic top plate and a dielectric.

FIGS. 8-9 illustrate different examples of cartridges that may be used. In FIG. 8, an exemplary two-plate cartridge 800 (similar to that shown in FIGS. 7A-7D) is shown over a seating surface 803 including electrodes. The cartridge 800 includes a microfluidics portion 805 formed above the air gap (not visible in FIG. 8), on one end of the cartridge. The other end of the cartridge includes a window region 807 through which a portion of the air gap may be imaged. The both the front (window) region and the back (microfluidics) regions of the cartridge may include access regions for accessing the air gap and/or microfluidics portions. In FIG.

9, three different DMF design configurations on paper are shown. Paper DMF devices were formed by inkjet printing arrays of silver driving electrodes and reservoirs connected to contact pads onto paper substrates.

Within the cartridge, the top plate may be any appropriate material, including transparent materials, such as acrylics. The top plate may be formed of (or may contain) one or more conductive polymers. A ground electrode(s) may be formed on the top plate. In some other examples of cartridges suitable for use in the DMF apparatuses described herein, the top plate of the cartridge may not include a ground electrode, but may include a hydrophobic surface and a dielectric.

Figure 15:
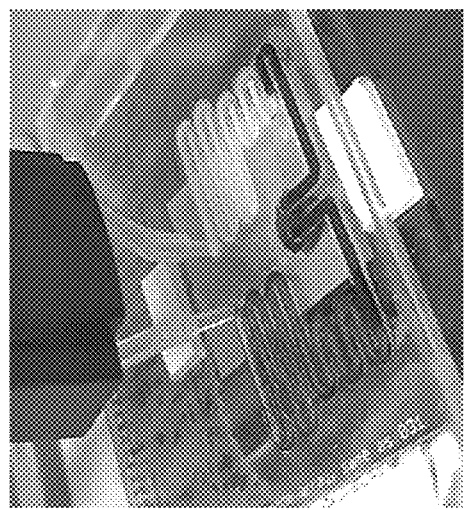
FIGS. 13-15 illustrate one example of a microfluidics channel interfacing with a DMF air gap region as described herein.
Figure 14:
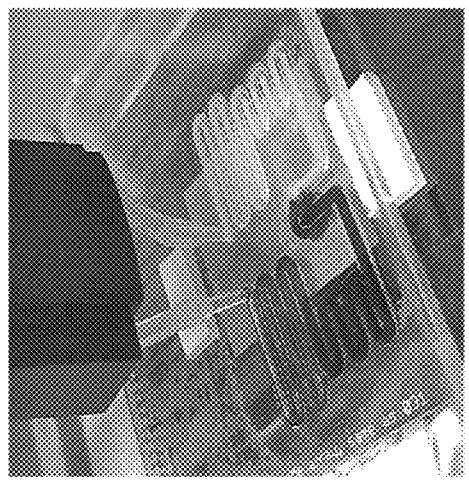
Figure 13:
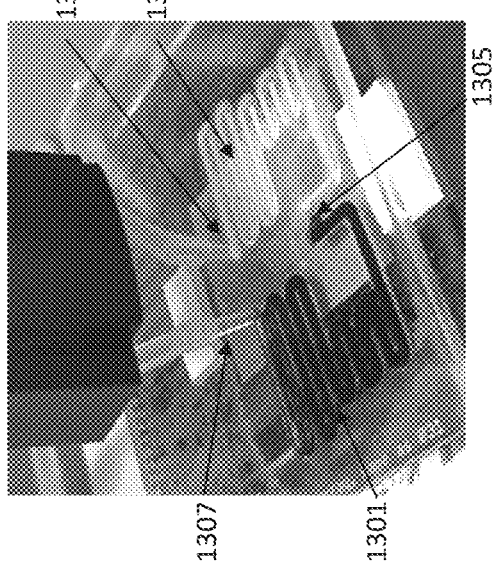

As already discussed above, any of these apparatuses and methods may include one or more microfluidics channel(s) integrated into the cartridge. In particular, the apparatus may include a microfluidics mixing and extraction region. This is illustrated in FIGS. 13-15. For example two microfluidics channels 1301, 1303 may be formed into the top plate of the air gap, and an opening in to the air gap may be positioned within a fixed distance from each other. Fluid may be passed from one microfluidics channel to another microfluidics channel, through the air gap. The region of the air gap between these openings may bridge these two regions 1305. This configuration may be used to mix a larger droplet (e.g., greater than 5 microliters, greater than 7 microliters, greater than 10 microliters, greater than 15 microliters, greater than 20 microliters, greater than 25 microliters, greater than 30 microliters, greater than 1 ml, etc.) than could be easily done within the air gap.

For example, in FIG. 13, a first pressure source 1307 (negative pressure and/or positive pressure) is shown attached to one end of the microfluidics channel, and a second pressure source 1309 (positive and/or negative pressure) is shown attached to another microfluidics channel. Fluid may be withdrawn from the air gap through the opening 1305 into the first channel 1301; alternatively or additionally, by applying positive pressure 1307, fluid may be moved from the first channel 1301 into the air gap through the opening 1305; concurrently, fluid may be drawn from the air gap at or near the same opening 1305 into the second channel by applying negative pressure 1309 within the second channel. Alternating positive and negative pressure may pass relatively larger volumes of solution between the two microfluidics channels, in and out of the air gap, as shown in FIGS. 14 and 15.

In the example shown in FIGS. 13-15, the top plate integrates microfluidic channels, as well as reservoirs and tubing; alternatively or additionally, one or more ports (e.g., for connecting to the pressure source(s), valves, and the like may be included. For example, a cover over the microfluidics channels may be included with port(s) and/or valves and the like. Positive and negative pressure may be applied within the microfluidics channel(s), for example, by reversing the polarity of a peristaltic pump.

FIGS. 16A and 16B illustrate schematically examples of a method for applying and removing (including washing) fluid to/from the air gap of a DMF apparatus 1620. In FIG. 16A, for example, the air gap 1621 of the cartridge is formed between the top plate 1617 and the bottom dielectric 1626. A connector interface 1627 connects a combined inlet/outlet port for a first fluid channel 1643 and a second fluid channel 1645. These fluid channels may be connected one or more reservoirs 1605, 1607. As already described above, in some variations, two separate connector interfaces (ports) may be used, one connected to each fluid line (e.g., which may be a microfluidics channel, as described above). A bridging droplet in the air gap region 1621 may connect to both inlet and outlet lines, and fluid may be drawn into and out of the fluid lines 1643, 1645 to mix the droplet, add fluid to the droplet, remove fluid from the droplet, expose a solid phase capture element (e.g., magnetic bead, non-magnetic bead, etc.) to the same fluid repetitively to deplete the fluid from the analyte of interest, e.g., to concentrate the analyte on the solid phase or other surfaces), etc. FIG. 16B illustrates a similar method for applying and removing fluid to/from the air gap of a DMF apparatus 1625, where introduction/removal is performed at a port at the side of the air gap 1621.

Alternatively, as shown in FIGS. 17A and 17B, the cartridge may include air gaps of different heights of a DMF apparatus 1720. For example, in FIG. 17A, the air gap 1719 for the region around the connector interface 1727 may be greater (e.g., between 0.5 and 2 mm) larger than the air gap 1721 between other regions of the top plate 1717 and the bottom dielectric 1726, as a portion of the top plate 1717 (or a separate top plate 1715 connected to another top plate 1717) may be spaced further from the dielectric 1726. The reservoirs 1705, 1707, connector interface 1727, first fluidic channel 1743, second fluidic channel 1745 may be similarly to the respective elements in FIGS. 16A-16B. Similarly, in FIG. 17B, the air gap 1719 near the connector interface at the edge of the apparatus may be larger than the air gap 1721 in other regions, e.g., by spacing a portion 1715 of the top plate 1717 further from the dielectric 1726 bottom layer.

A prototype DMF apparatus and cartridge illustrating the principle shown in FIG. 16A is illustrated in FIGS. 18A-18C, and was used to demonstrate the proof of principle for mixing larger volumes of solution in an air gap of a DMF cartridge. In FIG. 18A, the upper plate of the DMF cartridge included an opening through the top plate 1801 connected to a first fluid line 1843 and a second fluid line 1845. By alternating negative pressure (suction) between the first and second fluid line, fluid was moved back and forth between the first reservoir 1805 and the second reservoir 1807, as shown in the sequence of FIGS. 18A, 18B and 18C. In this example, magnetic particles holding an analyte of interest are magnetically held within the air gap (e.g., against the bottom, e.g., hydrophobic coated dielectric) by the DMF apparatus 1809 while the fluid is exchanged between the reservoirs, enhancing binding and/or rinsing.

In any of the air-gap apparatuses described herein, evaporation may be controlled or reduced, particularly when heating the droplets within the air gap. FIGS. 19A-19C illustrate the effects of evaporation on a droplet 1903 after only a few minutes. The intact droplet is shown in FIG. 19A. After one minute at 95 degrees C., the droplet volume has noticeably decreased (e.g., losing between 5-15% of the volume of the droplet, as shown in FIG. 19B. After two minutes (FIG. 19C), the droplet is between 20-34% smaller. To prevent this loss due to evaporation, the droplet within the air gap may be sheathed or covered in a nonpolar jacket, as illustrated in FIGS. 20A-20C. For example, a liquid paraffin material (e.g., a nonpolar material that is liquid at the working range described herein, e.g., between 10 degrees C. and 99 degrees C., may be used. In FIG. 20A, a droplet 2003 jacketed in liquid paraffin 2005 is heated (e.g., to 65 degrees C. or above). After one hour (FIG. 20B), the droplet has not appreciably evaporated. Similarly after 2 hours (FIG. 20C), the droplet has remained approximately the same volume.

In use, the nonpolar jacketing material may be added and removed at any point during a DMF procedure, as illustrated in FIGS. 21A-21I. Surprisingly, removal may be accomplished, for example, by drawing the jacketed droplet up out of the air gap, e.g., out of a port entering into a microfluidics channel as described above. The liquid paraffin, for example, may be removed into a waste reservoir by applying a negative pressure to a droplet from a port through the top or side of the air gap. The lower-density liquid paraffin may be the first layer that gets drawn up, leaving the aqueous droplet behind. Previously it was believed to be difficult or impossible to remove the jacket of nonpolar liquid.

For example, FIG. 21A shows a jacketed droplet in which the aqueous droplet 2101 is surrounded by a nonpolar liquid 2103 (e.g., liquid paraffin). In this example, a small bubble has also been formed in the liquid paraffin. The droplet may be easily moved, as shown in FIG. 21B, showing the droplet moving by the coordinated application of energy to the driving electrodes to alter the electrowetting of the aqueous droplet. In FIG. 21B, the jacketed droplet has been moved to the right. Initially, the aqueous droplet may be combined with the nonpolar liquid by applying the nonpolar liquid into the air gap either directly on the droplet, or in a region of the air gap that the droplet may be moved into. The jacketed droplet may also be combined with one or more additional droplets that may include a nonpolar liquid droplet of their own, or may be unjacketed. In some variations, a jacketing droplet (including a small aqueous droplet and a relatively large volume of nonpolar solution may be combined with the target droplet in order to jacket the target droplet. The small amount of aqueous liquid in the jacketing droplet may be a buffer, diluent, or other solution that allows the jacketing droplet to be moved in the air gap. This technique is particularly helpful when used with DMF cartridges having larger (e.g., 0.5 mm or greater) gap widths. A larger gap width may otherwise make it difficult for the larger droplets to maintain a jacket of typically less dense nonpolar jacketing material. FIGS. 21C and 21D illustrate a droplet 2101 that has been combined with another droplet, forming a larger jacketed droplet 2101'. The larger droplet may also be moved by controlled actuation of the driving electrodes, as shown in FIGS. 21C and 21D.

FIGS. 21E to 21I illustrate the use of a nonpolar liquid jacket in a sample including a magnetic bead material. In FIG. 21E, a jacketing droplet includes a small amount of aqueous liquid 2121 and a relatively large amount of nonpolar jacketing material 2123, the two may be combined, for example, by moving the jacketing droplet 2123 into the sample droplet 2121, as shown in FIG. 21F, allowing them to combine so that the jacketing material is now jacketing the sample droplet. In in his case, the sample droplet is quite large, and includes a concentration of sample absorption magnetic beads.

Once combined, the jacketed droplet 2121' may be moved (by DMF) to a port into the air gap from which solution may be extracted, as shown in FIG. 21H. In this example, the solution may be mixed by applying positive and negative pressure to move the solution into and out of the fluid channel 2131. The nonpolar solution jacketing the droplet may be removed by applying negative pressure to pull the solution out of the air gap though the top port; the first solution removed is the jacketing material. Thereafter, as shown in FIG. 21I, the magnetic particles to which a desired analyte has been bound may be held onto the bottom side of the air gap, e.g., by applying a magnetic field, and the droplet solution may be removed, and/or washed, in the absence of nonpolar jacketing solution, which may otherwise interfere with the binding or release of the analyte from the magnetic particles. In FIG. 21I, the magnetic particles 2133 are left in the air gap, and a separate washing buffer may be applied by moving a washing and/or elution droplet 2135 over the magnetic particles.

In addition to the techniques for controlling evaporation discussed above (e.g., using a jacket of nonpolar liquid), any of the methods and apparatuses described herein may also include controlling the partial pressure of water vapor inside the cartridge to create "zero evaporation" conditions, e.g., by balancing the rates of water molecules leaving and entering the water surfaces. The balance does not need to be perfect, but may be adjusted by adjusting the temperature and pressure so as to stay as close as possible to the zero evaporation condition. This may vary with temperature; for example, once relative humidity is controlled, it may be best to adjust the humidity up and down with the temperature, e.g., during hybridization or PCR cycling using the apparatus. Alternatively or additionally, any of these apparatuses may use local replenishment to adjust for evaporation by moving droplets slightly to recapture nearby condensation (see, e.g., FIGS. 19B-19C, showing evaporative droplets surrounding the main droplet). Any of these methods and apparatuses may also or alternatively use walled-in heating zones to reduce the surface area from which evaporation may occur. For example, as mentioned above, in some variations the seating surface of the DMF apparatus may include projections forming local regions within the cartridge, since the vacuum may be precisely applied to control the contact between the flexible dielectric and the electrodes, projection on the seating surface may create chambers or channels within the air gap, including forming partially wall-in heating zones that may reduce evaporative surface area. In some variations, the top plate may be spaced differently across the cartridge; the evaporation rate may be lower for thinner droplets compared to thicker droplets. Thus, any of the heating regions may have a narrower width of the air gap to reduce evaporation.

In any of the large-volume droplet DMF cartridges, e.g., DMF cartridges having a gap separation of 0.5 mm or greater (e.g., 0.6 mm or greater, 0.7 mm or greater, 0.8 mm or greater, 0.9 mm or greater 1 mm or greater, e.g., between 0.4 mm and 2 mm, between 0.5 mm and 2 mm, between 0.5 mm and 1.8 mm, between 0.5 mm and 1.7 mm, etc.), it has proven particularly difficult to dispense droplets having a predictable volume, as the surface tension of the relatively large droplets may require a greater amount of energy to release a smaller droplet from the larger droplet. In general, in digital DMF systems, the ratio between spacer (air gap) thickness and electrode size dictates the volume of droplet dispensing. In the conventional digital microfluidic approach, spacer thickness of less than about 500 micrometers (0.5 mm) allows for electrowetting forces to split a unit liquid droplet from a larger amount of liquid volume; this has not been possible with higher spacer thicknesses (e.g., greater than 500 micrometers). Described herein are methods for splitting unit droplets from larger volumes in air gaps having a width (e.g., spacer thicknesses) of 500 μm or greater. In some variations this may be performed by, e.g., flooding a region of the air gap with a solution to be dispensed from a port (which may be a side port, top port or bottom port), and then selectively activating a cell (corresponding to a driving electrode) in the flooded region, then withdrawing the solution back into the port (or another port) that is offset from the activated electrode so that a droplet remains on the activated electrode as the solution is withdrawn into the port; the droplet on the activated electrode breaks off from the larger flood volume (e.g., by necking off), leaving the dispensed droplet behind, where it may then be driven by the drive electrodes, combined with one or more other droplets, etc.

For example, an integrated companion pump may be used to drive a large volume of aqueous solution into a DMF device (e.g., into an air gap of the DMF cartridge) and over an activated electrode. The aqueous solution may then be withdrawn away from DMF device, dispensing behind a unit droplet over the activated electrode. FIGS. 22A-22D illustrate an example of this method. In FIG. 22A, a port 2201 into the air gap 2205 of the DMF cartridge connects to a fluid channel (e.g., a microfluidics channel as described above), shown in FIG. 22A as a tube 2209, holding an aqueous solution (reagent 2203). In this example, a single drive electrode 2207 has been actuated; alternatively in some variations, the electrode is not activated until after flooding the region of the DMF apparatus. Pre-activating it may help distribute a predefined amount onto the unit cell defined by the drive electrode. In any of these examples more than one contiguous drive electrodes may be activated to dispense larger-volume droplets.

Next, as shown in FIG. 22B, the region of the air gap including the activated drive electrode is flooded with the aqueous solution 2203. FIG. 22A shows the release of a large volume (e.g., 250 µL) from the channel (tube 2209). In some variations, as the reagent nears the distal end channel 2209, a drive electrode 2207 is activated (e.g., AC potential of 390 Vrms, or by otherwise creating an alternating field effect using a DC potential), which may generate an electrowetting force that further encourages transfer of the reagent from tube 2209 to the activated drive electrode 2207; further flow from the channel occurs so that the droplet grows to fully cover the activated drive electrode(s).

In FIG. 22C, the aqueous solution (reagent 2203) is then withdrawn from the air gap through the same port 2201 or a separate port, where the activated drive electrode(s) is/are separated from the port into which the solution is being drawn by a distance (e.g., the distance may be approximately equivalent to the width of the activated electrode); this distance is sufficient so that the droplet on the activated drive electrode(s) necks off of the liquid being withdrawn back into the channel 2209. For example, aspirating the reagent back into the tube as shown in FIG. 22C may result in necking of the droplet from the rest of the solution; the neck region continuously shrinks until a unit droplet (e.g., 10 µL) is left behind on activated drive electrode, as shown in FIG. 22D. The same process can be repeated with activating two, three and five electrodes to dispense approximate multiples of the unit droplet (e.g., 20, 30 and 50 µL), respectively as shown in FIG. 23A-23E. Multiple droplets may be separately dispensed and combined, or alternatively multiple electrodes may be used to dispense larger volumes at once, as mentioned. The size of the droplet (droplet volume) may be based in part by the size of the driving electrodes and the spacing of the air gap.

FIGS. 23A-23F illustrate the dispensing of various predefined volumes of solution from a reservoir above the cartridge using the method described above. In FIG. 23A, for example, the region of the air gap including the port connecting to a channel holding solution above the larger air gap (e.g., 0.5 mm width) is flooded with solution 2301, as shown, and a single activated electrode is used to break off a predetermined volume of solution (e.g., 10 microliters), shown in FIG. 23B. This droplet may be moved away from the flooding region, and the process repeated multiple times to produce multiple droplets of approximately uniform volume (e.g., 10 microliters+/−5%, 10%, 15%, 20%, 25%, etc.).

In FIG. 23D, a first unit droplet 2303 (e.g., having a 10 microliter volume) is shown adjacent to two combined unit droplets 2305, which form a second droplet having 2x the volume, e.g., 20 microliters. Similarly, FIG. 23E shows a large droplet 2307 (e.g., 50 microliters) formed by combining five unit droplets. FIG. 23F illustrates the use of a larger driving electrode 2315 (e.g., having approximately 4x the surface area) that may be activated when flooding the air gap region to form a larger unit droplet 2311 (e.g., a 40 µL unit droplet).

Thus, by flooding or flushing a dispensing region of the air gap with a large volume of aqueous solution, and activating a drive electrode (or over an already-active drive electrode), then removing the solution (e.g. pumping it out) a relatively precise volume droplet may be left behind. As mentioned, when using large-volume DMF apparatuses (which may include a cartridge), e.g. having a spacing of between 0.4 or 0.5 and up to 3 mm, this technique may be used to dispense smaller-volume droplets from larger-volume reservoirs with a reasonable amount of force; unlike air gap DMF apparatuses having smaller air gaps, which may directly dispense smaller volume droplets form a larger volume by applying electrowetting energy, the larger force effectively prevents directly dispensing by DMF in larger air-gap devices. In many of the examples provided herein, the gap spacing of the air gap is between 1 mm and 1.3 mm (e.g., approximately 1.14 mm), though at least up to a 3 mm spacing has been successfully used.

Dispensing of solution as described herein may be particularly important in processing samples (e.g., mixing, etc.) as well as replenishing solution lost due to evaporation in such systems.

User Control Interface. In any of the apparatuses and methods described herein, a DMF apparatus may be controlled by a user so that the DMF apparatus can execute one or more protocols (e.g., laboratory procedures) on a sample that is inserted into the DMF apparatus (e.g., cartridge). For example, a DMF apparatus may include a user interface that dynamically and flexibly allows the user to control operation of the DMF apparatus to perform a user-selected or user-entered protocol. In general, there are numerous considerations when translating a processing protocol for operation by a DMF apparatus, including preventing contamination during the procedure. Contamination may occur when moving a sample droplet, in which the protocol is being performed, over a path taken by earlier steps in the procedure (or parallel steps). Typically, the one or more reaction droplets that are being processed may need to be moved to different locations within the air gap of the DMF cartridge, and/or temporarily out of the air gap region. It would otherwise be difficult for the user to coordinate these movements both to avoid earlier or future paths (e.g., contamination) and to remember which locations are appropriate for heating, cooling, mixing, adding, removing, thermal cycling, etc.

Described herein are user interfaces for controlling the operation of the DMF apparatus that allow the user to more easily enter protocol information/steps into the DMF. This may be accomplished in part by providing a set of graphical step representations (e.g., showing mixing, adding, heating, cooling, cycling, washing, etc.) of steps that may be performed, and allowing the user to select/enter these steps in a manner that also intuitively provides the duration of the steps, or the degree (e.g., temperature, etc.) to be applied. Once entered, the apparatus may then determine an efficient pathway to perform the entered protocol within the predefined layout constraints of the DMF apparatus and/or cartridge to avoid contamination. For example, any of these apparatuses may determine a pathway (pathfinding) that prevents or reduces path crossing within the air gap where such crossovers may result in contamination.

FIG. 24 is an exemplary schematic, illustrating the steps involved in controlling any of the DMF apparatuses described herein. For example, in FIG. 24, the user may enter the protocol using a graphical/visual user interface (referred to herein as "SAM"). This may be described in greater detail in reference to FIGS. 25A-26B). The graphical protocol may then be translated into a series of target goals and this target protocol may then be used by the apparatus to tailor this protocol to the DMF apparatus. In FIG. 24, the system may determine a path, and derive the control of the drive electrodes, heater, cooling (e.g. Peltier), magnetic(s), microfluidics (pump(s), etc.), etc. in order to accomplish the protocol. The path may be optimized to require the shortest pathways, but constrained by limiting or reducing overlap in the path(s), to prevent contamination, loss of materials (including reagents and/or Teflon), heat dissipation, etc.

As mentioned, FIGS. 25A and 25B illustrate one example of a visual interface (e.g., graphical user interface) for entering a desired protocol. In FIG. 25A, a set of control icons ("move", "heat", "removal", "cycle", "mix", "breakoff", "dispense", and "wait") are shown. The user may select or arrange these icons in order to provide a graphical representation of a processing protocol, as shown in FIG. 25B. Each of the icons may have an associated duration, and thus, these icons may be used to select processing instructions, or steps, for a sample. In this example, the icons are uniquely identified by one or more of: color, image, and text.

The user may input the protocol directly into the apparatus, or into a computer or other processor in communication with the DMF apparatus.

Once entered, the protocol may be translated into a data structure format (e.g., a JSON format that indicates the name of the protocol and sample, where the sample goes, what volume to use, etc.). This data structure may then be directly used or converted into a format (e.g., java script) so that the apparatus may determine the paths to take in the cartridge in order to achieve the desired protocol. The path finding may be done locally (e.g., in the DMF apparatus) or remotely and communicated to the DMF apparatus. The path finding may be configured to maximize based on the shortest path length that also avoids cross over, or some cross-overs, to prevent contamination. Thus, the apparatus may determine the shortest route that avoids contamination. In general, the user interface can allow the user to easily select the desired actions and elements (e.g., mixing, etc.); the apparatus may already be familiar with the reagents (e.g., elements of the device). The user can then select the actions, durations, temperatures, etc.

Figure 26A:
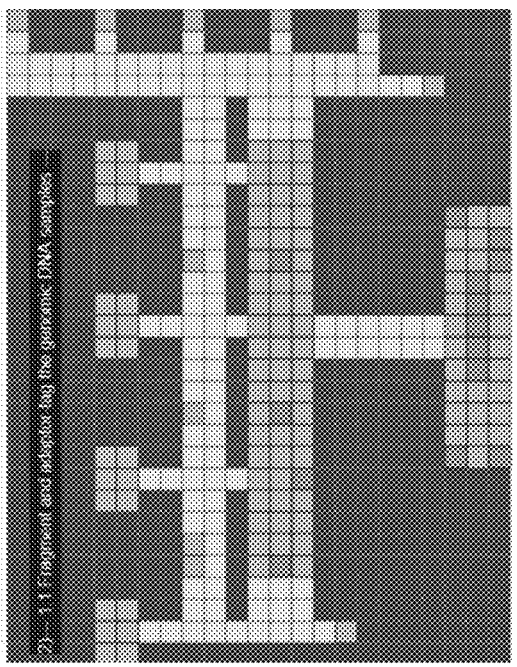
Figure 26B:
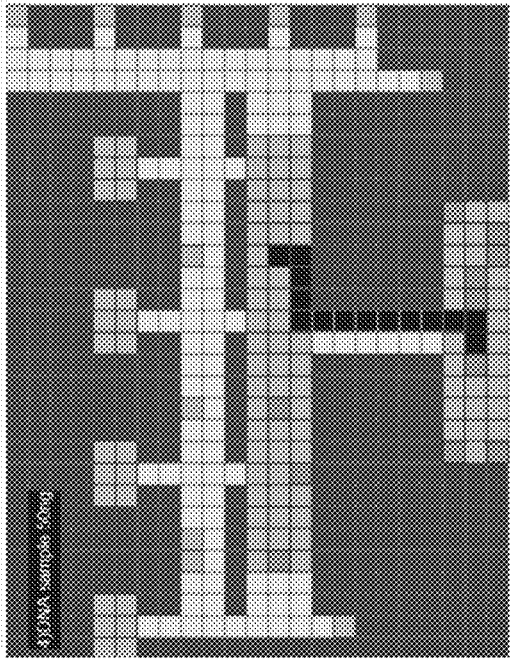
Figure 26C:
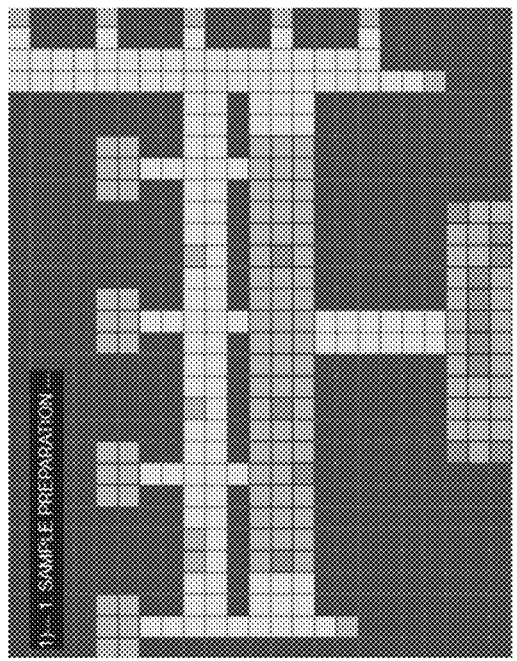
Figure 26D:
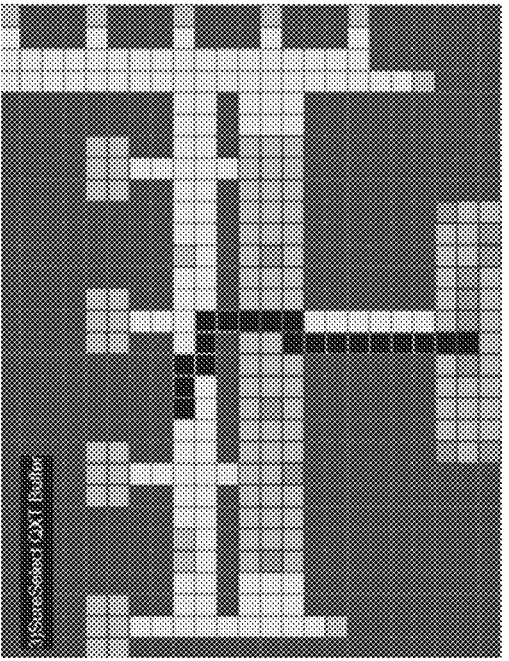

FIGS. 26A-26H illustrate one non-limiting example of an apparatus determining a pathway from an input protocol. For example, FIG. 26A shows a graphical illustration of a particular configuration of DMF cartridge air-gap planning a first set of steps, e.g., sample preparation. The apparatus may know the distribution of the cells within the air gap, as well as the configuration of the functional zones (heaters, coolers, mixing/microfluidics, waste removal, dispensing, etc.) in the DMF cartridge. FIG. 26B is a graphical illustration of the apparatus determining the path for tagging a sample having genomic DNA (or fragments of DNA) with an adapter tag. In FIG. 26C, a step of moving a first buffer (e.g., SureSelect QXT buffer) to an appropriate location for future processing is performed. The path may be chosen in light of both past movements and future movements and may be recursively modified as the future protocol steps are defined. In FIG. 26D, the path for moving the DNA sample is shown (in black). FIG. 26E shows the movement of an enzyme mix from a cooled region where it is beings stored to combine with the sample; FIG. 26F shows the user of mixing of the sample with the buffer and enzyme mix. The mixed sample may then be moved (FIG. 26G) along a calculated pathway to a heating/cooling zone for cycling (FIG. 26H). Additional steps may then be performed as indicated.

Thermal control. Any of the apparatuses described herein may include features for thermal control (e.g., heating and/or cooling), and/or droplet detection (e.g., tracking and/or identification). For example, the apparatus, including the cartridge and apparatus, may be configured to quickly and accurately cycle droplet temperatures. Alternatively or additionally, droplet detection may quickly and accurately scan the electrode grid for droplets (including, but not limited to reagents, wax, water, etc.).

As described above, the apparatus may be configured to include one or more thermal control elements, including cooling and/or heating. For example, the apparatus may include resistive heating in some of the cells, to heat a droplet within the air gap. For example, in some variations a resistive heater may be included in a layer of the printed circuit board (PCB), such as part of a first copper layer under the surface of the PCB. The apparatus may also include a heat sink or cooling element, such as a liquid cooler (chiller) that is in constant thermal connection with the PCB. Any of these variations may also include one or more of thermal mass reduction, which may enhance the rate of temperature change in a cell, and/or thermal conduction through the PCB (e.g., through the electrodes that form part of the PCB in the apparatus).

Thermal Mass Reduction may refer to the reduction or removal of thermal mass from the apparatus (e.g., system, device, etc.) to reduce the total required amount of energy to reach a temperature or temperature range. Ideally, when there is less thermal mass, less energy needs to be taken out of the system to decrease the sample temperature during thermal cycling, thus enabling faster cycle rates without the need for a very large heating and cooling system (i.e. no more liquid cooling to the stack up). The apparatuses and methods described herein may reduce thermal mass by reducing/removing thermal mass from above a droplet or region holding one or more droplets in the upper (top) plate of a cartridge. For example, when the upper/top plate is formed of an acrylic or polycarbonate material, the thermal mass above the air gap region may be reduced by including one or more cavities in the top plate (e.g., the polycarbonate and/or acrylic structure) and filling the cavity with a thermally insulating material, or a material that has a low thermal conductivity (such as air). The cavities may be positioned in the top plate of the cartridge over a thermally controller region, so that when a droplet of material is below the cavity, the heating/cooling applied by the apparatus, e.g., from the PCB, may more rapidly change the temperature of the droplet in the air gap region. Removing the thermal mass above the droplet may be incorporated in the design of any of the cartridges described herein. The cavity may be formed near the bottom surface of the top plate (e.g., immediately on one side of the air gap); the cavity may be partially through the thickness between the top and bottom surfaces of the top plate. FIG. 27 illustrates an example of a portion of a cartridge 2700 showing a thermally controlled region in the top plate 2701 of the cartridge 2704. The cartridge may be positioned onto the apparatus 2703. A droplet 2707 within the air gap region of the cartridge (e.g., the region bounded by the bottom surface of the upper plate 2701 and the top surface of the lower sheet of dielectric material 2709. Thus, in variations in which the cartridge body, including the top plate, is formed of a solid piece of polycarbonate, one or more cavities 2705 may be created and may be enclosed or filled with an insulating material that has a low thermal mass. This may prevent heat from the sample transferring to storage region above it. The void replacement material can be air or a similar material that has low thermal conductivity and low thermal mass.

Alternatively or additionally, thermal mass may be removed from the PCB by removing material (e.g., with precision milling) and/or using materials having a very low thermal mass. For example, one or more layers of the PCB may be removed in the heater zone (e.g., heating or thermally controlled region) to reduce thermal mass. This may be done from the bottom side of the board as to not disrupt the surface finish of the electrodes.

FIG. 28 is an example of a milled region in a PCB of an apparatus that has a lower thermal mass in order to increase the response time for temperature change of a droplet in the air gap of a cartridge (not shown for clarity). In This schematic example, showing sectional view, the layers of the bottom (e.g., PCB) may include one or more layers, e.g., of copper 2801 and dielectric 2803, beneath the droplet (in the PCB of the apparatus) has been milled to create a cavity or void which may be filled with a thermally insulating material, including air. Thus, thermal conduction through the PCB may be reduced. In general, the cavities in the top and/or bottom plate may help thermally isolate the droplet in the air gap between the top and bottom plates.

In addition to speeding temperature changes in the droplet by reducing thermal mass, any of the methods and apparatuses described herein may increase the thermal conductivity between a heater source and an electrode to improve performance. For example, if the heater layer on the PCB is in a layer underlying the PCB, then using a high thermally conductive dielectric layer will increase heat transfer from the heater layer to the electrodes, as illustrated in FIG. 29. FIG. 29 shows a high conductive dielectric 2905 between the heater 2903 and electrode 2901 copper regions.

In some variations, the apparatus (and in particular the PCB portion of the apparatus) may alternatively or additionally be configured to increase thermal conductivity by including one or more thermal vias near each active (e.g., driving) electrode/cell. The thermal via may be a channel or passage in thermal contact with the region near the electrode(s), including the region underlying the electrode(s), such as the PCB material, of the thermal control region, and may be filled with any thermally conductive material. For example filling the vias with a thermally conductive material (such as, but not limited to: copper, epoxy, resin, etc.) may further increase the thermal conductivity and may dramatically increase the thermal response time of the droplet or other material in the air gap. Thus heating and/or cooling may be much faster than without the vias. The thermally conductive vias can be implemented with or without a milled region in the PCB (shown in FIG. 30A, showing a milled region with thermally conductive vias, and 30B, showing thermally conductive vias without a milled region). For example, FIG. 30A illustrates a plurality of thermal conductive vias 3005 in an example of a bottom plate (e.g., PCB) with that has been milled to provide a region of thermal isolation around the thermally controlled active region. In each of FIGS. 30, 31A, 31B, a cartridge is not shown, for clarity, but apparatuses having the modifications described may utilize a removable cartridge as described herein.

The vias may be filled with any appropriate thermally conducive material. In some variations the vias are filled with a thermally conductive material that is not electrically conductive (e.g., epoxy, resin, etc.).

One end of the vias may be in thermal contact (e.g., may touch) with a region adjacent to the ultimate upper surface (e.g., the cartridge-contacting surface) and/or the electrodes of the apparatus. In particular, when the thermal vias are filled with an electrically conductive material (e.g., copper) the thermally conductive vias may contact a region immediately adjacent to the electrodes, but not in electrical contact with the electrodes. Another portion of the thermal via may be in thermal contact with a heat sink beneath the upper surface (e.g., on a side and/or bottom surface). In some variations the opposite end of the vias may be in contact with a temperature controlled surface (e.g., cooled surface, heated surface, etc.). In some variations the vias may be in thermal communication at one end region with a thermal controller (e.g., heater, cooler, heat sink, etc.); the vias may pass through a vacuum chuck on which the PCB sits.

The vias may be any appropriate dimensions. For example, the thermally conductive vias (referred to herein as thermal vias or simply vias) may have a dimeter of between 0.1 mm and 3 mm, 0.1 mm and 2 mm, 0.5 mm and 1.5 mm, about 0.8 mm, about 1 mm, about 1.2 mm, about 1.4 mm, etc. The thermal vias may have a round, oval, rectangular, square, triangular, or any other cross-section and may be cylindrical, extending through the printed circuit board from the thermal control (e.g., one or more of a heater, cooler, heat sink, etc.) to the region immediately beneath the electrode or immediately adjacent to the electrode (in some variations, without contacting the electrode, so that they remain electrically, but not thermally, isolated from the electrodes).

As mentioned, any appropriate number of vias may be formed per each cell (e.g., associated with each electrode driving movement of fluid in the air gap of a cartridge). For example, each cell in the thermally controlled region (which may include multiple thermally controlled cells) may be in contact with 2, 3, 4, 5, 6, 7, 8, 9, 10, 11, 12, etc., or more vias. For example, each thermally controlled cell may be in contact with more than 8 vias.

The use of thermal vias may provide a dramatic improvement over variations in the rate of heating and/or cooling of the thermally controlled regions, compared to systems that do not include thermal vias.

Cartridge Features and Seating Arrangement. In addition to the features described above, any of the cartridges may alternatively or additionally include one or more openings into or through the top plate over some of the cells (e.g., regions that will correspond to one or more drive electrodes). These openings may be open and may allow direct imaging by optics 3121, as illustrated in FIG. 31. Alternatively or additionally, an opening may be used for passive dispensing of fluid from the air gap. For example, in FIG. 31, an opening 3103 in the top plate of the cartridge 3105, seated on seating surface 3107 having actuation electrodes, may be used to passively dispense fluid from a droplet 3111 positioned beneath the opening; the droplet may be moved under the opening via DMF as described above. Once positioned, a predetermined amount of fluid may be passively dispensed from the droplet into the opening, e.g., via capillary action, and the droplet may be moved away from the opening. The sample material may then be analyzed or processed using the microfluidics in top of the cartridge and/or may be analyzed in place. Alternatively, the material sampled may be added to another droplet 3119 after the first droplet 3111 has been moved away; positioning the second droplet under the opening through the top plate that includes the sampled material 3103. This sampled material (fluid) from the first droplet may be a metered amount, based on the dimensions of the opening 3103. The top plate may include a hydrophilic surface or surface coating. In some variations, an opening in the top plate may be pre-loaded with a material, such as a liquid wax or other coating material that maybe combined with a droplet when the droplet is moved under the opening (e.g., to dispense a coating material, such as an anti-evaporation coating of liquid paraffin, oil, etc.). An opening in the top plate may also act as a thermal insulator. The opening may extend over a portion of the cell so that the return electrode may be on the edges of the opening. The opening may be any size and dimension (e.g., round, square, etc.). Although the variation shown in FIG. 31 illustrates imaging through the top plate (using optics 3121), in some variations the imaging may be done from the bottom, through the bottom of the cartridge. For example a region of the bottom of the cartridge (e.g., the dielectric film) may be transparent or optically permeable for imaging (e.g., fluorescence).

In any of the cartridges described herein, the top plate may include a plurality of manifold for delivery of one or more materials into the air gap. FIGS. 32A and 32B illustrate one example of a top plate, formed of a polymeric material (e.g., acrylic and/or polycarbonate). FIG. 32A shows the upper region of the top plate (which may be covered by one or more covers, not shown. In FIG. 32A, a plurality of dispensing regions 3204, 3206, 3208 of different sizes are included. For example a smaller 3206 (e.g., 2-20 microliter size), medium 3204 (e.g., 100 microliter to 1 mL) and large 3208 (e.g., 1 mL to 5 mL) are shown, as are waste and/or mixing regions 3210. These chambers may be preloaded with fluid, and each may include an opening into air gap region. A pressure control may be used to apply pressure to drive the fluid out of the opening of the dispensing region and into the air gap, which may be controlled by the apparatus or other device holding the cartridge. Thus, the apparatus may include one or more pressure interface(s) that may be used to control the release of fluid from and fluid handling in the top plate.

In some embodiments, the top of the cartridge may be covered by a protective film, such as a 200 μm thick top cover film. The bottom surface of the top plate of the cartridge body, forming the top surface of the air gap, may be covered in a conductive substrate material that may be hydrophobic or may include a hydrophobic coating. For example, the film may be a COC film sputtered with ITO (conductive material) and Cytop (omniphobic substrate) to seal the channels on the bottom side of the main cartridge body.

FIG. 32B illustrates a bottom side of the top plate portion shown in FIG. 32A. The bottom side may be coated or covered with the electrode and/or a dielectric and/or a hydrophobic coating, a described above. In FIG. 32B, the top plate may also or alternatively include one or more channels 3212 in the surface of the plate that may allow for mixing as described above. The bottom surface of these channels may be formed by the upper dielectric and/or return electrode (which, in some variations, may include a dielectric, hydrophobic film and/or electrode layer). In general, the cartridges described herein may include one or more serpentine mixing channels, which may provide a fluidic pathway for entire volumes of liquids so they can be chaotically mixed on the EWOD zone.

In any of the cartridges described herein, the bottom surface, which may be configured to contact the seating surface of the apparatus and in particular the drive electrodes in the apparatus, is formed of a dielectric material, as described above. The bottom surface may be a sheet of dielectric material having a first side and a second side (the first side forming an exposed bottom surface on the bottom of the cartridge). The second side of the sheet of dielectric material may comprise a hydrophobic surface and may form one side of the air gap. The bottom surface may be, for example, a film that is either itself dielectric, and/or that is coated with a dielectric material. For example, in some variations the film is a dielectric and/or hydrophobic film. It may be beneficial to have this bottom surface be substantially flat. Any of the cartridges described herein may be configured apply tension to the sheet of dielectric material. For example, any of these cartridges may include a frame to hold the dielectric material in tension. Thus the cartridge may include a tensioning frame holding the bottom sheet of the cartridge.

The dielectric and/or hydrophobic film tensioning design may pretension a sheet (e.g., a dielectric and/or hydrophobic film) such that the surface of the sheet is planar throughout, and remains planar during its interface with the apparatus seating surface (e.g., the PCB) and during use of the DMF apparatus. The goal of the tensioning frame holding the film (e.g., a dielectric and/or hydrophobic) in the cartridge is to interface with the seating surface (e.g., of the PCB interface) to ensure that the film remains in complete contact with the electrode grid (e.g., driving electrodes) throughout use of the apparatus.

In any of the cartridges described herein the bottom of the cartridge may include a sheet of dielectric material having a first side and a second side, the first side forming an exposed bottom surface on the bottom of the cartridge, as described above. Any of the cartridges described herein may include a tensioning frame to hold the sheet flat by applying tension. The sheet, while exposed as the bottom of the cartridge, may be slightly recessed compared to the outer perimeter of the cartridge bottom, which may fit into a lip or recess on the apparatus, as will be described in further detail below. Thus the sheet of dielectric material at the bottom of the cartridge need not be the bottommost surface.

For example, FIGS. 33A-35 illustrate one example of a cartridge assembly that includes a frame to stretch/smooth the bottom (e.g., dielectric sheet) of the cartridge. FIGS. 33A-33D illustrate one example of a tensioning frame. In this example, the cartridge body features a two-part film tensioning mechanism. The two parts, shown in FIGS. 33A-33B (and assembled views of cartridge 3300 in 33C-33D), may include a tensioning frame 3301 and a dielectric and/or hydrophobic film frame 3303. When assembled, the film forming the bottom of the cartridge may be adhered to the dielectric and/or hydrophobic film frame 3303. The film and film frame 3303 assembly may be inserted into a groove in the tensioning frame 3311 employing a connector (e.g., a snap-fit mechanism). Upon snapping into the tensioning frame, the film may be pulled taught in all directions in an X-Y plane. This frame assembly may then be fastened into the cartridge body. The assembled frame may include lower profile (e.g., cut-out) region 4909 that may provide access to electrically connect the return electrode on the upper plate, bypassing the film on the cartridge bottom surface.

One example of a cartridge including a frame for holding the bottom membrane flat is shown in the exploded view of FIG. 34A. In FIG. 34A, the individual components in the cartridge and film tensioning assembly are shown. This figure also outlines their arrangement during assembly. The first two components to assemble may include, e.g., an optically clear double-sided adhesive 3402, and a sheet of dielectric material 3403 (e.g., coated on conductive material, which may further have a hydrophobic coating or layer). The conductive material may be any conductive material such as ITO, aluminum film, amongst others. The frame (e.g., tensioning frame 3404) and the sheet including a dielectric material 3405 may also be included, and the film secured in place by a second portion of the film frame 3406. The air gap 3409 maybe formed between the film 3405 and the bottom surface 3403 of the top piece 3401 (which may include the return electrode(s)).

The film/cartridge and PCB interface may include a film tensioning frame as described above and a groove drilled out (trough) of the top surface of the PCB may form a boundary around the electrode grid of the apparatus. FIG. 35 shows an isometric, exploded view of an example of an assembly of a cartridge, including a film 3520 and film tensioning frame (outer frame 3521 and inner frame 3523), and an upper (top) portion of the cartridge 3509; FIG. 35 also shows a portion of an apparatus, including a PCB 3511 forming a seating surface for the cartridge. The seating surface also includes a trough 3505 to accept the lip around the bottom film of the cartridge (in this example, formed by the tensioning frame 3503). The trough may be a groove that is drilled out around the perimeter of the electrode grid. As the assembly arrangement in this embodiment shows, the film tensioning frame 3503 may slot into this trough 3505 around the electrode grid. Once assembled, the film tensioning frame 3503 may tension the film in X and Y, but also pulled downward in the Z direction at the edges of the film. The film may wrap over filleted edges of the trough, just slightly outside the boundaries of the electrode grid (not shown).

FIGS. 36A and 36B show top and cross-section views, respectively, of one example of a cartridge, including a bottom dielectric (and hydrophobic or hydrophobically coated) film, and film tensioning frames seated on a PCB assembly portion of an apparatus. The cross-section in FIG. 36B highlights how the dielectric and/or hydrophobic film may be pulled taught across the electrodes, and sealed down using the vacuum ports through at least some of the electrodes (drive electrodes) of the PCB, and also illustrates seating of an edge (extending proud of the film) in a trough formed in the PCB seating surface to seat the film. When fully assembled, these components may allow for a secure, fully tensioned, and planar dielectric (and/or hydrophobic) film to be secured to the driving electrode grid on the PCB. FIG. 37 is an exploded view showing individual components and their arrangement in assembly, including a cartridge upper body frame 3706, a dielectric film 3705 held in tension by a tensioning frame 3704, a PCB 3702 forming a seating surface on the apparatus, a groove or channel 3703 on the seating surface around the perimeter of the array of drive electrodes (driving electrodes) on the PCB, and a vacuum chuck 3701.

FIGS. 38A and 38B shows a top view of the assembly and a cross sectional view, respectively. The cross section view highlights the relationship of the vacuum chuck 3811 on the cartridge 3813 and film assembly, as well as on the PCB 3815. The section in FIG. 38B also highlights a few different effects of this system. The arrows 3805 depict the flow path for vacuum originating from a diaphragm vacuum pump 3807 on the outside of the chuck. This may be the same flow path as is described in more detail below in FIG. 41B. The arrows outline the downward force being applied to the film by the vacuum through the via holes in the PCB. The vacuum chuck and interface with the PCB securely adhere the film to the electrodes and apply downward force in Z. The film tensioning mechanism and PCB trough ensure the film remains planar by applying force in X and Y, while maintaining contact around the edges due to a fillet along the internal edge of the trough.

One-plate cartridge. In some embodiments, one or more one-plate cartridges may be used in the multiplex system. In this case, a one-plate cartridge includes a single plate and may be open to the air above the single (e.g., first) plate; the "air gap" may correspond to the region above the plate in which one or more droplet may travel while on the single plate. The ground electrode(s) may be positioned adjacent to (e.g., next to) each actuation electrode, e.g., in, on, or below the single plate. The plate may be coated with the hydrophobic layer (and an additional dielectric layer may be positioned between the hydrophobic layer and the dielectric layer, or the same layer may be both dielectric and hydrophobic).

The one-plate cartridge may be prepared similarly to the two-plate cartridges described herein, without the variety of layers that enclose and form the second plate of a two-plate cartridge of any of FIGS. 33-35. Similarly tensioned frames and bottom plates may be prepared using the same methods, to provide sufficiently rigid one-plate cartridges. One-plate cartridges offer advantages in providing full access to both droplet dispensing/withdrawal and optical imaging/activation from above the open air-gap. The one-plate cartridge may have any suitable feature described above for the two-plated cartridges in any combination. In some embodiments, the bottom of the one-plate cartridge may be optically permeable or transparent to permit imaging/photoactivation from below.

In any of the apparatuses described herein, the cartridge material of either a two-plate or a one-plate cartridge may allow for dimensional accuracy, hydrophobicity of channel surfaces, & bio-compatibility. As mentioned above, the use of one or more thermal windows above a region of a thermally controlled zone may be useful. Typically, the reduction of material in thermal heating zone may decrease thermal mass and increase PCR ramp rates, when the system is used to perform PCR on the apparatus.

Apparatus Features. In general, any of the apparatuses described herein may include a PCB portion, that may include the electrode array, active thermal control (e.g., heater, cooling, etc.), magnetic field applicator(s), etc., and a chuck (e.g., vacuum chuck) that may be mounted to the PCB. This portion of the apparatus may form the seating surface for the bottom of the cartridge, so that it may sit on the apparatus securely and in a predetermined orientation. For example, the cartridge may be keyed to fit onto the seating surface in a predetermined manner (e.g., by including one or more orientation slots, pins, etc.). The apparatus may also include one or more control units, including one or more processors, which may control the activity of the apparatus and may be configured to drive droplets and analyze information from the cartridge. The controller may also include memory, one or more datastores.

The seating surface of the apparatus may be configured both to seat a cartridge, but also to prevent arcing, sparking or shorting between the plurality of electrodes on the seating surface. For example, the seating surface may coated with an additional dielectric (onto which the dielectric bottom surface of the cartridge may sit) such as parylene and/or alternative or additional materials. The dielectric bottom surface may prevent arcing between the electrodes in the array or electrodes (driving electrodes) on the seating surface. The spacing between the driving electrodes may be between about 50-120 micrometers. This close packing between electrodes on the otherwise flat surface may otherwise be susceptible to arcing/shorting between electrodes, thus the use of an outer dielectric coating (in addition to the dielectric layer of the cartridge) may limit sparking/arcing between electrodes.

As discussed and described above, some or all of the electrodes may include an opening through them which may be connected to a vacuum source for seating the electrodes onto the device. For example, in some variations, every electrode in the array includes an opening therethrough; in other variations, every other electrode may include an opening (e.g., alternating). In some variations every third electrode, every fourth electrode, etc. In some variations only corner electrodes may include an opening.

Droplet Detection. Any of the apparatuses described herein may include droplet detection. As described above, droplet detection may be performed based on the capacitance of the electrode(s) in the array of driving electrodes by monitoring the current through the electrode(s). Also described herein are apparatuses (e.g., systems or devices, including apparatuses) in which droplet detection is based on a capacitance measurement by creating a capacitor divider. In this example, the top plate may form a reference frame (e.g., reference electrode, such an ITO electrode) and may be usually driven between 0 and 300 V to create the AC signal; during droplet detection the reference electrode (top electrode) may be disconnected from the driving signal and its voltage sensed by the controller (e.g., microprocessor), referred to in FIGS. 39A and 39B as "ITO sense" as it may act as a sensing electrode, and may be electrically coupled to one or more reference capacitors. One or a group of electrodes may be activated at a higher known voltage (e.g., 300V DC), while all other electrodes are grounded. This creates the divider as shown in FIG. 39A. FIG. 39A shows an ITO sensing circuit with a switch to toggle between sensing (e.g., capacitive sensing from the reference/top plate) and driving, e.g., to move one or more droplets.

In FIG. 39A, the voltage at the ITO sense node (the ITO sense electrode) is driven by the ratio of C_A to the total capacitance (C_A+C_B). The capacitance of C_A changes based on the material permittivity in between the plates of the capacitor (electrode to ITO). The capacitance of C_B also changes relative to what is present between the ITO and the remaining electrodes. Air, wax, water and reagents have different permittivity, and thus changing the capacitance and the voltage at ITO sense. This enables this droplet detection method to not only detect droplets (e.g., the presence/absence of a droplet) but also to differentiate between droplets and identify specific reagents within the electrode grid.

Due to the variability of base capacitance, two calibration capacitors may be included (e.g., in FIG. 39B, C_REF and C_REF_LARGE). FIG. 33B illustrates another example of a capacitive sensing circuit that includes multiple reference capacitors. By driving all electrodes (e.g., all of the drive electrodes) to 300V, the total capacitance C_Total can be calculated by using the reference capacitors. The reference capacitance can be increased if there is a large enough C_Total to saturate the voltage at ITO SENSE. The conditioning circuitry for the ITO SENSE may isolate the voltage from minor leakage currents.

FIG. 40A shows exemplary values for capacitance that may indicate the presence or absence (and/or identity of the material) of a droplet in one or more cells within the air gap. As discussed above, a 'cell' in the air gap may correspond to the region above a driving electrode when the cartridge including the air gap is placed into the DMF apparatus, which may have the array of drive electrodes on the cartridge seating region. In FIG. 40A, the "ITO" corresponds to the upper (e.g., return) electrode on the upper plate of the cartridge. In this example, C18, C21, C24, C27, C30 are the reference capacitor (e.g., 11.9 pF in this case) and C16, C19, C1, C25, C28 is the capacitance measured as described above, corresponding to the capacitance when different drive electrodes are measured (e.g., set to the high voltage, while grounding the other drive electrodes), either with or without a droplet. Water, wax and air (no droplet) have very different capacitances that can be used to identify the presence or absence of a droplet (e.g., capacitance greater than or equal to 0.09 pF, greater than or equal to 0.1 pF, etc.). In this example, a capacitance above this threshold (e.g., above 0.06 pF, 0.07 pF, 0.08 pF, 0.09 pF, 0.1 pF, 0.11 pF, etc.) indicates that the presence of a material in the air gap above the examined (set to high voltage, e.g., 300 V). Further, the range of the measured capacitance above this threshold may indicate the composition of the droplet, e.g., aqueous (water) and/or wax/oil. For example, a capacitance of greater than about 3 pF (e.g., 3 pF, 3.1 pF, 3.2 pF, 3.3 pF, 3.4 pF, 3.5 pF, etc.) may indicate that the droplet is aqueous, while a capacitance of between about 0.09 pF to about 3 pF may indicate that the droplet is wax or oil (e.g., between about 0.07 pF and about 3.3 pF, between about 0.09 pF and about 3.0 pF, etc.).

FIG. 40B is a graph showing example of measured voltages using this technique, based, showing the differences between different voltages measured with various droplets (water, wax) versus with no droplet (air) over a single test cell. In FIG. 40B, the voltage detected when an aqueous droplet is present is about 3.3V, compared to 0.085V when there is no droplet present and 0.176V when wax is present. The measurement for wax is double that of air (no droplet/material), and water is much higher; in this example the circuit caps the value at 3.3V. Different materials can be detected by their differing permittivities. The permittivity of water may also be a function of temperature. Thus, in some variations, the capacitance may change as a function of temperature when a droplet is present. This property may be further used to identify water, and may also be used to estimate temperature. Thus, in some variations the capacitance measurement of the droplet may be used to estimate their temperature as well. For example, FIG. 40C is a graph showing the static relative permittivity of water, showing a change in relative permittivity with change in temperature (between 0-300 degrees C.).

Chuck Design. Any of the apparatuses described herein, e.g., the apparatuses, may include a chuck (e.g., a vacuum chuck) that may form part of the seating surface, as mentioned above. The vacuum chuck may be attached to the electrode array (e.g., the drive electrodes that may be part of a printed circuit board) and may also be integrated with a magnet and/or heat dissipation features. Any of these elements or portions of these elements may be include or omitted, and may be used in any combination.

The vacuum chuck design may help ensure a reliable and effective vacuum adheres the bottom of the cartridge (e.g., in some variations a dielectric and/or hydrophobic forming the dielectric layer) to the electrode grid. The vacuum may be applied through one or more (e.g., a manifold) of vias (e.g., copper vias).

In addition, any of the apparatuses described herein may include a magnet that is integrated into the base, including the chuck and/or the seating surface. The integrated magnet(s) may be configured to allow an actuatable magnet to engage with material in the cartridge (e.g., magnetic beads in the liquid droplets in the air gap) through the vacuum chuck. The magnet(s) may rest slightly below the PCB forming the seating surface of the apparatus, without impacting the vacuum performance or function.

Any of the readers (apparatuses) described herein may also or alternatively include one or more thermal regulators, including one or more heat dissipation elements that may quickly and accurately dissipate heat from the heater(s) in the apparatus that control the temperature of one or more cells in the cartridge when it is seated and retained on the seating surface of the apparatus. For example, described herein are two designs for heat dissipation elements that may be used separately or tighter. One exemplary thermal dissipation designs is configured to dissipate heat from a thermoelectric heater and another design is configured to dissipate heat from an embedded heater.

FIGS. 41A-49 illustrate a vacuum chuck portion of the apparatus that may be used with any of the apparatus apparatuses described herein. In general, the vacuum chuck may be configured such that negative pressure is applied through the chuck (e.g., from a vacuum pump), and is directed underneath the seating surface (e.g., the PCB forming part of the seating surface) in an area that is pneumatically isolated, e.g., by an O-ring. The seating surface may have via holes (e.g., in the PCB) that allow for the negative pressure to act directly on the bottom of the cartridge (e.g., a dielectric and/or hydrophobic film) that is seated on the topside of the seating surface (e.g., the PCB forming the seating surface), pulling the cartridge bottom down in the Z direction, and adhering it onto the electrode grid.

The vacuum chuck may include one or more of: a vacuum channel with ports on either end, a groove for an O-ring, threaded holes to attach the PCB, and a recess under the electrode grid. For example, FIG. 41A is a top view and FIG. 41B is a cross sectional view of one example of a vacuum chuck 4100. Section A-A highlights the vacuum channel and its accompanying ports. The pneumatic flow 4105 follows the path of the arrows shown in FIG. 41B: first pulling through at least one inlet port, then flowing through the channel 4107, and finally flowing out of the side port 4109. A portion of the chuck (over which the seating surface formed by the PCB will be placed) is surrounded by an O-ring 4103.

For example, FIG. 42 shows an isometric view of the chuck shown in FIGS. 41A-41B. The groove 4211 (that may be designed using, e.g., a Parker O-Ring design standard) is configured to fit an O-ring. Once in place, and with the chuck fastened to the PCB, the O-ring may pneumatically isolate the vacuum directly under the electrode grid. The seating surface may be formed by securing a PCB having the electrodes (not shown) to the chuck. For example, as shown in FIG. 42, the chuck may include multiple threaded holes 4201 for attaching the seating surface (e.g., PCB). In some variations the chuck includes a minimum of four threaded holes (eight shown in FIG. 42), each equidistant apart in at least the X or Y directions, and centered about the origin of the chuck. The screw holes may serve a dual-purpose: first to fasten the PCB to the chuck such that the interface of the two components is planar, second to apply a downward force in the Z direction about the perimeter of the O-ring, effectively creating a pneumatic seal.

In FIG. 42, an opening 4213 for a magnet is present on the upper region and may include sufficient space for the magnet to be moved to/from the cartridge (e.g., by moving up/down within the space, or in some variations laterally). The region around the magnet opening may include a gasket or sealing ring (e.g., O-ring) 4215 for isolating the magnet region from the vacuum region, similar to the outer O-ring that fits in groove 4211. FIG. 43 shows a cross sectional and zoomed-in view of the chuck of FIG. 42. FIG. 43 shows an enlarged image of section A-A, showing the boundaries of the recess 4317, 4319 (along the X axis) that may create space between the PCB and the surface of the chuck, but only in the isolated area where the vacuum is active. This space may optimize the pneumatic flow of the vacuum as described in the herein.

As mentioned, any of the apparatuses described herein may include an integrated magnet. In FIGS. 41A-44, a recessed region 4421 may be used to hold an integrated magnet that may be moved up/down by the system to engage/disengage a magnetic field. Alternatively in some variations the magnet may be stationary, but may be toggled (on/off, and/or changing the intensity) by the apparatus's controller.

Thus, the vacuum chuck may include an integrated magnet and may therefore include one or both of: a cut-out that allows a magnet to travel through the chuck, and a second O-ring groove that isolates the magnet zone from the pneumatic flow of the vacuum, thus ensuring the vacuum is not compromised by the magnet cut-out. FIG. 44 shows a bottom view of a chuck similar to that shown in FIGS. 41A-41B. A through-cut region 4421 is shown, and can be sized to fit the desired magnet, and allows for uninterrupted travel of an actuatable magnet. A magnet can pass through the cut-out, landing directly below the PCB when engaged, or can be disengaged through the cut-out when not in use.

FIGS. 45A and 45B illustrate top and side sectional views, respectively, of a chuck similar to that shown in FIGS. 41A and 41B, but including a gap 4523 for thermally accessing a heating component, such as a heater (e.g., resistive heater) 4525. The heater 4525 is shown above the cavity 4523 in the chuck so that it may be easily thermally regulated (e.g., cooled). The resistive heater may be in the PCB (not shown in FIGS. 45A and 45B).

For example, FIG. 45A shows one example of a heat dissipation system that may be included in any of the apparatuses described herein. This heat dissipation system may be built such that any thermal load created by a heater 4525 in the apparatus (e.g., in the PCB) may be dissipated properly and effectively. A first heat dissipation configuration may be built to dissipate heat generated by a heater embedded in the PCB and is described below as a heat dissipation of an embedded heater. The second heat dissipation design may be built to dissipate heat generated by a thermoelectric cooler embedded in the vacuum chuck and describe below as Heat Dissipation of Thermoelectric cooler. Both heat dissipation designs may employ unique features in the vacuum chuck, as well as accompanying components to dissipate the heat. Both designs can be used together or in the assembly, or independently.

For example, the heat dissipation of the embedded heater in the vacuum chuck may be configured as a vented chamber. In FIG. 45A, the top view of the chuck shows the heat dissipation aspects of the chuck; FIG. 45B shows a pair of air channels 4527, 4527' that feed into a cooling chamber 4529 that may be part of or below (or otherwise connected to) the region where the heater is positioned. In FIG. 45B, the flow path of the multiple air elements (channels 4527, 4527') acting in this system are shown. The air drawn in 4527 may be warmed by the heat, including residual heat, from the heater in the PCB (e.g., seating region, not shown), and may flow over the through-cut 4523 region in the vacuum chuck, which may be covered or partially covered, or open to the heater in the PCB (or to one or more thermal vias in thermal communication with the heater). Section A-A (shown in FIG. 45B) shows a pneumatic flow of two air elements, warm air generated about heater 4525 and ambient air when a fan, fastened flush against the chuck and centered about the through-cut 4523, is turned on. The fan (not shown) may push the warm air generated by the heater out of the through-cut of the vacuum chuck. Simultaneously, the fan may pull ambient air into the chuck and through-cut via two channels in the chuck 4527, 4527'. The system can continuously or intermittently cycle ambient air into and warm air out of the chuck, effectively dissipating any heat generated by the PCB heater Also described herein are systems for heat dissipation of an embedded heater. For example, the assembly shown in FIG. 46 may be configured to include both the chuck 4631, which may be like any chuck described herein, and a fan 4633. The pneumatic flow described in the previous above may be controlled by a fan 4633 fastened to the bottom of the chuck 4631. FIG. 46 shows a front view of the chuck 4631 and the fan 4633. The set of arrows 4635, 4635' and 4637 depict the airflow path. FIG. 47 shows an example of an arrangement of the chuck 4731 (which may be like any chuck described herein), a fan 4733 (which may be like any fan described herein), a PCB 4739, like any PCB described here, forming a seating surface (e.g., including the array of electrodes, not shown) and a cartridge 4741, which may be like any cartridge described herein. The cartridge may be held down by the vacuum through the openings (e.g., in some of the electrodes).

FIG. 48 shows an example of a heat dissipation system for regulating the temperature of a thermoelectric cooler through a vacuum chuck. In FIG. 48, an isometric view of a chuck (similar to that shown in FIG. 41A) is shown. The chuck shown includes a recess 4843 designed such that a thermoelectric cooler (TEC) can slot into it.

FIGS. 49A-49B show top and sectional views, respectively, of a chuck similar to that shown in FIG. 41A. The section (though A-A) shown in FIG. 49B highlights the thermal path of the heat generated by a thermoelectric cooling element 4945. The rectangle 4945 represents the TEC, and the arrows within the chuck depict the heat spreading throughout the chuck. The apparatus may include one or more heat sinks of a desired size that may be fastened to the bottom of the chuck and below the TEC that absorbs the heat. Lastly, two fans, fastened to either side of the heat sink (shown in FIG. 50), may act in unison to push the hot air away from the entire system and funnel ambient air into the system.

FIGS. 50, 51A to 51C illustrate assembly of one or more devices configured for heat dissipation of a thermoelectric cooler. For example, FIG. 50 shows the front view of a chuck. The arrows 5047 in FIG. 52 directed downwards show a thermal path of the heat in the chuck as described in FIG. 49B. The arrows 5049, 5049' depict the flow path of air being pushed into the heatsink by a fan as well as the path of air being pulled out of the heatsink by a fan. The fans act in the same direction, simultaneously. FIGS. 51A-51C show an assembly process as well as multiple components that may be included in this apparatus and method of using it. For example, FIG. 51A shows a chuck 5131 (which may be like any chuck described herein, FIG. 51B shows the chuck 5131 plus a heatsink 5151, and FIG. 51C shows the chuck 5131, plus the heatsink 5151, plus two fans 5133, 5133'. FIG. 52 depicts an exploded view of a partial arrangement of an apparatus assembly, including the assembly in FIG. 51A-C (e.g., chuck 52315131, heat sink 5151, fans 5233, 5233') as well as the PCB 5239 including the driving electrodes and a heater (not visible), which may be like any PCB described herein; in addition a cartridge 5247, which may be like any cartridge described herein, is attached via vacuum to the seating surface of the PCB Action zones. Any of the apparatuses described herein may include one or more action zones that strategically position the different possible actions that a droplet can be subjected to for protocol execution. The goal of the plexing strategy is to adapt to different laboratory requirements in a more flexible, modular way. Different stages of the protocol to be executed may be grouped strategically into action zones to allow the protocol designer define abstract targets on the board. The action zones may be fixed regions under or over the electrode board used for reactions (i.e. mixing, merging, heating, cooling, thermocycling, magnet capture, waste, optical detection, etc.).

FIG. 53A shows an example of an electrode grid setup with independent action zones for either magnetic capture 5301 (three magnetic control zones, which may be used as mixing chambers, are shown), a heater (five heating zones 5303 are shown) which can be isothermal or thermocycler, a Peltier 5305 which is an active cooling zone down to 4° C. and may also heat, and a waste connection to the top plate through a channel and into a waste chamber (three waste zones 5307 are shown, which may connect to separate or the same waste chambers). The cartridge setup may also include a mixing connection to the top plate through a channel (e.g., one or more of the waste regions/zones 5307 may be used for mixing, as described herein) and one or more optical detection regions 5311. Thus, FIG. 53A shows an electrode grid with distinct action zones. These zones may be determined by the cartridge and the apparatus. For example, the cartridge may determine the waste zones, and the unit cells corresponding to the heating and/or cooling (e.g., thermal control), optics, and magnet(s) may correspond to regions of the apparatus, as described above.

FIG. 53B illustrates another example of a system (cartridge and apparatus) having a variety of action zones that are defined by either or both the cartridge and the apparatus. In FIG. 53B, the system includes 912 driving electrodes, corresponding to the 912 (0-911, e.g., a 38×24 grid) unit cells. Some of these cells within the air-gap of the cartridge may be action zones for loading, mixing, rinsing, imaging, etc. In general, these systems may include one or more loading inlets 5351 (in FIG. 53A, 10 loading inlets are shown, each corresponding to a single driving electrode unit cell; more than one unit cell may be used). Three thermocycling zones 5353 are shown in this example. One or more pinning features (e.g., protrusions, walls, barriers, etc.) may extend at least partially in to the air gap to pin or hold a droplet, and particularly the outer hydrophobic (e.g., liquid wax) material to maintain the position and droplet. In FIG. 53B, 10 pinning fixtures 5355 are shown. These pinning features may be a barrier (e.g., a fence, wall, stop, etc.). In general, the pinning features may be formed of a hydrophobic, oleophilic, hydrophilic, etc., material that may hold the coating material (e.g., the hydrophobic, liquid wax material) at least partially surrounding an encapsulated (e.g., coated) reaction droplet. The barrier may form a chamber that is open on one or more sides, as shown in FIG. 53B in which two or four pinning fixtures are used at the corners of the three thermocycling zones 5353. The barrier may extend from the top to the bottom of the air gap, or partially into the air gap. For example, the barrier may be formed of a material including a wax (e.g. paraffin) such a polymeric material mixed with a paraffin. In FIG. 53B, the pinning features are shown as PTFE posts that may be inserted into the main cartridge body (e.g., the top plate) and are hydrophobic but oleophilic and thus attracting the paraffin wax when a droplet is within the thermocycling zone, which may keep the droplet centered to the thermocycler zone when in use. In some variations the pinning feature may be formed of a material such as an acrylic, polycarbonate, Parafilm®, DuraSeal™, high melting temperature fluorowaxes/solid ski waxes, etc. The pinning feature may be formed as part of the top or bottom plate and/or may connect to both. In use, the barrier may pin the wax droplet around the reaction droplet. For example, a wax droplet may surround the aqueous reaction droplet 1501 and be held within the open chamber in the air gap formed by the barrier.

The systems described herein may also include one or more waste zones 5357 (in FIG. 53B, two zones are shown) that may be connected to a vacuum region for drawing, by suction, all or part of a droplet from the air gap. In FIG. 53B, one of the waste zones is a lower capacity (e.g., 1 mL) waste zone 5359 and the other may be higher capacity (e.g., 2 mL, 3 mL, 5 mL, etc.) waste zone 5357.

Any of the systems described herein may also include one or more magnetic regions 5363. In FIG. 53A, the system includes four magnetic unit cells distributed in the air gap, in some cases, overlapping with other regions, such as thermal control and/or isothermal regions. Generally, any of the zones described herein may overlap (e.g., magnetic, thermally regulated inlets, mixing channels, waste channels, etc. may overlap with each other).

The system may also include one or more isothermal regions 5361 (in FIG. 53B, a single isothermal region is shown, having 16 unit cells, 4×4, in which two of these unit cells are configured as magnetic control 5363 and waste 5357 zones.

Any of these systems may also include one or more mixing channels 5365. Four mixing channels are shown in the example of FIG. 53B. This example also shows a plurality of reservoir outlet holes 5369, from which fluid held in the cartridge's one or more reservoirs may be added to the air gap. Any of these systems may also include one or more recovery holes 5371 (one is shown in FIG. 53B). In general, the cartridge may include a smaller region than the number of possible active electrodes. For example, in FIG. 53B, the working region includes 912 active unit cells, as mentioned above, however they are surrounded by non-working (inactive) unit cells/electrodes 5373 that may be part of the apparatus. In FIG. 53B, approximate dimensions (e.g., 3.17 by 4.75 inches) of the cartridge base portion (forming the air gap dimensions) are shown, as examples only. As in any of the figures shown herein, these dimensions may be approximate only, and may be +/−1%, 5%, 10%, 15%, 20%, 25%, 30%, 40%, 50%, 75%, 100%, etc.

Figure 54A:
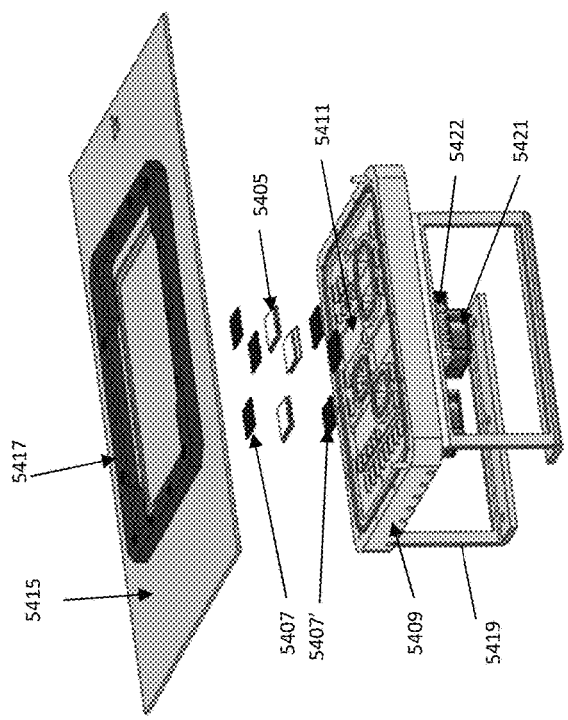
Figure 54B:
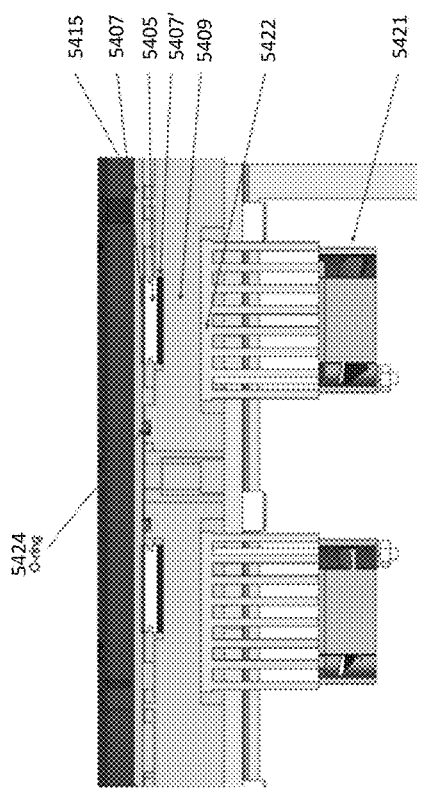

Thermal subsystems. Thermal subsystem may be like any described herein. FIGS. 54A-54B illustrate another example of a portion of the thermal subsystem, similar to that described above in FIGS. 47, 48, 49, 52 and 53A-C, above. In FIG. 54A, the thermal subsystem includes one or more TECs 5405 that may be sandwiched between a pair of thermal conductors (graphite pads 5407, 5407') and secured on the vacuum chuck 5409 in TEC slots 5411. The chuck may then be positioned beneath the electrode board 5415 that underlies the cartridge seat (including cartridge rim 5417 which is keyed to accept the cartridge and may seal with the clamp frame as described above). The chuck may be coupled to a frame 5419 within the housing (e.g., a housing frame), and may be positioned beneath one or more fans 5421 and one or more heat sinks 5422, as shown. FIG. 54B shows a cross-section through a side view of the thermal subsystem shown in FIG. 54A. The PCB of the electrode board 5415 is placed on top of the chuck 6409 holding the TECs. The chuck may be thermally conductive (e.g., formed of a thermally conductive metal and/or polymer) and one or more heat sinks 5422 and cooling fans 5421 may underlie each of the TECs.

Figure 54C:
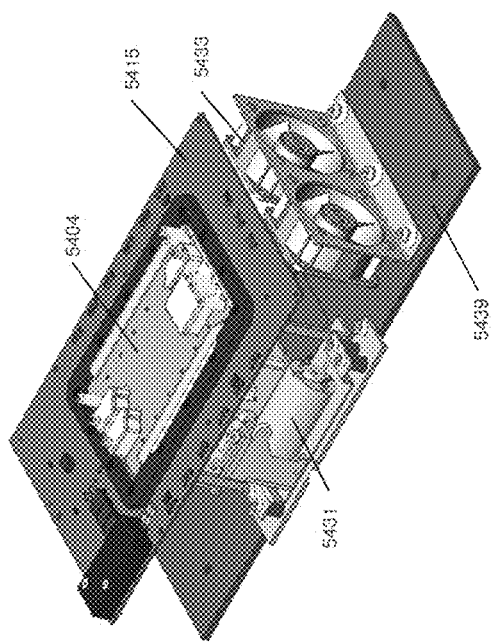
Figure 54D:
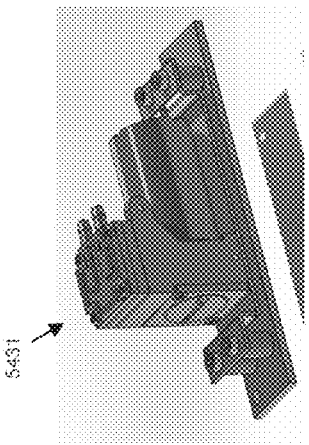

FIG. 54C shows a top perspective view of a portion of the apparatus including the thermal subsystem. In FIG. 56C the cartridge 5404 is shown housed within the cartridge seat on the electrode board 5415. A pump 5431 and additional front cooling fans 5433 (fan assembly) are mounted within the housing as part of the thermal control subsystem. The fan assembly, pump and housing frame are all mounted on a base plate 5439, which may be part of the housing or coupled to the housing. FIG. 54D shows an enlarged view of the pump 5431.

As mentioned above, any of the thermal control subsystems described herein may also include one or more resistive heater traces, drive circuitry and thermal protection (e.g., insulation); the resistive heater(s) may provide isothermal heating up to about 75 degrees C. in an action zone, as described above in reference to FIG. 53B (and may also include a magnet).

A resistive heater may include active cooling or passive (e.g., air) cooling, and the resistive heater may be in the electrode board, integral to, e.g., a second layer side.

The TEC thermal transfer regions may include the TEC, drive circuitry and protection (e.g., insulation), and may be configured to transfer energy from a TEC to the EWOD, including thermocycling with temperatures between about 4 degrees C. and 98 degrees C. Any of the apparatuses described herein may also include custom TECs and mountings, which may be used to provide a robust TEC that achieves ramp rates of up to 10 degrees C./sec and may have a high degree of temperature measurement accuracy.

In any of the apparatuses described herein, the TEC may be a high power thermocycling TEC (e.g., 30 W) soldered to the bottom of the electrode board directly. In some variations, the ramp rate may be 3 degrees C./sec or higher, and can be controlled by controlling the current applied to the TEC. For some variations of a control system, a closed feedback loop system may be used both in ramp rate and steady state with precision temperature control to at least 0.5 degrees C. accuracy. For example, the heaters (and ramp rates) may be configured to be in a 4×4 electrode grid array (heater zone), fitting approximately 200 μl droplets per heater zone.

Magnetic subsystems. A magnet control system (magnet control) may be included within the housing, and may coordinate (via the controller) one or more magnets to apply a local magnetic field to one or more zones of the cartridge. This is described briefly above in relation to FIGS. 41A-44. FIGS. 55A-55B also illustrate example of magnetic subsystems that may be included as part of an apparatus to apply and/or remove a local magnetic field to a region (zone) of a cartridge. For example, in FIG. 55A, the cartridge 5505 is seated in a cartridge seat in communication with the array of drive electrodes (on the electrode board 5515), beneath the vacuum chuck 5509. In this example, a magnet is shown as a Haibach array of magnets 5522 (an arrangement of permanent magnets that augments the magnetic field on one side of the array while cancelling the field to near zero or near-zero on the other side), and a magnetic jacket 5526 around the lower-filed side of the array; the jacket may be connected to a post that includes a bias (e.g., spring) 5524.

The magnet (e.g., jacket) on the post may also be connected to a motor (e.g., a stepper motor 5529) that can move the magnet up and down (e.g., in the z-axis, to/from the cartridge). A sensor, such as an optical sensor 5533 may determine the position of the magnet and this position may be used for feedback to help regulate the position of the magnet relative to the cartridge. For example, a flag 5537 or marker may be coupled to the magnet (e.g., through the post or jacket) and may be tracked by an optical sensor. The magnet may also be limited in movement to prevent it from crashing into the cartridge; for example, a hard stop 5538 (lip, rim, etc.) may be connected to the jacket or post to engage with a corresponding limit (rim, edge, etc.) on the chuck. The bias may help return the magnet back to a retracted position, away from the cartridge. FIG. 55B illustrates an enlarged view of the magnet assembly show in FIG. 55A. In this example, the spring compliance of the magnet head has a tolerance of about 1.5 mm, and the motor resolution is about 18°/step for about 80 steps/mm. As mentioned, the Halbach magnet array focalizes the magnetic field and amplifies the magnetic flux (in this example, of three neodymium magnets) at one point that is approximately 3.0 mm in diameter (roughly the dimensions of one unit cell, e.g., one electrode) and may generate enough force to achieve successful captures of magnetic beads in the cartridge. The magnet array housing ("magnet jacket") may secure the Halbach magnet array. The magnet actuator (e.g., a captive linear actuator, or stepper motor) may vertically actuate the magnet housings and magnet arrays to move it into both an engaged position and a disengaged position. The magnet assembly may also include an optical home sensor that detects the "home" position (e.g., disengaged position) of the stepper motor.

Electrode array. The apparatuses described herein generally include an electrode subsystem including the array of drive electrodes and the return electrode connection, as well as the control circuitry for controlling actuation of the EWOD to move droplets on the device. FIG. 56A is an example of the top of an electrode subsystem that may be included in an apparatus as described. In FIG. 56A, the electrode subsystem includes an electrode array 5605 (as mentioned, above, all or some, of the electrodes in the array, e.g., the peripheral rows of electrodes, may include a vacuum opening formed through the electrode), and one or more return (e.g., ground) contacts 5607 for connecting to the return electrode in the cartridge. The electrode array and return contacts may be mounted or formed on a circuit board (e.g., a PCB) 5601, which may be referred to as the electrode board. The electrode board may include a high voltage power supply 5609 for providing high voltage for the EWOD (e.g., the drive electrodes). The electrode board may also include the cartridge detection subsystem 5811 mentioned above, e.g., one or more sensors for detecting the presence of a cartridge in a desired location, and/or a clamp detection subsystem 5815, including one or more clamp latching sensors for detecting latching of a clamp securing the cartridge in a desired location.

The electrode board may also include an identification marker apparatus (e.g., optical apparatus, RFID apparatus) and/or a near-field communications apparatus (NFC apparatus) 5630 for reading an identifying marker from a cartridge seated in the apparatus. The electrode board may also include the high-voltage regulating circuitry 5633, and/or high-voltage measurement resistor strings 5635, as well as decoupling capacitors 5641, which may prevent electrical shock. Any of these boards may also include the circuitry including one or more thermistor amplifiers, TEC interlocks and optionally and accelerometer 5644.

FIG. 56B shows the bottom side of the electrode board, including the TECs (TEC1, TEC2, TEC3) as described above, as well as the isothermal heater power supply, the TEC power supply, the high voltage power supply regulation circuitry, and circuitry for power supply conditioning, droplet detection, digital and analog isolation circuitry, solid state relays, thermistor amplifiers, TEC and heater protection logic, vibrational motor for vortexing (vibe motor) and one or more pressure sensors.

In general, the electrode board forming at least part of the electrode sub-assembly may include a paralyne coating, as mentioned. The electrode board may also include the controller (e.g., one or more processors) of the control may be part of a separate board. The electrode board may also include the fan and/or vacuum pump drivers, for during the proper voltage to the fan and vacuum pump within the apparatus housing. As mentioned above, the electrode board may include the NFC electronics and/or antenna, for reading and writing to a NFC tag in the cartridge.

Vortexing on DMF. As mentioned above, and illustrated in FIG. 56B, any of the apparatuses described herein may include a mechanical vibration (e.g., vortexer), e.g., on the electrode board, configured to apply mechanical vibration to one or more regions of the DMF apparatus, including any sub-region or zone. The dynamics of vortexing liquids are key to implementing many standard molecular biology protocols steps including thorough mixing, dissolving compounds into solution, emulsion formation, cells and tissue dissociation and or disaggregation. Conventionally, many of these processes are carried using vortexer devices onto which small vials of liquid are placed on their base, pressed and in consequence vials rapidly oscillate in a circular motion creating a vortex inside the liquid. A standard vortexer can have variable speed control ranging from 100 to 3200 rpm.

The apparatuses described herein may mimic this process on DMF. Although the DMF chamber is stationary and circular motion cannot take place, the dynamics of vortices in droplets may be achieved by coupling a vibrational motor to the bottom of DMF PCB board. The vibrational motor speed may control ranges from 0 to 10,000 RPMs and a force of minimum 50 Newtons (11.241$bf$).

As shown in FIG. 57, vortexing on DMF can enable compartmentalized reactions which are useful in a wide range of protocols and applications such as single cell biology, single cell RNA-seq, droplet digital PCR, droplet barcode and single molecule sequencing, all of which may be performed in the systems described herein. For example, a mechanical vibrator motor (shown in FIG. 56B) may be mounted to the electrode board under or adjacent to the electrode array (drive electrode array). In FIG. 57, a schematic showing a vibration motor 5701 underlying the drive electrodes 5703 ("actuation electrodes") is shown, with a droplet 5705 held in an air gap 5707. The air gap 5707 is formed between the inner surface of an upper hydrophobic layer 5709" and the inner surface of a lower hydrophobic layer (or dielectric layer) 5811'. The upper hydrophobic layer may be part of a (top plate) 5709, which may include conductive layer 5709' or may be part of a cartridge upper plate having only the upper hydrophobic layer 5709". The lower hydrophobic layer 5711' may be the dielectric film of a cartridge vacuum-attached to the drive electrodes in the apparatus) or may be part of the bottom plate 5711, having the actuation electrodes 5703 therebetween.

Examples of different procedures using this vibration motor are shown. The vibration motor operates at, e.g., a voltage of 3 V DC, at a speed of approximately 14,000 RPM (and is approximately 6×14 mm). In FIG. 57, the vortex is applied through vibrational forces generated from digital microfluidic PCB board. On the left side, an emulsion formation by vortexing two droplets, aqueous droplet 5713 and oil droplet 5715 that merged using electrowetting forces to form a mixture of aqueous/oil 5717 is shown schematically. It is possible for hydrogel particles and sample solution or single cells to be contained in monodispersed oil emulsions 5717 upon vortexing on DMF. Using DMF, heterogeneous mixtures such as slurries and solid tissue blocks can be mobilized and manipulated in protocol steps. Tissue dissociation on DMF can be enabled mechanically through vortexing. Combining a set of DMF features can enhance the ability to dissociate otherwise difficult tissues 5719 through parallel on-chip vortexing (mechanical feature) and incubation with dissociative enzymes (enzymatic incubation at set temperatures) such as trypsin, papain, collagenase. Dissociation of tissues/organs/organisms on DMF can be followed by single cell partitioning by applying vortex forces to partition cells in emulsion as described above and the use of mixing/heating/cooling/magnetic actuation DMF features can allow to continue with downstream single cell 5721 protocol steps followed by library preparation steps to yield a sequence ready single cell library. Vortexing on DMF can help resuspend slurries, sedimented particles or heterogeneous mixtures 5723 such as magnetic or paramagnetic bead particles in suspension after they sediment during prolonged storage/incubation steps to provide freely suspended particles in the droplet 5725.

Non-transitory computer readable instructions. Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, intensity, etc.), determining, alerting, or the like.

In order to better adapt to different user needs and laboratory space, independent single modules, each with its own power, environmental, internal computer and connection to console unit for user interface may be multiplexed together. Additionally, a console unit for user interface can be integrated to control the different modules as well as other laboratory required functions such as scan the sample ID as well as the cartridge ID and integrate that information to the local laboratory or sample management system. Connection to console unit can be wireless or by cable.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A digital microfluidics method, the method comprising:
driving a droplet within an air gap of an air-matrix digital microfluidic (DMF) apparatus to a sub-region of the air gap by electrowetting;
coating the droplet with a liquid wax material within the air gap;
pinning the droplet within the sub-region by contacting the droplet with two or more protrusions extending from an upper surface of the air gap into the air gap, wherein the two or more protrusions extend only partially into the air gap;
vortexing a plurality of magnetic beads within the coated droplet within a thermal zone; and
performing one or more manipulations on the pinned droplet.

2. The method of claim 1, wherein pinning the droplet comprises pinning at least the liquid wax coating material coating the droplet.

3. The method of claim 1, wherein performing one or more manipulations comprises heating the sub-region of the air gap including the droplet.

4. The method of claim 1, further comprising driving the droplet away from the sub-region and off of the protrusions by electrowetting.

5. The method of claim 1, wherein the two or more protrusions comprise three to ten protrusions.

6. The method of claim 1, wherein each of the two or more protrusions have a cylindrical or rectangular shape.

7. The method of claim 1, wherein each of the two or more protrusions have a lateral dimension on the upper surface of the air gap between 0.5 mm to 2.8 mm.

8. The method of claim 1, wherein each of the two or more protrusions have a vertical dimension extending into the air gap of 1% to 90% of a vertical dimension of the air gap.

9. The method of claim 1, wherein each of the two or more protrusions have a vertical dimension extending into the air gap of 1% to 20% of a vertical dimension of the air gap.

10. The method of claim 1, wherein performing one or more manipulations comprises performing at least one of: vortexing a plurality of magnetic beads within the pinned droplet, cooling the sub-region of the air gap including the pinned droplet, detecting the pinned droplet; driving the pinned droplet to a channel hole within the sub-region of the air gap; aspirating the droplet into a channel of the channel hole; and driving the droplet from the sub-region by electrowetting.

11. A digital microfluidic (DMF) method comprising:
coating an aqueous reaction droplet with a liquid wax material within an air gap formed between a first hydrophobic layer of a first plate and a second hydrophobic layer of a second plate of a DMF apparatus;
pinning the liquid wax coating of the aqueous reaction droplet to at least two protrusions within a sub-region of the air gap, thereby distributing the liquid wax around the reaction droplet;
heating at least the sub-region of the air gap including the coated aqueous reaction droplet, whereby the liquid wax coating limits or prevents evaporation from the aqueous reaction droplet; and
vortexing a plurality of magnetic beads within the coated reaction droplet within a thermal zone.

12. The method of claim 11, wherein pinning comprises pinning the liquid wax coating to the at least two protrusions disposed adjacent to the second hydrophobic layer of the second plate.

13. The method of claim 11, wherein the at least two protrusions comprise two to ten protrusions.

14. The method of claim 11, wherein each of the at least two protrusions has a cylindrical or rectangular shape.

15. The method of claim 11, wherein each of the at least two protrusions has a lateral dimension between 0.5 mm to 2.8 mm.

16. The method of claim 11, wherein each of the at least two protrusions has a vertical dimension extending into the air gap of 1% to 90% of a vertical dimension of the air gap.

17. The method of claim 11, wherein each of the at least two protrusions has a vertical dimension into the air gap extending less than 40% of a vertical dimension of the air gap.

18. The method of claim 11, wherein each of the at least two protrusions has a vertical dimension extending into the air gap between 1% to 20% of a vertical dimension of the air gap.

19. The method of claim 11, further comprising moving the coated aqueous reaction droplet away from the sub-region of the air gap after completing heating.

20. The method of claim 19, wherein moving comprises driving the coated aqueous reaction droplet by energizing a sub-set of a plurality of driving electrodes adjacent to the first hydrophobic layer of the first plate of the DMF apparatus.

21. The method of claim 19, wherein moving further comprises withdrawing at least a portion of the coated aqueous reaction droplet from a surface of the air gap of the DMF apparatus before energizing a sub-set of the plurality of driving electrodes; and
reintroducing the at least portion of the coated aqueous reaction droplet back to the surface of the air gap of the DMF apparatus as a front of the aqueous reaction droplet exits the sub-region.

22. The method of claim 21, wherein withdrawing comprises withdrawing the at least portion of the coated reaction droplet via a channel from a surface of the second hydrophobic layer of the second plate to at least partially through the second plate.

23. The method of claim 11, wherein the first plate comprises a bottom plate of a cartridge configured to be seated on a seating surface of the DMF apparatus comprising a plurality of actuation electrodes.

24. A digital microfluidic (DMF) method comprising:
coating an aqueous reaction droplet with a liquid wax material within an air gap formed between a first hydrophobic layer of a first plate and a second hydrophobic layer of a second plate of a DMF apparatus, wherein the first plate comprises a bottom plate of a cartridge configured to be seated on a seating surface of the DMF apparatus comprising a plurality of actuation electrodes;
pinning the liquid wax coating of the aqueous reaction droplet to at least two protrusions within a sub-region of the air gap, thereby distributing the liquid wax around the reaction droplet; and
heating at least the sub-region of the air gap including the coated aqueous reaction droplet, whereby the liquid wax coating limits or prevents evaporation from the aqueous reaction droplet.

* * * * *